US009877981B2

(12) United States Patent
Sinclair et al.

(10) Patent No.: US 9,877,981 B2
(45) Date of Patent: Jan. 30, 2018

(54) NAD BIOSYNTHESIS AND PRECURSORS FOR THE TREATMENT AND PREVENTION OF CANCER AND PROLIFERATION

(71) Applicants: President and Fellows of Harvard College, Cambridge, MA (US); NewSouth Innovations Pty Limited, Sydney (AU)

(72) Inventors: David A. Sinclair, Chestnut Hill, MA (US); Ana P. Gomes, New York, NY (US); Lindsay Wu, Coogee (AU)

(73) Assignees: President and Fellows of Harvard College, Cambridge, MA (US); NewSouth Innovations Pty Limited, Sydney (AU)

( * ) Notice: Subject to any disclaimer, the term of this patent is extended or adjusted under 35 U.S.C. 154(b) by 47 days.

(21) Appl. No.: 14/434,573

(22) PCT Filed: Oct. 9, 2013

(86) PCT No.: PCT/US2013/064154
§ 371 (c)(1),
(2) Date: Apr. 9, 2015

(87) PCT Pub. No.: WO2014/059034
PCT Pub. Date: Apr. 17, 2014

(65) Prior Publication Data
US 2015/0313930 A1 Nov. 5, 2015

Related U.S. Application Data

(60) Provisional application No. 61/711,552, filed on Oct. 9, 2012, provisional application No. 61/832,414, filed on Jun. 7, 2013, provisional application No. 61/832,203, filed on Jun. 7, 2013.

(51) Int. Cl.
*A01N 43/04* (2006.01)
*A61K 31/70* (2006.01)
*A61K 31/7064* (2006.01)
*A61K 38/45* (2006.01)
*A61K 48/00* (2006.01)
*A61K 31/706* (2006.01)

(52) U.S. Cl.
CPC .......... *A61K 31/7064* (2013.01); *A61K 38/45* (2013.01); *A61K 48/005* (2013.01); *A01K 2217/075* (2013.01); *A01K 2227/105* (2013.01); *A01K 2267/035* (2013.01); *A61K 31/706* (2013.01); *C12Y 204/02012* (2013.01); *C12Y 207/07001* (2013.01)

(58) Field of Classification Search
None
See application file for complete search history.

(56) References Cited

U.S. PATENT DOCUMENTS

| 4,816,567 | A | 3/1989 | Cabilly et al. |
|---|---|---|---|
| 4,933,324 | A | 6/1990 | Shashoua |
| 5,225,539 | A | 7/1993 | Winter |
| 5,284,876 | A | 2/1994 | Shashoua et al. |
| 5,530,188 | A | 6/1996 | Ausich et al. |
| 5,565,332 | A | 10/1996 | Hoogenboom et al. |
| 5,994,392 | A | 11/1999 | Shashoua |
| 6,369,086 | B1 | 4/2002 | Davis et al. |
| 6,369,087 | B1 | 4/2002 | Whittle et al. |
| 6,372,733 | B1 | 4/2002 | Caldwell et al. |
| 6,372,778 | B1 | 4/2002 | Tung et al. |
| 7,544,497 | B2 | 6/2009 | Sinclair |
| 7,977,049 | B2 | 7/2011 | Sinclair |
| 8,017,634 | B2 | 9/2011 | Sinclair |
| 8,242,171 | B2 | 8/2012 | Sinclair |
| 8,846,724 | B2 | 9/2014 | Sinclair et al. |
| 9,241,916 | B2 | 1/2016 | Sinclair |
| 9,597,347 | B2 | 3/2017 | Sinclair et al. |
| 2004/0224039 | A1 | 11/2004 | Brucker |
| 2005/0004052 | A1 | 1/2005 | Baasov et al. |
| 2005/0096256 | A1 | 5/2005 | Sinclair |
| 2005/0136537 | A1 | 6/2005 | Sinclair |

(Continued)

FOREIGN PATENT DOCUMENTS

| CA | 2 529 510 A1 | 1/2005 |
|---|---|---|
| EP | 2431480 A2 | 3/2012 |

(Continued)

OTHER PUBLICATIONS

Chaplin et al. Journal of the National Cancer Institute (1990), vol. 82, pp. 672-676.*

(Continued)

*Primary Examiner* — Patrick T Lewis
(74) *Attorney, Agent, or Firm* — Wolf, Greenfield & Sacks, P.C.

(57) ABSTRACT

Disclosed herein are novel compositions and methods for the treatment of age-related diseases, mitochondrial diseases, the improvement of stress resistance, the improvement of resistance to hypoxia and the extension of life span. Also described herein are methods for the identification of agents useful in the foregoing methods.

Methods and compositions are provided for the treatment of diseases or disorders associated with mitochondrial dysfunction.

The invention relates to methods for treatment and prevention of cancer by administering agents that increase levels of NAD+, such as NAD+ precursors or agents involved in NAD+ biosynthesis.

19 Claims, 72 Drawing Sheets

(56) References Cited

U.S. PATENT DOCUMENTS

| | | |
|---|---|---|
| 2005/0171027 A1 | 8/2005 | Sinclair |
| 2005/0267023 A1 | 12/2005 | Sinclair et al. |
| 2006/0002914 A1 | 1/2006 | Milbrandt et al. |
| 2006/0025337 A1 | 2/2006 | Sinclair |
| 2006/0084085 A1 | 4/2006 | Sinclair |
| 2006/0111435 A1 | 5/2006 | Sinclair et al. |
| 2008/0020413 A1 | 1/2008 | Tong et al. |
| 2008/0194803 A1 | 8/2008 | Sinclair |
| 2010/0035885 A1 | 2/2010 | Sinclair |
| 2010/0074897 A1 | 3/2010 | Huang |
| 2011/0082189 A1 | 4/2011 | Sinclair |
| 2011/0123510 A1 | 5/2011 | Imai et al. |
| 2012/0021924 A1 | 1/2012 | Sinclair |
| 2012/0022013 A1 | 1/2012 | Sinclair |
| 2012/0029065 A1 | 2/2012 | Sinclair |
| 2012/0164670 A1 | 6/2012 | Hubbard et al. |
| 2013/0028862 A1 | 1/2013 | Fyfe et al. |
| 2015/0133396 A1 | 5/2015 | Sinclair et al. |
| 2015/0233949 A1 | 8/2015 | Hafner et al. |
| 2015/0265642 A1 | 9/2015 | Sinclair et al. |
| 2015/0266946 A1 | 9/2015 | Sinclair et al. |
| 2016/0263140 A1 | 9/2016 | Sinclair et al. |
| 2016/0287621 A1 | 10/2016 | Sinclair et al. |

FOREIGN PATENT DOCUMENTS

| | | |
|---|---|---|
| WO | WO 99/33792 | 7/1999 |
| WO | WO 99/33793 | 7/1999 |
| WO | WO 99/33795 A1 | 7/1999 |
| WO | WO 99/33815 A1 | 7/1999 |
| WO | WO 2004/006887 A2 | 1/2004 |
| WO | WO 2005/002555 A2 | 1/2005 |
| WO | WO 2005/002672 A2 | 1/2005 |
| WO | WO 2006/105403 A2 | 5/2006 |
| WO | WO 2006/086454 A2 | 8/2006 |
| WO | WO 2006/105440 A2 | 10/2006 |
| WO | WO 2010/036230 A2 | 4/2010 |
| WO | WO 2012/114204 A2 | 8/2012 |
| WO | WO 2012/142191 A1 | 10/2012 |

OTHER PUBLICATIONS

Yoshino et al. Cell Metabolism (2011), vol. 14, pp. 528-536.*
Tan et al. The Journal of Biological Chemistry (2015), vol. 290, pp. 15812-15824.*
Andziak et al., Disparate patterns of age-related changes in lipid peroxidation in long-lived naked mole-rats and shorter-lived mice. Aging Cell. Dec. 2006;5(6):525-32.
Andziak et al., High oxidative damage levels in the longest-living rodent, the naked mole-rat. Aging Cell. Dec. 2006;5(6):463-71. Epub Oct. 27, 2006.
Balan et al., Life span extension and neuronal cell protection by *Drosophila* nicotinamidase. J Biol Chem Oct. 10, 2008;283(41):27810-9. Epub Aug. 4, 2008. Supplemental Materials Included.
Banks et al., SirT1 gain of function increases energy efficiency and prevents diabetes in mice. Cell Metab. Oct. 2008;8(4):333-41. doi:10.1016/j.cmet.2008.08.014.
Baur et al., Resveratrol improves health and survival of mice on a high-calorie diet. Nature. Nov. 16, 2006;444(7117):337-42. Epub Nov. 1, 2006.
Beidler et al. Cloning and high level expression of a chimeric antibody with specificity for human carcinoembryonic antigen. J Immunol. Dec. 1, 1988;141(11):4053-60.
Bell et al., SirT3 suppresses hypoxia inducible factor 1α and tumor growth by inhibiting mitochondrial ROS production. Oncogene. Jun. 30, 2011;30(26):2986-96. doi: 10.1038/onc.2011.37. Epub Feb. 28, 2011.
Bell et al., The Qo site of the mitochondrial complex III is required for the transduction of hypoxic signaling via reactive oxygen species production. J Cell Biol. Jun. 18, 2007;177(6):1029-36. Epub Jun. 11, 2007.
Berge et al., Pharmaceutical salts. J Pharm Sci. Jan. 1977;66(1):1-19.
Better et al., *Escherichia coli* secretion of an active chimeric antibody fragment. Science. May 20, 1988;240(4855):1041-3.
Bieganowski et al., Discoveries of nicotinamide riboside as a nutrient and conserved NRK genes establish a preiss-handler independent route to NAD+ in fungi and humans. Cell, May 4, 2004;117:495-502.
Boffoli et al., Decline with age of the respiratory chain activity in human skeletal muscle. Biochim Biophys Acta. Apr. 12, 1994;1226(1):73-82.
Boily et al., SirT1 regulates energy metabolism and response to caloric restriction in mice. PLoS One. Mar. 12, 2008;3(3):e1759. doi: 10.1371/journal.pone.0001759.
Bordone et al., SIRT1 transgenic mice show phenotypes resembling calorie restriction. Aging Cell. Dec. 2007;6(6):759-67. Epub Sep. 17, 2007.
Bowling et al., Age-dependent impairment of mitochondrial function in primate brain. J Neurochem. May 1993;60(5):1964-7.
Braidy et al., Age related changes in NAD+ metabolism oxidative stress and Sirt1 activity in wistar rats. PLoS One. Apr. 26, 2011;6(4):e19194. doi: 10.1371/journal.pone.0019194.
Brautigan et al., Mitochondrial cytochrome c:preparation and activity of native and chemically modified cytochromes c. Methods Enzymol. 1978;53:128-64.
Bresett, Would you suspect this skin-eating infection? Modern Medicine. Mar. 1, 2006.
Cadenas et al., Mitochondrial reprogramming through cardiac oxygen sensors in ischaemic heart disease. Cardiovasc Res. Nov. 1, 2010;88(2):219-28. doi: 10.1093/cvr/cvq256. Epub Aug. 2, 2010.
Cantó et al., AMPK regulates energy expenditure by modulating NAD+ metabolism and SIRT1 activity. Nature. Apr. 23, 2009;458(7241):1056-60. doi:10.1038/nature07813.
Cantó et al., NAD+ as a signaling molecule modulating metabolism. Cold Spring Harb Symp Quant Biol. 2011;76:291-8. doi: 10.1101/sqb.2012.76.010439. Epub Feb. 17, 2012.
Cantó et al., Targeting sirtuin 1 to improve metabolism: all you need is NAD(+)? Pharmacol Rev. Jan. 2012;64(1):166-87. doi: 10.1124/pr.110.003905. Epub Nov. 21, 2011.
Carabelli et al., High fat diet-induced liver steatosis promotes an increase in liver mitochondrial biogenesis in response to hypoxia. J Cell Mol Med. Jun. 2011;15(6):1329-38. doi: 10.1111/j.1582-4934.2010.01128.x. Epub Jul. 12, 2010.
Cerqueira et al., Long-term intermittent feeding, but not caloric restriction, leads to redox imbalance, insulin receptor nitration, and glucose intolerance. Free Radic Biol Med. Oct. 1, 2011;51(7):1454-60. doi: 10.1016/j.freeradbiomed.2011.07.006. Epub Jul. 21, 2011.
Chandel et al., Cells depleted of mitochondrial DNA (rho0) yield insight into physiological mechanisms. FEBS Lett. Jul. 9, 1999;454(3):173-6.
Chandel et al., Reactive oxygen species generated at mitochondrial complex III stabilize hypoxia-inducible factor-1alpha during hypoxia: a mechanism of O2 sensing. J Biol Chem. Aug. 18, 2000;275(33):25130-8.
Chen et al., HIF-1 modulates dietary restriction-mediated lifespan extension via IRE-1 in Caenorhabditis elegans. PLoS Genet. May 2009;5(5):e1000486. doi: 10.1371/journal.pgen.1000486. Epub May 22, 2009.
Chen et al., The Role of Nicotinamide Phosphoribosyltransferase in Cerebral Ischemia. Curr Top Med Chem. 2015;15(21):2211-21.
Cheng et al., Developmental defects and p53 hyperacetylation in Sir2 homolog (SIRT1)-deficient mice. Proc Natl Acad Sci U S A. Sep. 16, 2003;100(19):10794-9. Epub Sep. 5, 2003.
Choi et al., Caloric restriction improves efficiency and capacity of the mitochondrial electron transport chain in *Saccharomyces cerevisiae*. Biochem Biophys Res Commun. Jun. 3, 2011;409(2):308-14. doi:10.1016/j.bbrc.2011.05.008. Epub May 7, 2011.
Civitarese et al., Calorie restriction increases muscle mitochondrial biogenesis in healthy humans. PLoS Med. Mar. 2007;4(3):e76.
Cohen et al., Calorie restriction promotes mammalian cell survival by inducing the SIRT1 deacetylase. Science. Jul. 16, 2004;305(5682):390-2. Epub Jun. 17, 2004.

(56) References Cited

OTHER PUBLICATIONS

Coskun et al., A mitochondrial etiology of Alzheimer and Parkinson disease. Biochim Biophys Acta. May 2012;1820(5):553-64. doi: 10.1016/j.bbagen.2011.08.008. Epub Aug. 16, 2011.
Couzin-Frankel, Genetics. Aging genes: the sirtuin story unravels. Science. Dec. 2, 2011;334(6060):1194-8.
Creighton-Gutteridge et al., Cell type-specific, topoisomerase II-dependent inhibition of hypoxia-inducible factor-1alpha protein accumulation by NSC 644221. Clin Cancer Res. Feb. 1, 2007;13(3):1010-8.
Dai et al., SIRT1 activation by small molecules: kinetic and biophysical evidence for direct interaction of enzyme and activator. J Biol Chem. Oct. 22, 2010;285(43):32695-703. Epub Aug. 11, 2010. Supplemental Materials included.
De Moura et al., Mitochondrial dysfunction in neurodegenerative diseases and cancer. Environ Mol Mutagen. Jun. 2010;51(5):391-405. doi: 10.1002/em.20575.
De Oliveira et al., Sirtuins: common targets in aging and in neurodegeneration. Curr Drug Targets. Oct. 2010;11(10):1270-80.
Dillin et al., Rates of behavior and aging specified by mitochondrial function during development. Science. Dec. 20, 2002;298(5602):2398-401. Epub Dec. 5, 2002.
Dioum et al., Regulation of hypoxia-inducible factor 2alpha signaling by the stress-responsive deacetylase sirtuin 1. Science. Jun. 5, 2009;324(5932):1289-93. doi:10.1126/science.1169956.
Dominy et al., The deacetylase Sirt6 activates the acetyltransferase GCN5 and suppresses hepatic gluconeogenesis. Mol Cell. Dec. 28, 2012;48(6):900-13. doi:10.1016/j.molcel.2012.09.030. Epub Nov. 8, 2012.
Donmez et al., SIRT1 suppresses beta-amyloid production by activating the alpha-secretase gene ADAM10. Cell. Jul. 23, 2010;142(2):320-32. doi: 10.1016/j.cell.2010.06.020. Erratum in: Cell. Aug. 6, 2010;142(3):494-5. Retraction in: Cell. Aug. 14, 2014;158(4):959.
Durieux et al., The cell-non-autonomous nature of electron transport chain-mediated longevity. Cell. Jan. 7, 2011;144(1):79-91. doi:10.1016/j.cell.2010.12.016.
Dutta et al., Contribution of impaired mitochondrial autophagy to cardiac aging: mechanisms and therapeutic opportunities. Circ Res. Apr. 13, 2012;110(8):1125-38. doi:10.1161/CIRCRESAHA.111.246108.
Emaus et al., Rhodamine 123 as a probe of transmembrane potential in isolated rat-liver mitochondria: spectral and metabolic properties. Biochim Biophys Acta. Jul. 23, 1986;850(3):436-48.
Evans et al., NRF-1: a trans-activator of nuclear-encoded respiratory genes in animal cells. Genes Dev. Jun. 1990;4(6):1023-34.
Falk et al., NMNAT1 mutations cause Leber congenital amaurosis. Nat Genet. Sep. 2012;44(9):1040-5. doi: 10.1038/ng.2361. Epub Jul. 29, 2012.
Falkenberg et al., DNA replication and transcription in mammalian mitochondria. Annu Rev Biochem. 2007;76:679-99.
Felkai et al., CLK-1 controls respiration, behavior and aging in the nematode *Caenorhabditis elegans*. EMBO J. Apr. 1, 1999;18(7):1783-92.
Feng et al., Mitochondrial electron transport is a key determinant of life span in *Caenorhabditis elegans*. Dev Cell. Nov. 2001;1(5):633-44.
Fernandez-Marcos et al., Regulation of PGC-1α, a nodal regulator of mitochondrial biogenesis. Am J Clin Nutr. Apr. 2011;93(4):884S-90. doi:10.3945/ajcn.110.001917. Epub Feb. 2, 2011.
Ferrer et al., Phosphorylated c-MYC expression in Alzheimer disease, Pick's disease, progressive supranuclear palsy and corticobasal degeneration. Neuropathol Appl Neurobiol. Oct. 2001;27(5):343-51.
Figueiredo et al., Aging impairs skeletal muscle mitochondrial bioenergetic function. J Gerontol A Biol Sci Med Sci. Jan. 2009;64(1):21-33. doi: 10.1093/gerona/gln048. Epub Feb. 5, 2009.
Figueiredo et al., The role of mitochondria in aging of skeletal muscle. Biogerontology. Apr. 2008;9(2):67-84. doi:10.1007/s10522-007-9121-7. Epub Jan. 4, 2008.
Finley et al., SIRT3 opposes reprogramming of cancer cell metabolism through HIF1α destabilization. Cancer Cell. Mar. 8, 2011;19(3):416-28. doi: 10.1016/j.ccr.2011.02.014.
Finsterer, Mitochondriopathies. Eur J Neurol. Mar. 2004;11(3):163-86.
Frezza et al., Organelle isolation: functional mitochondria from mouse liver, muscle and cultured fibroblasts. Nat Protoc. 2007;2(2):287-95.
Gallo et al., Increased longevity of some C. elegans mitochondrial mutants explained by activation of an alternative energy-producing pathway. Mech Ageing Dev. Oct. 2011;132(10):515-8. doi: 10.1016/j.mad.2011.08.004. Epub Aug. 22, 2011.
Geng et al., HDAC4 protein regulates HIF1α protein lysine acetylation and cancer cell response to hypoxia. J Biol Chem. Nov. 4, 2011;286(44):38095-102. doi: 10.1074/jbc.M111.257055. Epub Sep. 14, 2011.
Gerhart-Hines et al., Metabolic control of muscle mitochondrial function and fatty acid oxidation through SIRT1/PGC-1alpha. EMBO J. Apr. 4, 2007;26(7):1913-23. Epub Mar. 8, 2007.
Gomes et al., Berberine protects against high fat diet-induced dysfunction in muscle mitochondria by inducing SIRT1-dependent mitochondrial biogenesis. Biochim Biophys Acta. Feb. 2012;1822(2):185-95. doi:10.1016/j.bbadis.2011.10.008. Epub Oct. 17, 2011.
Gordan et al., HIF and c-Myc: sibling rivals for control of cancer cell metabolism and proliferation. Cancer Cell. Aug. 2007;12(2):108-13.
Greenberger et al., A RNA antagonist of hypoxia-inducible factor-1alpha, EZN-2968, inhibits tumor cell growth. Mol Cancer Ther. Nov. 2008;7(11):3598-608. doi: 10.1158/1535-7163.MCT-08-0510. Epub Oct. 30, 2008.
Gumucio et al., Atrogin-1, MuRF-1, and sarcopenia. Endocrine. Feb. 2013;43(1):12-21. doi: 10.1007/s12020-012-9751-7. Epub Jul. 20, 2012.
Gunther et al., Caspase-8 regulates TNF-α-induced epithelial necroptosis and terminal ileitis. Nature. Sep. 14, 2011;477(7364):335-9. doi: 10.1038/nature10400.
Gunther et al., Programmed cell death in crohn's disease. 2011.
Haigis et al., Mammalian sirtuins: biological insights and disease relevance. Annu Rev Pathol. 2010;5:253-95. doi:10.1146/annurev.pathol.4.110807.092250.
Hancock et al., Does calorie restriction induce mitochondrial biogenesis? A reevaluation. FASEB J. Feb. 2011;25(2):785-91. doi: 10.1096/fj.10-170415. Epub Nov. 3, 2010.
Harman, The biologic clock: the mitochondria? J Am Geriatr Soc. Apr. 1972;20(4):145-7.
Hartmann et al., Mitochondrial DNA copy number and function decrease with age in the short-lived fish *Nothobranchius furzeri*. Aging Cell. Oct. 2011;10(5):824-31. doi: 10.1111/j.1474-9726.2011.00723.x. Epub Jun. 27, 2011.
Herranz et al., Sirt1 improves healthy ageing and protects from metabolic syndrome-associated cancer. Nat Commun. Apr. 12, 2010;1:3. doi:10.1038/ncomms1001.
Houtkooper et al., Mitonuclear protein imbalance as a conserved longevity mechanism. Nature. May 23, 2013;497(7450):451-7. doi: 10.1038/nature12188.
Howes, The free radical fantasy: a panoply of paradoxes. Ann N Y Acad Sci. May 2006;1067:22-6.
Huang, Carrot and stick: HIF-alpha engages c-Myc in hypoxic adaptation. Cell Death Differ. Apr. 2008;15(4):672-7. doi: 10.1038/sj.cdd.4402302. Epub Jan. 11, 2008.
Hubbard et al., Evidence for a common mechanism of SIRT1 regulation by allosteric activators. Science. Mar. 8, 2013;339(6124):1216-9. doi: 10.1126/science.1231097.
Jäger et al., AMP-activated protein kinase (AMPK) action in skeletal muscle via direct phosphorylation of PGC-1alpha. Proc Natl Acad Sci U S A. Jul. 17, 2007;104(29):12017-22. Epub Jul. 3, 2007.
Jayaram et al., NMNAT expression and its relation to NAD metabolism. Curr Med Chem. 2011;18(13):1962-72.
Johnson et al., Skeletal muscle aging and the mitochondrion. Trends Endocrinol Metab. May 2013;24(5):247-56. doi: 10.1016/j.tem.2012.12.003. Epub Feb. 1, 2013.

(56) References Cited

OTHER PUBLICATIONS

Jones et al. Replacing the complementarity-determining regions in a human antibody with those from a mouse. Nature. May 29-Jun. 4, 1986;321(6069):522-5.

Kaeberlein et al., Increased life span due to calorie restriction in respiratory-deficient yeast. PLoS Genet. Nov. 2005;1(5):e69. Epub Nov. 25, 2005.

Kaelin, The von Hippel-Lindau tumour suppressor protein: O2 sensing and cancer. Nat Rev Cancer. Nov. 2008;8(11):865-73. doi: 10.1038/nrc2502. Epub Oct. 16, 2008.

Kessler et al., HIF-1α inhibition by siRNA or chetomin in human malignant glioma cells: effects on hypoxic radioresistance and monitoring via CA9 expression. BMC Cancer. Nov. 4, 2010;10:605. doi: 10.1186/1471-2407-10-605.

Kim et al., Expression and functional significance of nicotinamide N-methyl transferase in skeletal muscles of patients with chronic obstructive pulmonary disease. Am J Respir Crit Care Med. Apr. 15, 2010;181(8):797-805. doi:10.1164/rccm.200906-0936OC.

Kim et al., Global identification of Myc target genes reveals its direct role in mitochondrial biogenesis and its E-box usage in vivo. PLoS One. Mar. 12, 2008;3(3):e1798. doi: 10.1371/journal.pone.0001798.

Koh et al., Molecular mechanisms for the activity of PX-478, an antitumor inhibitor of the hypoxia-inducible factor-1alpha. Mol Cancer Ther. Jan. 2008;7(1):90-100. doi: 10.1158/1535-7163.MCT-07-0463.

Koshiji et al., HIF-1alpha induces cell cycle arrest by functionally counteracting Myc. EMBO J. May 5, 2004;23(9):1949-56. Epub Apr. 8, 2004.

Koshiji et al., HIF-1alpha induces genetic instability by transcriptionally downregulating MutSalpha expression. Mol Cell. Mar. 18, 2005;17(6):793-803.

Krishnan et al., Dietary obesity-associated HIF1α activation in adipocytes restricts fatty acid oxidation and energy expenditure via suppression of the Sirt2-NAD+ system. Genes Dev. Feb. 1, 2012;26(3):259-70. doi: 10.1101/gad.180406.111.

Kwong et al., Age-related changes in activities of mitochondrial electron transport complexes in various tissues of the mouse. Arch Biochem Biophys. Jan. 1, 2000;373(1):16-22.

Laemmle et al., Inhibition of SIRT1 impairs the accumulation and transcriptional activity of HIF-1α protein under hypoxic conditions. PLoS One. 2012;7(3):e33433. doi: 10.1371/journal.pone.0033433. Epub Mar. 30, 2012.

Lagouge et al., Resveratrol improves mitochondrial function and protects against metabolic disease by activating SIRT1 and PGC-1alpha. Cell. Dec. 15, 2006;127(6):1109-22. Epub Nov. 16, 2006.

Lanza et al., Mitochondrial function as a determinant of life span. Pflugers Arch. Jan. 2010;459(2):277-89. doi: 10.1007/s00424-009-0724-5. Epub Sep. 11, 2009.

Lapointe et al., Reversal of the mitochondrial phenotype and slow development of oxidative biomarkers of aging in long-lived Mclk1+/− mice. J Biol Chem. Jul. 24, 2009;284(30):20364-74. doi:10.1074/jbc.M109.006569. Epub May 28, 2009.

Lapointe et al., When a theory of aging ages badly. Cell Mol Life Sci. Jan. 2010;67(1):1-8. doi: 10.1007/s00018-009-0138-8.

Larsson, Somatic mitochondrial DNA mutations in mammalian aging. Annu Rev Biochem. 2010;79:683-706. doi: 10.1146/annurev-biochem-060408-093701.

Ledford, Much ado about ageing. Nature. Mar. 2010;464:480-481.

Lee et al., LW6, a novel HIF-1 inhibitor, promotes proteasomal degradation of HIF-1 alpha via upregulation of VHL in a colon cancer cell line. Biochem Pharmacol. Oct. 1, 2010;80(7):982-9. doi: 10.1016/j.bcp.2010.06.018. Epub Jun. 23, 2010.

Leiser et al., The hypoxia-inducible factor HIF-1 functions as both a positive and negative modulator of aging. Biol Chem. Oct. 2010;391(10):1131-7. doi: 10.1515/BC.2010.123.

Li et al., Myc stimulates nuclearly encoded mitochondrial genes and mitochondrial biogenesis. Mol Cell Biol. Jul. 2005;25(14):6225-34.

Lim et al., Sirtuin 1 modulates cellular responses to hypoxia by deacetylating hypoxia-inducible factor 1alpha. Mol Cell. Jun. 25, 2010;38(6):864-78. doi: 10.1016/j.molcel.2010.05.023.

Liu et al., Chimeric mouse-human IgG1 antibody that can mediate lysis of cancer cells. Proc Natl Acad Sci U S A. May 1987;84(10):3439-43.

Liu et al., Production of a mouse-human chimeric monoclonal antibody to CD20 with potent Fc-dependent biologic activity. J Immunol. Nov. 15, 1987;139(10):3521-6.

López-Lluch et al., Calorie restriction induces mitochondrial biogenesis and bioenergetic efficiency. Proc Natl Acad Sci U S A. Feb. 7, 2006;103(6):1768-73. Epub Jan. 30, 2006.

Majmundar et al., Hypoxia-inducible factors and the response to hypoxic stress. Mol Cell. Oct. 22, 2010;40(2):294-309. doi:10.1016/j.molcel.2010.09.022.

Manohar et al., A novel inhibitor of hypoxia-inducible factor-1α P3155 also modulates PI3K pathway and inhibits growth of prostate cancer cells. BMC Cancer. Aug. 5, 2011;11:338. doi: 10.1186/1471-2407-11-338.

Mao et al., Sirt1 deacetylates c-Myc and promotes c-Myc/Max association. Int J Biochem Cell Biol. Nov. 2011;43(11):1573-81. doi: 10.1016/j.biocel.2011.07.006. Epub Jul. 22, 2011.

Marshall et al., SIRT1 promotes N-Myc oncogenesis through a positive feedback loop involving the effects of MKP3 and ERK on N-Myc protein stability. PLoS Genet. Jun. 2011;7(6):e1002135. doi:10.1371/journal.pgen.1002135. Epub Jun. 16, 2011.

Massudi et al., Age-associated changes in oxidative stress and NAD+ metabolism in human tissue. PLoS One. 2012;7(7):e42357. doi: 10.1371/journal.pone.0042357. Epub Jul. 27, 2012.

McBurney et al., The mammalian SIR2alpha protein has a role in embryogenesis and gametogenesis. Mol Cell Biol. Jan. 2003;23(1):38-54.

Menssen et al., The c-MYC oncoprotein, the NAMPT enzyme, the SIRT1-inhibitor DBC1, and the SIRT1 deacetylase form a positive feedback loop. Proc Natl Acad Sci U S A. Jan. 24, 2012;109(4):E187-96. doi: 10.1073/pnas.1105304109. Epub Dec. 21, 2011.

Michel et al., Crosstalk between mitochondrial (dys)function and mitochondrial abundance. J Cell Physiol. Jun. 2012;227(6):2297-310. doi: 10.1002/jcp.23021.

Minamishima et al., Somatic inactivation of the PHD2 prolyl hydroxylase causes polycythemia and congestive heart failure. Blood. Mar. 15, 2008;111(6):3236-44. Epub Dec. 20, 2007.

Minor et al., SRT1720 improves survival and healthspan of obese mice. Sci Rep. 2011;1:70. doi:10.1038/srep00070. Epub Aug. 18, 2011. Erratum in: Sci Rep. 2013;3():1131.

Mirzoeva et al., Inhibition of HIF-1 alpha and VEGF expression by the chemopreventive bioflavonoid apigenin is accompanied by Akt inhibition in human prostate carcinoma PC3-M cells. Mol Carcinog. Sep. 2008;47(9):686-700. doi: 10.1002/mc.20421.

Morrison, Transfectomas provide novel chimeric antibodies. Science. Sep. 20, 1985;229(4719):1202-7.

Moslehi et al., Telomeres and mitochondria in the aging heart. Circ Res. Apr. 27, 2012;110(9):1226-37. doi: 10.1161/CIRCRESAHA.111.246868.

Nehlin et al., The Werner Syndrome. A Model for the Study of Human Aging. Annals NY Acad Sci. 2000; 980:167-179.

Niemann et al., Caloric restriction delays cardiac ageing in rats: role of mitochondria. Cardiovasc Res. Nov. 1, 2010;88(2):267-76. doi: 10.1093/cvr/cvq273. Epub Aug. 25, 2010.

Nishimura et al., Recombinant human-mouse chimeric monoclonal antibody specific for common acute lymphocytic leukemia antigen. Cancer Res. Feb. 15, 1987;47(4):999-1005.

Oberdoerffer et al., SIRT1 redistribution on chromatin promotes genomic stability but alters gene expression during aging. Cell. Nov. 28, 2008;135(5):907-18. doi: 10.1016/j.cell.2008.10.025.

Oi et al., Chimeric Antibodies. BioTechniques. 1986;4:214-221.

Osiewacz, Mitochondrial quality control in aging and lifespan control of the fungal aging model Podospora anserina. Biochem Soc Trans. Oct. 2011;39(5):1488-92. doi: 10.1042/BST0391488.

Pacholec et al., SRT1720, SRT2183 and SRT1460 do not activate Sirt1 with native substrates. Poster 30. FASEB Summer Research Conferences. Arizona. Jun. 21-26, 2009.

(56) References Cited

OTHER PUBLICATIONS

Pacholec et al., SRT1720, SRT2183, SRT1460, and resveratrol are not direct activators of SIRT1. J Biol Chem. Mar. 12, 2010;285(11):8340-51. Epub Jan. 8, 2010. Supplemental Materials Included.

Parisi et al., Similarity of human mitochondrial transcription factor 1 to high mobility group proteins. Science. May 17, 1991;252(5008):965-9.

Park et al., Resveratrol ameliorates aging-related metabolic phenotypes by inhibiting cAMP phosphodiesterases. Cell. Feb. 3, 2012;148(3):421-33. doi:10.1016/j.cell.2012.01.017.

Peterson et al., Skeletal muscle mitochondria and aging:a review. J Aging Res. 2012;2012:194821. doi: 10.1155/2012/194821. Epub Jul. 19, 2012.

Pfluger et al., Sirt1 protects against high-fat diet-induced metabolic damage. Proc Natl Acad Sci U S A. Jul. 15, 2008;105(28):9793-8. doi: 10.1073/pnas.0802917105. Epub Jul. 3, 2008.

Podar et al., A therapeutic role for targeting c-Myc/Hif-1-dependent signaling pathways. Cell Cycle. May 2010;9(9):1722-8. Epub May 1, 2010.

Powers et al., Mitochondrial signaling contributes to disuse muscle atrophy. Am J Physiol Endocrinol Metab. Jul. 1, 2012;303(1):E31-9. doi: 10.1152/ajpendo.00609.2011. Epub Mar. 6, 2012.

Price et al., SIRT1 is required for AMPK activation and the beneficial effects of resveratrol on mitochondrial function. Cell Metab. May 2, 2012;15(5):675-90. doi: 10.1016/j.cmet.2012.04.003.

Qin et al., Neuronal SIRT1 activation as a novel mechanism underlying the prevention of Alzheimer disease amyloid neuropathology by calorie restriction. J Biol Chem. Aug. 4, 2006;281(31):21745-54. Epub Jun. 2, 2006.

Rasbach et al., PGC-1alpha regulates a HIF2alpha-dependent switch in skeletal muscle fiber types. Proc Natl Acad Sci U S A. Dec. 14, 2010;107(50):21866-71. doi:10.1073/pnas.1016089107. Epub Nov. 24, 2010.

Rodgers et al., Nutrient control of glucose homeostasis through a complex of PGC-1alpha and SIRT1. Nature. Mar. 3, 2005;434(7029):113-8.

Rolo et al., Mitochondrially mediated synergistic cell killing by bile acids. Biochim Biophys Acta. Jan. 20, 2003;1637(1):127-32.

Sahin et al., Telomere dysfunction induces metabolic and mitochondrial compromise. Nature. Feb. 17, 2011;470(7334):359-65. doi: 10.1038/nature09787. Epub Feb. 9, 2011. Erratum in: Nature. Jul. 14, 2011;475(7355):254.

Sanders, Pseudohypoxia, Mitochondrial mutations, the Warburg Effect and Cancer. Biomed Research. 2012;23:109-131.

Santos et al., Quantitative PCR-based measurement of nuclear and mitochondrial DNA damage and repair in mammalian cells. Methods Mol Biol. 2006;314:183-99.

Scarpulla, Metabolic control of mitochondrial biogenesis through the PGC-1 family regulatory network. Biochim Biophys Acta. Jul. 2011;1813(7):1269-78. doi:10.1016/j.bbamcr.2010.09.019. Epub Oct. 13, 2010.

Scarpulla, Nucleus-encoded regulators of mitochondrial function:integration of respiratory chain expression, nutrient sensing and metabolic stress. Biochim Biophys Acta. Sep.-Oct. 2012;1819(9-10):1088-97. doi:10.1016/j.bbagrm.2011.10.011. Epub Nov. 4, 2011.

Schriner et al. Extension of murine life span by overexpression of catalase targeted to mitochondria. Science. Jun. 24, 2005;308(5730):1909-11. Epub May 5, 2005.

Schulz et al., Glucose restriction extends Caenorhabditis elegans life span by inducing mitochondrial respiration and increasing oxidative stress. Cell Metab. Oct. 2007;6(4):280-93.

Sequeira et al., sirt1-null mice develop an autoimmune-like condition. Exp Cell Res. Oct. 1, 2008;314(16):3069-74. doi:10.1016/j.yexcr.2008.07.011. Epub Jul. 23, 2008.

Shaw et al., Mouse/human chimeric antibodies to a tumor-associated antigen: biologic activity of the four human IgG subclasses. J Natl Cancer Inst. Dec. 7, 1988;80(19):1553-9.

Singer, Determination of the activity of succinate, NADH, choline, and alpha-glycerophosphate dehydrogenases. Methods Biochem Anal. 1974;22:123-75.

Sun et al., Chimeric antibody with human constant regions and mouse variable regions directed against carcinoma-associated antigen 17-1A. Proc Natl Acad Sci U S A. Jan. 1987;84(1):214-8.

Tan et al., Pharmacological inhibition of nicotinamide phosphoribosyltransferase (NAMPT), an enzyme essential for NAD+ biosynthesis, in human cancer cells: metabolic basis and potential clinical implications. J Biol Chem. Feb. 1, 2013;288(5):3500-11. doi:10.1074/jbc.M112.394510.

Tennen et al., Finding a target for resveratrol. Cell. Feb. 3, 2012;148(3):387-9.

Trifunovic et al., Premature ageing in mice expressing defective mitochondrial DNA polymerase. Nature. May 27, 2004;429(6990):417-23.

Trifunovic et al., Somatic mtDNA mutations cause aging phenotypes without affecting reactive oxygen species production. Proc Natl Acad Sci U S A. Dec. 13, 2005;102(50):17993-8. Epub Dec. 6, 2005.

Tyner et al., p53 mutant mice that display early ageing-associated phenotypes. Nature. Jan. 3, 2002;415(6867):45-53.

Verhoeyen et al., Reshaping human antibodies: grafting an antilysozyme activity. Science. Mar. 25, 1988;239(4847):1534-6.

Vermulst et al., DNA deletions and clonal mutations drive premature aging in mitochondrial mutator mice. Nat Genet. Apr. 2008;40(4):392-4. doi: 10.1038/ng.95. Epub Mar. 2, 2008.

Wallace et al., Mitochondrial energetics and therapeutics. Annu Rev Pathol. 2010;5:297-348. doi: 10.1146/annurev.pathol.4.110807.092314.

Wang et al., Elevated mitochondrial reactive oxygen species generation affects the immune response via hypoxia-inducible factor-1alpha in long-lived Mclk1+/− mouse mutants. J Immunol. Jan. 15, 2010;184(2):582-90. doi:10.4049/jimmunol.0902352. Epub Dec. 9, 2009.

Wang et al., NAMPT overexpression in prostate cancer and its contribution to tumor cell survival and stress response. Oncogene. Feb. 24, 2011;30(8):907-21. doi: 10.1038/onc.2010.468.

Wang et al., Nicotinamidase participates in the salvage pathway of NAD biosynthesis in *Arabidopsis*. Plant J. Mar. 2007;49(6):1020-9.

Wang et al., The anti-neurodegeneration drug clioquinol inhibits the aging-associated protein CLK-1. J Biol Chem. Jan. 2, 2009;284(1):314-23. doi:10.1074/jbc.M807579200. Epub Oct. 15, 2008.

Warburg, On the origin of cancer cells. Science. Feb. 24, 1956;123(3191):309-14.

Williams et al., Antagonistic pleiotropy, mortality source interactions, and the evolutionary theory of senescence. Evolution. Jul. 2003;57(7):1478-88.

Williamson et al., Hyperglycemic pseudohypoxia and diabetic complications. Diabetes. Jun. 1993;42(6):801-13.

Wood et al., The synthesis and in vivo assembly of functional antibodies in yeast. Nature. Apr. 4-10, 1985;314(6010):446-9.

Yang et al., NAD metabolism and sirtuins: metabolic regulation of protein deacetylation in stress and toxicity. AAPS J. Oct. 6, 2006;8(4):E632-43.

Yoshino et al., Nicotinamide mononucleotide, a key NAD(+) intermediate, treats the pathophysiology of diet- and age-induced diabetes in mice. Cell Metab. Oct. 5, 2011;14(4):528-36. doi: 10.1016/j.cmet.2011.08.014.

Yuan et al., A c-Myc-SIRT1 feedback loop regulates cell growth and transformation. J Cell Biol. Apr. 20, 2009;185(2):203-11. doi:10.1083/jcb.200809167. Epub Apr. 13, 2009.

Zechner et al., Total skeletal muscle PGC-1 deficiency uncouples mitochondrial derangements from fiber type determination and insulin sensitivity. Cell Metab. Dec. 1, 2010;12(6):633-42. doi: 10.1016/j.cmet.2010.11.008. Erratum in:Cell Metab. Jan. 5, 2011;13(1):114.

Zhang et al., Endothelium-specific overexpression of class III deacetylase SIRT1 decreases atherosclerosis in apolipoprotein E-deficient mice. Cardiovasc Res. Nov. 1, 2008;80(2):191-9. doi: 10.1093/cvr/cvn224. Epub Aug. 9, 2008.

(56) References Cited

OTHER PUBLICATIONS

Zhang et al., Enzymes in the NAD+ salvage pathway regulate SIRT1 activity at target gene promoters. J Biol Chem. Jul. 24, 2009;284(30):20408-17. doi: 10.1074/jbc.M109.016469. Epub May 28, 2009.
Zhang et al., Regulation of poly(ADP-ribose) polymerase-1-dependent gene expression through promoter-directed recruitment of a nuclear NAD+ synthase. J Biol Chem. Apr. 6, 2012;287(15):12405-16. doi: 10.1074/jbc.M111.304469. Epub Feb. 13, 2012.
[No Author Listed] FDA Guidance for Industry. Estimating the Maximum Safe Starting Dose in Initial Clinical Trials for Therapeutics in Adult Healthy Volunteers. Jul. 1-27, 2005.
Imai et al., NAD+ and sirtuins in aging and disease. Trends Cell Biol. Aug. 2014;24(8):464-71. doi: 10.1016/j.tcb.2014.04.002. Epub Apr. 29, 2014.
Rongvaux et al., Pre-B-cell colony-enhancing factor, whose expression is up-regulated in activated lymphocytes, is a nicotinamide phosphoribosyltransferase, a cytosolic enzyme involved in NAD biosynthesis. Eur J Immunol. Nov. 2002;32(11):3225-34.
Van Der Horst et al., The *Caenorhabditis elegans* nicotinamidase PNC-1 enhances survival. Mech Ageing Dev. Apr. 2007;128(4):346-9. Epub Feb. 2, 2007.
Villalba et al., Sirtuin activators and inhibitors. Biofactors. Sep.-Oct. 2012;38(5):349-59. doi: 10.1002/biof.1032.
Yang et al., Nutrient-sensitive mitochondrial NAD+ levels dictate cell survival. Cell. Sep. 21, 2007;130(6):1095-107.

\* cited by examiner

HIF-1a Homo sapiens NCBI Reference Sequence: NP_001521.1
SEQ ID NO: 1
MEGAGGANDKKKISSERRKEKSRDAARSRRSKESEVFYELAHQLPLPHNVSSHLDKASVMRLTISYL
RVRKLLDAGDLDIEDDMKAQMNCFYLKALDGFVMVLTDDGDMIYISDNVNKYMGLTQFELTGHSVFD
FTHPCDHEEMREMLTRNGLVKKGKEQNTQRSFFLRMKCTLTSRGRTMNIKSATWKVLHCTGHIHVY
DTNSNQPQCGYKKPPMTCLVLICEPIPHPSNIEIPLDSKTFLSRHSLDMKFSYCDERITELMGYEPE
ELLGRSIYEYYHALDSDHLTKTHHDMFTKGQVTTGQYRMLAKRGGYVWVETQATVIYNTKNSQPQCI
VCVNYVVSGIIQHDLIFSLQQTECVLKPVESSDMKMTQLFTKVESEDTSSLFDKLKKEPDALTLLAP
AAGDTIISLDFGSNDTETDDQQLEEVPLYNDVMLPSPNEKLQNINLAMSPLPTAETPKPLRSSADPA
LNQEVALKLEPNPESLELSFTMPQIQDQTPSPSDGSTRQSSPEPNSPSEYCFYVDSDMVNEFKLELV
EKLFAEDTEAKNPFSTQDTDLDLEMLAPYIPMDDDFQLRSFDQLSPLESSSASPESASPQSTVTVFQ
QTQIQEPTANATTTTATTDELKTVTKDRMEDIKILIASPSPTHIHKETTSATSSPYRDTQSRTASPN
RAGKGVIEQTEKSHPRSPNVLSVALSQRTTVPEEELNPKILALQNAQRKRKMEHDGSLFQAVGIGTL
LQQPDDHAATTSLSWKRVKGCKSSEQNGMEQKTIILIPSDLACPLLGQSMDESGLPQLTSYDCEVNA
PIQGSRNLLQGEELLRALDQVN HIF1a Pan troglodytes NCBI Reference Sequence: XP_001168972.1
SEQ ID NO: 2
MEGAGGANDKKKISSERRKEKSRDAARSRRSKESEVFYELAHQLPLPHNVSSHLDKASVMRLTISYL
RVRKLLDAGDLDIEDDMKAQMNCFYLKALDGFVMVLTDDGDMIYISDNVNKYNGLTQFELFGHSVFD
FTHPCDHEEMREMLTHRNGLVKKGKEQNTQRSFFLRMKCTLTSRGRTMNIKSATWKVLHCTGHIHVY
DTNSNQPQCGYKKPFMTCLVLICEPIPHPSNIEIPLDSKTFLSRHSLDMKFSYCDERITELMGYEPE
ELLGRSIYEYYHALDSDHLTKTHHDMFTKGQVTTGQYRMLAKRGGYVWVETQATVIYNTKNSQPQCI
VCVNYVVSGIIQHDLIFSLQQTECVLKPVESSDMKMTQLFTKVESEDTSSLFDKLKKEPDALTLLAP
AAGDTIISLDFGSNDTETDDQQLEEVPLYNDVNLPSPNEKLQNINLAMSPLPTAETPKPLRSSADPA
LNQEVALKLEPNPESLELSFTMPQIQDQTPSPSDGSTRQSSPEPNSPSEYCFYVDSLMVNEFKLELV
EKLFAEDTEAKNPFSTQDTDLDLEMLAPYIPMDDDFQLRSFDQLSPLESSSASPESASPQSTVTVFQ
QTQIQEPTANATTTTATTDELKTVTKDCMEDIKILIASPSPTHIHKETTSATSSPYRDTQSRTASPN
RAGKGVIEQTEKSHPRSPNVLSVALSQRTTVPEEELNPKILALQNAQRKRKMEHDGSLFQAVGIGTL
LQQPDDHAATTSLSWKRVKGCKSSEQNGMEQKTIILIPSDLACRLLGQSMDESGLPQLTSYDCEVNA
PIQGSPNLLQGEELLRALDQVN HIF1a Macaca mulatta NCBI Reference Sequence: XP_001099149.1
SEQ ID NO: 3
MEGAGGANDKKKISSERRKEKSRDAARSRRSKESEVFYELAHQLPLPHNVSSHLDKASVMRLTISYL
RVRKLLDAGDLDIEDEMKAQMNCFYLKALDGFVMVLTDDGDMIYISDNVNKYMGLTQFELTGHSVFD
FTHPCDHEEMREMLTHRNGPVKKGKEQNTQRSFFLRMKCTLTSRGRTMNIKSATWKVLHCTGHIHVY
DTNSNQPQCGYKKPPMTCLVLICEPIPHPSNIEIPLDSKTFLSRHSLDMKFSYCDERITELMGYEPE
ELLGRSIYEYYHALDSDHLTKTHHDMFTKGQVTTGQYRMLAKRGGYVWVETQATVIYNTKNSQPQCI
VCVNYVVSGIIQHDLIFSLQQTECVLKPVESSDMKMTQLFTKVESEDTSSLFDKLKKEPDALTLLAP
AAGDTIISLDFGSNDTETDDQQLEEVPLYNDVMLPSSNEKLQNINLAMSPLPTSETPKPLRSSADPA
LNQEVALKLEPNPESLELSFTMPQIQDQPPSPSDGSTRQSSPEPNSPSEYCFYVDSDMVNEFKLELV
EKLFAEDTEAKNPFSTQDTDLDLEMLAPYIPMDDDFQLRSFDQLSPLESSSASPESASPQSTVTVFQ
QTQIQEPTANATTTTATTDELKTVTKDRMEDIKILIASPSSTHIHKETTSATSSPYRDTQSRTASPN
RAGKGVIEQTEKSHPRSPNVLSVTLSQRTTVPEEELNPKILALQNAQRKRKMEHDGSLFQAVGIGTL
LQQPDDHAATTSLSWKRVKGCKSSEQNGMEQKTIILIPSDLACRLLGQSMDESGLPQLTSYDCEVNA
PIQGSRNLLQGEELLRALDQVN

FIG. 1

HIF1a Canis lupus familiaris NCBI Reference Sequence:
XP_003639249.1
SEQ ID NO: 4
MEGAGGANDKKKISSERRKEKSRDAARSRRSKESEVFYELAHQLPLPHNVSSHLDKASVMRLTISYL
RVRKLLDAGDLDIEDEMKAQMNCFYLKALDGFVMVLTDDGDMIYISDNVNKYMGLTQFELTGHSVFD
FTHPCDHEEMREMLTHRNGLVKKGKEQNTQRSFFLRMKCTLTSRGRTMNIKSATWKVLHCTGHIHVY
DTNSNQSQCGYKKPPMTCLVLICEPIPHPSNIEIPLDSKTFLSRHSLDMKFSYCDERITELMGYEPE
ELLGRSIYEYYHALDSDHLTKTHHDMFTKGQVTTGQYRMLAKRGGYVWVETQATVIYNTKNSQPQCI
VCVNYVVSGIIQHDLIFSLQQTECVLKPVESSDMKMTQLFTKVESEDTSSLFDKLKKEPDALTLLAP
AAGDTIISLDFGSNDTETDDQQLEEVPLYNDVMLPSSNEKLQNINLAMSPLPASETPKPLRSSADPA
LNQEVALKLEPNPESLELSFTMPQIQDQPASPSDGSTRQSSPEPNSPSEYCFDVDSLMVNEFKLELV
EKLFAEDTEAKNPFSTQDTDLDLEMLAPYIPMDDDFQLRSFDQLSPLESNSTSPQSASTITVFQPTP
MQEPPLTTTSTTATTDELKTVTKDGIEDIKILIAAPSPTHVPKVTTSATTSPYSDTGSRTASPNRAG
KGVIEQTEKSHPRSPNVLSVTLSQRTTIPEEELNPKILALQNAQRKRKIEHDGSLFQAVGIGTLLQQ
PDDRATTTSLSWKRVKGCKSSEQNGMEQKTIILIPSDLACRLLGQSMDESGLPQLTSYDCEVNAPIQ
GSRNLLQGEELLRALDQVN HIF1a Bos Taurus NCBI Reference Sequence: NP_776764.2
SEQ ID NO: 5
MEGAGGANDKKKISSERRKEKSRDAARSRRSKESEVFYELAHQLPLPHNVSSHLDKASVMRLTISYL
RVRKLLDAGDLDIEDEMKAQMNCFYLKALDGFVMVLTDDGDMIYISDNVNKYMGLTQFELTGHSVFD
FTHPCDHEEMREMLTHRNGLVKKGKEQNTQRSFFLRMKCTLTSRGRTMNIKSATWKVLHCTGHIHVY
DTNSNQSQCGYKKPPMTCLVLICEPIPHPSNIEIPLDSKTFLSRHSLDMKFSYCDERITELMGYEPE
ELLGRSIYEYYHALDSDHLTKTHHDMFTKGQVTTGQYRMLAKRGGYVWIETQATVIYNTKNSQPQCI
VCVNYVVSGIIQHDLIFSLQQTECVLKPVESSDMKMTQLFTKVESEDTSSLFDKLKKEPDALTLLAP
AAGDTIISLDFGSNDTETDDQQLEEVPLYNDVMLPSSNEKLQNINLAMSPLPASETPKPLRSSADPA
LNQEVALKLEPNPESLELSFTMPQIQDQPASPSDGSTRQSSPEPNSPSEYCFDVDSLMVNEFKLELV
EKLFAEDTEAKNPFSTQDTDLDLEMLAPYIPMDDDFQLRSFDQLSPLENSSTSPQSASTNTVFQPTQ
MQEPPIATVTTTATSDELKTVTKDGMEDIKILIAFPSFPHVFKEPPCATTSPYSDTGSRTASPNRAG
KGVIEQTEKSHPRSPNVLSVALSQRTTAPEEELNPKILALQNAQRKRKIEHDGSLFQAVGIGTLLQQ
PDDRATTTSLSWKRVKGCKSSEQNGMEQKTIILIPSDLACRLLGQSMDESGLPQLTSYDCEVNAPIQ
GSRNLLQGEELLRALDQVN HIF1a Mus musculus NCBI Reference Sequence: NP_034561.2
SEQ ID NO: 6
MEGAGGENEKKKMSSERRKEKSRDAARSRRSKESEVFYELAHQLPLPHNVSSHLDKASVMRLTISYL
RVRKLLDAGGLDSEDEMKAQMDCFYLKALDGFVMVLTDDGDMVYISDNVNKYMGLTQFELTGHSVFD
FTHPCDHEEMREMLTHRNGPVRKGKELNTQRSFFLRMKCTLTSRGRTMNIKSATWKVLHCTGHIHVY
DTNSNQPQCGYKKPPMTCLVLICEPIPHPSNIEIPLDSKTFLSRHSLDMKFSYCDERITELMGYEPE
ELLGRSIYEYYHALDSDHLTKTHHDMFTKGQVTTGQYRMLAKRGGYVWVETQATVIYNTKNSQPQCI
VCVNYVVSGIIQHDLIFSLQQTESVLKPVESSDMKMTQLFTKVESEDTSCLFDKLKKEPDALTLLAP
AAGDTIISLDFGSDDTETEDQQLEDVPLYNDVMFPSSNEKLNINLAMSPLPSSETPKPLRSSADFAL
NQEVALKLESSPESLGLSFTMPQIQDQPASPSDGSTRQSSPERLLQENVNTPNFSQPNSPSEYCFDV
DSDMVNEFKLELVEKLFAEDTEAKNPFSTQDTDLDLEMLAPYIPMDDDFQLRSFLQLSPLESNSPSP
PSMSTVTGFQQTQLQKPTITATATTTATTDESKTETKDNKEDIKILIASPSSTQVPQETTTAKASAY
SGTHSRTASPDRAGKPVIEQTDKASPRSLNLSATLNQRNTVPEEELNPKTIASQNAQRKRKMEHDGS
LFQAAGIGTLLQQPGDCAPTMSLSWKRVKGFISSEQNGTEQKTIILIPSDLACRLLGQSMDESGLPQ
LTSYDCEVNAPIQGSRNLLQGEELLRALDQVN

FIG. 1 continued

HIF1a Rattus norvegicus NCBI Reference Sequence: NP_077335.1
SEQ ID NO: 7
MEGAGGENEKKNPMSSERRKEKSRDAARSRRSKESEVFYELAHQLPLPHNVSSHLDKASVMRLTISY
LRVRKLLGAGDLDIEDEMRAQMNCFYLKALDGFVMVLTDDGDMIYISDNVNKYMGLTQFELTGHSVF
DFTHPCDHEEMREMLTHRNGPVRKGKEQNTQRSFFLRMKCTLTSRGRTMNIKSATWKVLHCTGHIHV
YDTSSNQPQCGYKKPPMTCLVLICEPIPHPSNIEIPLDSKTFLSRHSLDMKFSYCDERITELMGYEP
EELLGRSIYEYYHALDSDHLTKTHHDMFTKGQVTTGQYRMLAKRGGYVWVETQATVIYNTKNSQPQC
IVCVNYVVSGIIQHDLIFSLQQTESVLKPVESSDMRMTQLFTKVESEDTSCLFDKLKKEPDALTLIA
PAAGDTIISLDFGSDDTETEDQQLEDVPLYNDVMFPSSNEKLNINIAMSPLPASETPKPLRSSADPA
LNQEVALKLESSPESLGLSFTMPQIQDQPASPSDGSTRQSSPEPNSPSEYCFDVDSDMVNVFKLELV
EKLFAEDTEAKNPFSAQDTDLDLEMLAPYIPMDDDPQLRSFDQLSPLESNSPSPPSVSTVTGFQQTQ
LQKPTITVTATATATTDESKAVTKDNIEDIKILIASPPSTQVPQEMTTAKASAYSGTHSPTASPDRA
GKRVIEKTDKAHPRSLNLSVTLNQENTVPEEELNPKTIALQNAQRKRKMEHDGSLFQAAGIGTLLQQ
PGDRAPTMSLSWKRVKGYISSEQDGMEQKTIFLIPSDLACRLLGQSMDESGLPQLTSYDCEVNAPIQ
GSRNLLQGEELLRALDQVN HIF1a Gallus gallus NCBI Reference Sequence: NP_989628.1
SEQ ID NO: 8
MDSPGGVTDKKRISSERRKEKSRDAARCRRSKESEVFYELAHQLPLPHTVSAHLDKASIMRLTISYL
RMRKLLDAGELETEANMEKELNCFYLKALDGFVMVLSEDGDMIYMSENVNKCMGLTQFDLTGHSVFD
FTHPCDHEELREMLTHRNGPVKKGKEQNTERSFFLRMKCTLTSRGRTVNIKSATWKVLHCTGHIRVY
DTCNNQTHCGYKKPPMTCLVLICEPIPHPSNIEVPLDSKTFLSRHSLDMKFSYCDERITELMGYEPE
ELLGRSIYEYYHALDSDHLTKTHHDMFTKGQVTTGQYRMLAKQGGYVWVETQATVIYNTENSQPQCI
VCVNYVLSGIVQKDLIFSLGQTECNLKPVESPEMKMTKIFSKDDWDDTNSLFEKLKQEPDALTVLAP
AAGDTIISLDFSSNESDEQQCDEVPLYNDVMLPSSSEKLQNINIAMSPLPASETTKPLRSNADPALN
REVVSRLEPNTETLELSFTMPQVQEQPTSPSDASTSQSSPEPSSPNDYCFDVDNDMANEFKLELVEK
LFAIDTEAKNPFSTQETDLDLEMLAPYIPMDDDPQLRSFDQLSPLESSSSGSQNAATITILQQTQTP
STAADEIKPVAERVDDVKALIVPSSPVHVINDFSSAPASPYSGNRSRTASFIRAGKGTLEQTEKSCP
GAPSLITVTLNKRSTAMDEELNPKMLALHNAQRKRKMEHDGSLFQAVGIGSLFQQTGDRGGNASLAW
KRVKACKTNGHNGVEQKTIILLSTDIASKLLGQSMDESGLPQLTSYDCEVNAPIQGNRNLLQGEELL
RALDQVN HIF1a Danio rerio NCBI Reference Sequence: NP_956527.1
SEQ ID NO: 9
MDTGVVTEKKRVSSERRKGKSRDAARSRRGKESEVFYELAHQLPLPHNVTSHLDKASIMRLTISYLR
MRKLLNSDEKEEKEENELESQLNGFYLKALEGFLMVLSEDGDMVYLSENVSKSNGLTQFDLTGHSIF
EFSHPCDHEELREMLVHRTGSKKTKEQNTERSFFLRMKCTLTSRGRTVNIKSATWKVLHCAGHVRVH
EGSEASEDGGFKEPPVTYLVLICEPIPHPSNIEVPLDSKTFLSRATLDMKFSYCDERITELMGYEPD
DLLNRSVYEYYHALDSDHLTKTHHNLFAKGQAFTGQYRMLAKKGGFVWVETQATVIYNFKNSQPQCI
VCVNYVLSGIVEGDVVLSLQQTVTEPKAVEKESEETEEKTSELDILKLFKPESLNCSLESSTLYNKL
KEEPEALTVLAPAAGDAIISLDFNNSDSDIQLLKEVPLYNDVMLPSSSEKLFLSLSPLTFSDSLSSH
ATTAKSTLPCRRRHPGPLHPYTCCRRCAVHLSRSSVAVGMPHLFDPAPHRAAVSSTTEKCLQRC

FIG. 1 continued

HIF1 Caenorhabditis elegans GenBank: CAB07381.2
SEQ ID NO: 10
MEDNRKRNMERRRETSRHAARDPRSKESSIFDDLKMCVPIVEEGTVTHLDRIALLRVAATICRLRKT
AGNVLENNLDNEITNEVWTEDTIAECLDGFVMIVDSDSSILYVTESVAMYLGLTQTDLTGRALRDFL
HPSDYDEFDKQSKMLHKPRGEDTDTTGINMVLRMKTVISPRGRCLNLKSALYKSVSFLVHSKVSTGG
HVSFMQGITIPAGQGTTNANASAMTKYTESPMGAFTTRHTCDMRITFVSDKFNYILKSELKTLMSTS
FYELVHPADMMIVSKSMKELFAKGHIRTFYYRLIAANDTLAWIQTEATTITHTTKGQKGQYVICVHY
VLGIQGAEESLVVCTDSMPAGMQVDIKKEVDDTRDYIGRQFEIVECVDFTPLIEPEDPFDTVIEFVV
GGEEFVKQADMGARKNSYDDVLQWLFRDQPSSPPPARYRSADRFRTTEPSNFGSALASPDFMDSSSR
TSRPKTSYGPRAQGQGSRTTGSSSTSASATLPHSANYSPLAEGISQCGLNSPPSCSIRSGQVVYGDA
RSMGPSCDPSDSSRRFSALSPSDTLNVSSTRGINPVIGSNDVFSTMPFADSIAIAERIDSSPTLTSG
EPILCDDLQWEEPDLSCLAPFVDTYDMNQMDEGLPPELQALYDLPDFTPAVPQAPAARPVHIDRSPF
AKRMHQSGPSDLDFMYTQHYQFFQQDETYWQGQQQQNEQQPSSYSPFPMLS

FIG. 1 continued

HIF-1a Homo sapiens c-Myc interaction domain
SEQ ID NO: 11
FFLRMKCTLTSRGRTMNIKSATWKVLHCTGHIHVYDTNSNQPQCGYKKPPMTCLVLICEPIPHPSNI
EIPLDSKTFLSRHSLDMKFSYCDERITELMGYEPEELLGRSIYEYYHALDSDHLTKTHHDMFTKGQV
TTGQYRMLAKRGGYVWVETQATVIYNTKN HIF1a Pan troglodytes c-Myc interaction domain
SEQ ID NO: 12
FFLRMKCTLTSRGRTMNIKSATWKVLHCTGHIHVYDTNSNQPQCGYKKPPMTCLVLICEPIPHPSNI
EIPLDSKTFLSRHSLDMKFSYCDERITELMGYEPEELLGRSIYEYYHALDSDHLTKTHHDMFTKGQV
TTGQYRMLAKRGGYVWVETQATVIYNTKN HIF1a Macaca mulatta c-Myc interaction domain
SEQ ID NO: 13
FFLRMKCTLTSRGRTMNIKSATWKVLHCTGHIHVYDTNSNQPQCGYKKPPMTCLVLICEPIPHPSNI
EIPLDSKTFLSRHSLDMKFSYCDERITELMGYEPEELLGRSIYEYYHALDSDHLTKTHHDMFTKGQV
TTGQYRMLAKRGGYVWVETQATVIYNTKN HIF1a Canis lupus familiaris c-Myc interaction domain
SEQ ID NO: 14
FFLRMKCTLTSRGRTMNIKSATWKVLHCTGHIHVYDTNSNQSQCGYKKPPMTCLVLICEPIPHPSNI
EIPLDSKTFLSRHSLDMKFSYCDERITELMGYEPEELLGRSIYEYYHALDSDHLTKTHHDMFTKGQV
TTGQYRMLAKRGGYVWVETQATVIYNTKN HIF1a Bos Taurus c-Myc interaction domain
SEQ ID NO: 15
FFLRMKCTLTSRGRTMNIKSATWKVLHCTGHIHVYDTNSNQSQCGYKKPPMTCLVLICEPIPHPSNI
EIPLDSKTFLSRHSLDMKFSYCDERITELMGYEPEELLGRSIYEYYHALDSDHLTKTHHDMFTKGQV
TTGQYRMLAKRGGYVWIETQATVIYNTKN HIF1a Mus musculus c-Myc interaction domain
SEQ ID NO: 16
FFLRMKCTLTSRGRTMNIKSATWKVLHCTGHIHVYDTNSNQPQCGYKKPPMTCLVLICEPIPHPSNI
EIPLDSKTFLSRHSLDMKFSYCDERITELMGYEPEELLGRSIYEYYHALDSDHLTKTHHDMFTKGQV
TTGQYRMLAKRGGYVWVETQATVIYNTKN HIF1a Rattus norvegicus c-Myc interaction domain
SEQ ID NO: 17
FFLRMKCTLTSRGRTMNIKSATWKVLHCTGHIHVYDTSSNQPQCGYKKPPMTCLVLICEPIPHPSNI
EIPLDSKTFLSRHSLDMKFSYCDERITELMGYEPEELLGRSIYEYYHALDSDHLTKTHHDMFTKGQV
TTGQYRMLAKRGGYVWVETQATVIYNTKN HIF1a Gallus gallus NCBI Reference Sequence: NP_989628.1
SEQ ID NO: 18
FFLRMKCTLTSRGRTVNIKSATWKVLHCTGHIRVYDTCNNQTHCGYKKPPMTCLVLICEPIPHPSNI
EVPLDSKTFLSRHSLDMKFSYCDERITELMGYEPEELLGPSIYEYYHALDSDHLTKTHHDMFTKGQV
TTGQYRMLAKQGGYVWVETQATVIYNTKN HIF1a Danio rerio c-Myc interaction domain
SEQ ID NO: 19
FFLRMKCTLTSRGRTVNIKSATWKVLHCAGHVRVHEGSEASEDSGFKEPPVTYLVLICEPIPHPSNI
EVPLDSKTFLSRHTLDMKFSYCDERITELMGYEPDDLLNRSVYEYYHALDSDHLTKTHHNLFAKGQA
TTGQYPMLAKKGGFVWVETQATVIYNPKNSQP

FIG. 2

HIF1 Caenorhabditis elegans c-Myc interaction domain
SEQ ID NO: 20
MVLRMKTVISPRGRCLNLKSALYKSVSFLVHSKVSTGGHVSFMQGITIPAGQGTTNANASAMTKYTE
SPMGAFTTPHTCDMRITFVSDKFNYILKSELKTLMGTSFYELVHPADMMIVSKSMKELFAKGHIRTP
YYRLIAANDTLANIQTEATTITHTTKG

FIG. 2 continued myc proto-oncogene protein Homo sapiens NCBI Reference Sequence:
NP_002458.2
SEQ ID NO: 21
MDFFRVVENQQPPATMPLNVSFTNRNYDLDYDSVQPYFYCDEEENFYQQQQQSELQPPAPSEDIWKKFEL
LPTPPLSPSRRSGLCSPSYVAVTPFSLRGDNDGGGGSFSTADQLEMVTELLGGDMVNQSFICDPDDETFI
KNIIIQDCMWSGFSAAAKLVSEKLASYQAARKDSGSPNPARGHSVCSTSSLYLQDLSAAASECIDPSVVF
PYPLNDSSSPKSCASQDSSAFSPSSDSLLSSTESSPQGSPEPLVLHEETPPTTSSDSEEEQEDEEEIDVV
SVEKRQAPGKRSESGSPSAGGHSKPPHSPLVLKRCHVSTHQHNYAAPPSTRKDYPAAKRVKLDSVRVLRQ
ISNNRKCTSPRSSDTEENVKRRTHNVLERQRRNELKRSFFALRDQIPELENNEKAPKVVILKKATAYILS
VQAEEQKLISEEDLLRKRREQLKHKLEQLRNSCA myc proto-oncogene protein Pan troglodytes NCBI Reference Sequence:
NP_001136266.1
SEQ ID NO: 22
MDFFRIVENQQPPATMPLNVSFTNRNYDLDYDSVQPYFYCDEEENFYQQQQQSELQPPAPSEDIWKKFEL
LPTPPLSPSRRSGLCSPSYVAVTPFSLRGDNDGGGGSFSTADQLEMVTELLGGDMVNQSFICDPDDETFI
KNIIIQDCMWSGFSAAAKLVSEKLASYQAARKDSGSPNPARGHSVCSTSSLYLQDLSAAASECIDPSVVF
PYPLNDSSSPKSCPSQDSSAFSPSSDSLLSSTESSPQGSPEPLVLHEETPPTTSSDSEEEQEDEEEIDVV
SVEKRQAPGKRSESGSPSAGGHSKPPHSPLVLKRCHVSTHQHNYAAPPSTRKDYPAAKRVKLDSVRVLRQ
ISNNRKCTSPRSSDTEENDKRRTHNVLERQRRNELKRSFFALRDQIPELENNEKAPKVVILKKATAYILS
VQAEEQKLISEEDLLRKRREQLKHKLEQLRNSCA myc proto-oncogene protein Macaca mulatta NCBI Reference Sequence:
NP_001136345.1
SEQ ID NO: 23
MPLNVSFTNRNYDLDYDSVQPYFYCDEEENFYQQQQQSELQPPAPSEDIWKKFELLPTPPLSPSRRSGLC
SPSYVAVTPFSFRGDNDGGGGSFSTADQLEMVTELLGGDMVNQSFICDPDDETFIKNIIIQDCMWSGFSA
AAKLVSEKLASYQAARKDSGSPNPARGHSVCSTSSLYLQDLSAAASECIDPSVVFPYPLNDSSSPKSCAS
PDSSAFSPSSDSLLSSTESSPQASPEPLVLHEETPPTTSSDSEEEQEEEEIDVVSVEKRQAPGKRSESG
SPSAGGHSKPPHSPLVLKRCHVSTHQHNYAAPPSTRKDYPAAKRVKLDSVRVLRQISNNRKCTSPRSSDT
EENDKRRTHNVLERQRRNELKRSFFALRDQIPELENNEKAPKVVILKKATAYILSVQAEEQKLISEKDLL
RKRREQLKHKLEQLRNSCA

FIG. 3 myc proto-oncogene Canis lupus familiaris NCBI Reference Sequence: NP_001003246.2
SEQ ID NO: 24
MDLLRRVETPAAAMPLNVSFANRNYDLDYDSVQPYFYCDEEENFYQQQQSELQPPAPSEDIWKKFELLP
TPPLSPSRRSGLCSPSYVAVASFSPRGDDDGGGGSFSTADQLEMVTELLGGDMVNQSFICDPDDETFIKN
IIIQDCMWSGFSAAAKLVSEKLASYQAARKDSGSPSPARGPGGCSTSSLYLQDLSAAASECIDPSVVFPY
PLNDSSSEKPCASPDSAAFSPSSDGLLSSAESSPRASPEPLALHEETPPTTSSDSEEEQEDEEEIDVVSV
EKRQPPAKRSESGSPSAGGHSKPPHSPLVLKRCHVSTHQHNYAAPPSTRKDYPAAKRARLDSGRVLKQIS
NNRKCASPRSSDTEENDKRRTHNVLERQRRNELKRSFFALRDQIPELENNEKAPKVVILKKATAYILSVQ
AEEQKLLSEKDLLRKRREQLKHKLEQLRNSGA myc proto-oncogene Bos taurus NCBI Reference Sequence: NP_001039539.1
SEQ ID NO: 25
MPLNVSFANKNYDLDYDSVQPYFYCDEEENFYHQQQQSELQPPAPSEDIWKKFELLPTPPLSPSRRSGLC
SPSYVAVASFSPRGDDDGGGGSFSSADQLEMVTELLGGDMVNQSFICDPDDETLIKNIIIQDCMWSGFSA
AAKLVSEKLASYQAARKDGGSPSPARGHGGCSTSSLYLQDLSAAASECIDPSVVFPYPLNDSSSPKPCAS
PDSTAFSPSSDSLLSSAESSPRASPEPLALHEETPPTTSSDSEEEQEDEEEIDVVSVEKRQPPAKRSESG
SPSAGSHSKPPHSPLVLKRCHVSTHQHNYAAPPSTRKDYPAAKRAKLDSGRVLKQISNNRKCASPRSSDT
EENDKRRTHNVLERQRRNELKRSFFALRDQIPELENNEKAPKVVILKKATAYILSVQAEQQKLKSEIDVL
QKRREQLKLKLEQIRNSCA myc proto-oncogene Mus musculus NCBI Reference Sequence: NP_034979.3
SEQ ID NO: 26
MDFLWALETPQTATTMPLNVNFTNRNYDLDYDSVQPYFICDEEENFYHQQQQSELQPPAPSEDIWKKFEL
LPTPPLSPSRRSGLCSPSYVAVATSFSPREDDDGGGGNFSTADQLEMMTELLGGDMVNQSFICDPDDETF
IKNIIIQDCMWSGFSAAAKLVSEKLASYQAARKDSTSLSPARGHSVCSTSSLYLQDLTAAASECIDPSVV
FPYPLNDSSSPKSCTSSDSTAFSPSSDSLLSSESSPRASPEPLVLHEETPPTYSSDSEEEQEDEEEIDVV
SVEKRQTPAKRSESGSSPSRGHSKPFHSPLVLKRCHVSTHQHNYAAPPSTRKDYPAAKRAKLDSGRVLKQ
ISNNRKCSSPRSSDTEENDKRRTHNVLERQRRNELKRSFFALRDQIPELENNEKAPKVVILKKATAYILS
IQADEHKLTSEKDLLRKRREQLKHKLEQLRNSGA myc proto-oncogene Rattus norvegicus NCBI Reference Sequence: NP_036735.2
SEQ ID NO: 27
MNFLWEVENFTVTTMPLNVSFANRNYDLDYDSVQPYFICDEEENFYHQQQQSELQPPAPSEDIWKKFELL
PTPPLSPSRRSGLCSPSYVAVATSFSPREDDDGGGGNFSTADQLEMMTELLGGDMVNQSFICDPDDETFI
KNIIIQDCMWSGFSAAAKLVSEKLASYQAARKDSTSLSPARGHSVCSTSSLYLQDLTAAASECIDPSVVF
PYPLNDSSSPKSCTSSDSTAFSSSSDSLLSZESSPRATPEPLVLHEETPPTTSSDSEEEQDDSEEEIDVVS
VEKRQPPAKRSESGSSPSRGHSKPPHSPLVLKRCHVSTHQHNYAAPPSTRKDYPAAKRAKLDSGRVLKQI
SNNRKCSSPRSSDTEENDKRRTHNVLERQRRNELKRSFFALRDQIPELENNEKAPKVVILKKATAYILSV
QADEHKLISEKDLLRKRREQLKHKLEQLRNSGA myc proto-oncogene Gallus gallus NCBI Reference Sequence: NP_001026123.1
SEQ ID NO: 28
MPLSASLPSKNYDYDYDSVQPYFYFEEEEENFYLAAQQRGSELQPPAPSEDIWKKFELLPTPPLSPSRRS
SLAAASCFPSTADQLEMVTELLGGDMVNQSFICDPDDESFVKSIIIQDCMWSGFSAAAKLEKVVSEKLAT
YQASRREGGFAAASRPGPPPSGPPPPFAGPAASAGLTLHDLGAAAALCIDPSVVFPYPLSERAPRAAPPG
ANPAALLGVDTPPTTSSDSEEEQEEDEEIDVVTLAEANESESSTESSTEASEEHCKPHHSPLVLKRCHVN
IHQHNYAAPPSTKVEYPAAKRLKLDSGRVLKQISNNRKCSSPRTSDSEENDKRRTHNVLERQRRNELKLS
FFALRDQIPEVANNEKAPKVVILKKATEYVLSIQSDEHRLAEKEQLRRREQLKHKLEQLRNSRA

FIG. 3 continued transcriptional regulator Myc-A Danio rerio NCBI Reference Sequence:
NP_571487.2
SEQ ID NO: 29
MERHSLNTSVKMPVSASLACKNYDYDYDSIQPYFYFDNDDEDFYHHQQGQTQPSAPSEDIWKKFELLPTP
PLSPSRQSLSTAEQLEMVSEFLGDDVVSQSFICDLADYSQSFIKSIIIQDCMWSGFSAAAKLEKVVSER
LASLHAERKELMSDSNSNRLNASYLQDLSTSASECIDPSVVFPYPLTECGKAGKVASPQFMLVLDTPPNS
SSSSGSDSEDEEEEDEEEEEEEEEEEEEEEIDVVTVEKRQKRHETDASESRYPSPLVLKRCHVSTHQ
HNYAAHPSTRHDQFAVKRLRLEASNNHSINSSSSNRHVKQRKCASPRTSDSEDNDKRRTHNVLERQRRNE
LKLSFFALRDEIPEVANNEKAAKVVILKKATECIHSMQLDEQRLLSIKEQLRRKSEQLKHRLQQLRSSH transcriptional regulator Myc-B Danio rerio NCBI Reference Sequence:
NP_956466.1
SEQ ID NO: 30
MPLNSSMECKNYDYDYDSYQPYFYFDNEDEDFYNHQHGQPPAPSEDIWKKFELLPTPPLSPSRRPSLSDP
FPSTADKLEMVSEFLGDDVVNHSIICDADYSQSFLKSIIIQDCMWSGFSAAAKLEKVVSERLASLQAARK
ESSRTESADICRSVGFLQEMSTPASQCIDPSVVFPFPLTDSTKPCKPAFTPASTTLPLDTPPNSGSSSSS
SDSESDDEDDEDEEEEEEIDVVTVEKRKSVKKSDANATHQSPVVLKRCHVNIHQHNYAAHFSTRNEQPAV
KRIKFESKIRVFKQISHNRKCASPRTSDSEDNDKRRTHNVLERQRRNELKLSFFALRDVIPDVANNEKAA
KVVILKKATECIASMQEDEQRLISLKEQLRRKCEHLKQRLEQLSCS

FIG. 3 continued

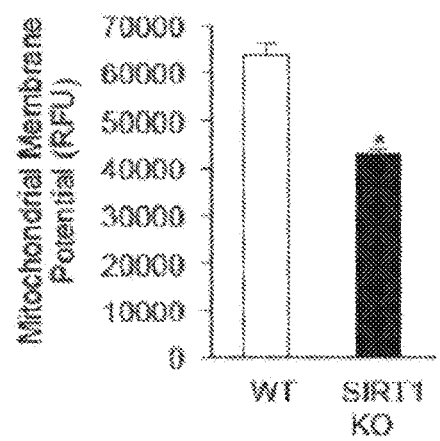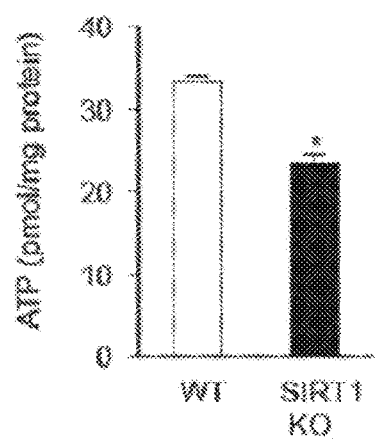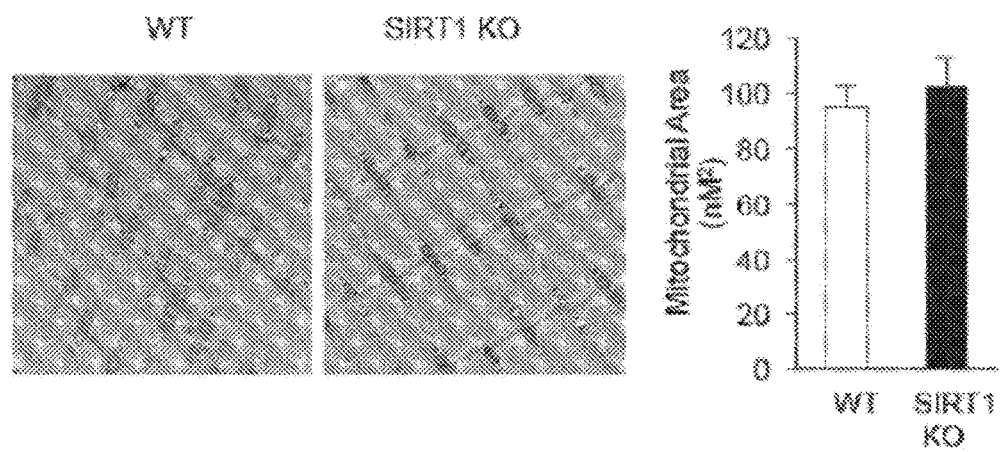
FIG. 4A-C

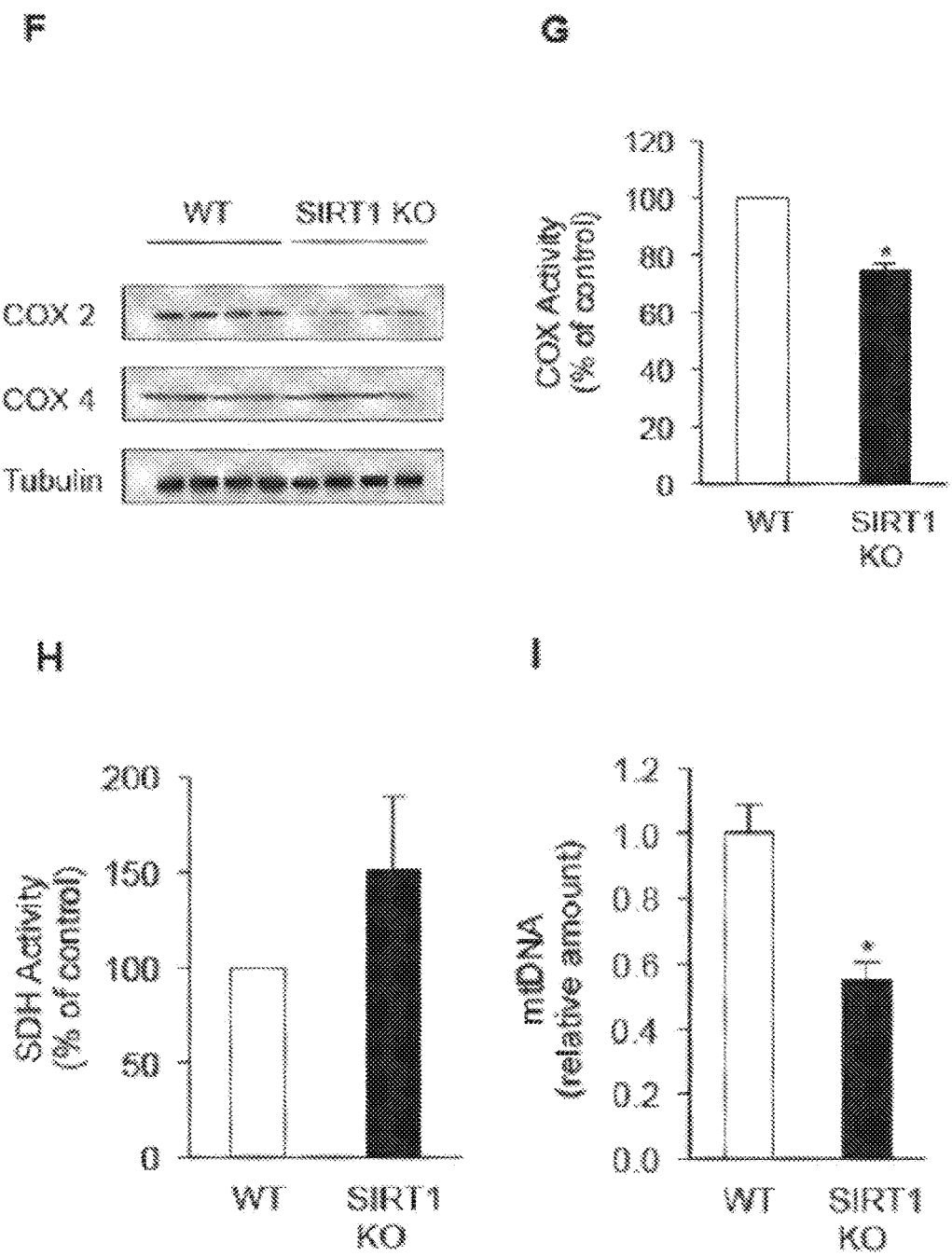
FIG. 4F-I

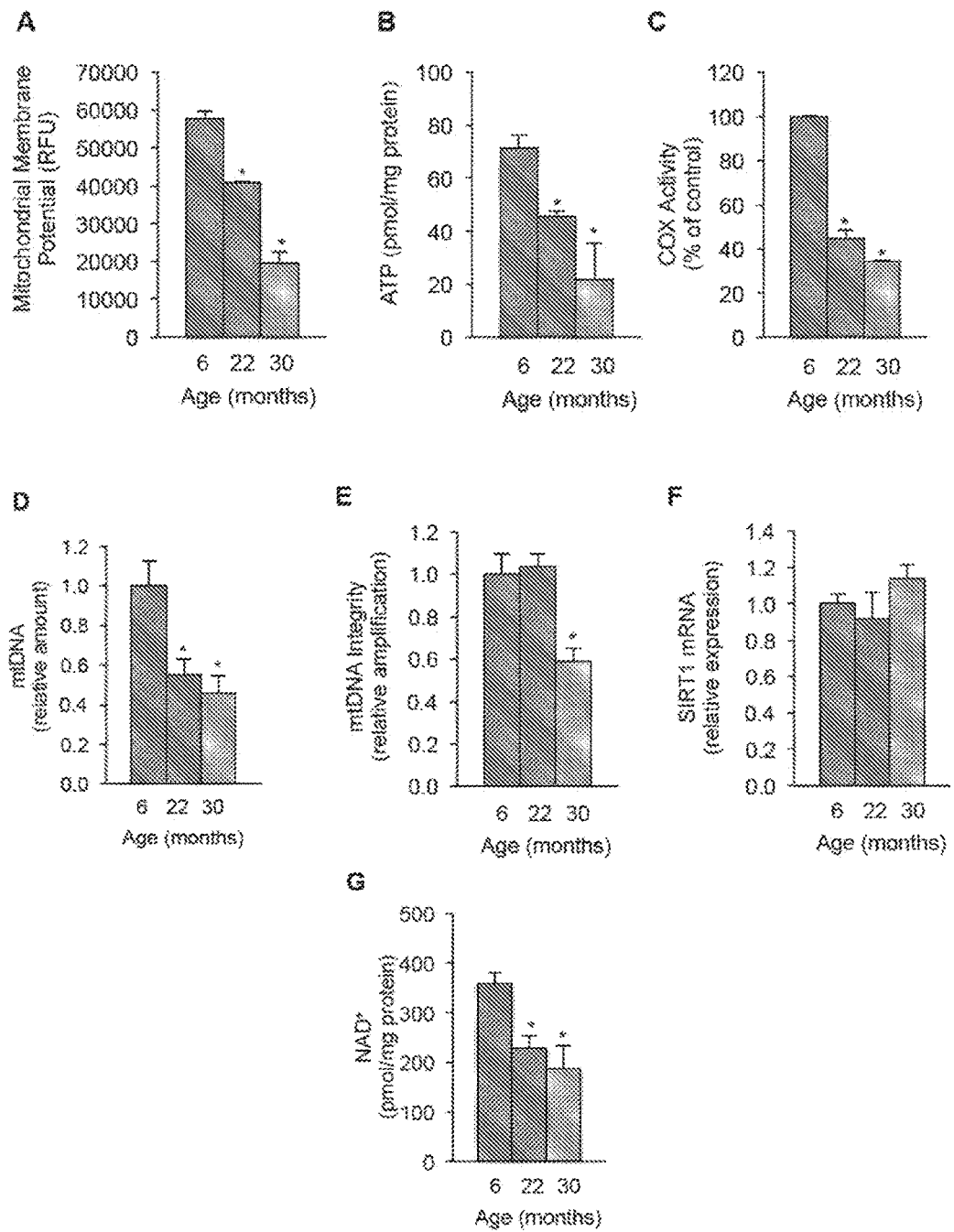
FIG. 5A-G

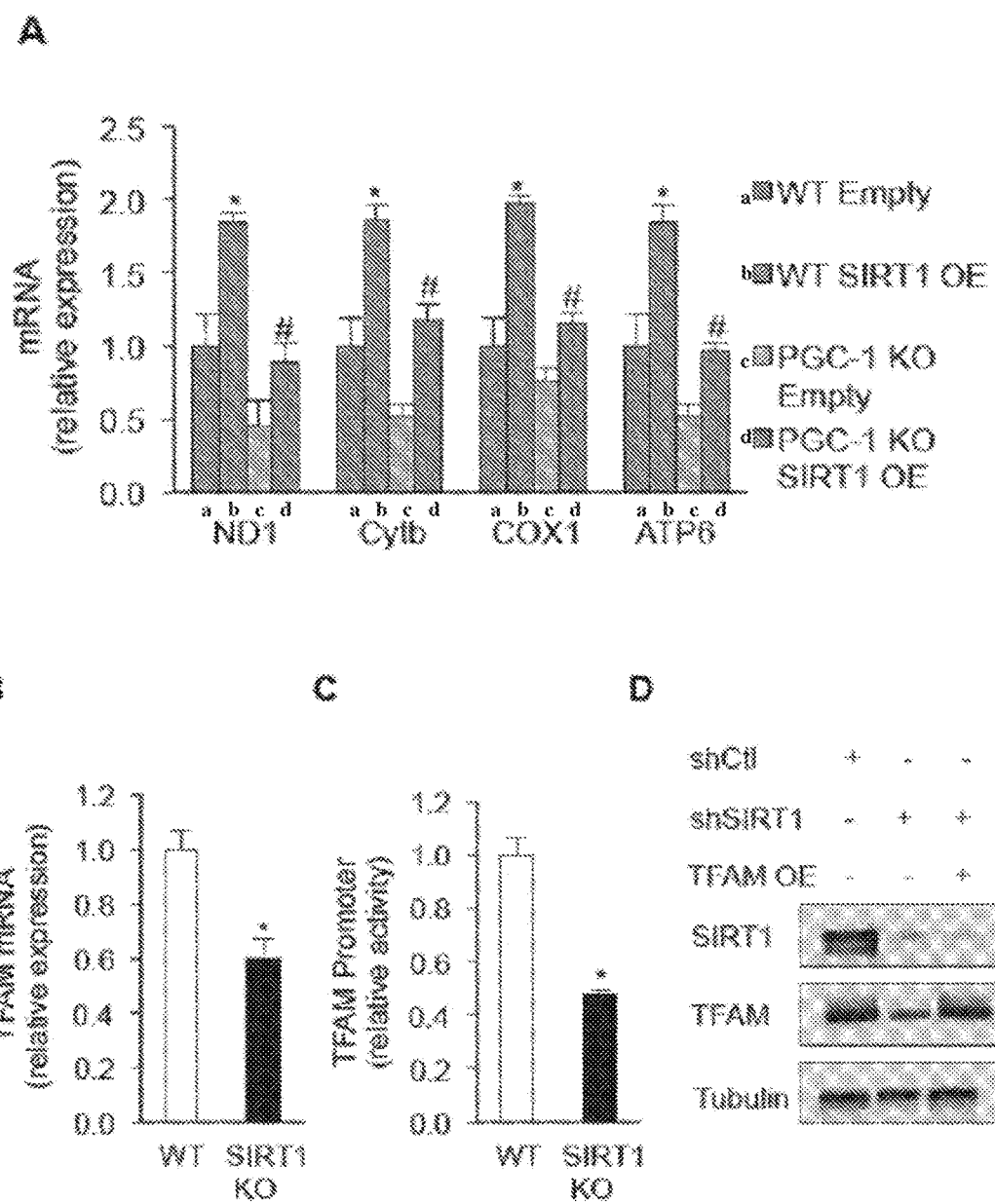
FIG. 6A-D

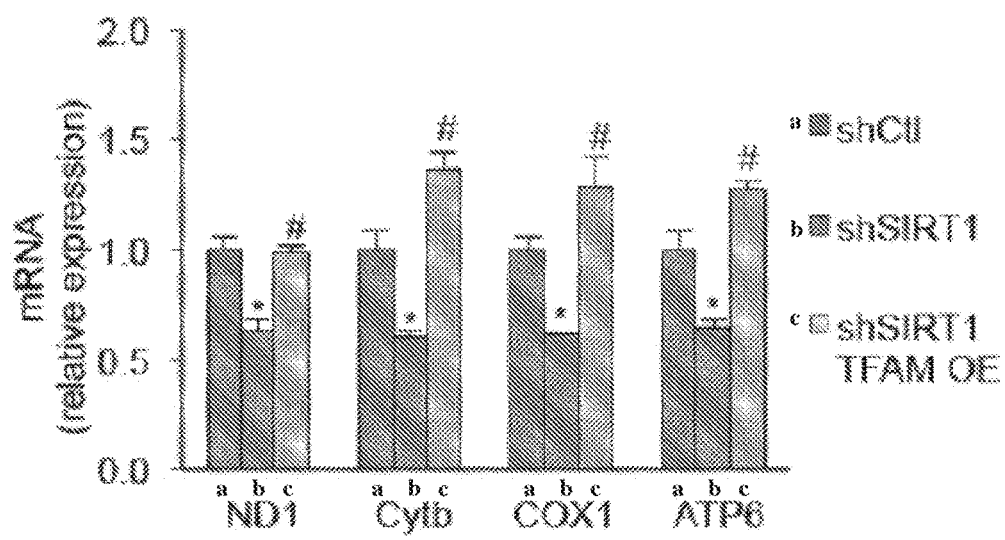
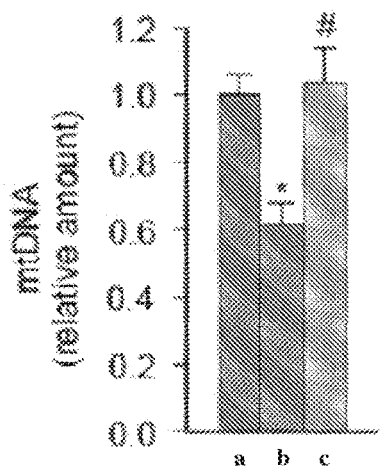
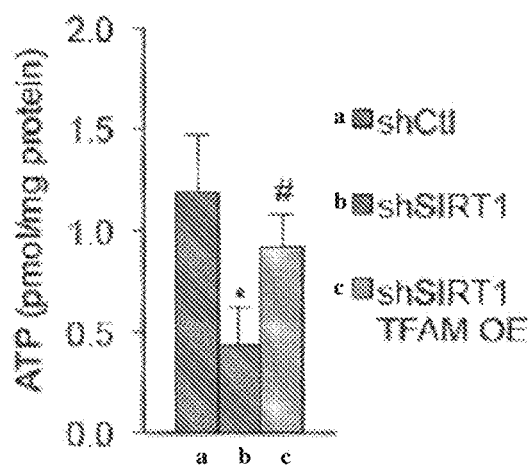
FIG. 6E-G

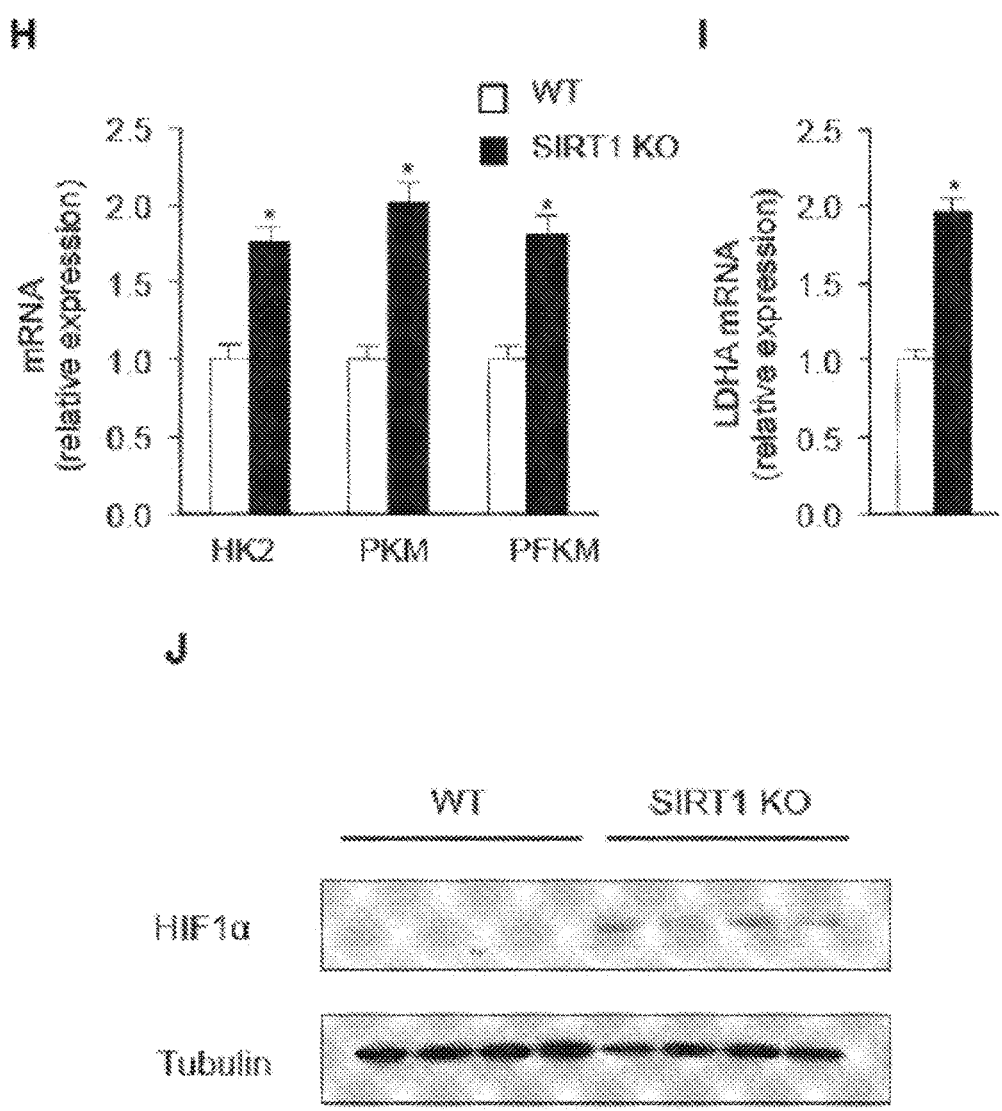
FIG. 6H-J

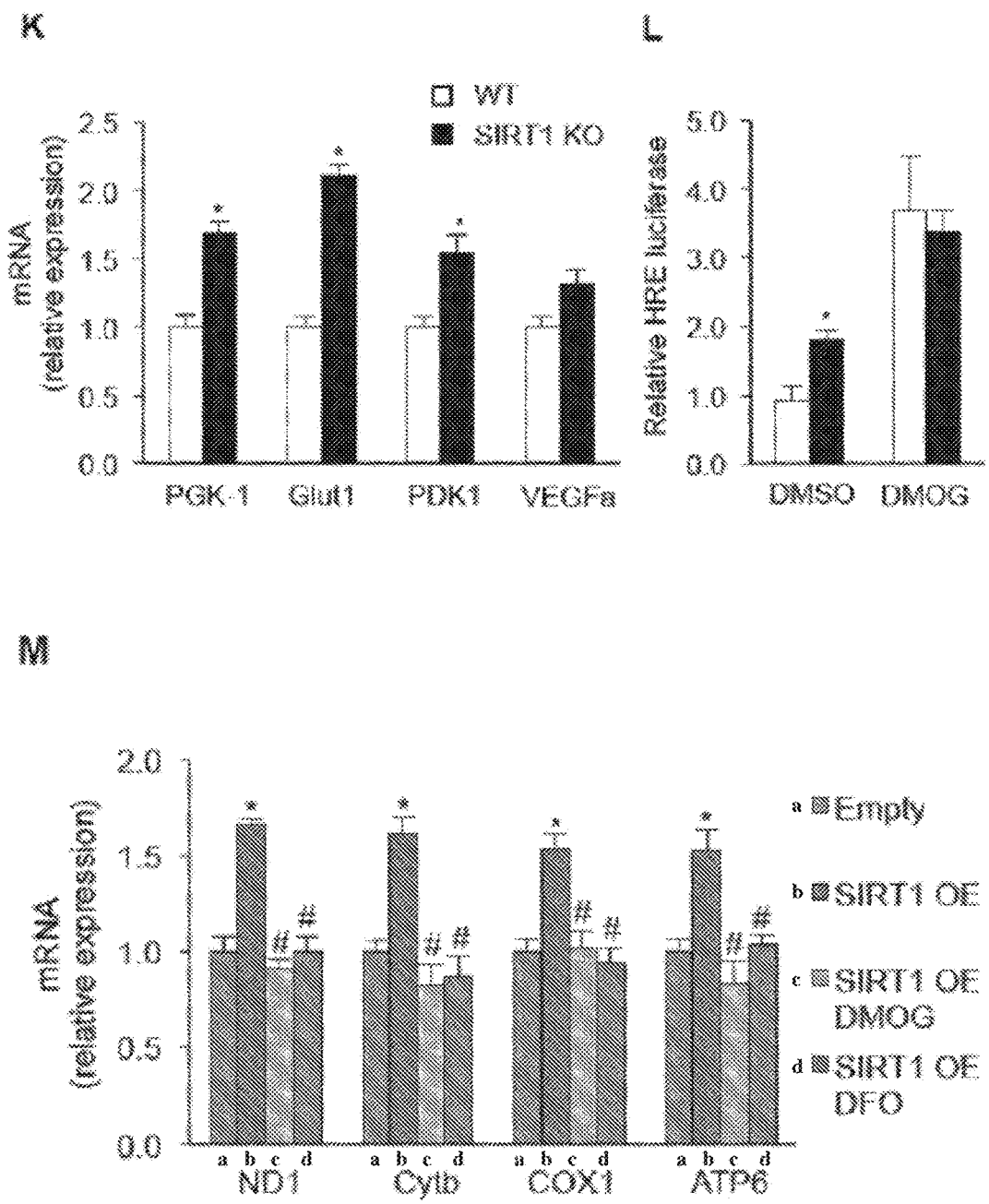
FIG. 6K-M

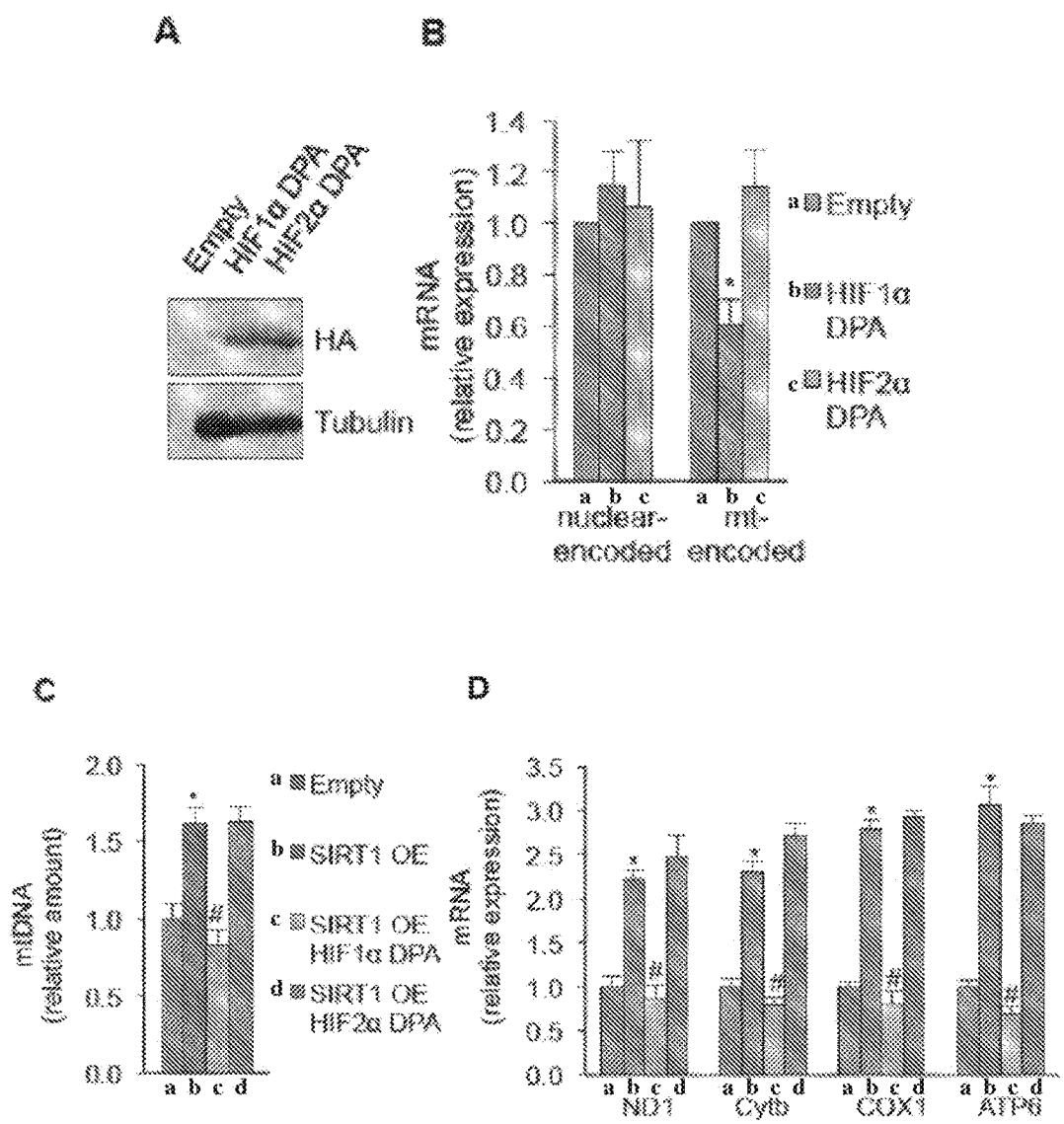
FIG. 7A-D

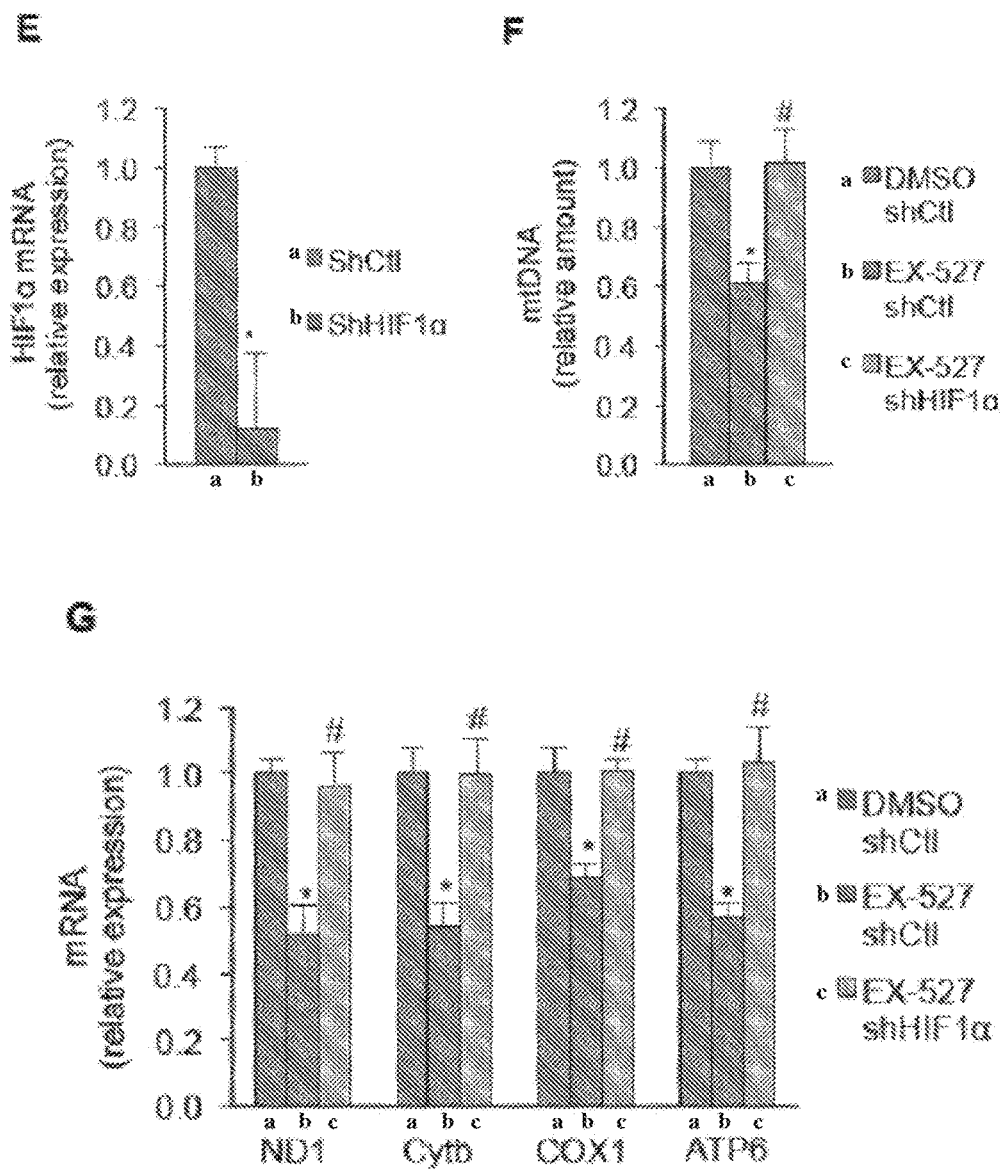
FIG. 7E-G

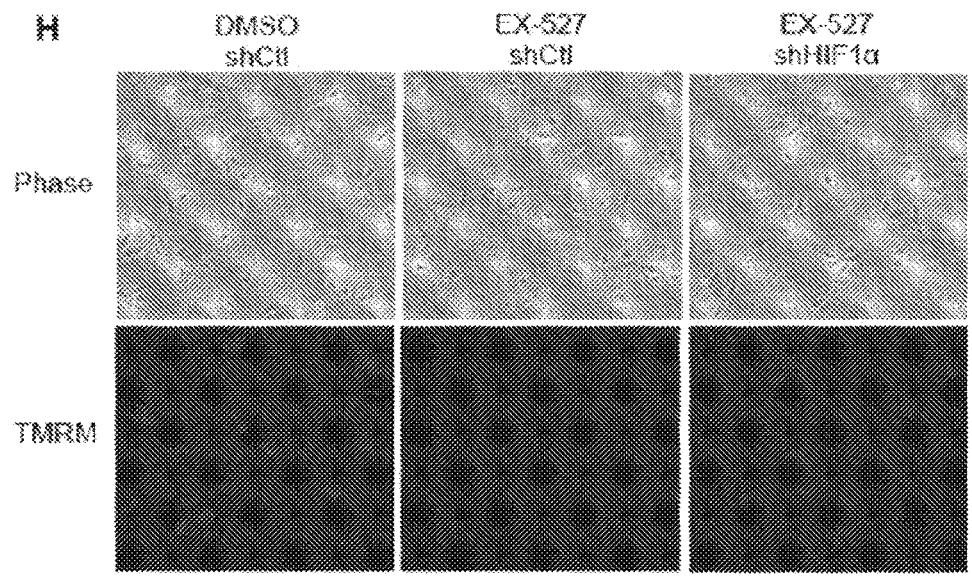
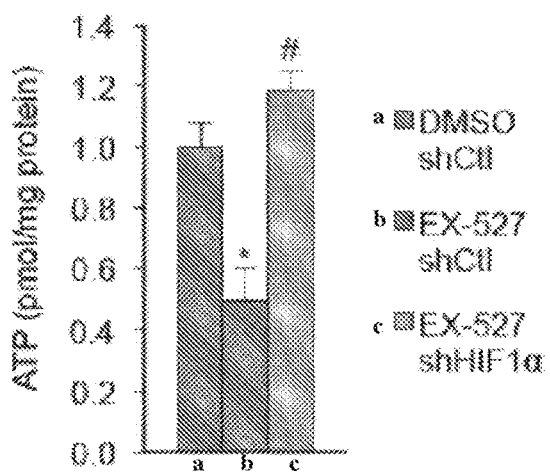
FIG. 7H-I

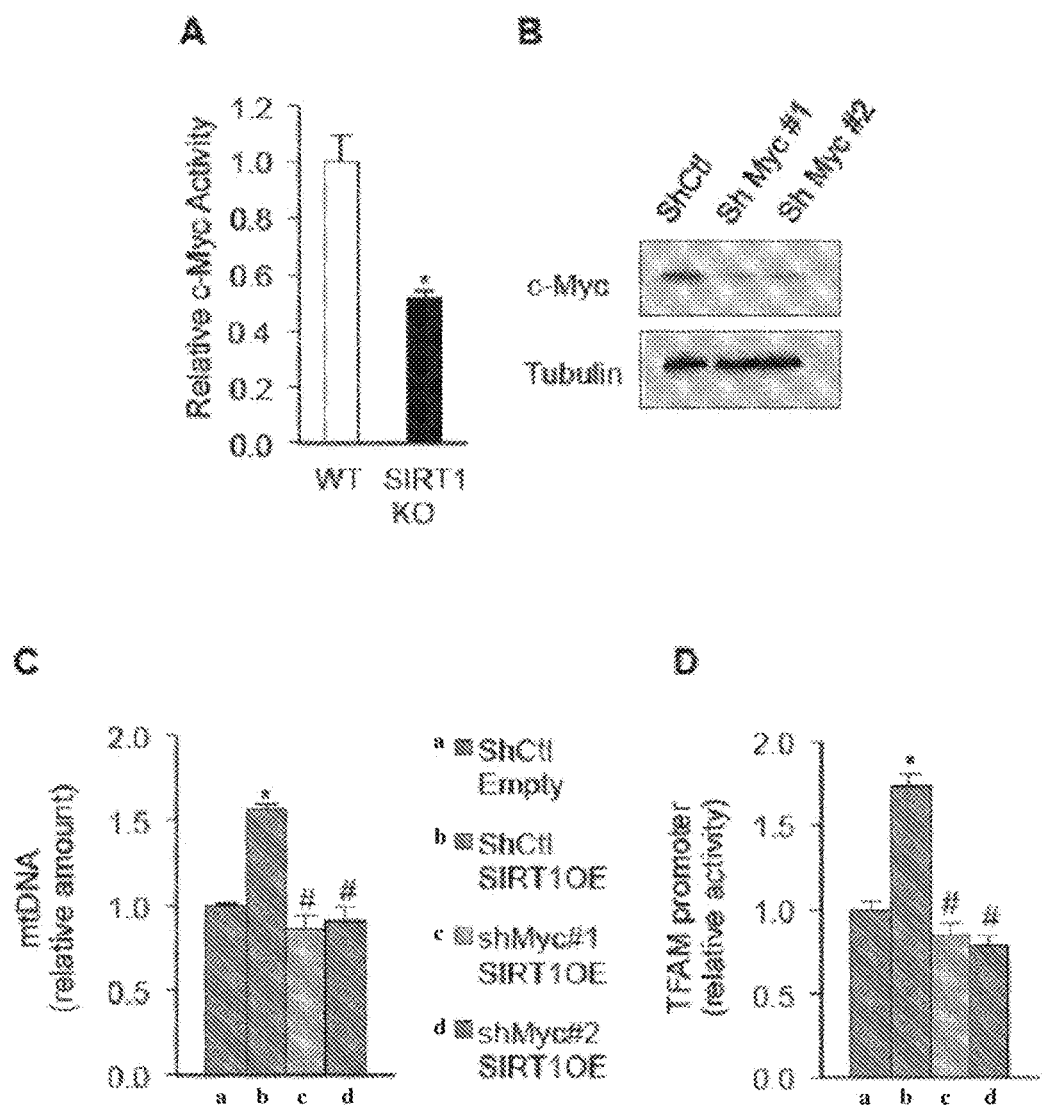
FIG. 8A-D

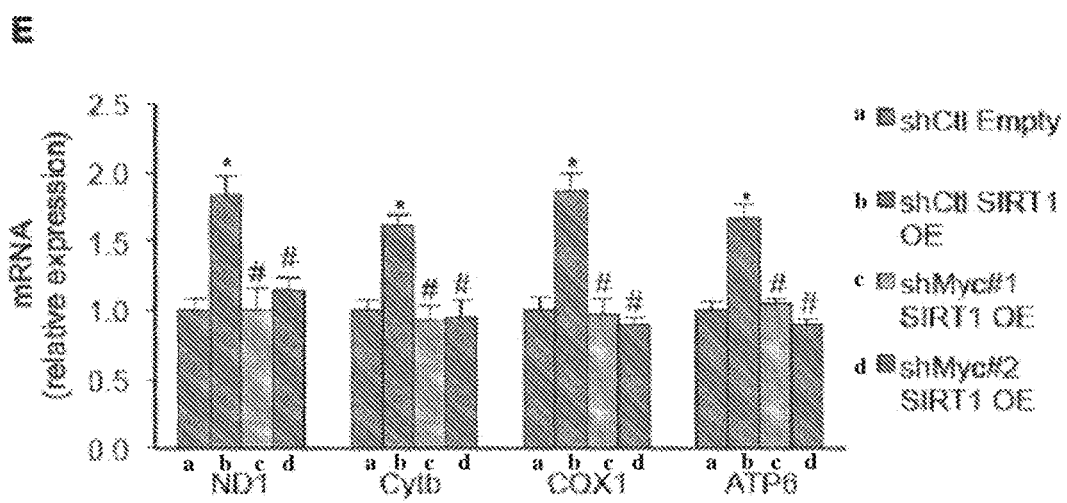
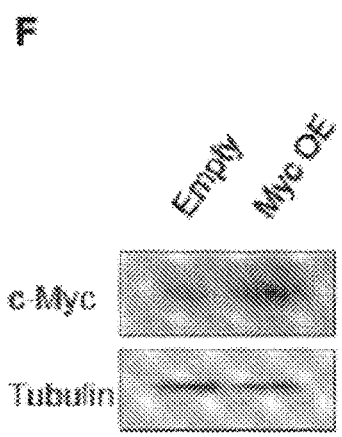
FIG. 8E-F

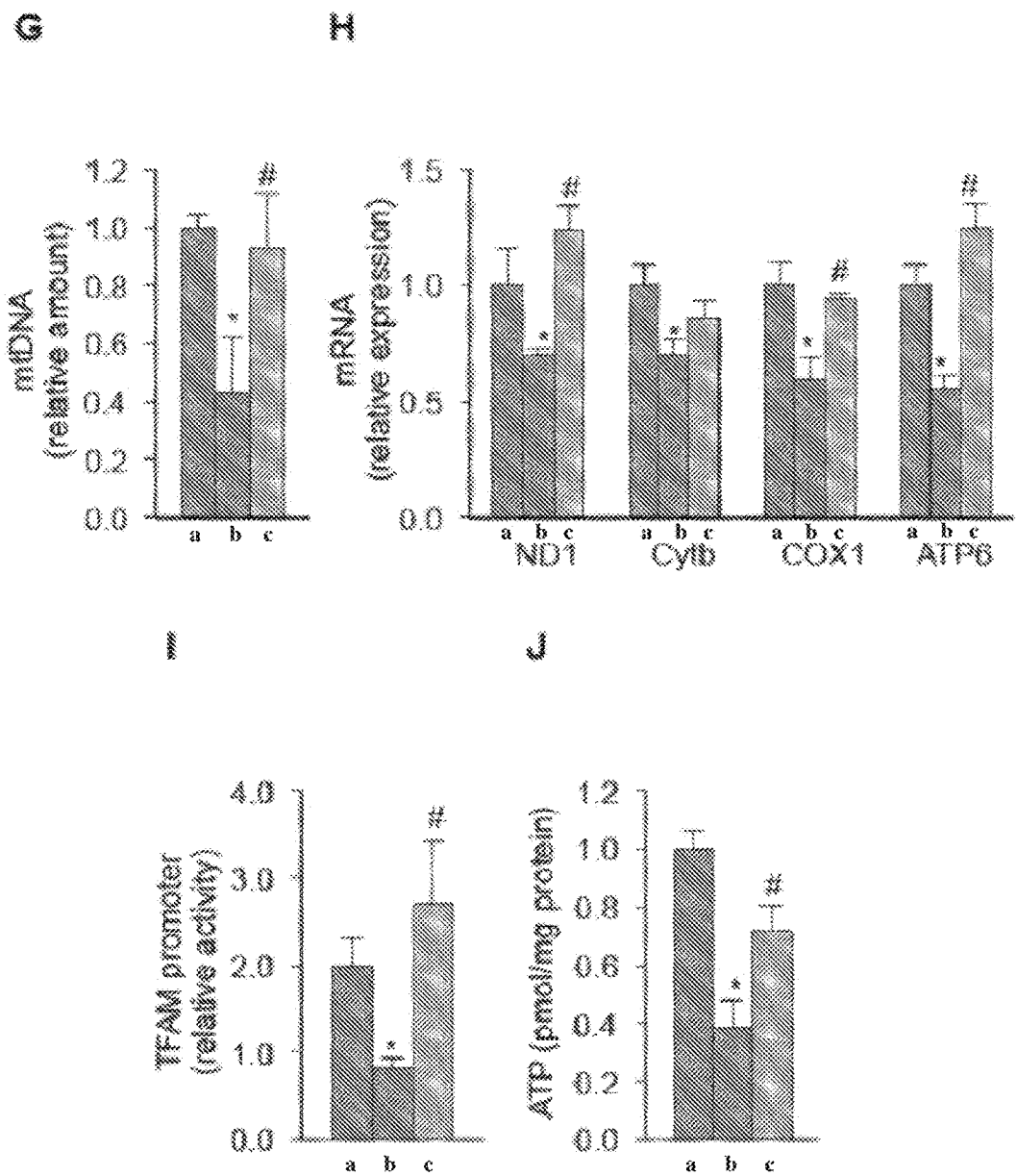
FIG. 8G-J

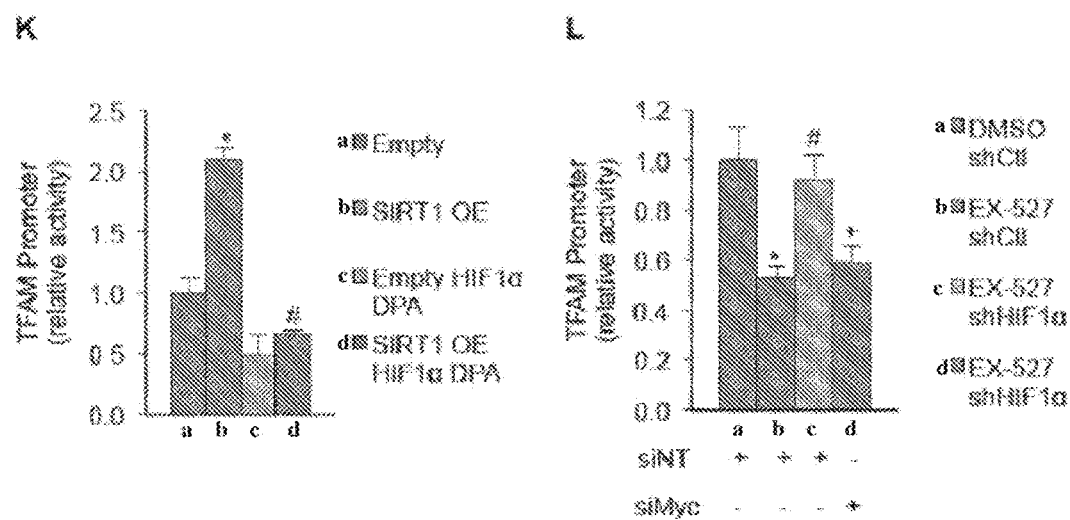
FIG. 8K-L

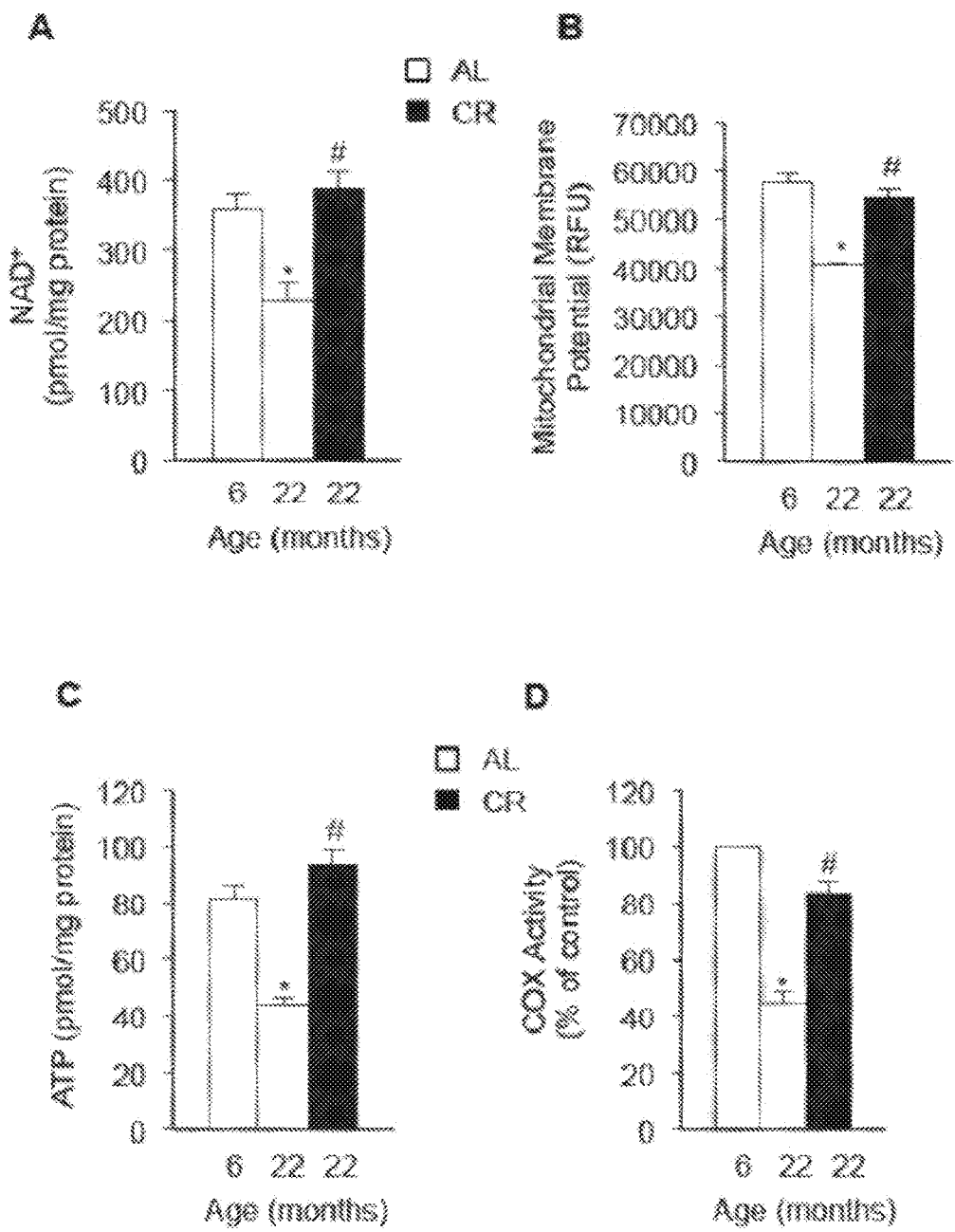
FIG. 9A-D

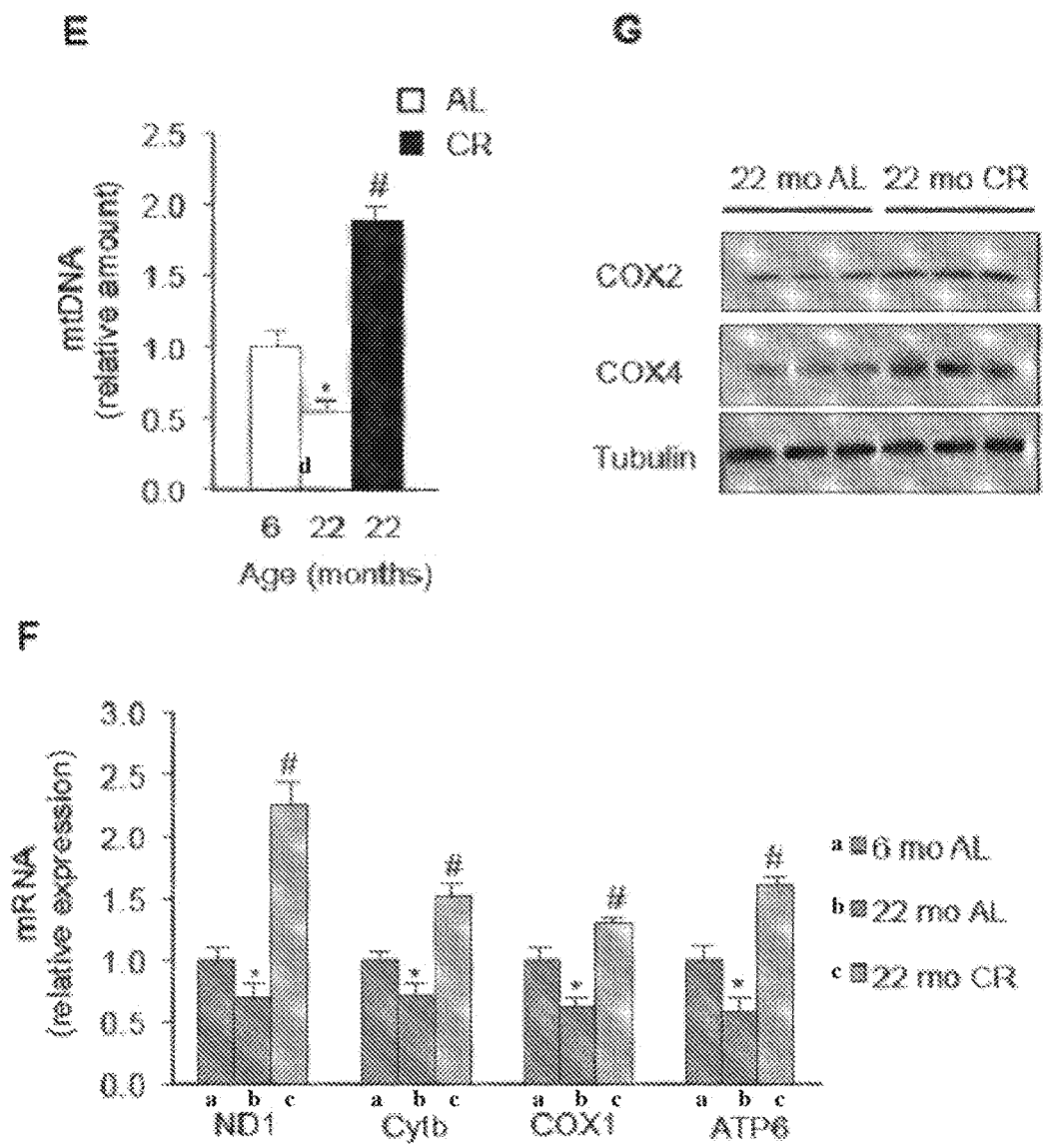
FIG. 9E-F

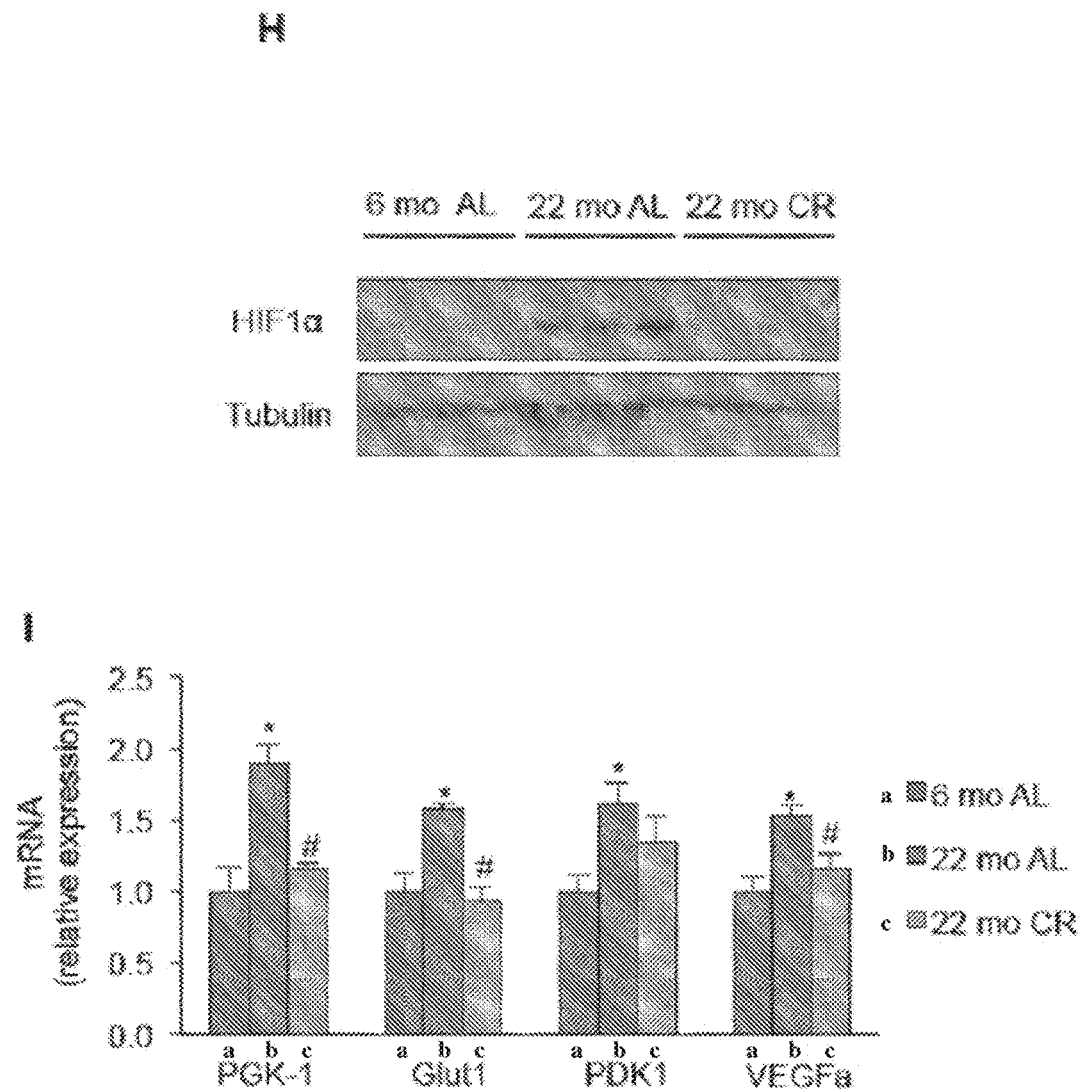
FIG. 9H-I

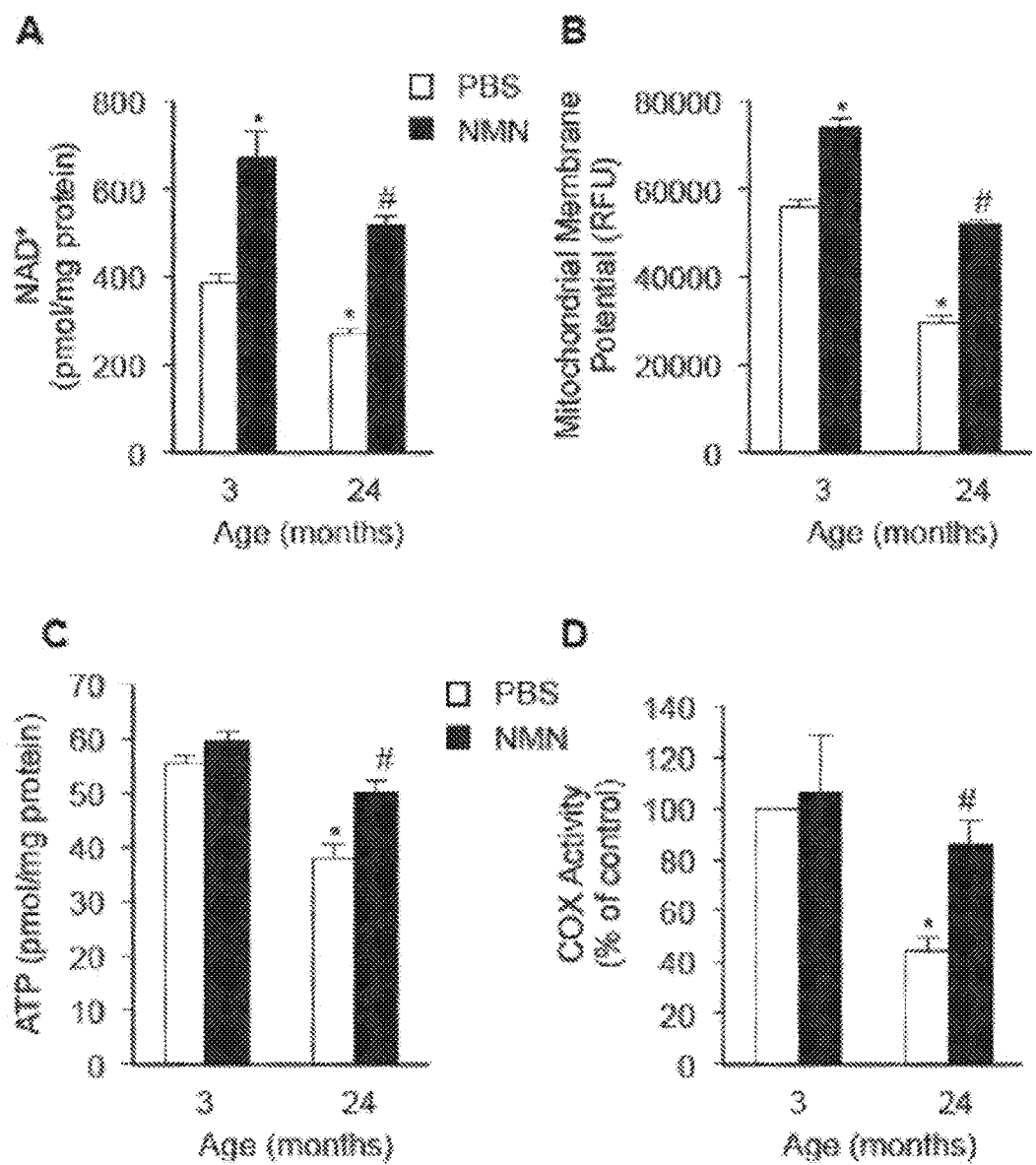
FIG. 10A-D

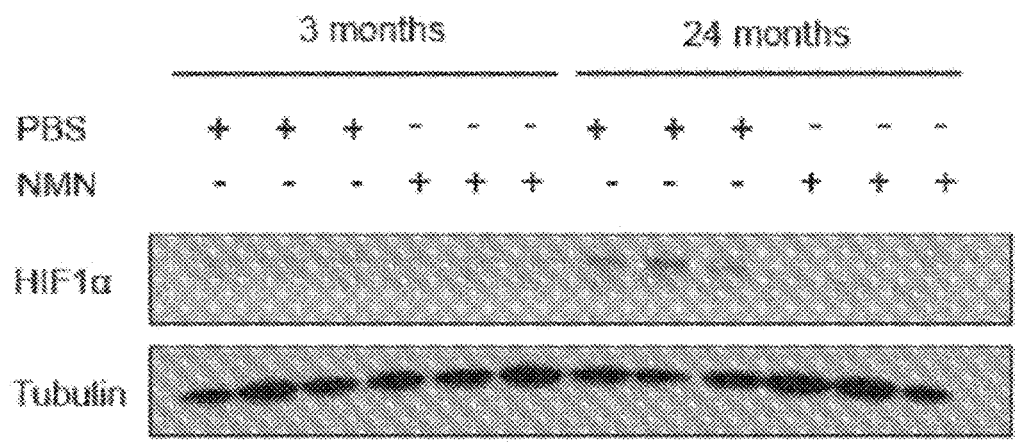
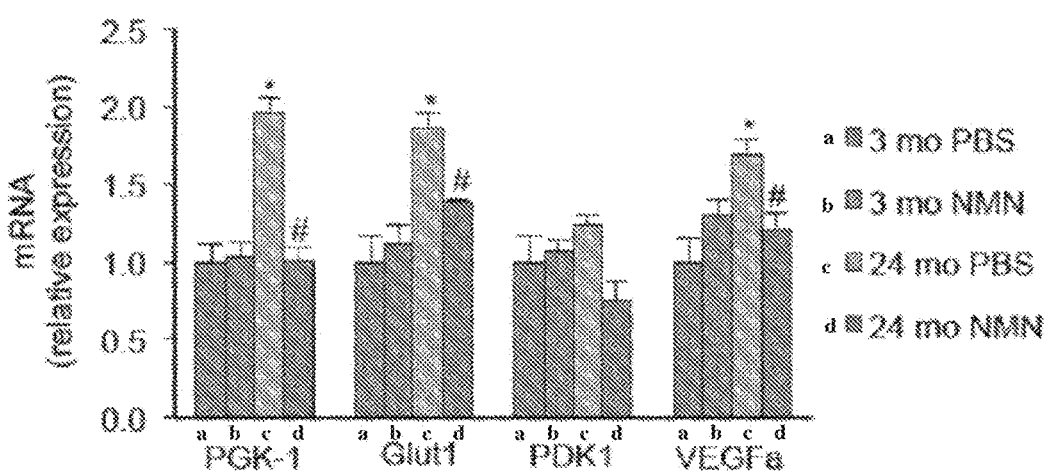
FIG. 10E-F

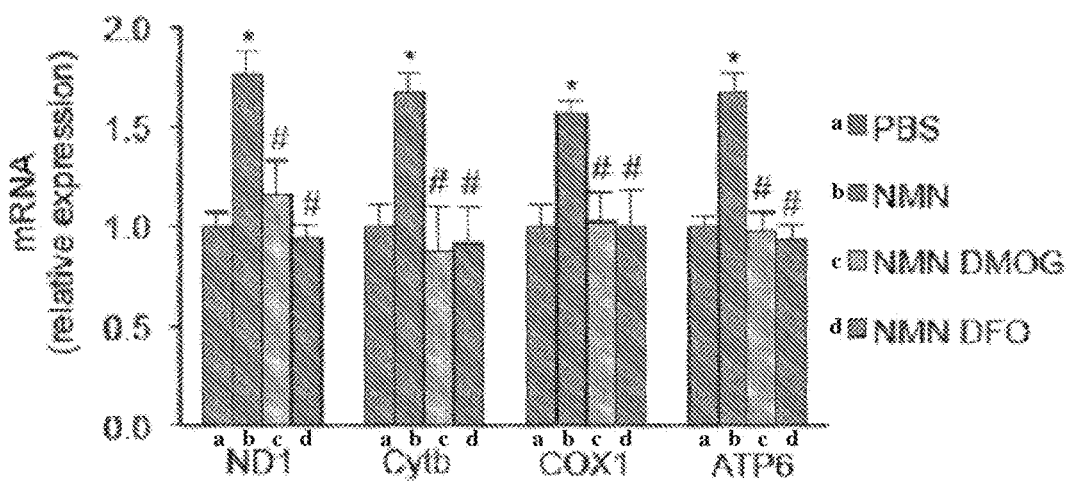
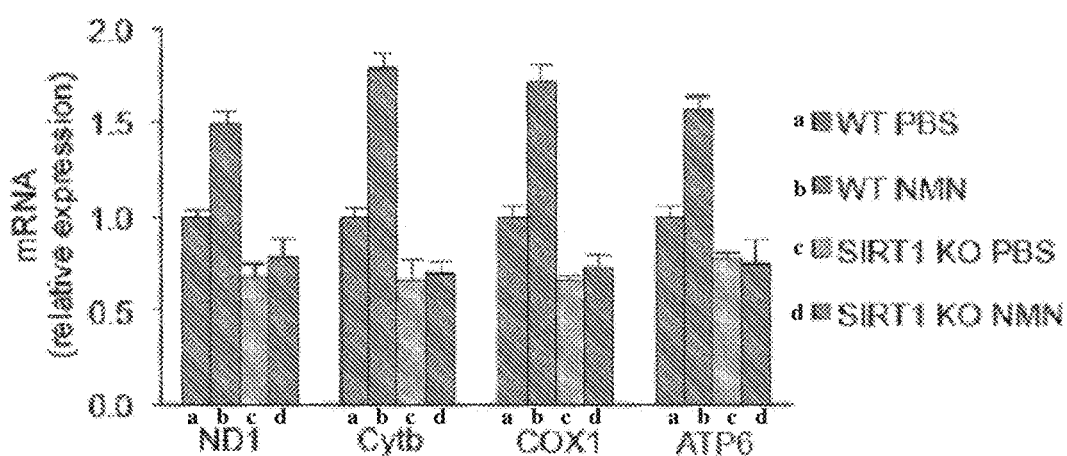
FIG. 10G-H

I
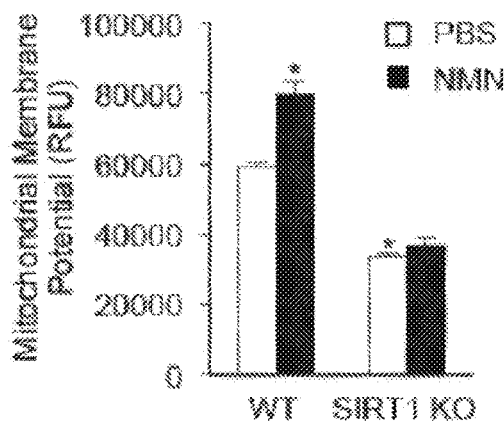
J
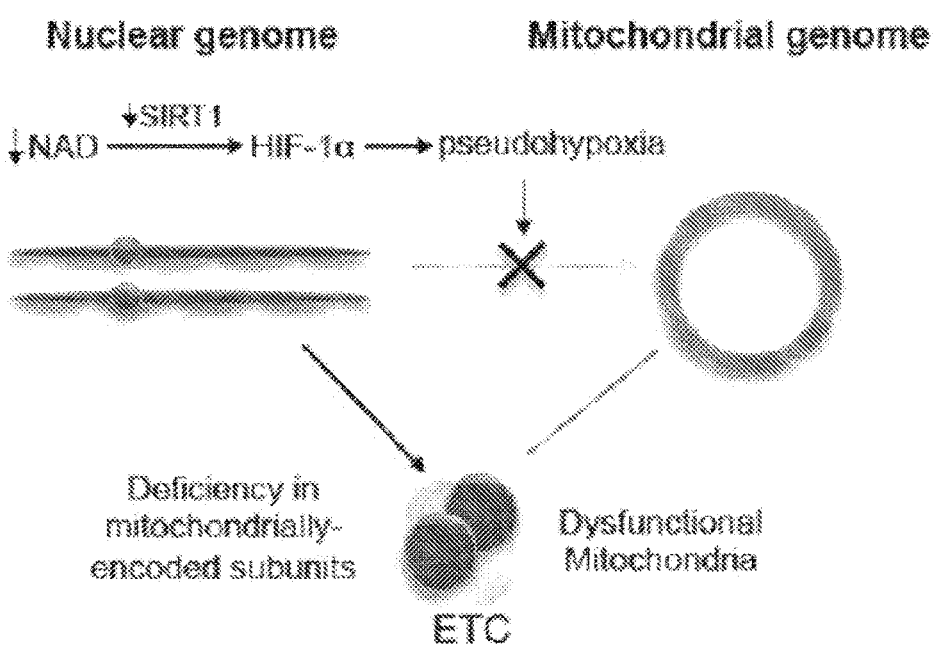
FIG. 10I-J

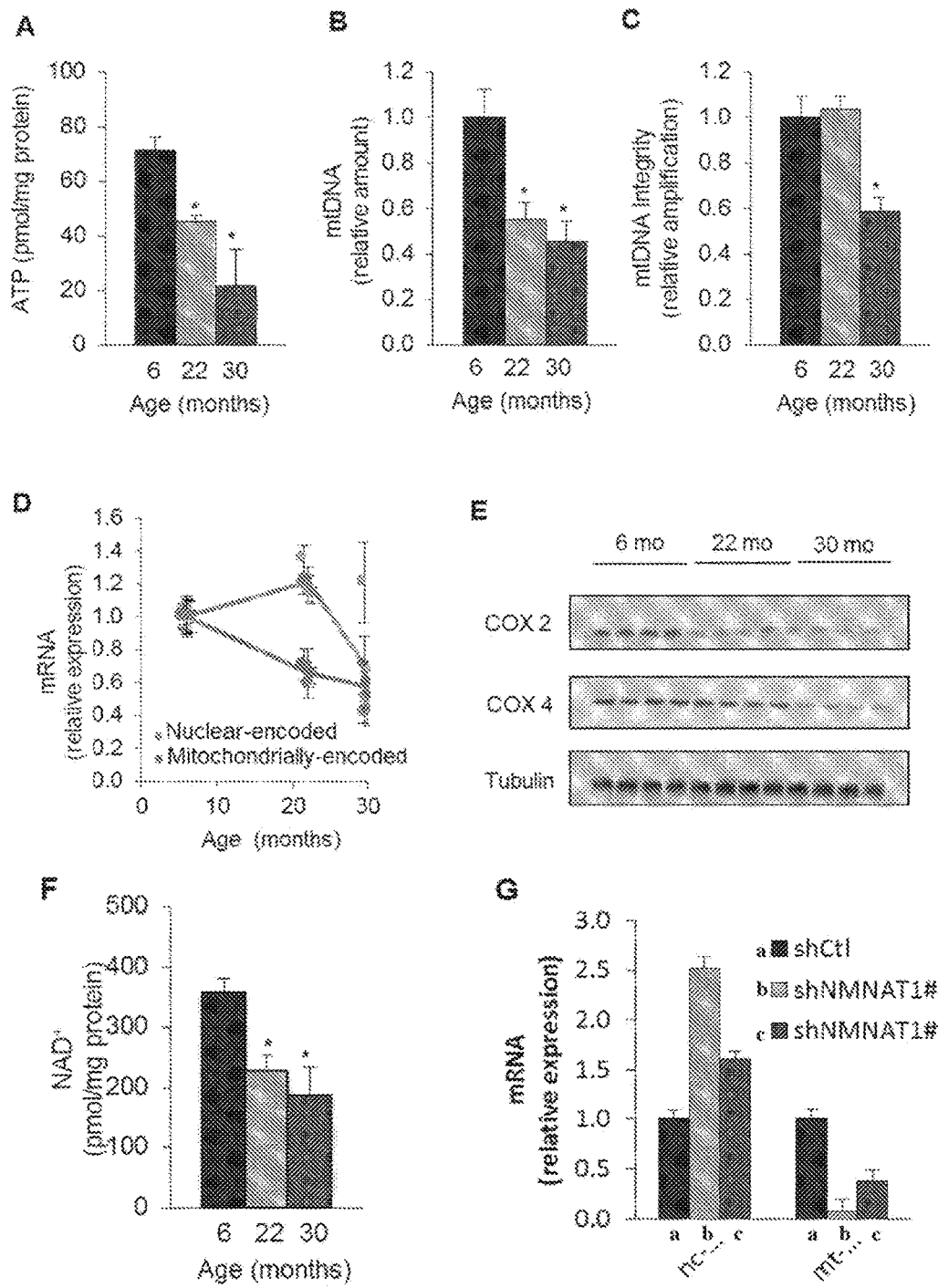
FIG. 11A-G

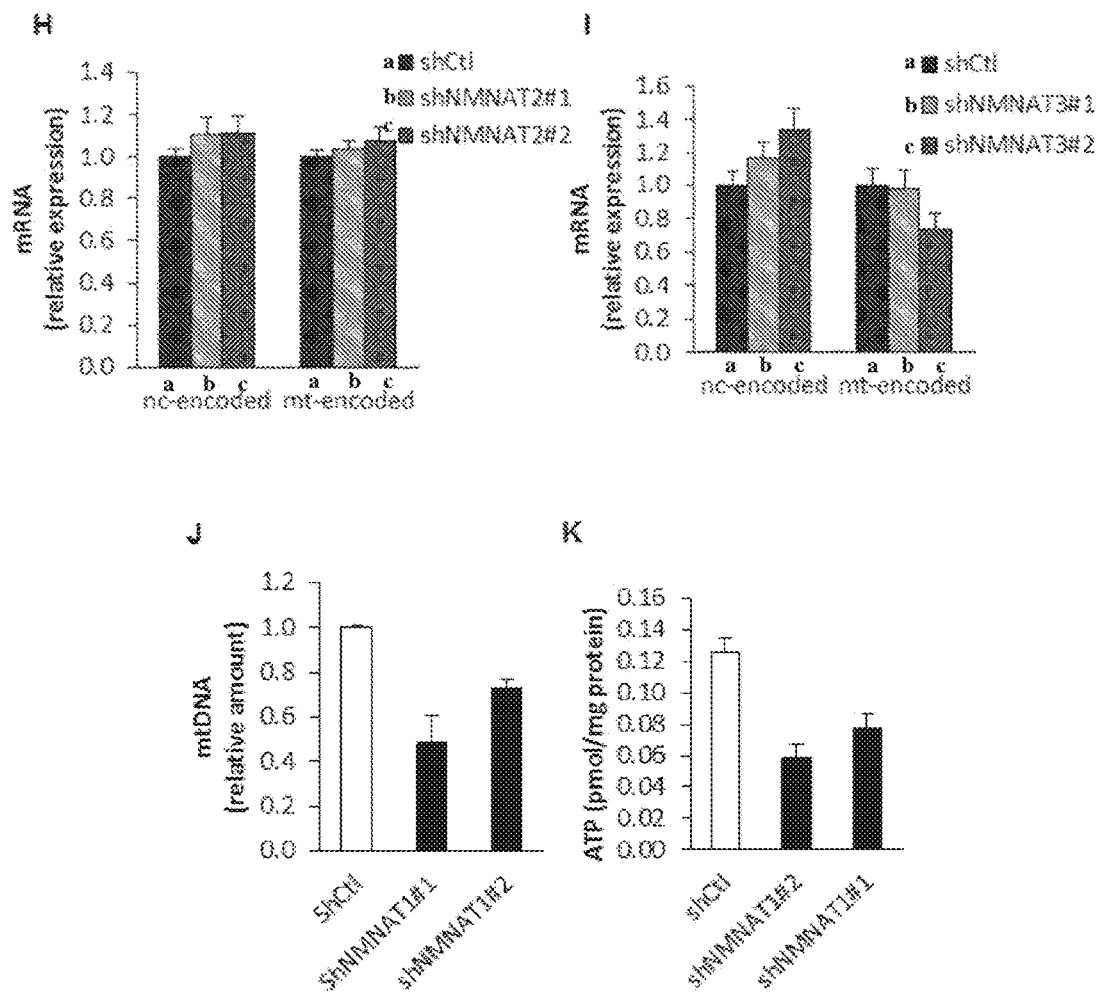
FIG. 11H-K

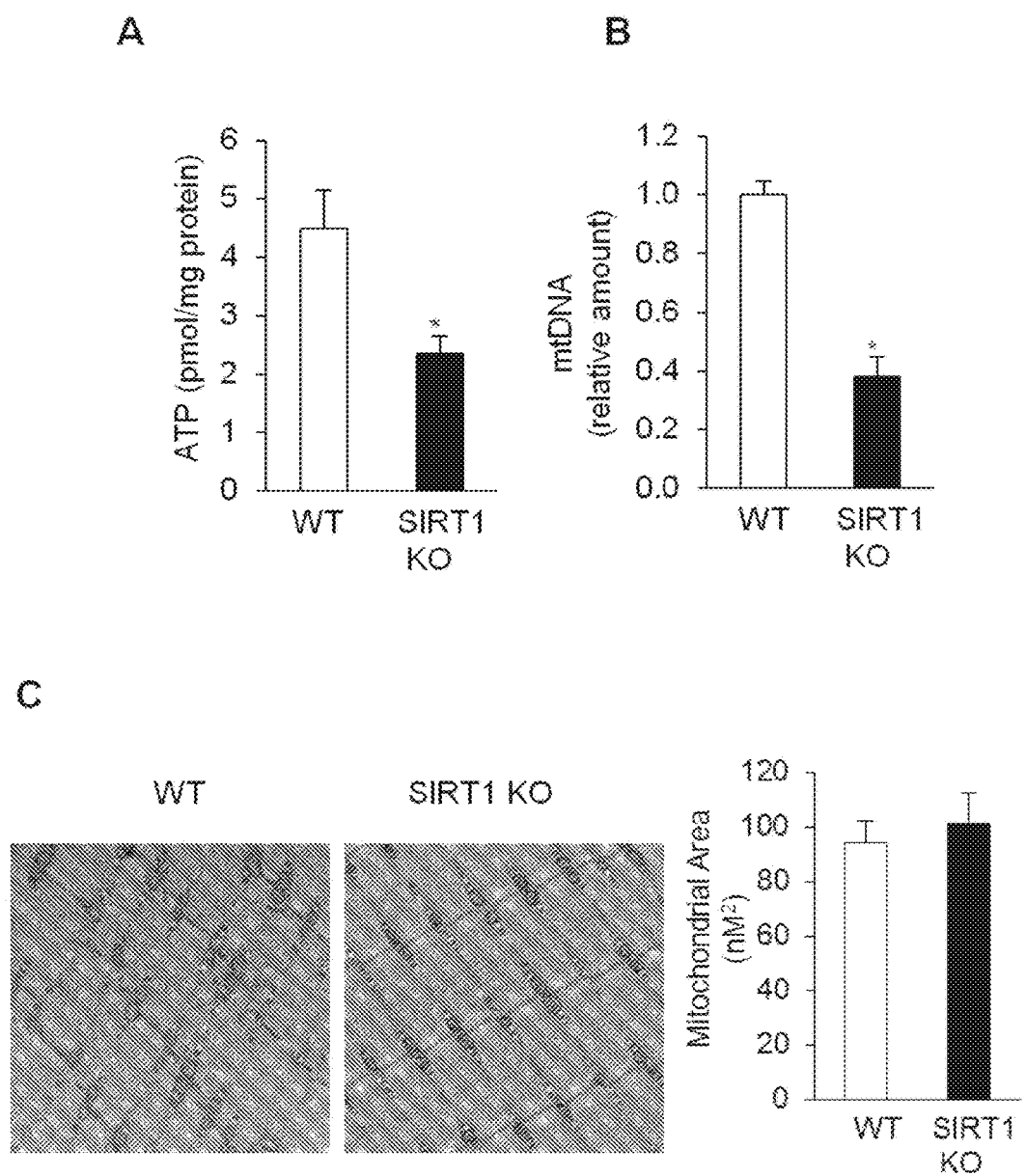
FIG. 12A-C

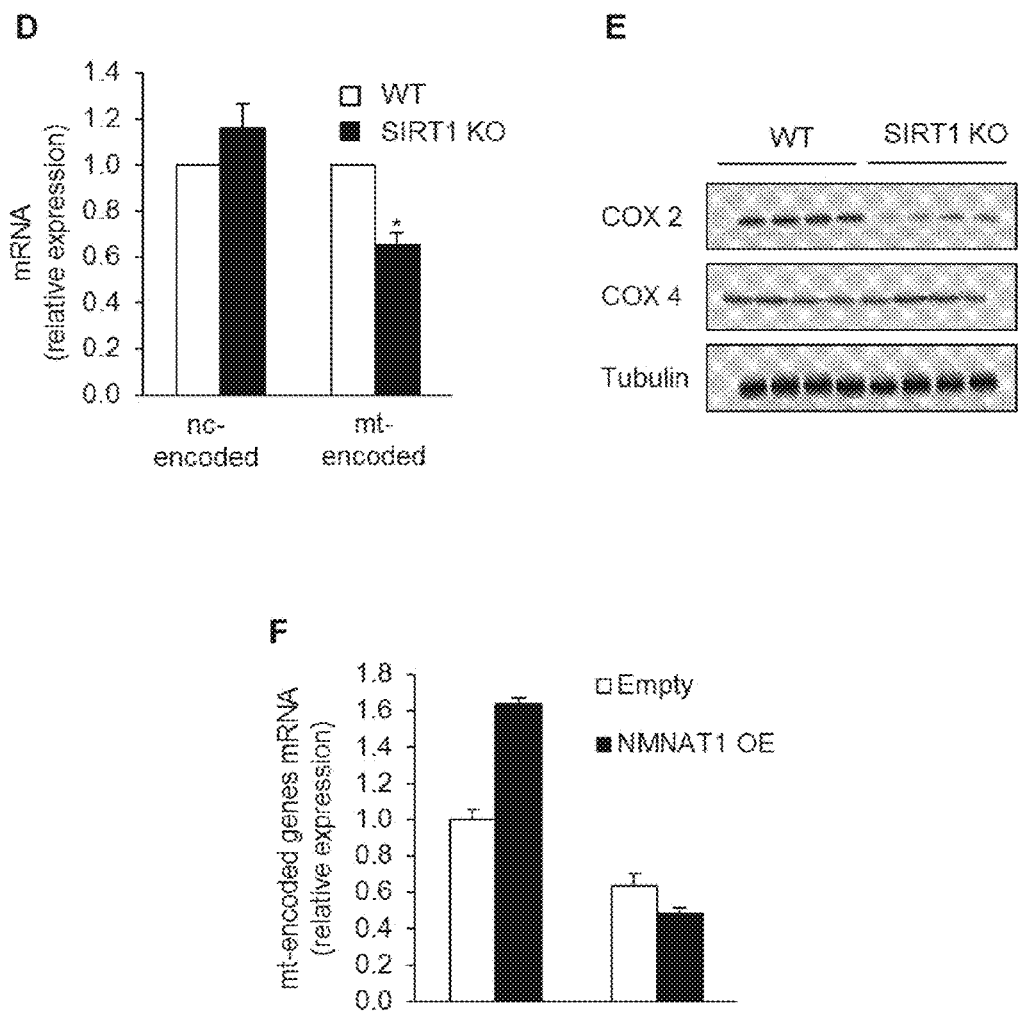
FIG. 12D-F

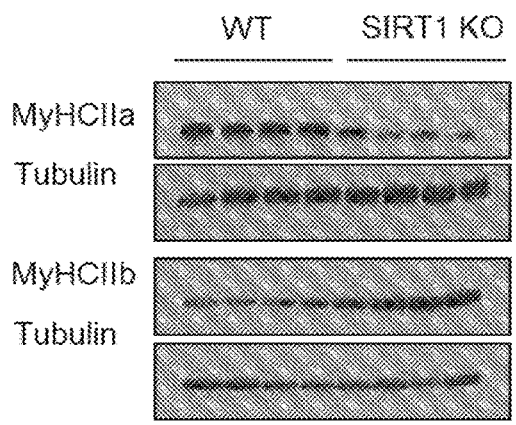
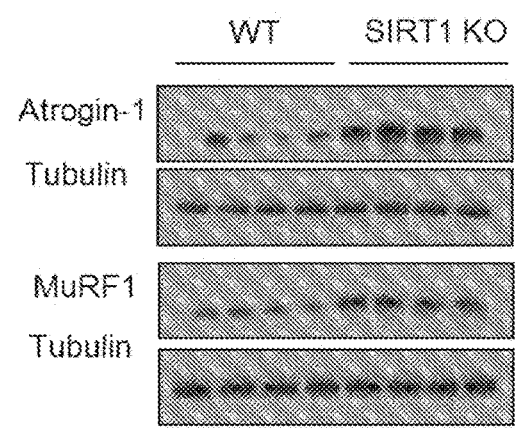
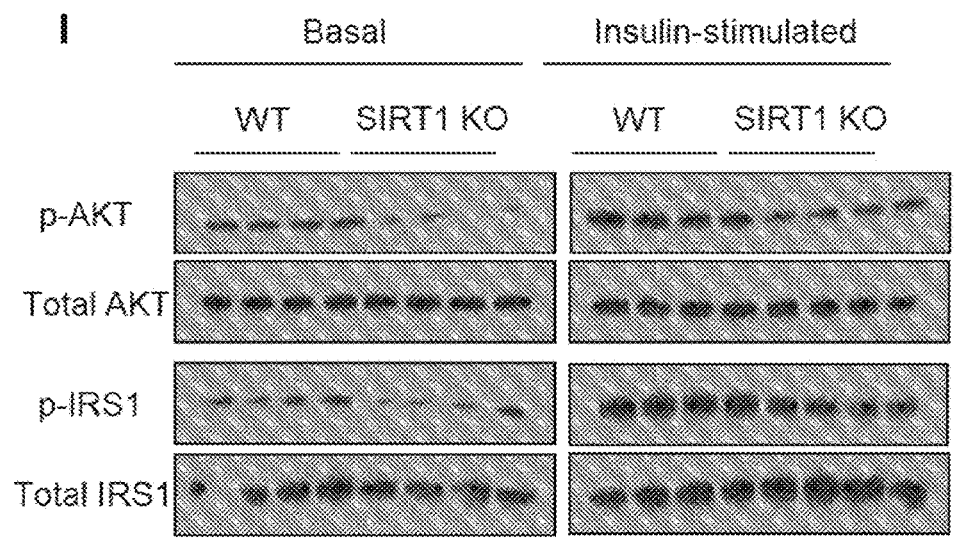
FIG. 12G-I

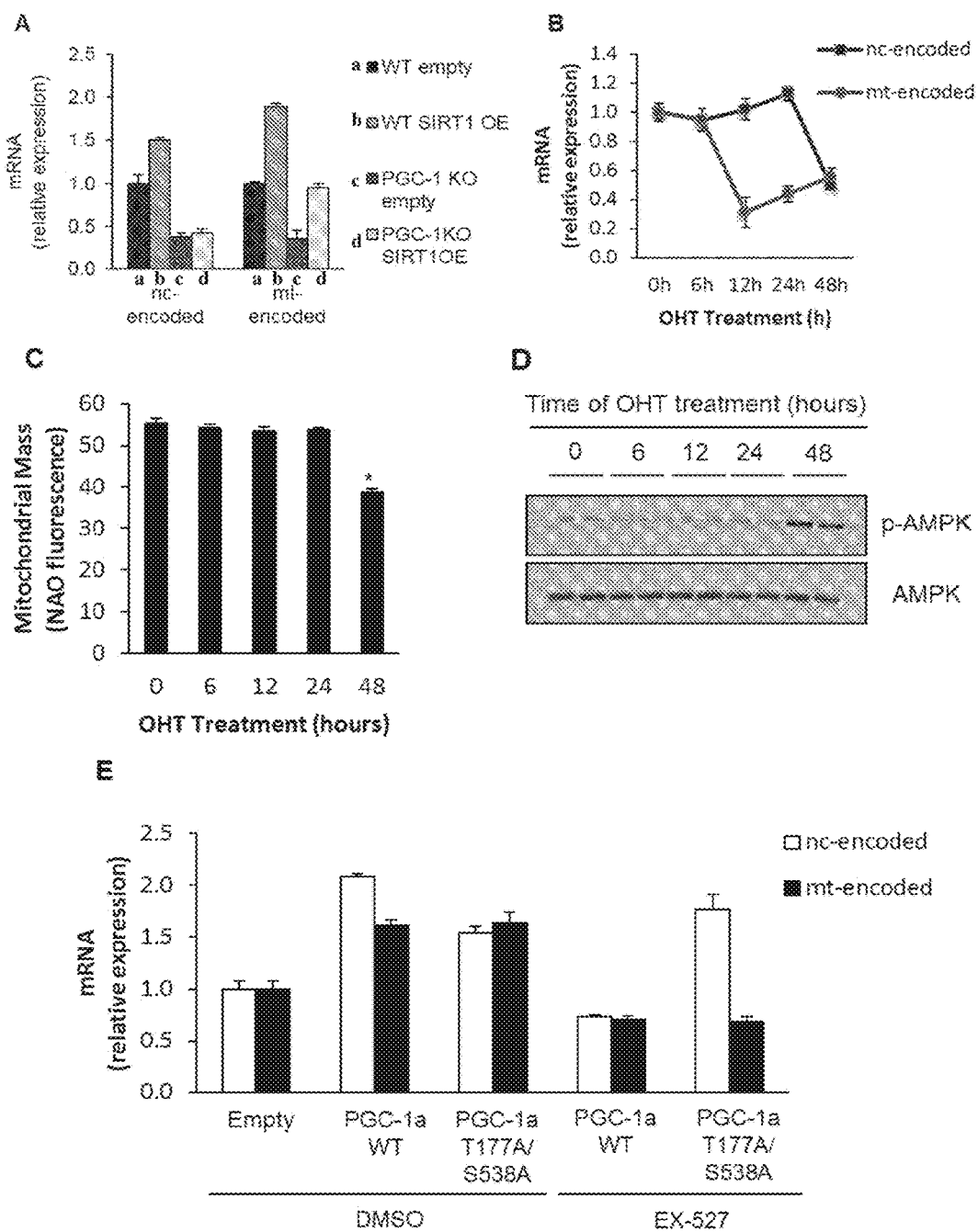
FIG. 13A-E

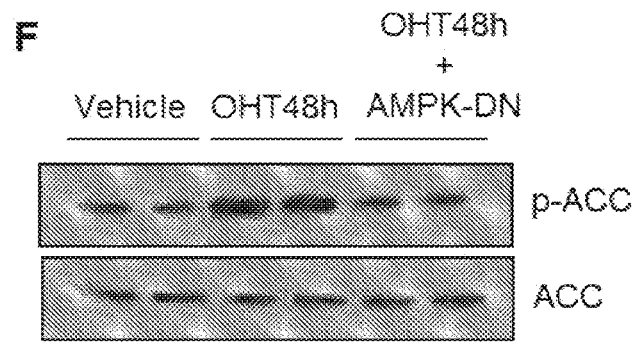
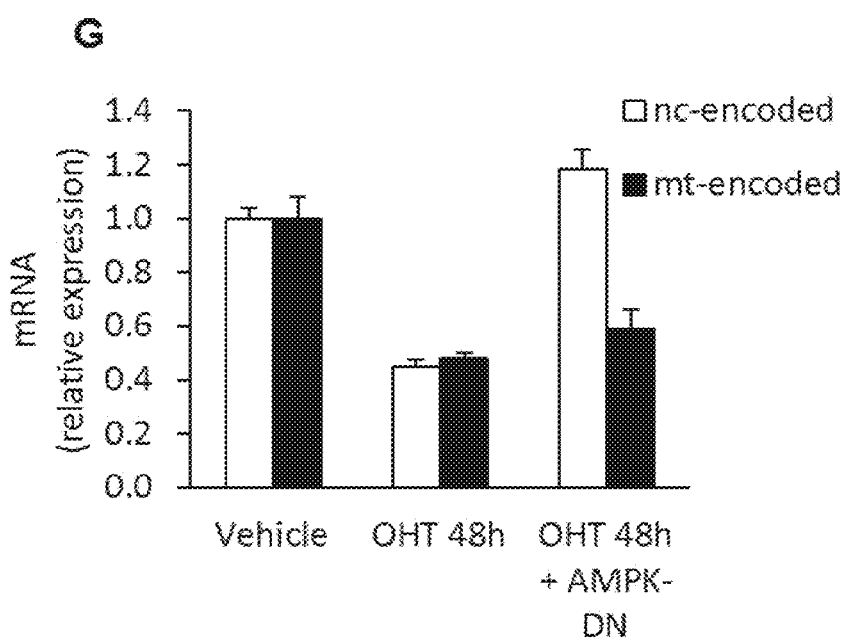
FIG. 13F-G

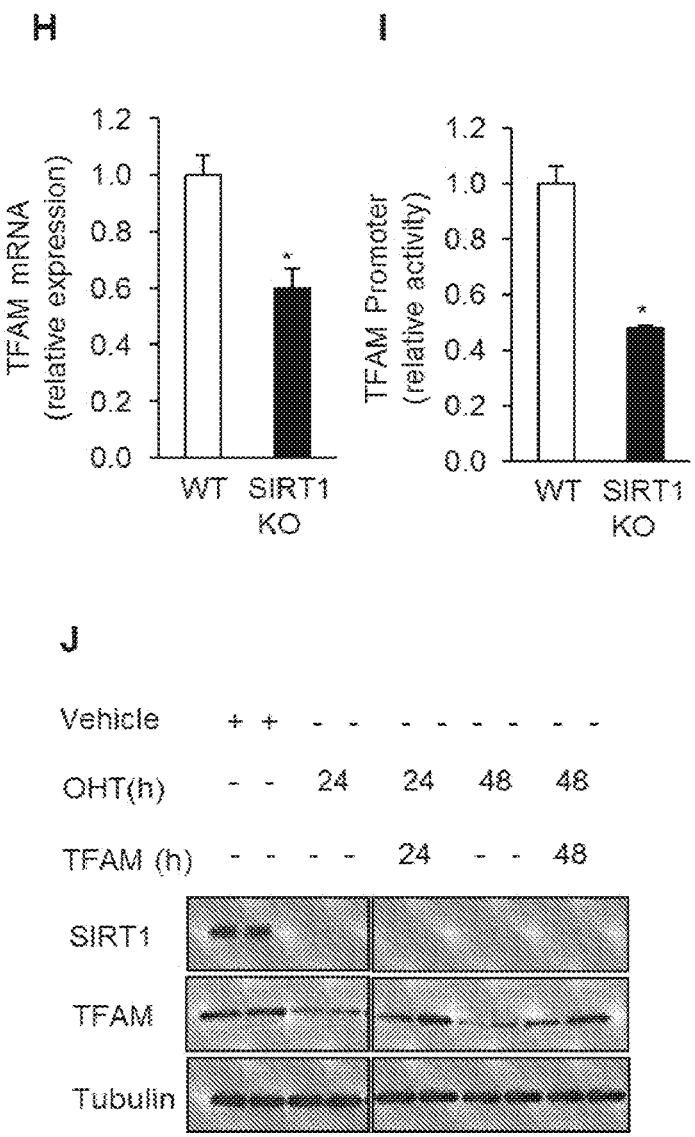
FIG. 13H-J

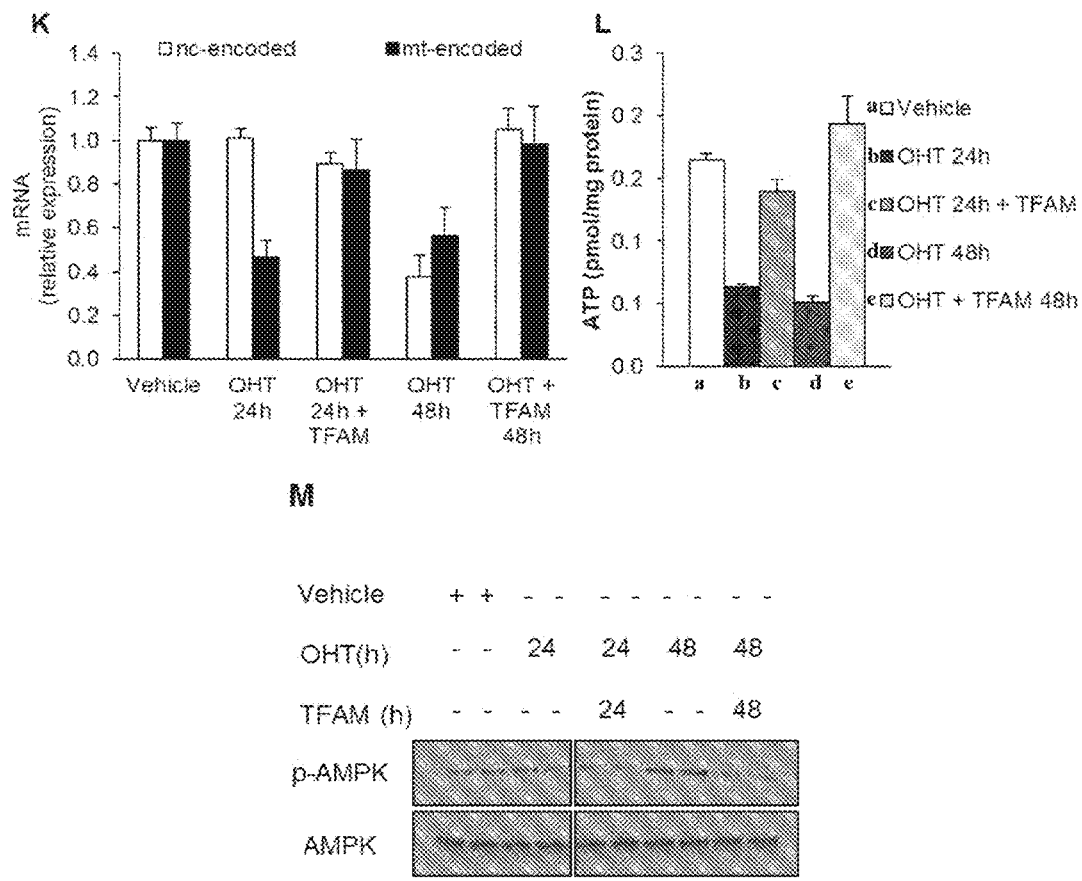
FIG. 13K-M

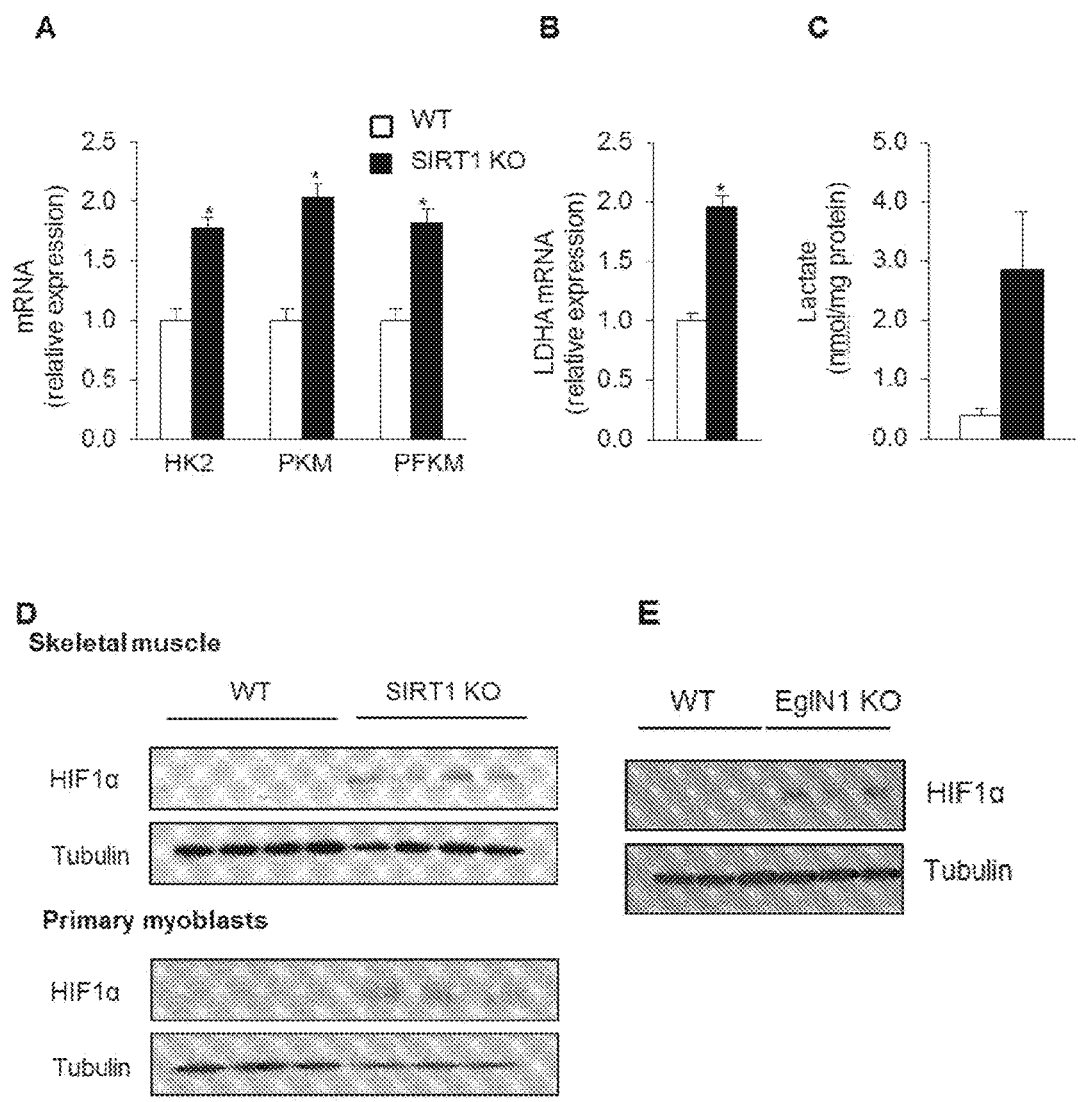
FIG. 14A-E

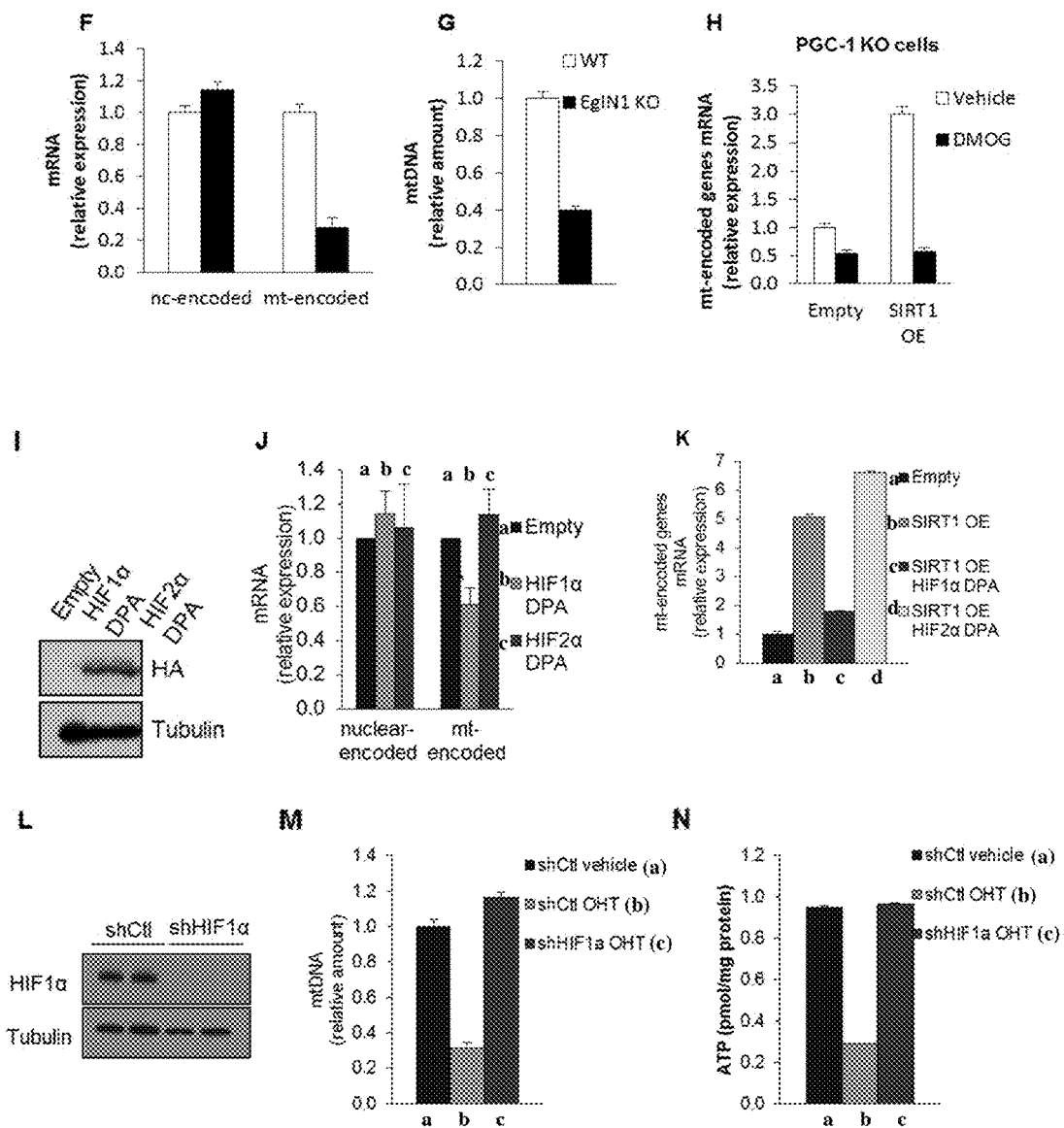
FIG. 14F-N

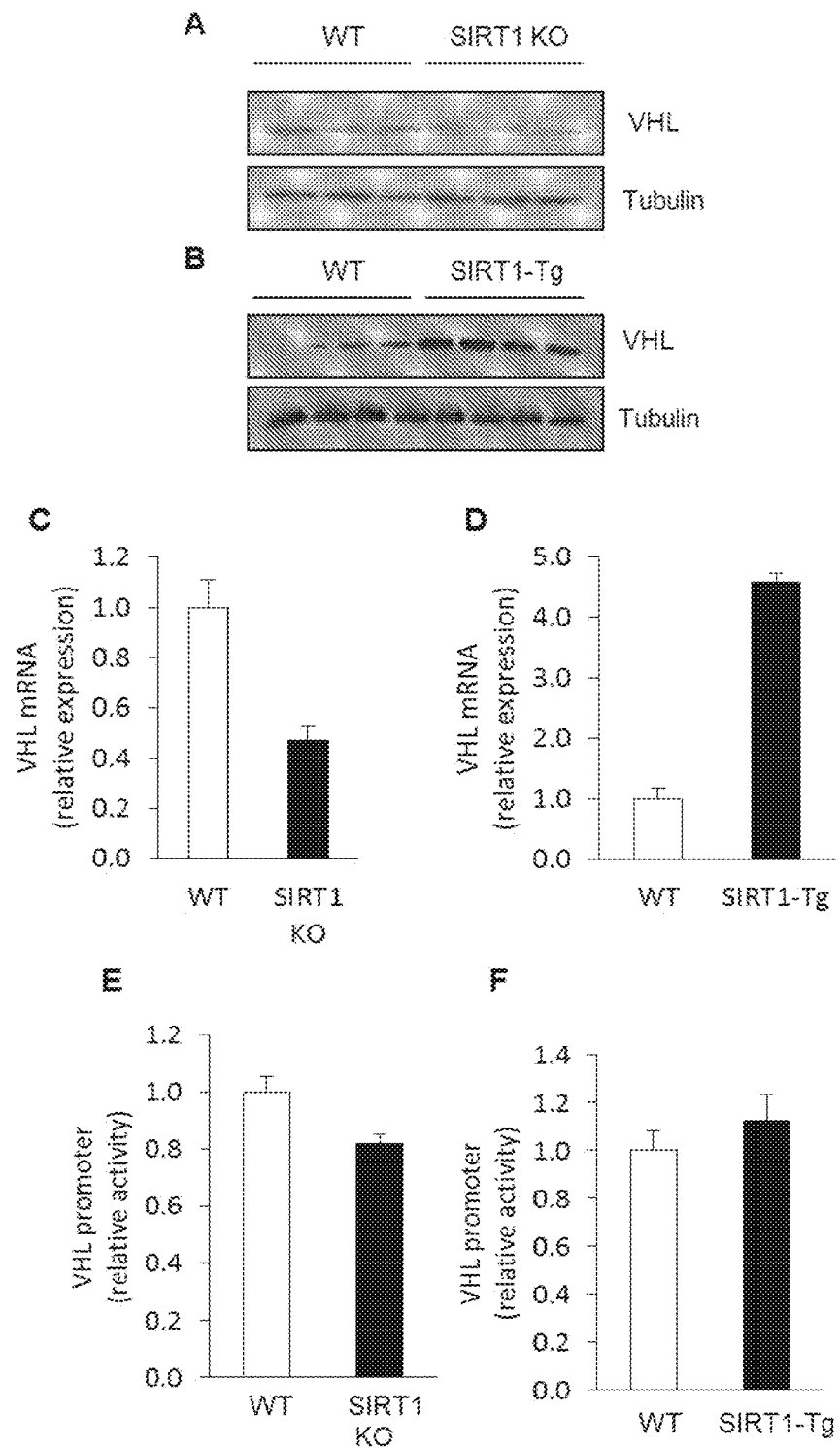
FIG. 15A-F

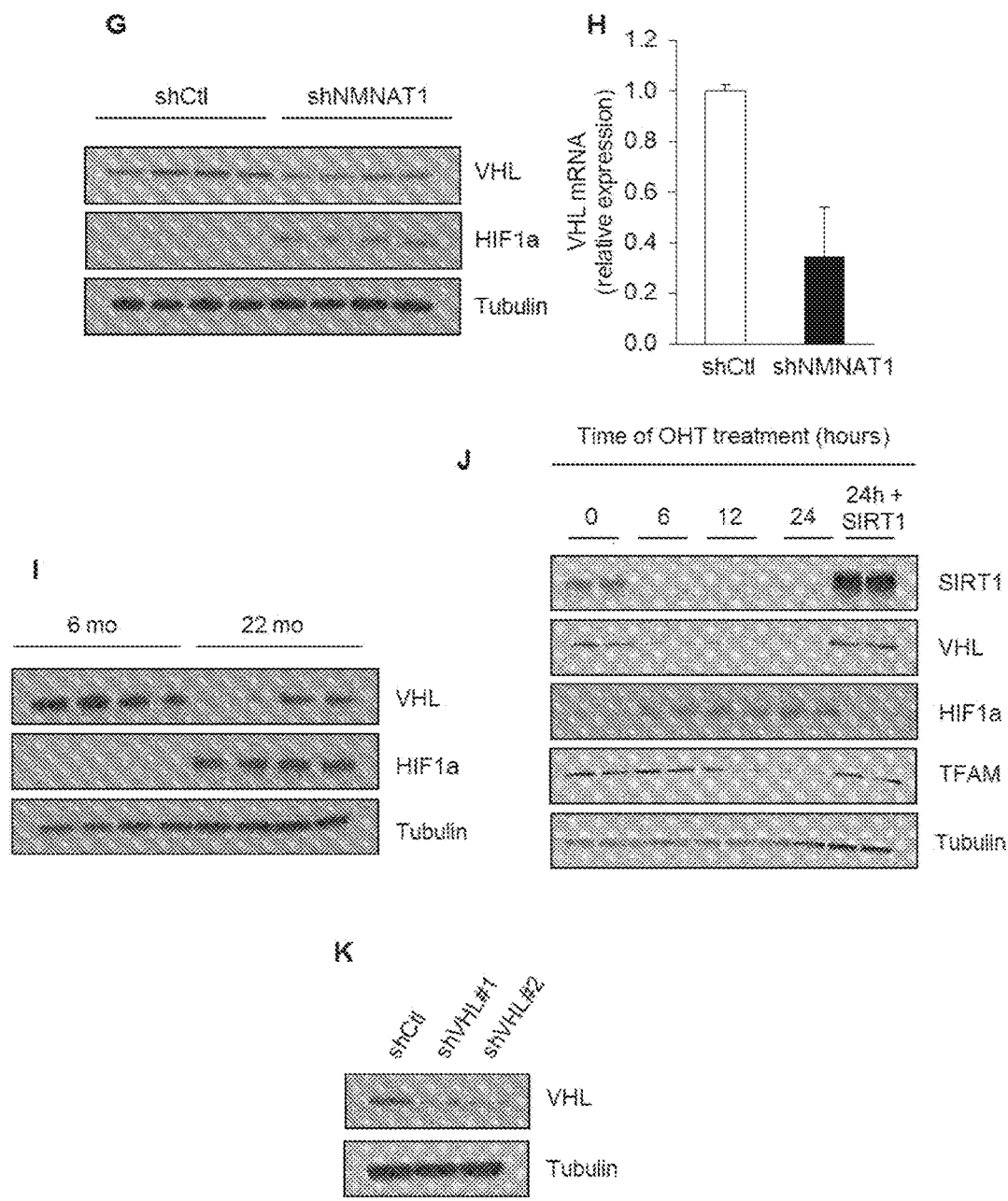
FIG. 15G-K

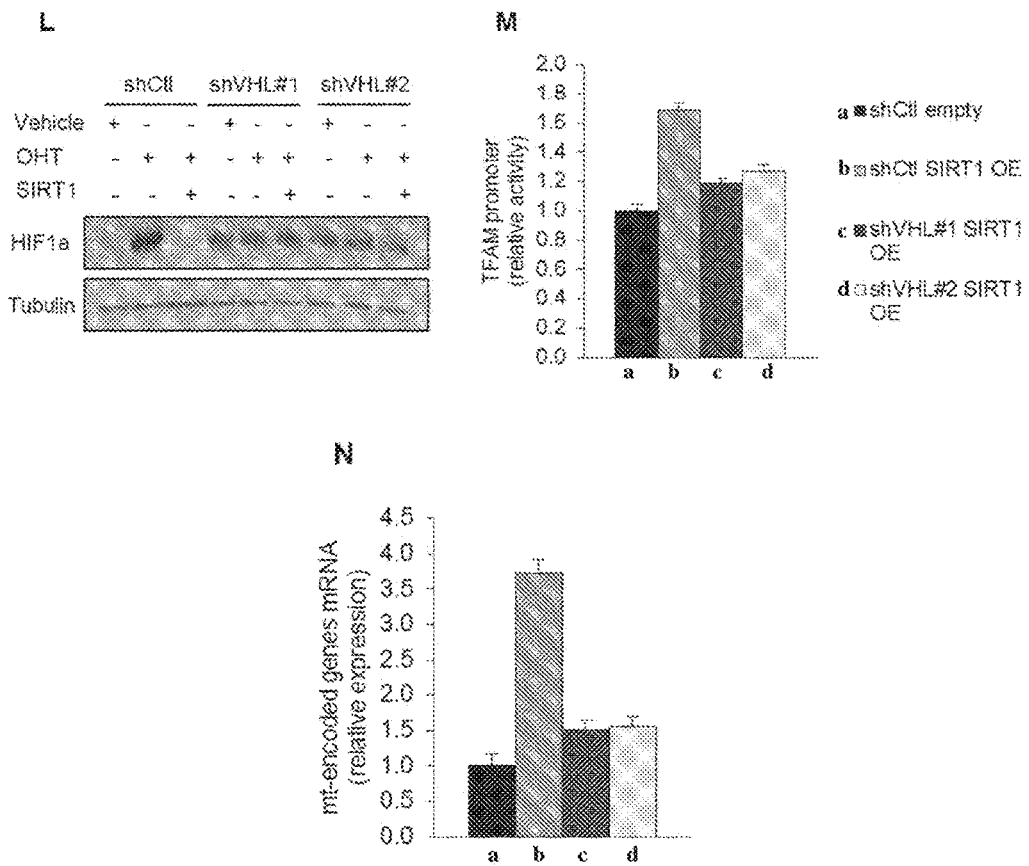
FIG. 15L-N

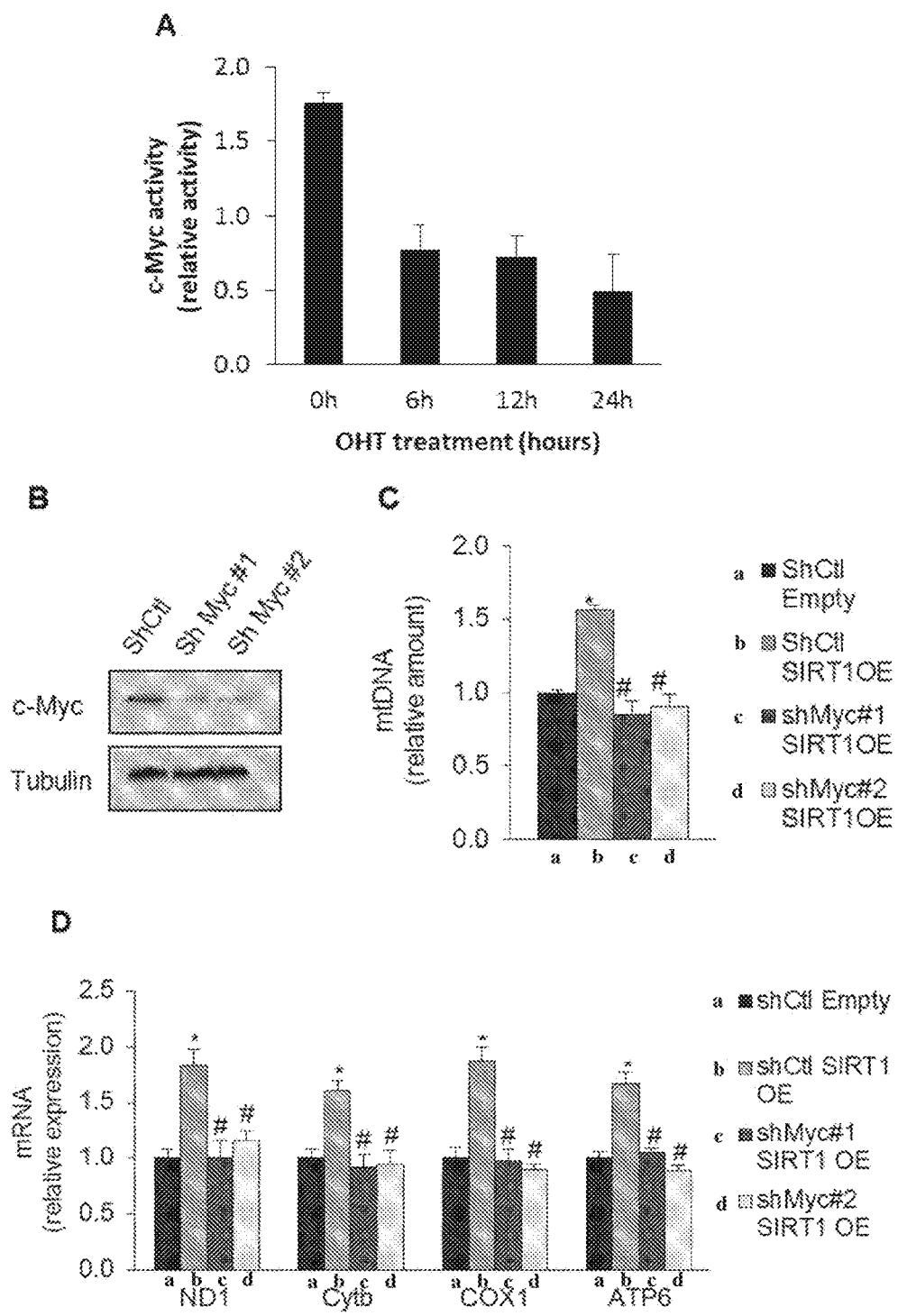
FIG. 16A-D

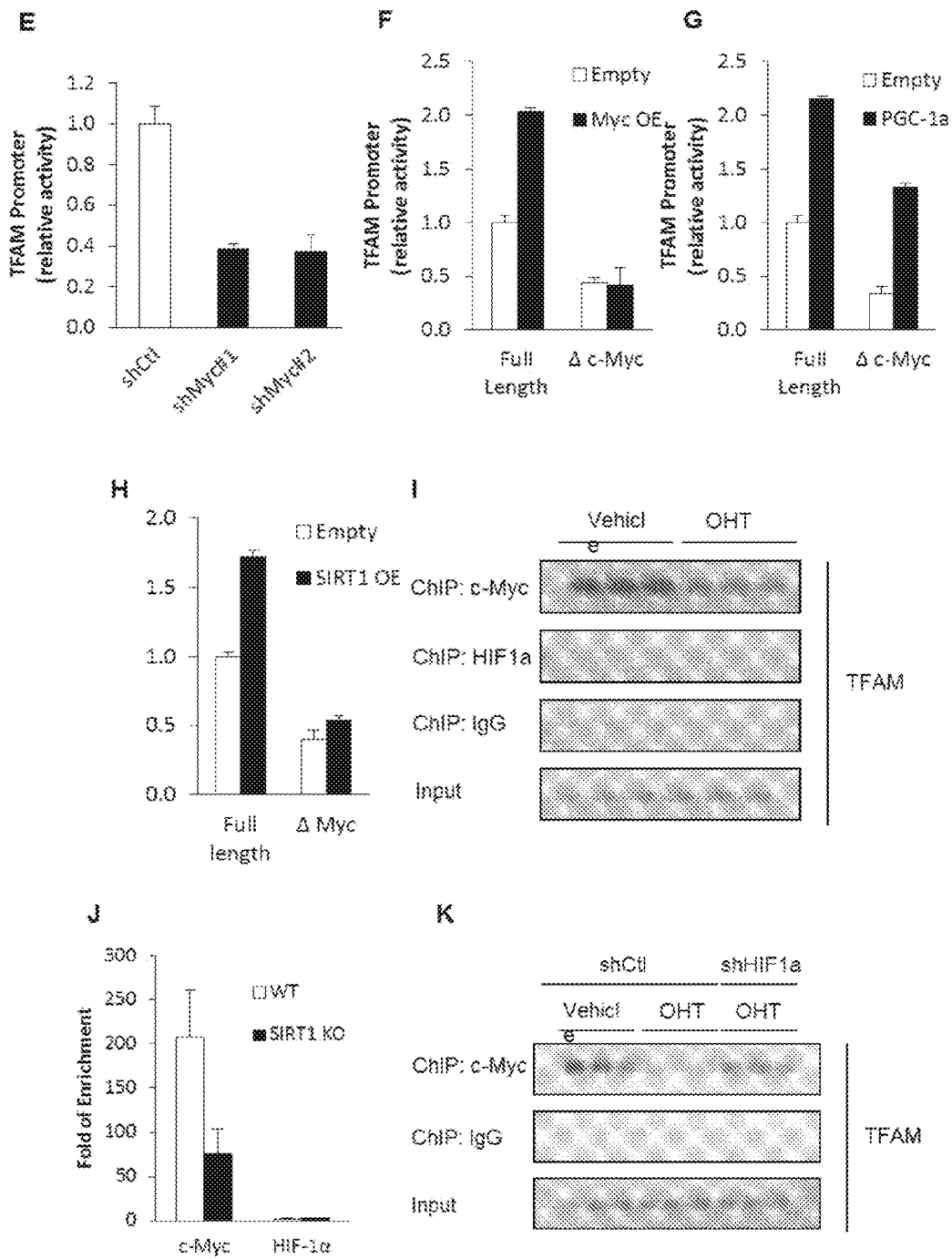
FIG. 16E-K

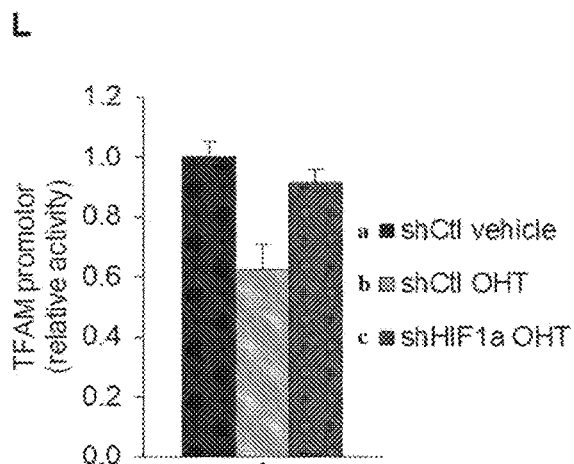
FIG. 16L
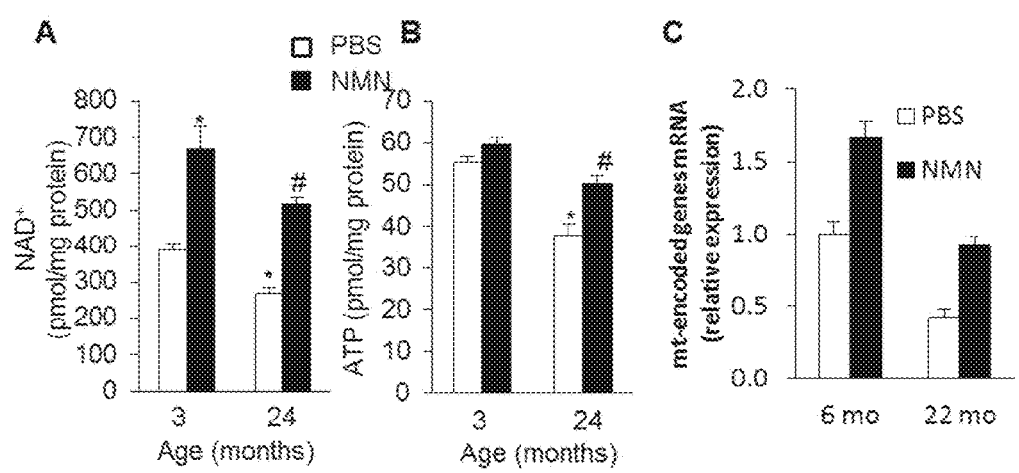
FIG. 17A-C

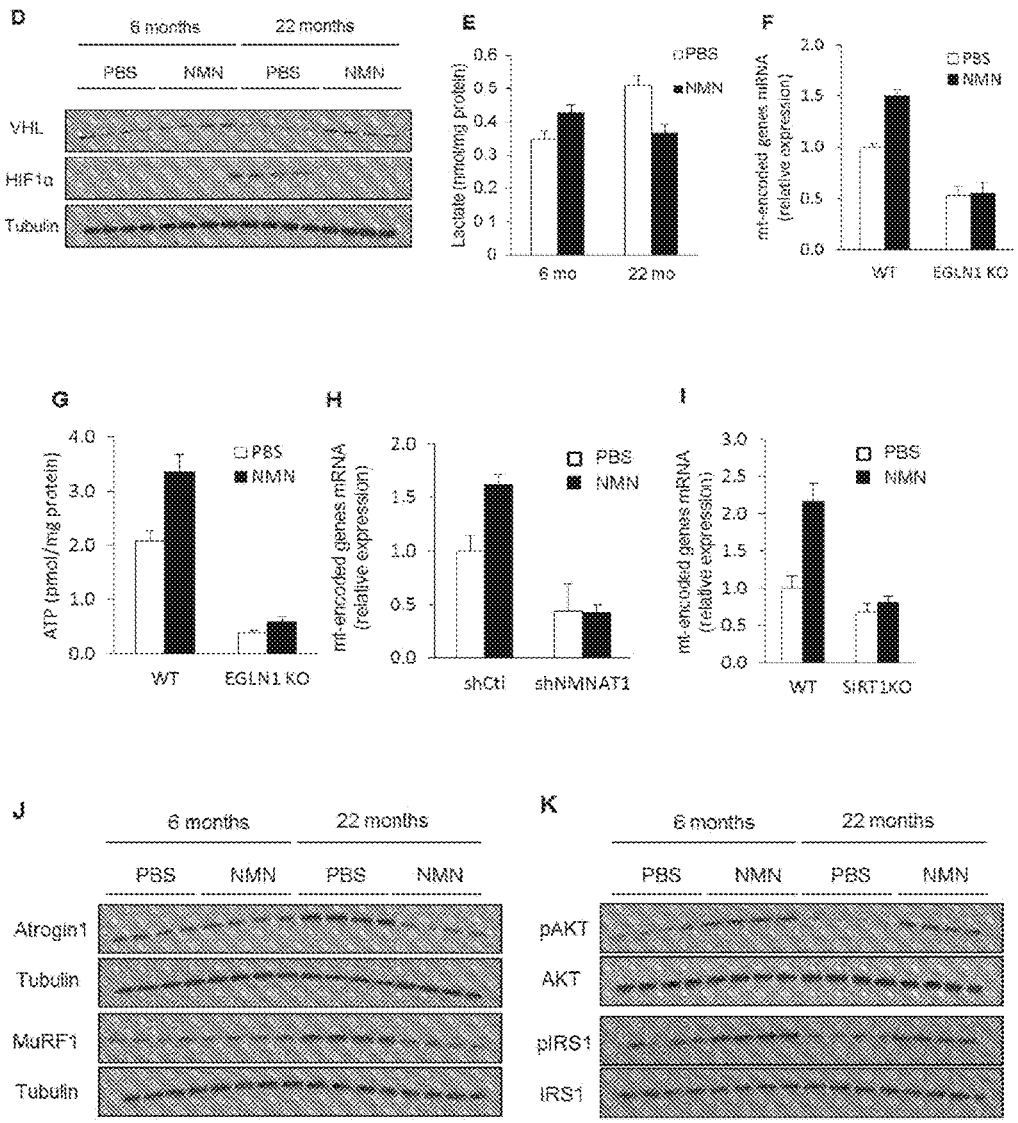
FIG. 17D-K

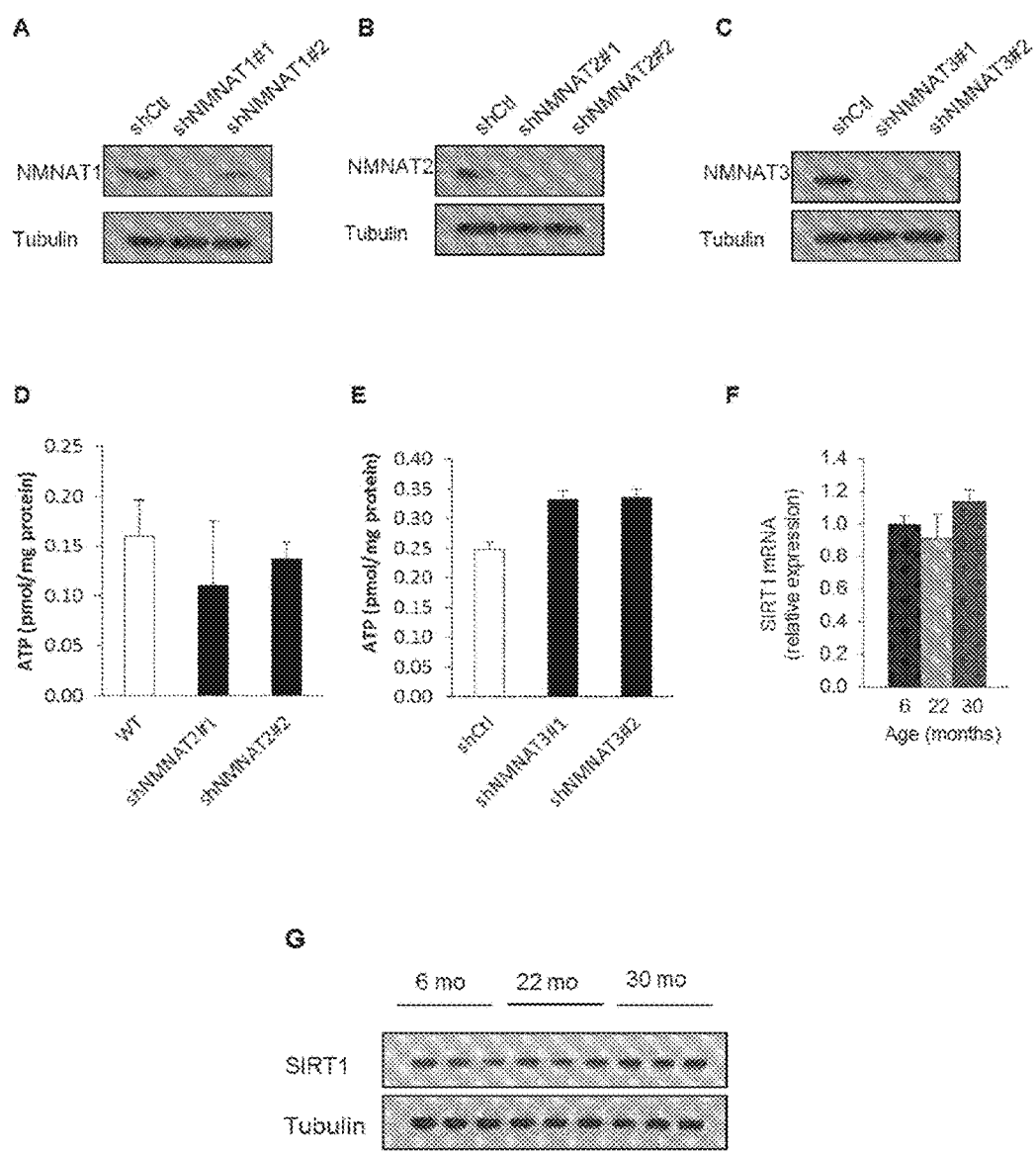
FIG. 18A-G

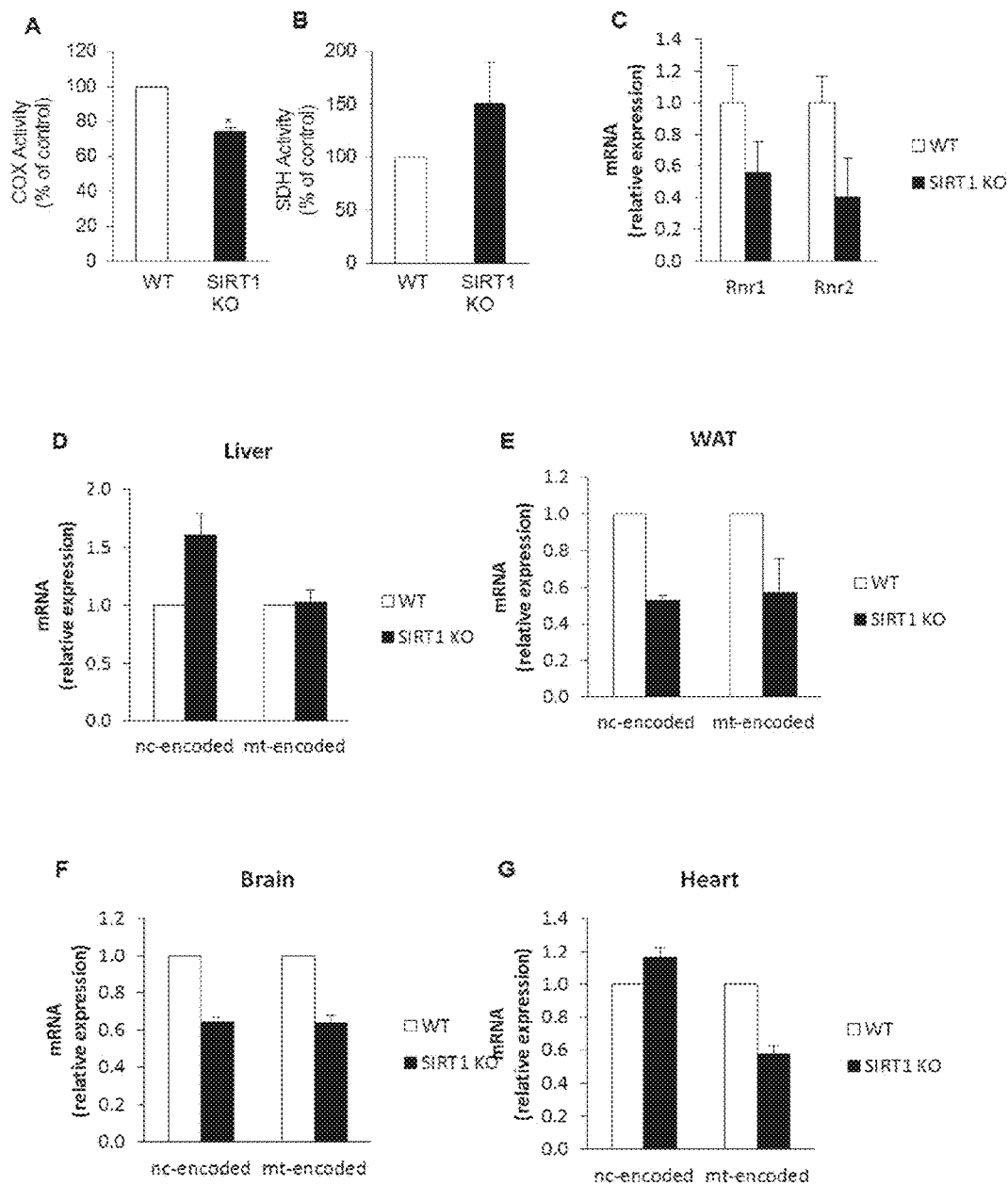
FIG. 19A-G

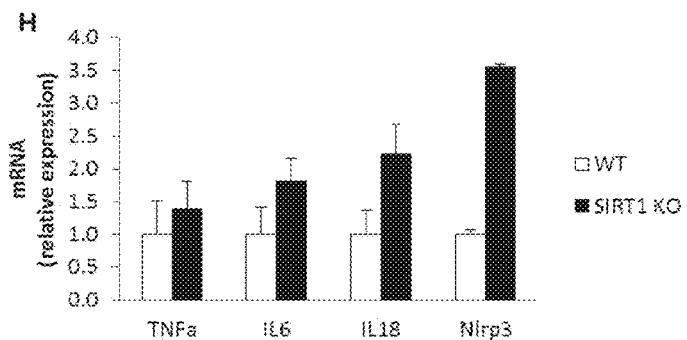
FIG. 19H
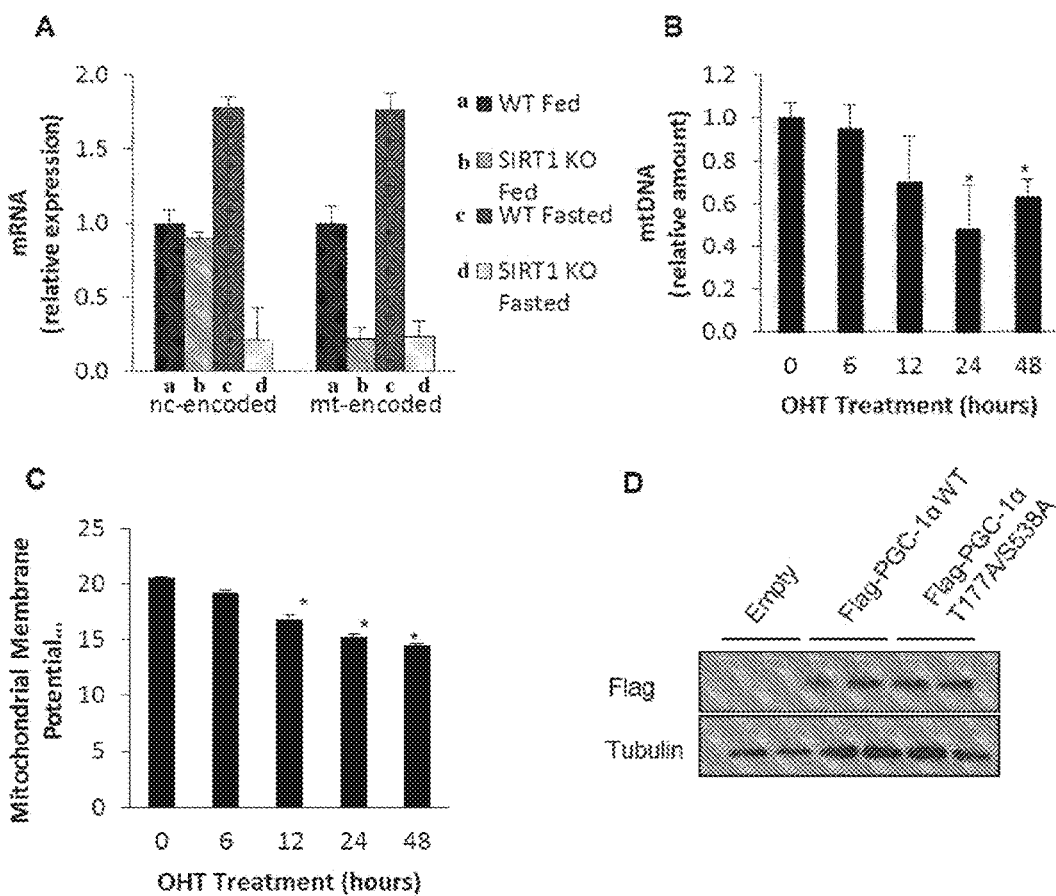
FIG. 20A-D

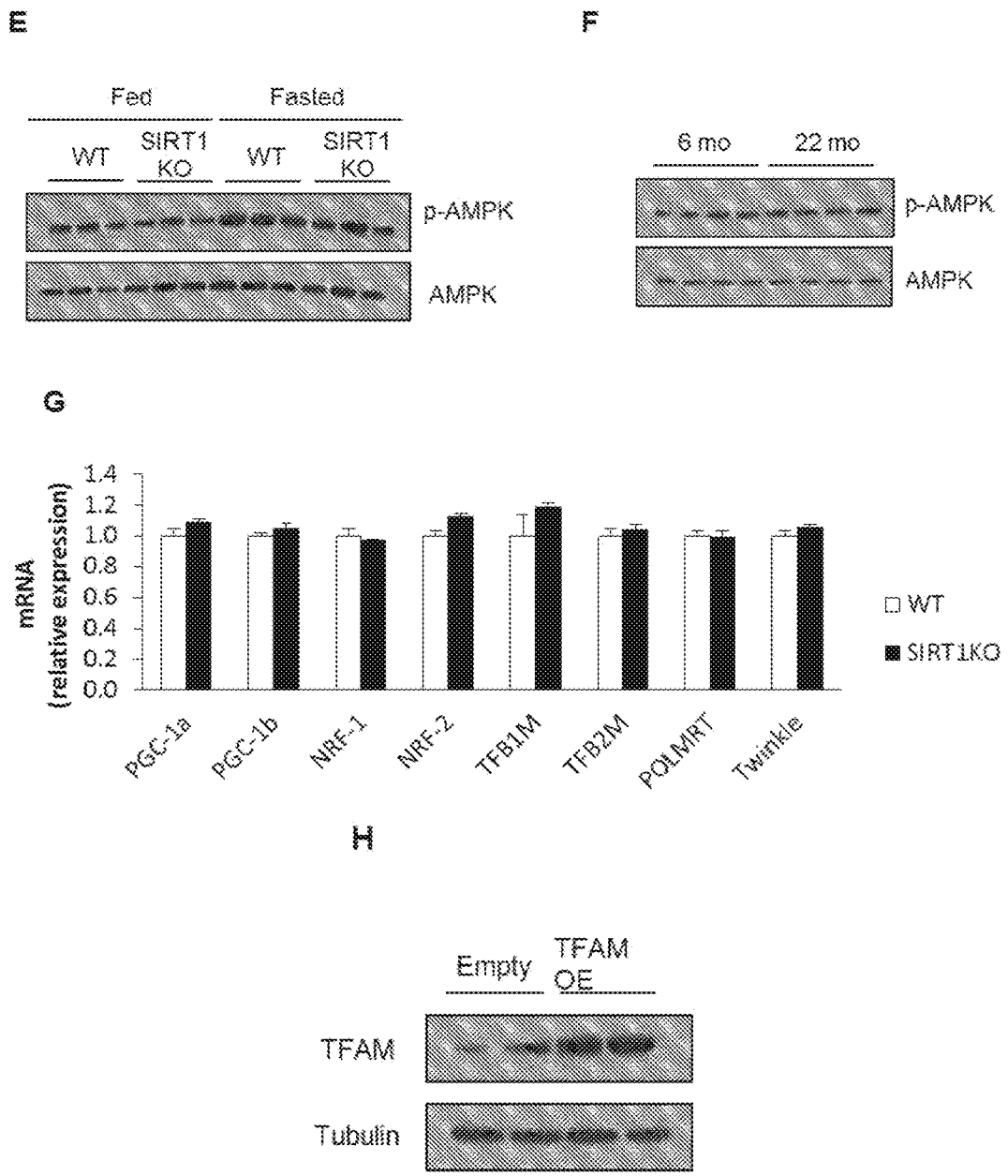
FIG. 20E-H

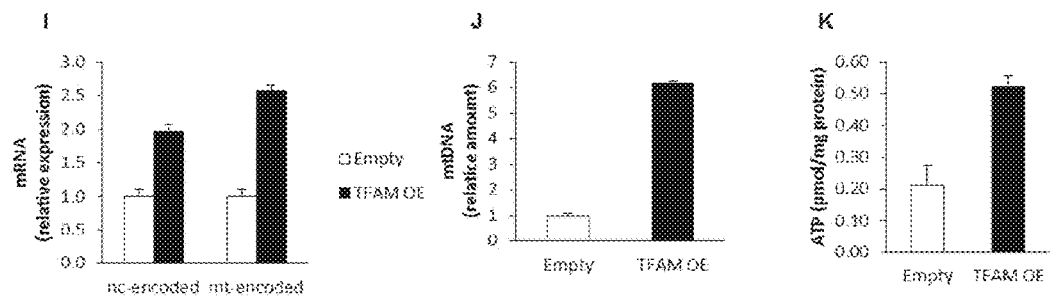
FIG. 20I-K
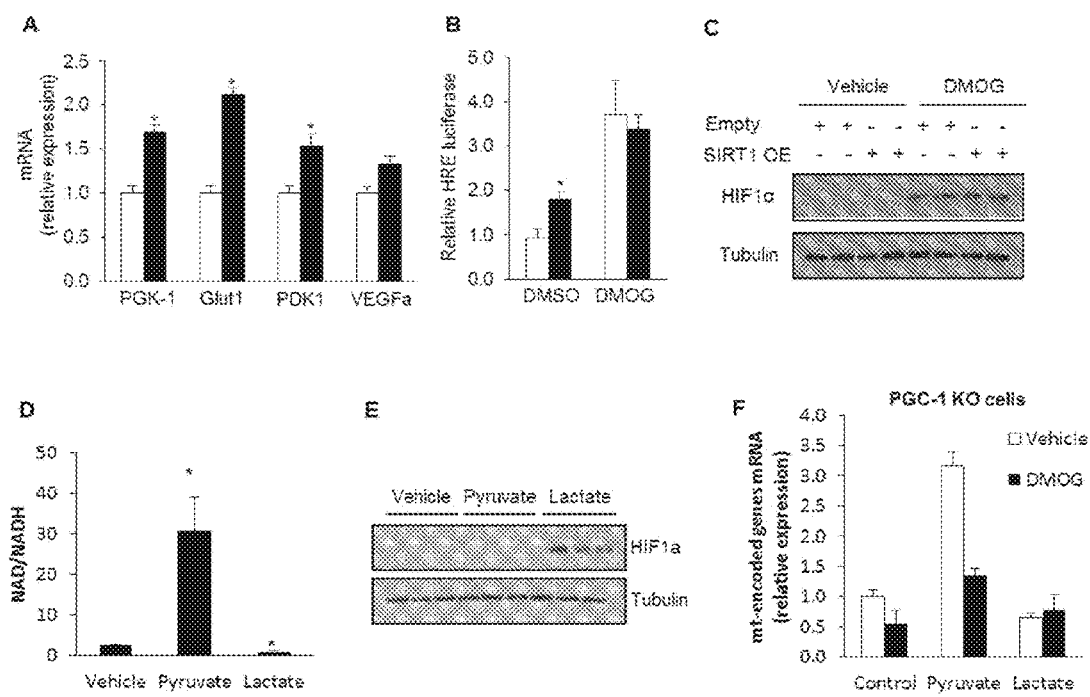
FIG. 21A-F

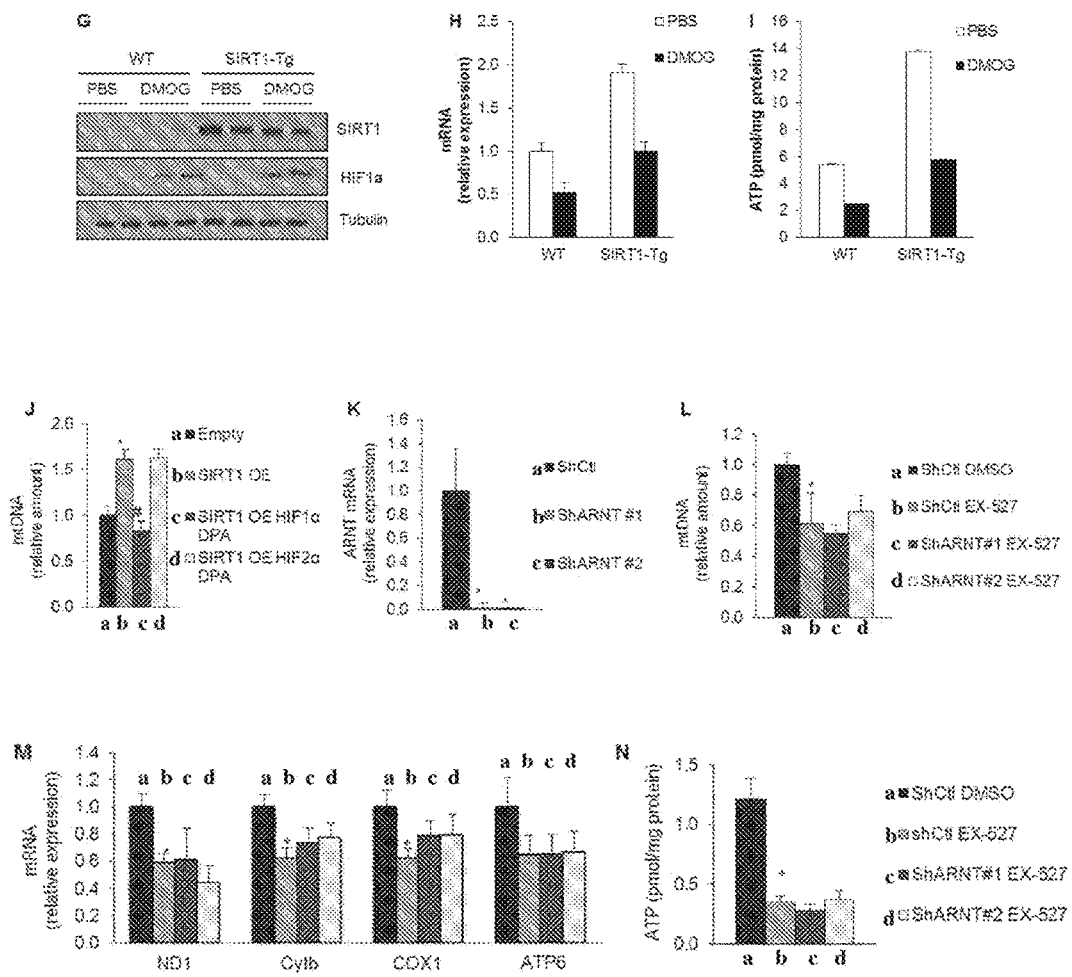
FIG. 21G-N

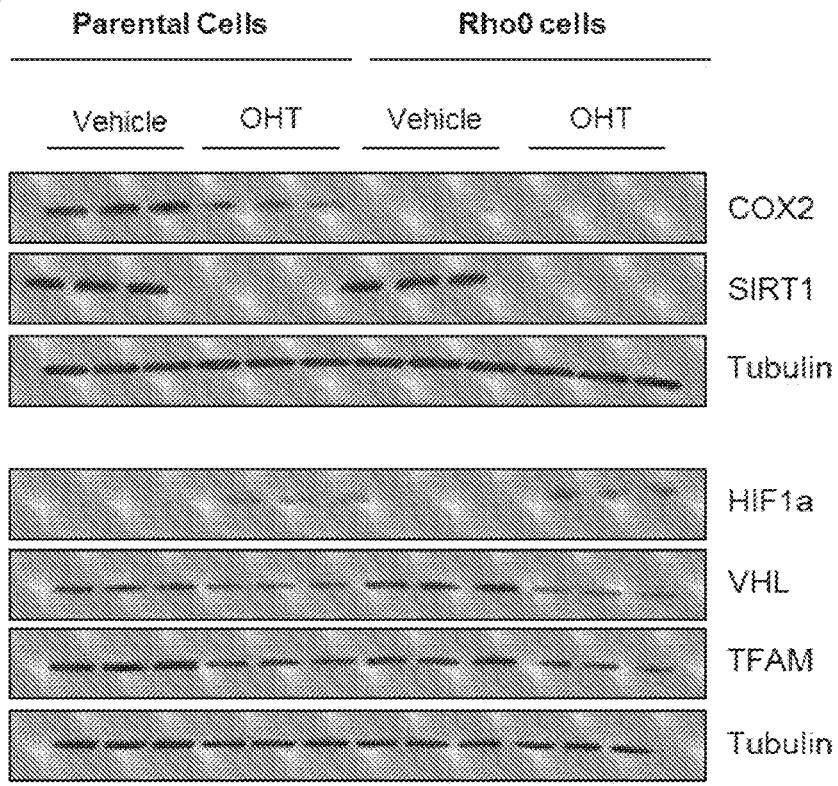
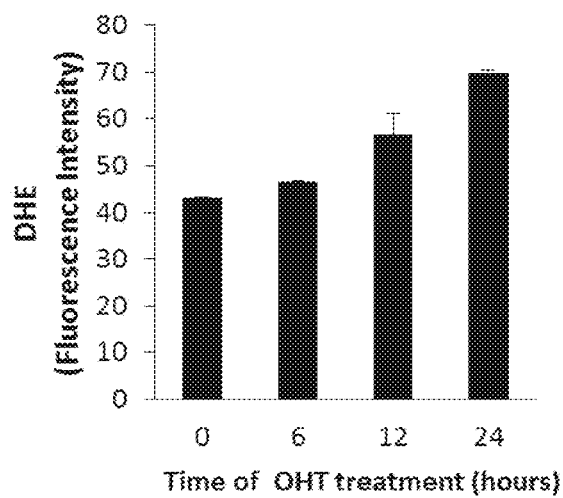
FIG. 22A-B

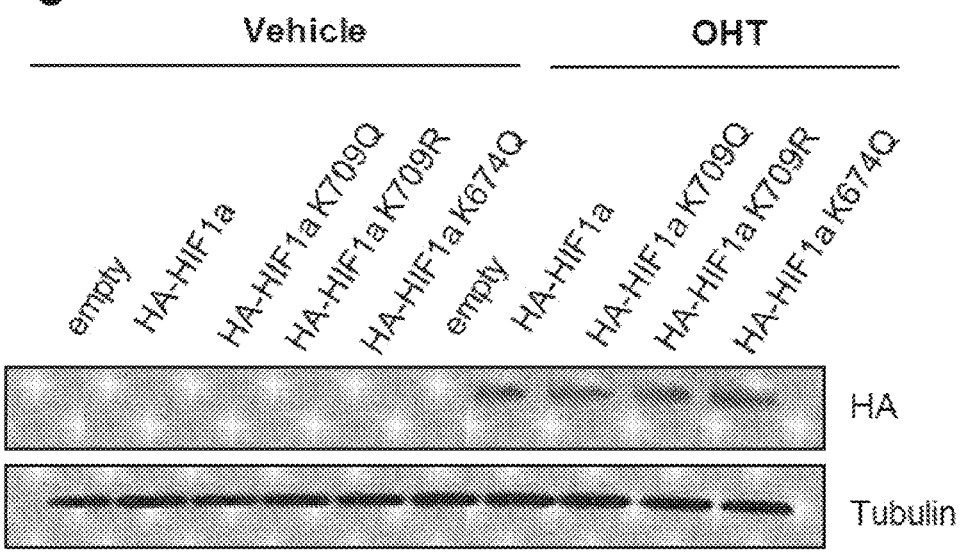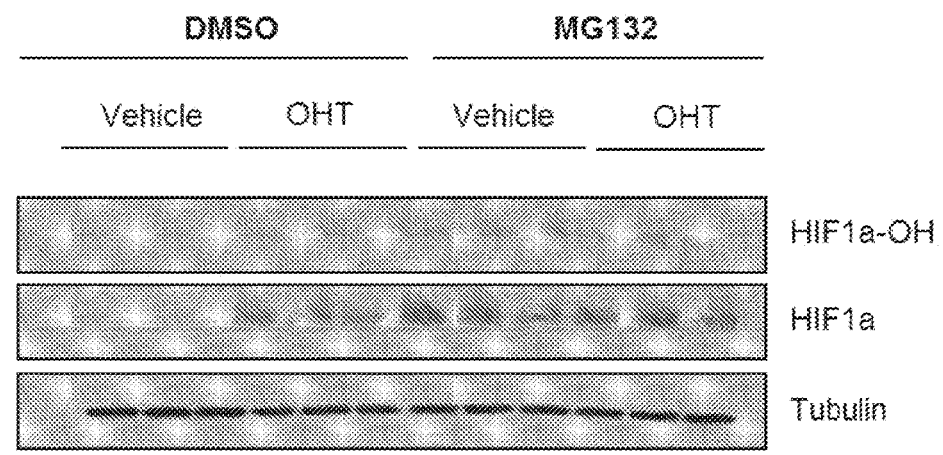
FIG. 22C-D

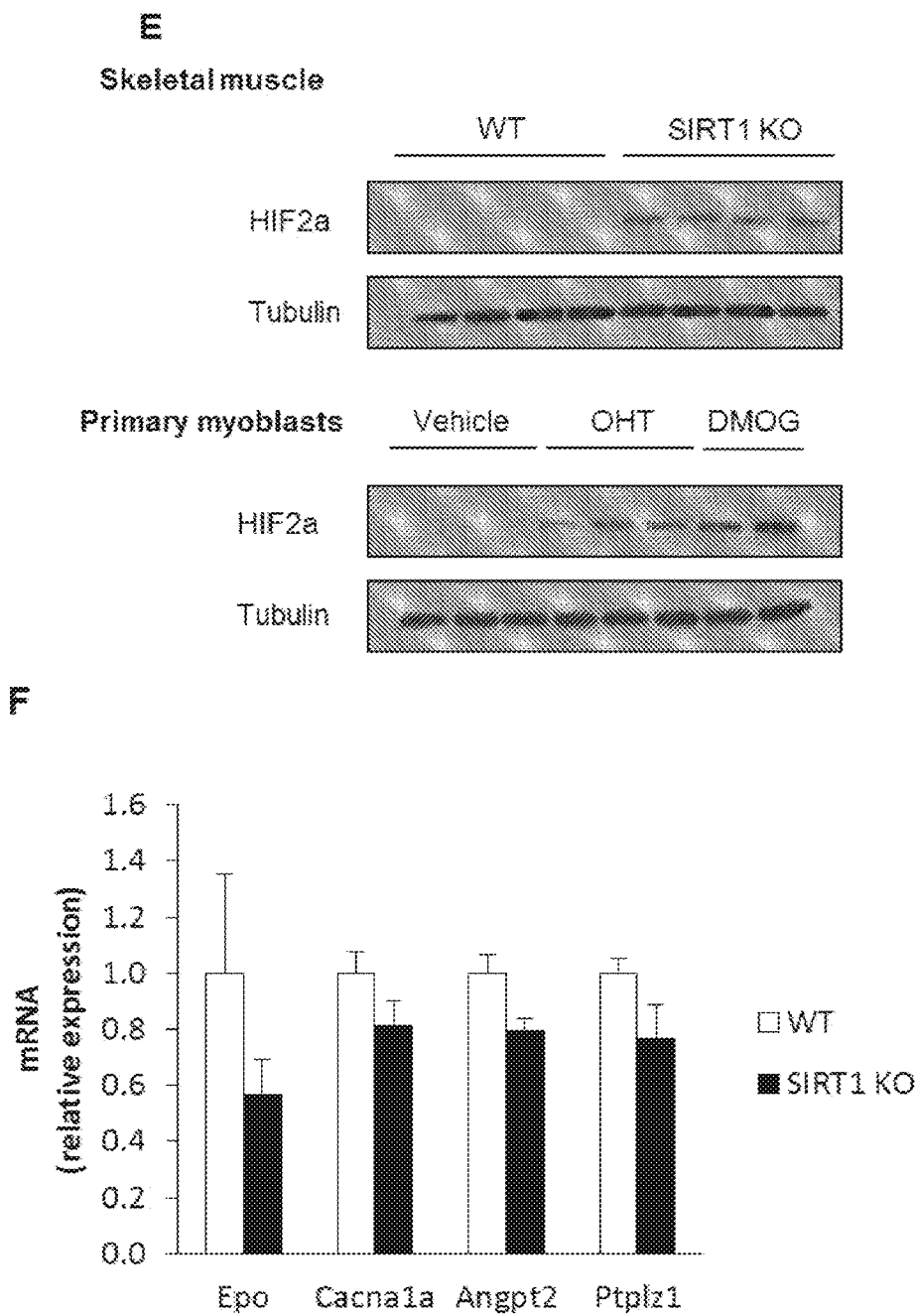
FIG. 22E-F

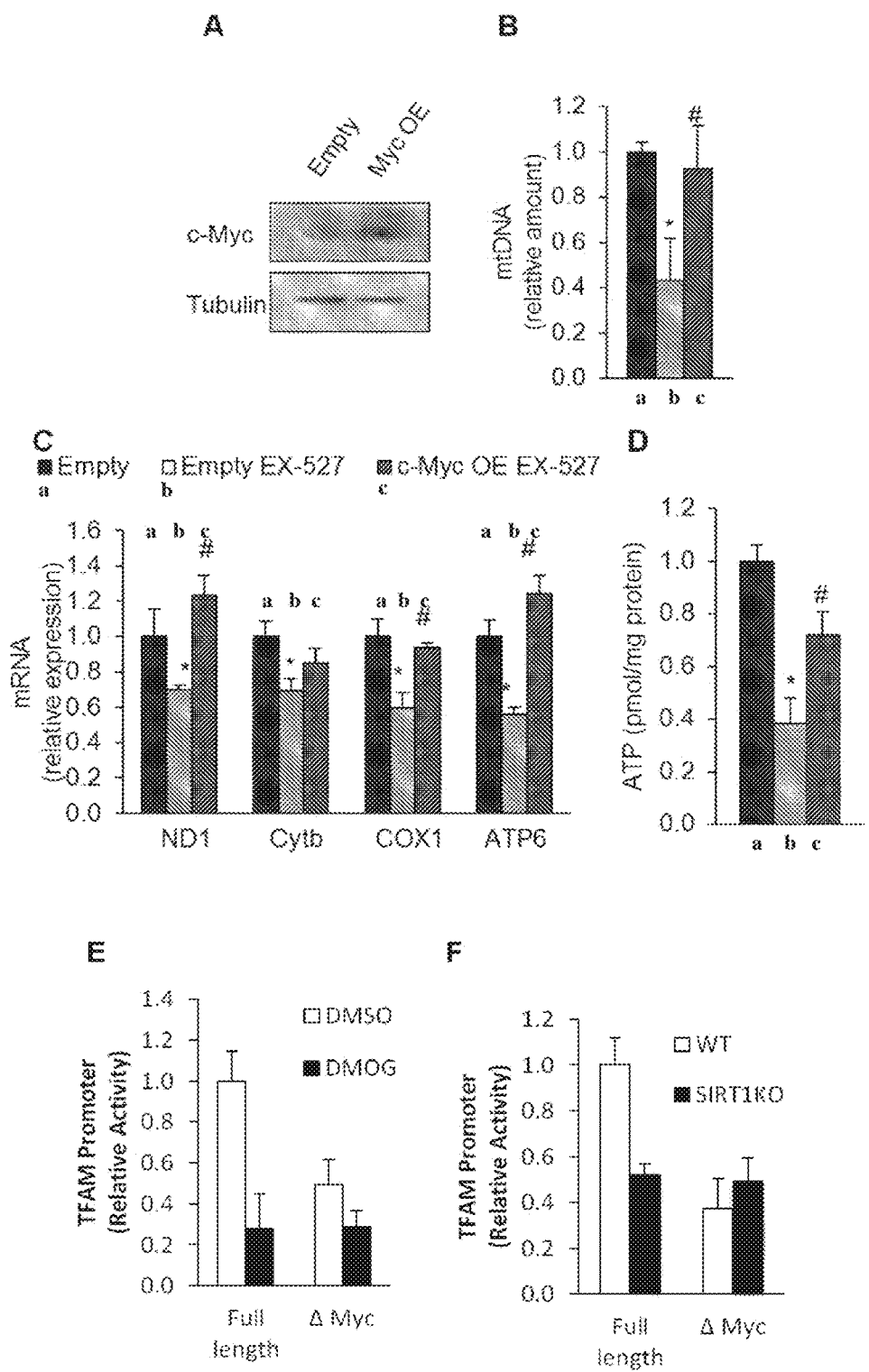
FIG. 23A-F

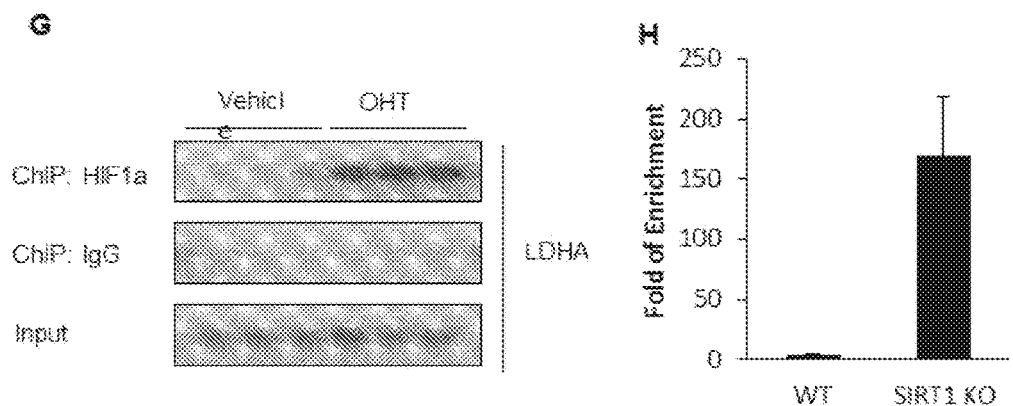
FIG. 23G-H
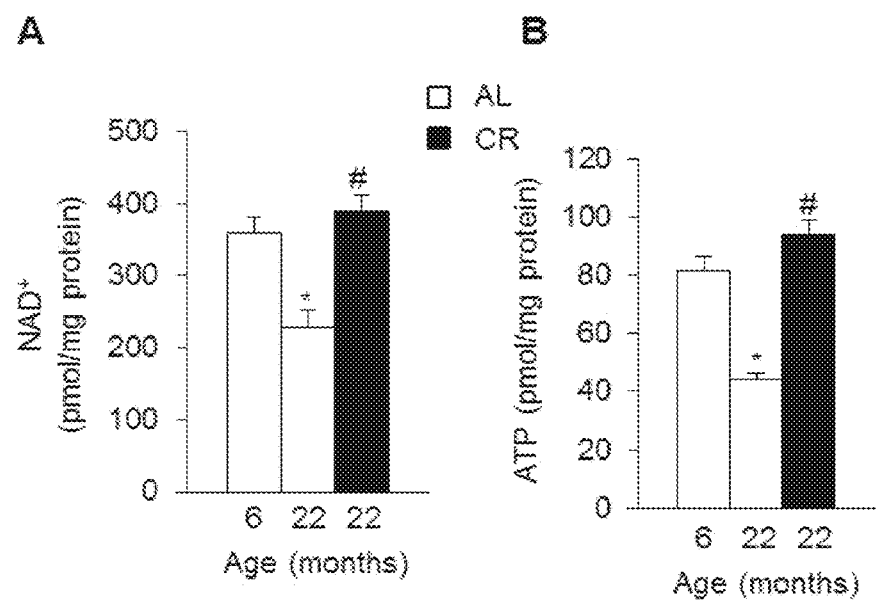
FIG. 24A-B

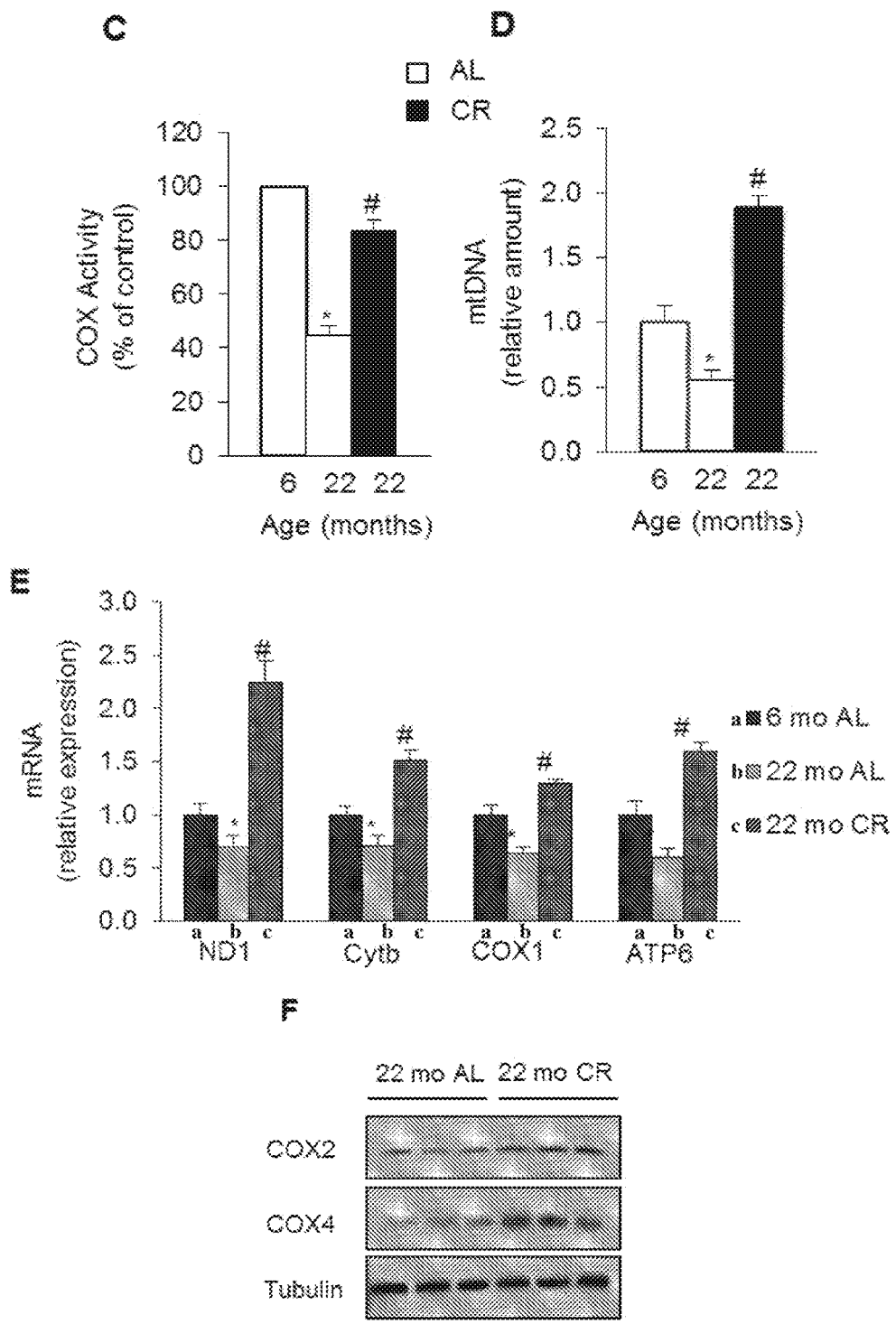
FIG. 24C-F

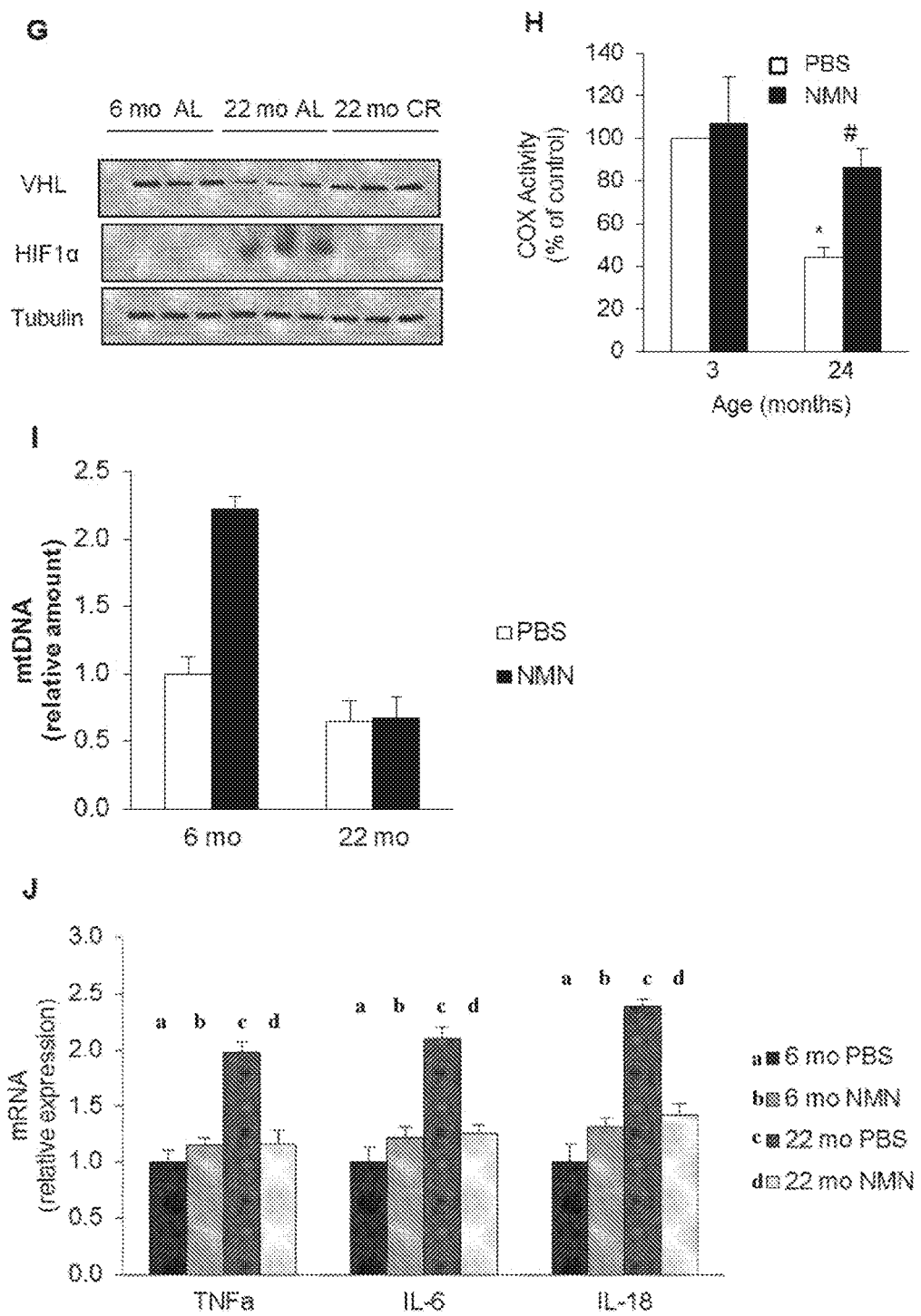
FIG. 24G-J

A
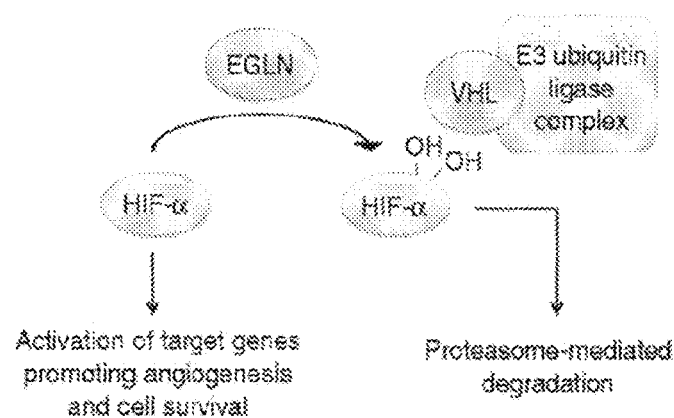
B
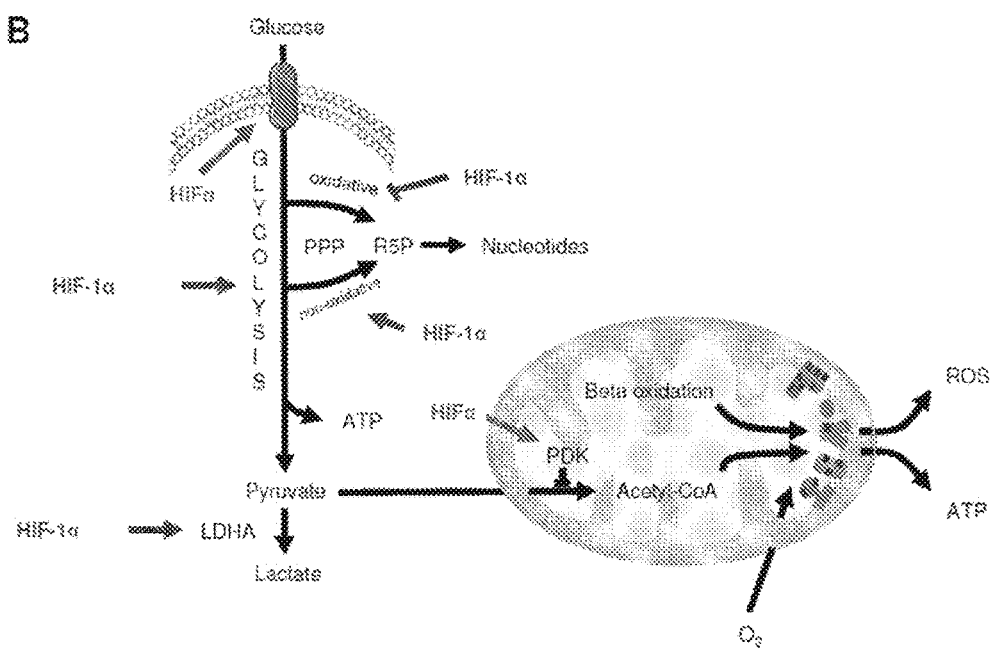
FIG. 26A-B

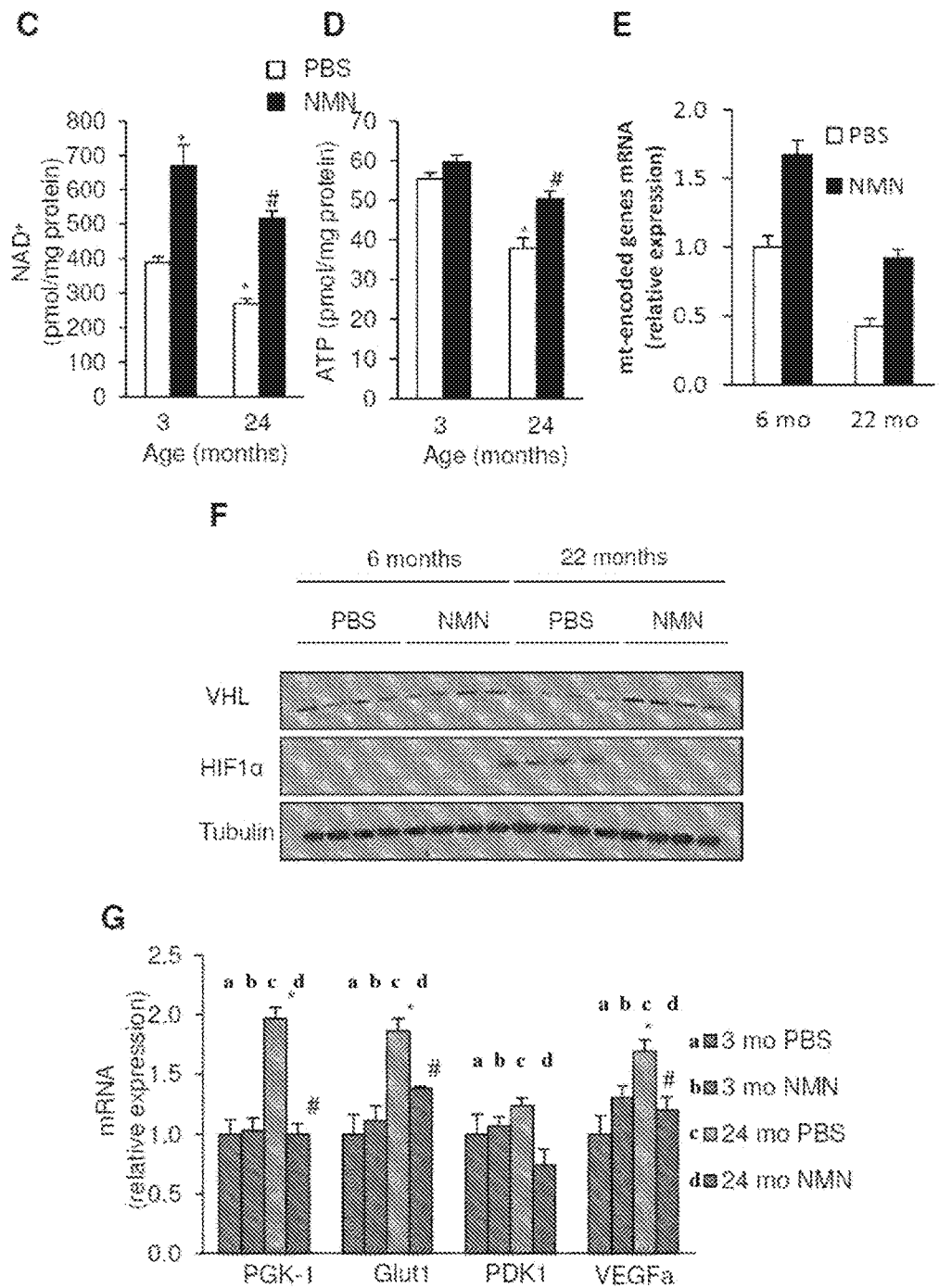
FIG. 26C-G

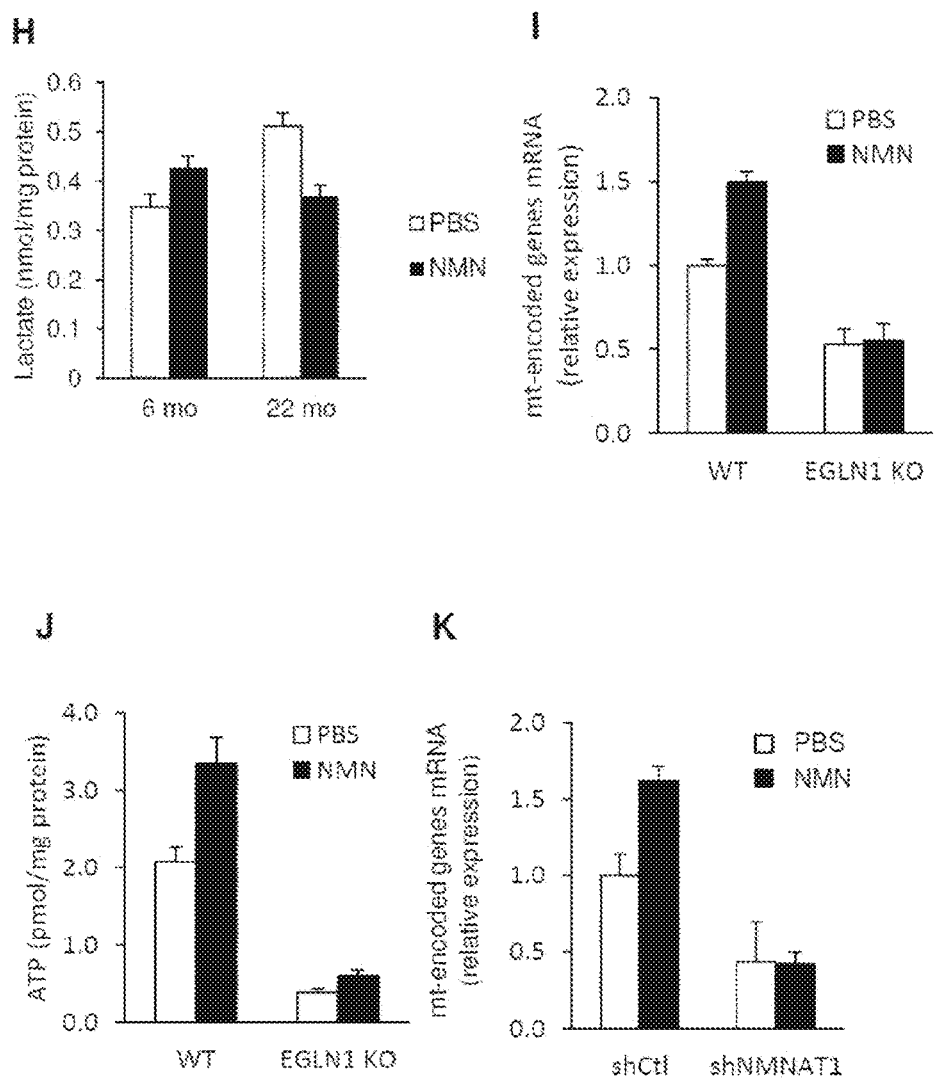
FIG. 26H-K

A
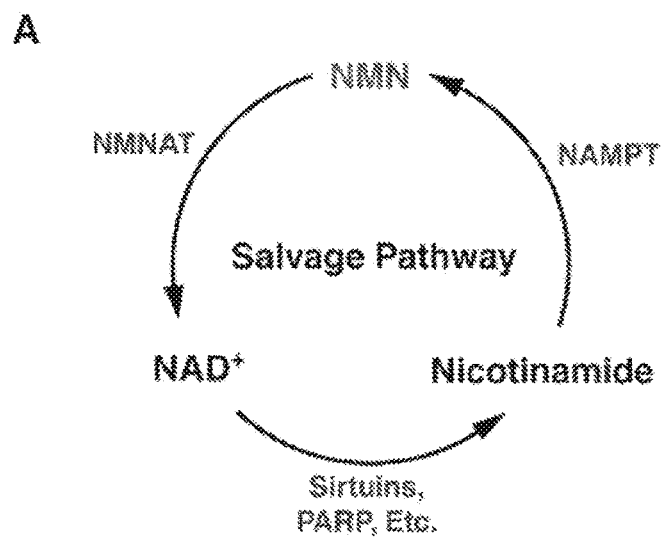
B
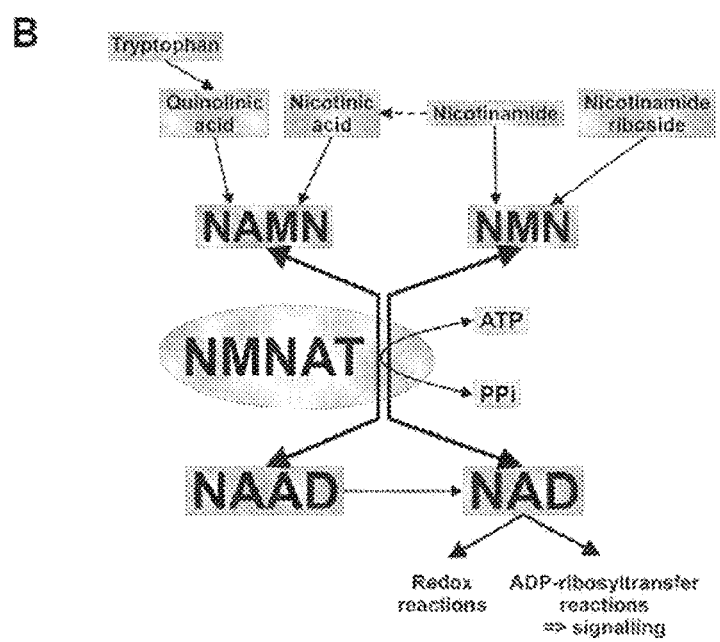
FIG. 27A-B

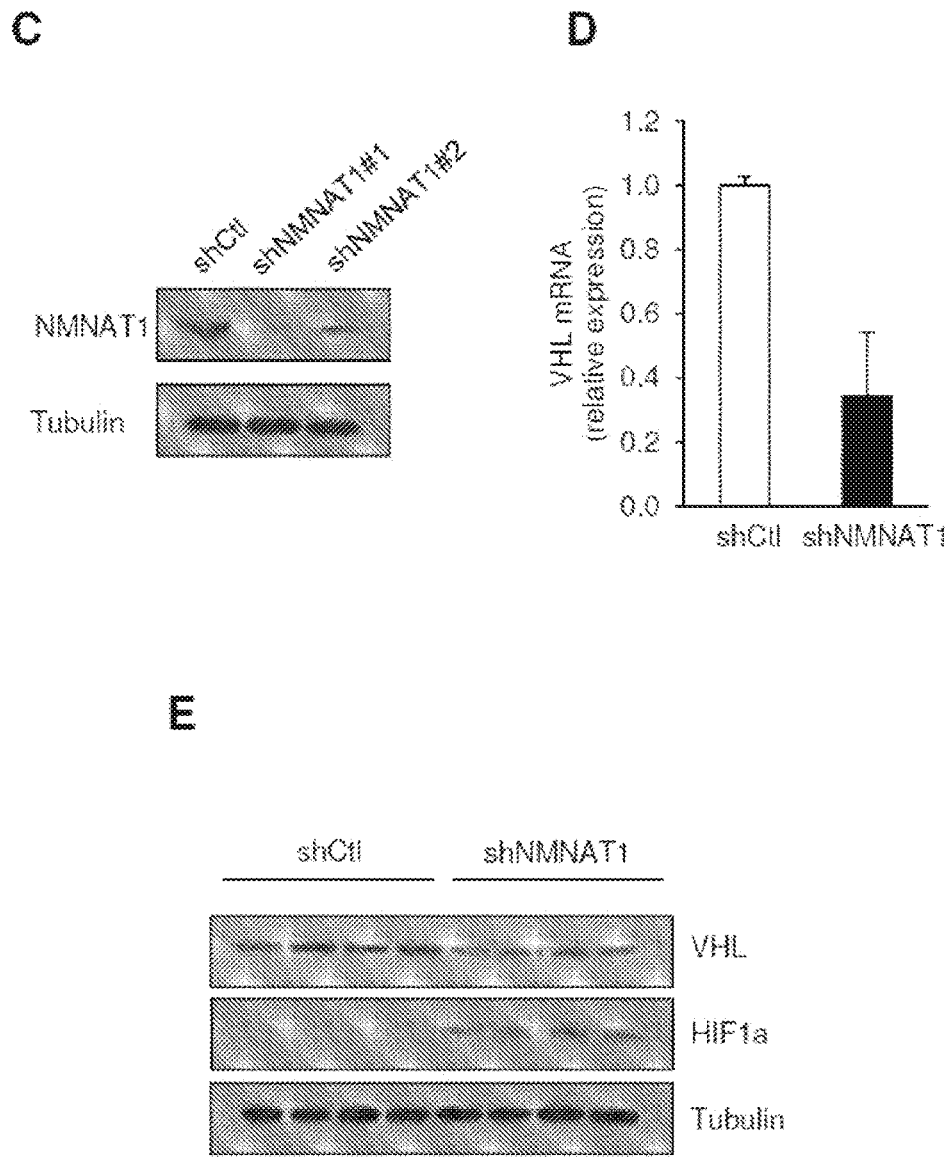
FIG. 27C-E

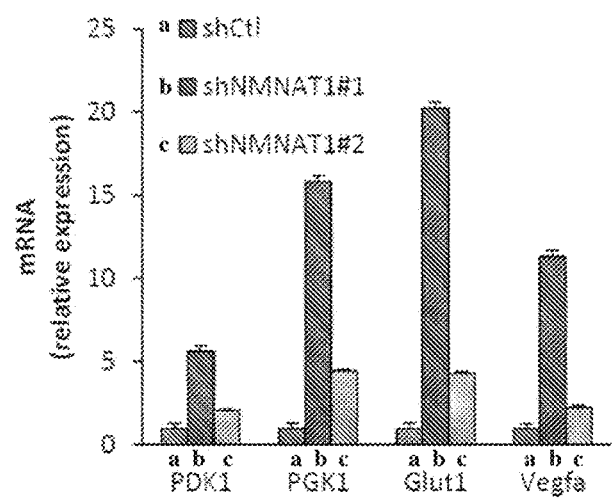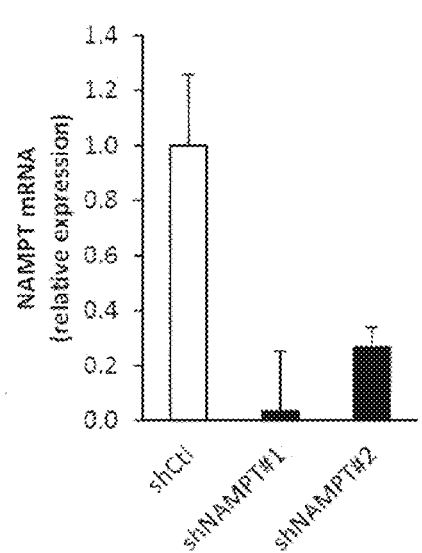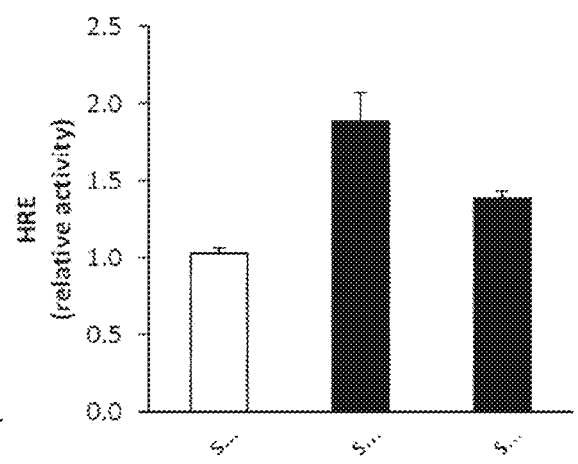
FIG. 27F-H

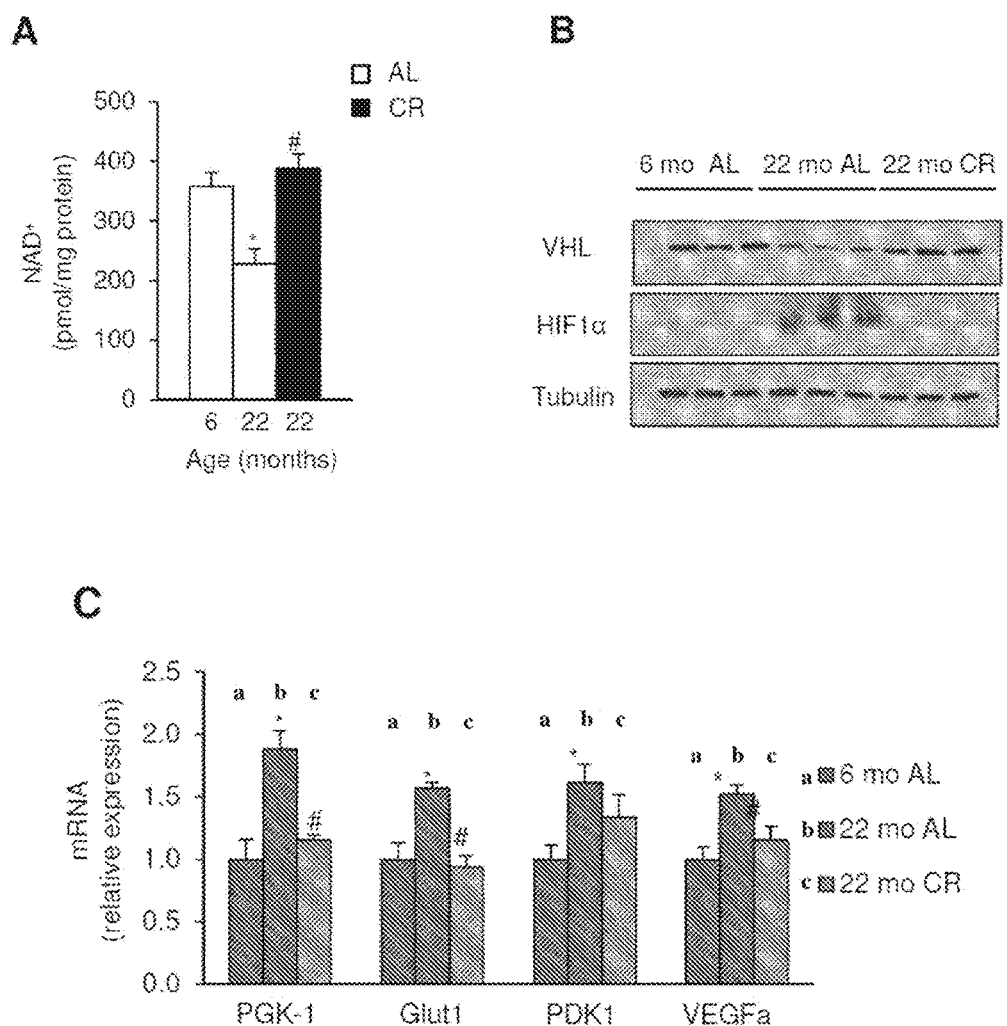
FIG. 28A-C

SEQUENCE LISTING

```
<160> NUMBER OF SEQ ID NOS: 114

<210> SEQ ID NO 1
<211> LENGTH: 826
<212> TYPE: PRT
<213> ORGANISM: Homo sapiens

<400> SEQUENCE: 1

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205
```

```
Gln Cys Gly Tyr Lys Lys Pro Pro Met Thr Cys Leu Val Leu Ile Cys
        210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
                260                 265                 270

Arg Ser Ile Tyr Glu Tyr Tyr His Ala Leu Asp Ser Asp His Leu Thr
            275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
                340                 345                 350

Ser Leu Gln Gln Thr Glu Cys Val Leu Lys Pro Val Glu Ser Ser Asp
            355                 360                 365

Met Lys Met Thr Gln Leu Phe Thr Lys Val Glu Ser Glu Asp Thr Ser
    370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
    435                 440                 445

Ala Met Ser Pro Leu Pro Thr Ala Glu Thr Pro Lys Pro Leu Arg Ser
450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
    515                 520                 525

Asn Glu Phe Lys Leu Glu Leu Val Glu Lys Leu Phe Ala Glu Asp Thr
530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590

Ala Ser Pro Gln Ser Thr Val Thr Val Phe Gln Gln Thr Gln Ile Gln
    595                 600                 605

Glu Pro Thr Ala Asn Ala Thr Thr Thr Thr Ala Thr Thr Asp Glu Leu
    610                 615                 620
```

```
Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
            645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
            690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
                740                 745                 750

Lys Arg Val Lys Gly Cys Lys Ser Ser Glu Gln Asn Gly Met Glu Gln
                755                 760                 765

Lys Thr Ile Ile Leu Ile Pro Ser Asp Leu Ala Cys Arg Leu Leu Gly
770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
                820                 825

<210> SEQ ID NO 2
<211> LENGTH: 826
<212> TYPE: PRT
<213> ORGANISM: Pan troglodytes

<400> SEQUENCE: 2

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
                20                  25                  30

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
        50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175
```

```
Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
                260                 265                 270

Arg Ser Ile Tyr Glu Tyr Tyr His Ala Leu Asp Ser Asp His Leu Thr
            275                 280                 285

Lys Thr His His Asp Met Phe Thr Lys Gly Gln Val Thr Thr Gly Gln
        290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
                340                 345                 350

Ser Leu Gln Gln Thr Glu Cys Val Leu Lys Pro Val Glu Ser Ser Asp
            355                 360                 365

Met Lys Met Thr Gln Leu Phe Thr Lys Val Glu Ser Glu Asp Thr Ser
        370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
                420                 425                 430

Asp Val Met Leu Pro Ser Pro Asn Glu Lys Leu Gln Asn Ile Asn Leu
            435                 440                 445

Ala Met Ser Pro Leu Pro Thr Ala Glu Thr Pro Lys Pro Leu Arg Ser
        450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
                530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590
```

Ala Ser Pro Gln Ser Thr Val Thr Val Phe Gln Gln Thr Gln Ile Gln
            595                 600                 605

Glu Pro Thr Ala Asn Ala Thr Thr Thr Ala Thr Thr Asp Glu Leu
    610                 615                 620

Lys Thr Val Thr Lys Asp Cys Met Glu Asp Ile Lys Ile Leu Ile Ala
625                 630                 635                 640

Ser Pro Ser Pro Thr His Ile His Lys Glu Thr Thr Ser Ala Thr Ser
            645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
    690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
            725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
            755                 760                 765

Lys Thr Ile Ile Leu Ile Pro Ser Asp Leu Ala Cys Arg Leu Leu Gly
            770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
            805                 810                 815

Glu Leu Leu Arg Ala Leu Asp Gln Val Asn
            820                 825

<210> SEQ ID NO 3
<211> LENGTH: 826
<212> TYPE: PRT
<213> ORGANISM: Macaca mulatta

<400> SEQUENCE: 3

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Glu Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

-continued

```
Arg Glu Met Leu Thr His Arg Asn Gly Pro Val Lys Lys Gly Lys Glu
145                 150                 155                 160

Gln Asn Thr Gln Arg Ser Phe Phe Leu Arg Met Lys Cys Thr Leu Thr
            165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
            195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
            245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
    275                 280                 285

Lys Thr His His Asp Met Phe Thr Lys Gly Gln Val Thr Thr Gly Gln
290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
            325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
        355                 360                 365

Met Lys Met Thr Gln Leu Phe Thr Lys Val Glu Ser Glu Asp Thr Ser
    370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
            405                 410                 415

Asp Thr Glu Thr Asp Asp Gln Gln Leu Glu Glu Val Pro Leu Tyr Asn
            420                 425                 430

Asp Val Met Leu Pro Ser Ser Asn Glu Lys Leu Gln Asn Ile Asn Leu
            435                 440                 445

Ala Met Ser Pro Leu Pro Thr Ser Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
            485                 490                 495

Gln Pro Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
            515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560
```

Met Leu Ala Pro Tyr Ile Pro Met Asp Asp Phe Gln Leu Arg Ser
                565                 570                 575

Phe Asp Gln Leu Ser Pro Leu Glu Ser Ser Ala Ser Pro Glu Ser
            580                 585                 590

Ala Ser Pro Gln Ser Thr Val Thr Val Phe Gln Gln Thr Gln Ile Gln
        595                 600                 605

Glu Pro Thr Ala Asn Ala Thr Thr Thr Ala Thr Thr Asp Glu Leu
    610                 615                 620

Lys Thr Val Thr Lys Asp Arg Met Glu Asp Ile Lys Ile Leu Ile Ala
625                 630                 635                 640

Ser Pro Ser Ser Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
        675                 680                 685

Asn Val Leu Ser Val Thr Leu Ser Gln Arg Thr Thr Val Pro Glu Glu
    690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
        755                 760                 765

Lys Thr Ile Ile Leu Ile Pro Ser Asp Leu Ala Cys Arg Leu Leu Gly
    770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 4
<211> LENGTH: 823
<212> TYPE: PRT
<213> ORGANISM: Canis lupus familiaris

<400> SEQUENCE: 4

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
                20                  25                  30

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Glu Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

```
Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
                180                 185                 190

His Cys Thr Gly His Ile His Val Tyr Asp Thr Asn Ser Asn Gln Ser
                195                 200                 205

Gln Cys Gly Tyr Lys Lys Pro Met Thr Cys Leu Val Leu Ile Cys
210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
                260                 265                 270

Arg Ser Ile Tyr Glu Tyr Tyr His Ala Leu Asp Ser Asp His Leu Thr
                275                 280                 285

Lys Thr His His Asp Met Phe Thr Lys Gly Gln Val Thr Thr Gly Gln
                290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
                340                 345                 350

Ser Leu Gln Gln Thr Glu Cys Val Leu Lys Pro Val Glu Ser Ser Asp
                355                 360                 365

Met Lys Met Thr Gln Leu Phe Thr Lys Val Glu Ser Glu Asp Thr Ser
370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
                420                 425                 430

Asp Val Met Leu Pro Ser Ser Asn Glu Lys Leu Gln Asn Ile Asn Leu
                435                 440                 445

Ala Met Ser Pro Leu Pro Ala Ser Glu Thr Pro Lys Pro Leu Arg Ser
450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Pro Ala Ser Pro Ser Asp Gly Ser Thr Arg Gln Ser Ser Pro Glu
                500                 505                 510

Pro Asn Ser Pro Ser Glu Tyr Cys Phe Asp Val Asp Ser Asp Met Val
                515                 520                 525
```

```
Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Phe Gln Leu Arg Ser
                565                 570                 575

Phe Asp Gln Leu Ser Pro Leu Glu Ser Asn Ser Thr Ser Pro Gln Ser
            580                 585                 590

Ala Ser Thr Ile Thr Val Phe Gln Pro Thr Pro Met Gln Glu Pro Pro
        595                 600                 605

Leu Thr Thr Thr Ser Thr Thr Ala Thr Thr Asp Glu Leu Lys Thr Val
    610                 615                 620

Thr Lys Asp Gly Ile Glu Asp Ile Lys Ile Leu Ile Ala Ala Pro Ser
625                 630                 635                 640

Pro Thr His Val Pro Lys Val Thr Thr Ser Ala Thr Thr Ser Pro Tyr
                645                 650                 655

Ser Asp Thr Gly Ser Arg Thr Ala Ser Pro Asn Arg Ala Gly Lys Gly
            660                 665                 670

Val Ile Glu Gln Thr Glu Lys Ser His Pro Arg Ser Pro Asn Val Leu
        675                 680                 685

Ser Val Thr Leu Ser Gln Arg Thr Thr Ile Pro Glu Glu Glu Leu Asn
    690                 695                 700

Pro Lys Ile Leu Ala Leu Gln Asn Ala Gln Arg Lys Arg Lys Ile Glu
705                 710                 715                 720

His Asp Gly Ser Leu Phe Gln Ala Val Gly Ile Gly Thr Leu Leu Gln
                725                 730                 735

Gln Pro Asp Asp Arg Ala Thr Thr Thr Ser Leu Ser Trp Lys Arg Val
            740                 745                 750

Lys Gly Cys Lys Ser Ser Glu Gln Asn Gly Met Glu Gln Lys Thr Ile
        755                 760                 765

Ile Leu Ile Pro Ser Asp Leu Ala Cys Arg Leu Leu Gly Gln Ser Met
    770                 775                 780

Asp Glu Ser Gly Leu Pro Gln Leu Thr Ser Tyr Asp Cys Glu Val Asn
785                 790                 795                 800

Ala Pro Ile Gln Gly Ser Arg Asn Leu Leu Gln Gly Glu Glu Leu Leu
                805                 810                 815

Arg Ala Leu Asp Gln Val Asn
            820

<210> SEQ ID NO 5
<211> LENGTH: 823
<212> TYPE: PRT
<213> ORGANISM: Bos Taurus

<400> SEQUENCE: 5

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80
```

```
Glu Asp Glu Met Lys Ala Gln Met Asn Cys Phe Tyr Leu Lys Ala Leu
                85                  90                  95
Asp Gly Phe Val Met Val Leu Thr Asp Asp Gly Asp Met Ile Tyr Ile
            100                 105                 110
Ser Asp Asn Val Asn Lys Tyr Met Gly Leu Thr Gln Phe Glu Leu Thr
        115                 120                 125
Gly His Ser Val Phe Asp Phe Thr His Pro Cys Asp His Glu Glu Met
    130                 135                 140
Arg Glu Met Leu Thr His Arg Asn Gly Leu Val Lys Lys Gly Lys Glu
145                 150                 155                 160
Gln Asn Thr Gln Arg Ser Phe Phe Leu Arg Met Lys Cys Thr Leu Thr
                165                 170                 175
Ser Arg Gly Arg Thr Met Asn Ile Lys Ser Ala Thr Trp Lys Val Leu
            180                 185                 190
His Cys Thr Gly His Ile His Val Tyr Asp Thr Asn Ser Asn Gln Ser
        195                 200                 205
Gln Cys Gly Tyr Lys Lys Pro Pro Met Thr Cys Leu Val Leu Ile Cys
    210                 215                 220
Glu Pro Ile Pro His Pro Ser Asn Ile Glu Ile Pro Leu Asp Ser Lys
225                 230                 235                 240
Thr Phe Leu Ser Arg His Ser Leu Asp Met Lys Phe Ser Tyr Cys Asp
                245                 250                 255
Glu Arg Ile Thr Glu Leu Met Gly Tyr Glu Pro Glu Glu Leu Leu Gly
            260                 265                 270
Arg Ser Ile Tyr Glu Tyr Tyr His Ala Leu Asp Ser Asp His Leu Thr
        275                 280                 285
Lys Thr His His Asp Met Phe Thr Lys Gly Gln Val Thr Thr Gly Gln
    290                 295                 300
Tyr Arg Met Leu Ala Lys Arg Gly Gly Tyr Val Trp Ile Glu Thr Gln
305                 310                 315                 320
Ala Thr Val Ile Tyr Asn Thr Lys Asn Ser Gln Pro Gln Cys Ile Val
                325                 330                 335
Cys Val Asn Tyr Val Val Ser Gly Ile Ile Gln His Asp Leu Ile Phe
            340                 345                 350
Ser Leu Gln Gln Thr Glu Cys Val Leu Lys Pro Val Glu Ser Ser Asp
        355                 360                 365
Met Lys Met Thr Gln Leu Phe Thr Lys Val Glu Ser Glu Asp Thr Ser
    370                 375                 380
Ser Leu Phe Asp Lys Leu Lys Lys Glu Pro Asp Ala Leu Thr Leu Leu
385                 390                 395                 400
Ala Pro Ala Ala Gly Asp Thr Ile Ile Ser Leu Asp Phe Gly Ser Asn
                405                 410                 415
Asp Thr Glu Thr Asp Asp Gln Gln Leu Glu Glu Val Pro Leu Tyr Asn
            420                 425                 430
Asp Val Met Leu Pro Ser Ser Asn Glu Lys Leu Gln Asn Ile Asn Leu
        435                 440                 445
Ala Met Ser Pro Leu Pro Ala Ser Glu Thr Pro Lys Pro Leu Arg Ser
    450                 455                 460
Ser Ala Asp Pro Ala Leu Asn Gln Glu Val Ala Leu Lys Leu Glu Pro
465                 470                 475                 480
Asn Pro Glu Ser Leu Glu Leu Ser Phe Thr Met Pro Gln Ile Gln Asp
                485                 490                 495
```

Gln Pro Ala Ser Pro Ser Asp Gly Ser Thr Arg Gln Ser Ser Pro Glu
            500                 505                 510

Pro Asn Ser Pro Ser Glu Tyr Cys Phe Asp Val Asp Ser Asp Met Val
            515                 520                 525

Asn Glu Phe Lys Leu Glu Leu Val Glu Lys Leu Phe Ala Glu Asp Thr
            530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
            565                 570                 575

Phe Asp Gln Leu Ser Pro Leu Glu Asn Ser Ser Thr Ser Pro Gln Ser
            580                 585                 590

Ala Ser Thr Asn Thr Val Phe Gln Pro Thr Gln Met Gln Glu Pro Pro
            595                 600                 605

Ile Ala Thr Val Thr Thr Thr Ala Thr Ser Asp Glu Leu Lys Thr Val
            610                 615                 620

Thr Lys Asp Gly Met Glu Asp Ile Lys Ile Leu Ile Ala Phe Pro Ser
625                 630                 635                 640

Pro Pro His Val Pro Lys Glu Pro Pro Cys Ala Thr Thr Ser Pro Tyr
            645                 650                 655

Ser Asp Thr Gly Ser Arg Thr Ala Ser Pro Asn Arg Ala Gly Lys Gly
            660                 665                 670

Val Ile Glu Gln Thr Glu Lys Ser His Pro Arg Ser Pro Asn Val Leu
            675                 680                 685

Ser Val Ala Leu Ser Gln Arg Thr Thr Ala Pro Glu Glu Glu Leu Asn
            690                 695                 700

Pro Lys Ile Leu Ala Leu Gln Asn Ala Gln Arg Lys Arg Lys Ile Glu
705                 710                 715                 720

His Asp Gly Ser Leu Phe Gln Ala Val Gly Ile Gly Thr Leu Leu Gln
            725                 730                 735

Gln Pro Asp Arg Ala Thr Thr Thr Ser Leu Ser Trp Lys Arg Val
            740                 745                 750

Lys Gly Cys Lys Ser Ser Glu Gln Asn Gly Met Glu Gln Lys Thr Ile
            755                 760                 765

Ile Leu Ile Pro Ser Asp Leu Ala Cys Arg Leu Leu Gly Gln Ser Met
            770                 775                 780

Asp Glu Ser Gly Leu Pro Gln Leu Thr Ser Tyr Asp Cys Glu Val Asn
785                 790                 795                 800

Ala Pro Ile Gln Gly Ser Arg Asn Leu Leu Gln Gly Glu Glu Leu Leu
            805                 810                 815

Arg Ala Leu Asp Gln Val Asn
            820

<210> SEQ ID NO 6
<211> LENGTH: 836
<212> TYPE: PRT
<213> ORGANISM: Mus musculus

<400> SEQUENCE: 6

Met Glu Gly Ala Gly Gly Glu Asn Glu Lys Lys Met Ser Ser Glu
1               5                   10                  15

Arg Arg Lys Glu Lys Ser Arg Asp Ala Ala Arg Ser Arg Arg Ser Lys
                20                  25                  30

Glu Ser Glu Val Phe Tyr Glu Leu Ala His Gln Leu Pro Leu Pro His
            35                  40                  45

-continued

```
Asn Val Ser Ser His Leu Asp Lys Ala Ser Val Met Arg Leu Thr Ile
         50                  55                  60

Ser Tyr Leu Arg Val Arg Lys Leu Leu Asp Ala Gly Gly Leu Asp Ser
 65                  70                  75                  80

Glu Asp Glu Met Lys Ala Gln Met Asp Cys Phe Tyr Leu Lys Ala Leu
                 85                  90                  95

Asp Gly Phe Val Met Val Leu Thr Asp Asp Gly Asp Met Val Tyr Ile
                100                 105                 110

Ser Asp Asn Val Asn Lys Tyr Met Gly Leu Thr Gln Phe Glu Leu Thr
            115                 120                 125

Gly His Ser Val Phe Asp Phe Thr His Pro Cys Asp His Glu Glu Met
130                 135                 140

Arg Glu Met Leu Thr His Arg Asn Gly Pro Val Arg Lys Gly Lys Glu
145                 150                 155                 160

Leu Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
            195                 200                 205

Gln Cys Gly Tyr Lys Lys Pro Pro Met Thr Cys Leu Val Leu Ile Cys
210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
            275                 280                 285

Lys Thr His His Asp Met Phe Thr Lys Gly Gln Val Thr Thr Gly Gln
290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Ser Val Leu Lys Pro Val Glu Ser Ser Asp
            355                 360                 365

Met Lys Met Thr Gln Leu Phe Thr Lys Val Glu Ser Glu Asp Thr Ser
370                 375                 380

Cys Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asp
                405                 410                 415

Asp Thr Glu Thr Glu Asp Gln Gln Leu Glu Asp Val Pro Leu Tyr Asn
            420                 425                 430

Asp Val Met Phe Pro Ser Ser Asn Glu Lys Leu Asn Ile Asn Leu Ala
            435                 440                 445

Met Ser Pro Leu Pro Ser Ser Glu Thr Pro Lys Pro Leu Arg Ser Ser
450                 455                 460
```

-continued

```
Ala Asp Pro Ala Leu Asn Gln Glu Val Ala Leu Lys Leu Glu Ser Ser
465                 470                 475                 480

Pro Glu Ser Leu Gly Leu Ser Phe Thr Met Pro Gln Ile Gln Asp Gln
            485                 490                 495

Pro Ala Ser Pro Ser Asp Gly Ser Thr Arg Gln Ser Ser Pro Glu Arg
        500                 505                 510

Leu Leu Gln Glu Asn Val Asn Thr Pro Asn Phe Ser Gln Pro Asn Ser
    515                 520                 525

Pro Ser Glu Tyr Cys Phe Asp Val Asp Ser Asp Met Val Asn Val Phe
530                 535                 540

Lys Leu Glu Leu Val Glu Lys Leu Phe Ala Glu Asp Thr Glu Ala Lys
545                 550                 555                 560

Asn Pro Phe Ser Thr Gln Asp Thr Asp Leu Asp Leu Glu Met Leu Ala
                565                 570                 575

Pro Tyr Ile Pro Met Asp Asp Asp Phe Gln Leu Arg Ser Phe Asp Gln
            580                 585                 590

Leu Ser Pro Leu Glu Ser Asn Ser Pro Ser Pro Ser Met Ser Thr
        595                 600                 605

Val Thr Gly Phe Gln Gln Thr Gln Leu Gln Lys Pro Thr Ile Thr Ala
    610                 615                 620

Thr Ala Thr Thr Thr Ala Thr Thr Asp Glu Ser Lys Thr Glu Thr Lys
625                 630                 635                 640

Asp Asn Lys Glu Asp Ile Lys Ile Leu Ile Ala Ser Pro Ser Ser Thr
                645                 650                 655

Gln Val Pro Gln Glu Thr Thr Thr Ala Lys Ala Ser Ala Tyr Ser Gly
            660                 665                 670

Thr His Ser Arg Thr Ala Ser Pro Asp Arg Ala Gly Lys Arg Val Ile
        675                 680                 685

Glu Gln Thr Asp Lys Ala His Pro Arg Ser Leu Asn Leu Ser Ala Thr
    690                 695                 700

Leu Asn Gln Arg Asn Thr Val Pro Glu Glu Leu Asn Pro Lys Thr
705                 710                 715                 720

Ile Ala Ser Gln Asn Ala Gln Arg Lys Arg Lys Met Glu His Asp Gly
                725                 730                 735

Ser Leu Phe Gln Ala Ala Gly Ile Gly Thr Leu Leu Gln Gln Pro Gly
            740                 745                 750

Asp Cys Ala Pro Thr Met Ser Leu Ser Trp Lys Arg Val Lys Gly Phe
        755                 760                 765

Ile Ser Ser Glu Gln Asn Gly Thr Glu Gln Lys Thr Ile Ile Leu Ile
    770                 775                 780

Pro Ser Asp Leu Ala Cys Arg Leu Leu Gly Gln Ser Met Asp Glu Ser
785                 790                 795                 800

Gly Leu Pro Gln Leu Thr Ser Tyr Asp Cys Glu Val Asn Ala Pro Ile
                805                 810                 815

Gln Gly Ser Arg Asn Leu Leu Gln Gly Glu Glu Leu Leu Arg Ala Leu
            820                 825                 830

Asp Gln Val Asn
        835

<210> SEQ ID NO 7
<211> LENGTH: 823
<212> TYPE: PRT
<213> ORGANISM: Rattus norvegicus

<400> SEQUENCE: 7
```

-continued

```
Met Glu Gly Ala Gly Gly Asn Glu Lys Lys Asn Arg Met Ser Ser
1               5                   10                  15

Glu Arg Arg Lys Glu Lys Ser Arg Asp Ala Ala Arg Ser Arg Arg
                20                  25                  30

Ser Lys Glu Ser Glu Val Phe Tyr Glu Leu Ala His Gln Leu Pro Leu Pro
            35                  40                  45

His Asn Val Ser Ser His Leu Asp Lys Ala Ser Val Met Arg Leu Thr
        50                  55                  60

Ile Ser Tyr Leu Arg Val Arg Lys Leu Leu Gly Ala Gly Asp Leu Asp
65                  70                  75                  80

Ile Glu Asp Glu Met Lys Ala Gln Met Asn Cys Phe Tyr Leu Lys Ala
                85                  90                  95

Leu Asp Gly Phe Val Met Val Leu Thr Asp Asp Gly Asp Met Ile Tyr
                100                 105                 110

Ile Ser Asp Asn Val Asn Lys Tyr Met Gly Leu Thr Gln Phe Glu Leu
            115                 120                 125

Thr Gly His Ser Val Phe Asp Phe Thr His Pro Cys Asp His Glu Glu
    130                 135                 140

Met Arg Glu Met Leu Thr His Arg Asn Gly Pro Val Arg Lys Gly Lys
145                 150                 155                 160

Glu Gln Asn Thr Gln Arg Ser Phe Phe Leu Arg Met Lys Cys Thr Leu
                165                 170                 175

Thr Ser Arg Gly Arg Thr Met Asn Ile Lys Ser Ala Thr Trp Lys Val
            180                 185                 190

Leu His Cys Thr Gly His Ile His Val Tyr Asp Thr Ser Ser Asn Gln
        195                 200                 205

Pro Gln Cys Gly Tyr Lys Lys Pro Pro Met Thr Cys Leu Val Leu Ile
    210                 215                 220

Cys Glu Pro Ile Pro His Pro Ser Asn Ile Glu Ile Pro Leu Asp Ser
225                 230                 235                 240

Lys Thr Phe Leu Ser Arg His Ser Leu Asp Met Lys Phe Ser Tyr Cys
                245                 250                 255

Asp Glu Arg Ile Thr Glu Leu Met Gly Tyr Glu Pro Glu Glu Leu Leu
            260                 265                 270

Gly Arg Ser Ile Tyr Glu Tyr Tyr His Ala Leu Asp Ser Asp His Leu
        275                 280                 285

Thr Lys Thr His His Asp Met Phe Thr Lys Gly Gln Val Thr Thr Gly
    290                 295                 300

Gln Tyr Arg Met Leu Ala Lys Arg Gly Gly Tyr Val Trp Val Glu Thr
305                 310                 315                 320

Gln Ala Thr Val Ile Tyr Asn Thr Lys Asn Ser Gln Pro Gln Cys Ile
                325                 330                 335

Val Cys Val Asn Tyr Val Val Ser Gly Ile Ile Gln His Asp Leu Ile
            340                 345                 350

Phe Ser Leu Gln Gln Thr Glu Ser Val Leu Lys Pro Val Glu Ser Ser
        355                 360                 365

Asp Met Lys Met Thr Gln Leu Phe Thr Lys Val Glu Ser Glu Asp Thr
    370                 375                 380

Ser Cys Leu Phe Asp Lys Leu Lys Lys Glu Pro Asp Ala Leu Thr Leu
385                 390                 395                 400

Leu Ala Pro Ala Ala Gly Asp Thr Ile Ile Ser Leu Asp Phe Gly Ser
                405                 410                 415
```

```
Asp Asp Thr Glu Thr Glu Asp Gln Gln Leu Glu Asp Val Pro Leu Tyr
            420                 425                 430

Asn Asp Val Met Phe Pro Ser Ser Asn Glu Lys Leu Asn Ile Asn Leu
            435                 440                 445

Ala Met Ser Pro Leu Pro Ala Ser Glu Thr Pro Lys Pro Leu Arg Ser
        450                 455                 460

Ser Ala Asp Pro Ala Leu Asn Gln Glu Val Ala Leu Lys Leu Glu Ser
465                 470                 475                 480

Ser Pro Glu Ser Leu Gly Leu Ser Phe Thr Met Pro Gln Ile Gln Asp
                485                 490                 495

Gln Pro Ala Ser Pro Ser Asp Gly Ser Thr Arg Gln Ser Ser Pro Glu
            500                 505                 510

Pro Asn Ser Pro Ser Glu Tyr Cys Phe Asp Val Asp Ser Asp Met Val
        515                 520                 525

Asn Val Phe Lys Leu Glu Leu Val Glu Lys Leu Phe Ala Glu Asp Thr
530                 535                 540

Glu Ala Lys Asn Pro Phe Ser Ala Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Asn Ser Pro Ser Pro Pro Ser
            580                 585                 590

Val Ser Thr Val Thr Gly Phe Gln Gln Thr Gln Leu Gln Lys Pro Thr
        595                 600                 605

Ile Thr Val Thr Ala Thr Ala Thr Ala Thr Thr Asp Glu Ser Lys Ala
610                 615                 620

Val Thr Lys Asp Asn Ile Glu Asp Ile Lys Ile Leu Ile Ala Ser Pro
625                 630                 635                 640

Pro Ser Thr Gln Val Pro Gln Glu Met Thr Thr Ala Lys Ala Ser Ala
                645                 650                 655

Tyr Ser Gly Thr His Ser Arg Thr Ala Ser Pro Asp Arg Ala Gly Lys
            660                 665                 670

Arg Val Ile Glu Lys Thr Asp Lys Ala His Pro Arg Ser Leu Asn Leu
        675                 680                 685

Ser Val Thr Leu Asn Gln Arg Asn Thr Val Pro Glu Glu Leu Asn
690                 695                 700

Pro Lys Thr Ile Ala Leu Gln Asn Ala Gln Arg Lys Arg Lys Met Glu
705                 710                 715                 720

His Asp Gly Ser Leu Phe Gln Ala Ala Gly Ile Gly Thr Leu Leu Gln
                725                 730                 735

Gln Pro Gly Asp Arg Ala Pro Thr Met Ser Leu Ser Trp Lys Arg Val
            740                 745                 750

Lys Gly Tyr Ile Ser Ser Glu Gln Asp Gly Met Glu Gln Lys Thr Ile
        755                 760                 765

Phe Leu Ile Pro Ser Asp Leu Ala Cys Arg Leu Leu Gly Gln Ser Met
770                 775                 780

Asp Glu Ser Gly Leu Pro Gln Leu Thr Ser Tyr Asp Cys Glu Val Asn
785                 790                 795                 800

Ala Pro Ile Gln Gly Ser Arg Asn Leu Leu Gln Gly Glu Glu Leu Leu
                805                 810                 815

Arg Ala Leu Asp Gln Val Asn
            820
```

```
<210> SEQ ID NO 8
<211> LENGTH: 811
<212> TYPE: PRT
<213> ORGANISM: Gallus gallus

<400> SEQUENCE: 8

Met Asp Ser Pro Gly Gly Val Thr Asp Lys Lys Arg Ile Ser Ser Glu
1               5                   10                  15

Arg Arg Lys Glu Lys Ser Arg Asp Ala Ala Arg Cys Arg Arg Ser Lys
            20                  25                  30

Glu Ser Glu Val Phe Tyr Glu Leu Ala His Gln Leu Pro Leu Pro His
        35                  40                  45

Thr Val Ser Ala His Leu Asp Lys Ala Ser Ile Met Arg Leu Thr Ile
    50                  55                  60

Ser Tyr Leu Arg Met Arg Lys Leu Leu Asp Ala Gly Glu Leu Glu Thr
65                  70                  75                  80

Glu Ala Asn Met Glu Lys Glu Leu Asn Cys Phe Tyr Leu Lys Ala Leu
                85                  90                  95

Asp Gly Phe Val Met Val Leu Ser Glu Asp Gly Asp Met Ile Tyr Met
            100                 105                 110

Ser Glu Asn Val Asn Lys Cys Met Gly Leu Thr Gln Phe Asp Leu Thr
        115                 120                 125

Gly His Ser Val Phe Asp Phe Thr His Pro Cys Asp His Glu Glu Leu
    130                 135                 140

Arg Glu Met Leu Thr His Arg Asn Gly Pro Val Lys Lys Gly Lys Glu
145                 150                 155                 160

Gln Asn Thr Glu Arg Ser Phe Phe Leu Arg Met Lys Cys Thr Leu Thr
                165                 170                 175

Ser Arg Gly Arg Thr Val Asn Ile Lys Ser Ala Thr Trp Lys Val Leu
            180                 185                 190

His Cys Thr Gly His Ile Arg Val Tyr Asp Thr Cys Asn Asn Gln Thr
        195                 200                 205

His Cys Gly Tyr Lys Lys Pro Pro Met Thr Cys Leu Val Leu Ile Cys
    210                 215                 220

Glu Pro Ile Pro His Pro Ser Asn Ile Glu Val Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Gln Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Leu Ser Gly Ile Val Gln Lys Asp Leu Ile Phe
            340                 345                 350

Ser Leu Gly Gln Thr Glu Cys Met Leu Lys Pro Val Glu Ser Pro Glu
        355                 360                 365

Met Lys Met Thr Lys Ile Phe Ser Lys Asp Asp Trp Asp Asp Thr Asn
    370                 375                 380
```

```
Ser Leu Phe Glu Lys Leu Lys Gln Glu Pro Asp Ala Leu Thr Val Leu
385                 390                 395                 400

Ala Pro Ala Ala Gly Asp Thr Ile Ile Ser Leu Asp Phe Ser Ser Asn
            405                 410                 415

Glu Ser Asp Glu Gln Gln Cys Asp Glu Val Pro Leu Tyr Asn Asp Val
            420                 425                 430

Met Leu Pro Ser Ser Ser Glu Lys Leu Gln Asn Ile Asn Ile Ala Met
            435                 440                 445

Ser Pro Leu Pro Ala Ser Glu Thr Thr Lys Pro Leu Arg Ser Asn Ala
450                 455                 460

Asp Pro Ala Leu Asn Arg Glu Val Val Ser Lys Leu Glu Pro Asn Thr
465                 470                 475                 480

Glu Thr Leu Glu Leu Ser Phe Thr Met Pro Gln Val Gln Glu Gln Pro
                485                 490                 495

Thr Ser Pro Ser Asp Ala Ser Thr Ser Gln Ser Ser Pro Glu Pro Ser
            500                 505                 510

Ser Pro Asn Asp Tyr Cys Phe Asp Val Asp Asn Asp Met Ala Asn Glu
            515                 520                 525

Phe Lys Leu Glu Leu Val Glu Lys Leu Phe Ala Ile Asp Thr Glu Ala
            530                 535                 540

Lys Asn Pro Phe Ser Thr Gln Glu Thr Asp Leu Asp Leu Glu Met Leu
545                 550                 555                 560

Ala Pro Tyr Ile Pro Met Asp Asp Asp Phe Gln Leu Arg Ser Phe Asp
                565                 570                 575

Gln Leu Ser Pro Leu Glu Ser Ser Ser Gly Ser Gln Asn Ala Ala
            580                 585                 590

Thr Ile Thr Ile Leu Gln Gln Thr Gln Thr Pro Ser Thr Ala Ala Asp
            595                 600                 605

Glu Ile Lys Pro Val Ala Glu Arg Val Asp Asp Val Lys Ala Leu Ile
610                 615                 620

Val Pro Ser Ser Pro Val His Val Ile Asn Asp Thr Ser Ser Ala Pro
625                 630                 635                 640

Ala Ser Pro Tyr Ser Gly Asn Arg Ser Arg Thr Ala Ser Pro Ile Arg
                645                 650                 655

Ala Gly Lys Gly Thr Leu Glu Gln Thr Glu Lys Ser Cys Pro Gly Ala
            660                 665                 670

Pro Ser Leu Ile Thr Val Thr Leu Asn Lys Arg Ser Thr Ala Met Asp
            675                 680                 685

Glu Glu Leu Asn Pro Lys Met Leu Ala Leu His Asn Ala Gln Arg Lys
            690                 695                 700

Arg Lys Met Glu His Asp Gly Ser Leu Phe Gln Ala Val Gly Ile Gly
705                 710                 715                 720

Ser Leu Phe Gln Gln Thr Gly Asp Arg Gly Gly Asn Ala Ser Leu Ala
                725                 730                 735

Trp Lys Arg Val Lys Ala Cys Lys Thr Asn Gly His Asn Gly Val Glu
            740                 745                 750

Gln Lys Thr Ile Ile Leu Leu Ser Thr Asp Ile Ala Ser Lys Leu Leu
            755                 760                 765

Gly Gln Ser Met Asp Glu Ser Gly Leu Pro Gln Leu Thr Ser Tyr Asp
            770                 775                 780

Cys Glu Val Asn Ala Pro Ile Gln Gly Asn Arg Asn Leu Leu Gln Gly
785                 790                 795                 800

Glu Glu Leu Leu Arg Ala Leu Asp Gln Val Asn
```

<210> SEQ ID NO 9
<211> LENGTH: 533
<212> TYPE: PRT
<213> ORGANISM: Danio rerio

<400> SEQUENCE: 9

```
Met Asp Thr Gly Val Val Thr Glu Lys Lys Arg Val Ser Ser Glu Arg
1               5                   10                  15

Arg Lys Gly Lys Ser Arg Asp Ala Ala Arg Ser Arg Arg Gly Lys Glu
            20                  25                  30

Ser Glu Val Phe Tyr Glu Leu Ala His Gln Leu Pro Leu Pro His Asn
        35                  40                  45

Val Thr Ser His Leu Asp Lys Ala Ser Ile Met Arg Leu Thr Ile Ser
    50                  55                  60

Tyr Leu Arg Met Arg Lys Leu Leu Asn Ser Asp Glu Lys Glu Glu Lys
65                  70                  75                  80

Glu Glu Asn Glu Leu Glu Ser Gln Leu Asn Gly Phe Tyr Leu Lys Ala
                85                  90                  95

Leu Glu Gly Phe Leu Met Val Leu Ser Glu Gly Asp Met Val Tyr
            100                 105                 110

Leu Ser Glu Asn Val Ser Lys Ser Met Gly Leu Thr Gln Phe Asp Leu
        115                 120                 125

Thr Gly His Ser Ile Phe Glu Phe Ser His Pro Cys Asp His Glu Glu
    130                 135                 140

Leu Arg Glu Met Leu Val His Arg Thr Gly Ser Lys Lys Thr Lys Glu
145                 150                 155                 160

Gln Asn Thr Glu Arg Ser Phe Phe Leu Arg Met Lys Cys Thr Leu Thr
                165                 170                 175

Ser Arg Gly Arg Thr Val Asn Ile Lys Ser Ala Thr Trp Lys Val Leu
            180                 185                 190

His Cys Ala Gly His Val Arg Val His Glu Gly Ser Glu Ala Ser Glu
        195                 200                 205

Asp Ser Gly Phe Lys Glu Pro Pro Val Thr Tyr Leu Val Leu Ile Cys
    210                 215                 220

Glu Pro Ile Pro His Pro Ser Asn Ile Glu Val Pro Leu Asp Ser Lys
225                 230                 235                 240

Thr Phe Leu Ser Arg His Thr Leu Asp Met Lys Phe Ser Tyr Cys Asp
                245                 250                 255

Glu Arg Ile Thr Glu Leu Met Gly Tyr Glu Pro Asp Asp Leu Leu Asn
            260                 265                 270

Arg Ser Val Tyr Glu Tyr Tyr His Ala Leu Asp Ser Asp His Leu Thr
        275                 280                 285

Lys Thr His His Asn Leu Phe Ala Lys Gly Gln Ala Thr Thr Gly Gln
    290                 295                 300

Tyr Arg Met Leu Ala Lys Lys Gly Gly Phe Val Trp Val Glu Thr Gln
305                 310                 315                 320

Ala Thr Val Ile Tyr Asn Pro Lys Asn Ser Gln Pro Gln Cys Ile Val
                325                 330                 335

Cys Val Asn Tyr Val Leu Ser Gly Ile Val Glu Gly Asp Val Val Leu
            340                 345                 350

Ser Leu Gln Gln Thr Val Thr Glu Pro Lys Ala Val Glu Lys Glu Ser
        355                 360                 365
```

-continued

```
Glu Glu Thr Glu Glu Lys Thr Ser Glu Leu Asp Ile Leu Lys Leu Phe
    370                 375                 380

Lys Pro Glu Ser Leu Asn Cys Ser Leu Glu Ser Ser Thr Leu Tyr Asn
385                 390                 395                 400

Lys Leu Lys Glu Glu Pro Glu Ala Leu Thr Val Leu Ala Pro Ala Ala
                405                 410                 415

Gly Asp Ala Ile Ile Ser Leu Asp Phe Asn Asn Ser Asp Ser Asp Ile
            420                 425                 430

Gln Leu Leu Lys Glu Val Pro Leu Tyr Asn Asp Val Met Leu Pro Ser
        435                 440                 445

Ser Ser Glu Lys Leu Pro Leu Ser Leu Ser Pro Leu Thr Pro Ser Asp
450                 455                 460

Ser Leu Ser Ser His Ala Thr Thr Ala Lys Ser Thr Leu Pro Cys Arg
465                 470                 475                 480

Arg Arg His Pro Gly Pro Leu His Pro Tyr Thr Cys Cys Arg Arg Cys
                485                 490                 495

Ala Val His Leu Ser Arg Ser Ser Val Ala Val Gly Met Pro His Leu
            500                 505                 510

Phe Asp Pro Ala Pro His Arg Ala Ala Val Ser Ser Thr Thr Glu Lys
        515                 520                 525

Cys Leu Gln Arg Cys
        530

<210> SEQ ID NO 10
<211> LENGTH: 721
<212> TYPE: PRT
<213> ORGANISM: Caenorhabditis elegans

<400> SEQUENCE: 10

Met Glu Asp Asn Arg Lys Arg Asn Met Glu Arg Arg Glu Thr Ser
1               5                   10                  15

Arg His Ala Ala Arg Asp Arg Arg Ser Lys Glu Ser Asp Ile Phe Asp
            20                  25                  30

Asp Leu Lys Met Cys Val Pro Ile Val Glu Glu Gly Thr Val Thr His
        35                  40                  45

Leu Asp Arg Ile Ala Leu Leu Arg Val Ala Ala Thr Ile Cys Arg Leu
    50                  55                  60

Arg Lys Thr Ala Gly Asn Val Leu Glu Asn Asn Leu Asp Asn Glu Ile
65                  70                  75                  80

Thr Asn Glu Val Trp Thr Glu Asp Thr Ile Ala Glu Cys Leu Asp Gly
                85                  90                  95

Phe Val Met Ile Val Asp Ser Asp Ser Ser Ile Leu Tyr Val Thr Glu
                100                 105                 110

Ser Val Ala Met Tyr Leu Gly Leu Thr Gln Thr Asp Leu Thr Gly Arg
            115                 120                 125

Ala Leu Arg Asp Phe Leu His Pro Ser Asp Tyr Asp Glu Phe Asp Lys
        130                 135                 140

Gln Ser Lys Met Leu His Lys Pro Arg Gly Glu Asp Thr Asp Thr Thr
145                 150                 155                 160

Gly Ile Asn Met Val Leu Arg Met Lys Thr Val Ile Ser Pro Arg Gly
                165                 170                 175

Arg Cys Leu Asn Leu Lys Ser Ala Leu Tyr Lys Ser Val Ser Phe Leu
            180                 185                 190

Val His Ser Lys Val Ser Thr Gly Gly His Val Ser Phe Met Gln Gly
        195                 200                 205
```

```
Ile Thr Ile Pro Ala Gly Gln Gly Thr Thr Asn Ala Asn Ala Ser Ala
    210                 215                 220

Met Thr Lys Tyr Thr Glu Ser Pro Met Gly Ala Phe Thr Thr Arg His
225                 230                 235                 240

Thr Cys Asp Met Arg Ile Thr Phe Val Ser Asp Lys Phe Asn Tyr Ile
                245                 250                 255

Leu Lys Ser Glu Leu Lys Thr Leu Met Gly Thr Ser Phe Tyr Glu Leu
                260                 265                 270

Val His Pro Ala Asp Met Met Ile Val Ser Lys Ser Met Lys Glu Leu
            275                 280                 285

Phe Ala Lys Gly His Ile Arg Thr Pro Tyr Tyr Arg Leu Ile Ala Ala
    290                 295                 300

Asn Asp Thr Leu Ala Trp Ile Gln Thr Glu Ala Thr Thr Ile Thr His
305                 310                 315                 320

Thr Thr Lys Gly Gln Lys Gly Gln Tyr Val Ile Cys Val His Tyr Val
                325                 330                 335

Leu Gly Ile Gln Gly Ala Glu Glu Ser Leu Val Val Cys Thr Asp Ser
                340                 345                 350

Met Pro Ala Gly Met Gln Val Asp Ile Lys Lys Glu Val Asp Asp Thr
            355                 360                 365

Arg Asp Tyr Ile Gly Arg Gln Pro Glu Ile Val Glu Cys Val Asp Phe
    370                 375                 380

Thr Pro Leu Ile Glu Pro Glu Asp Pro Phe Asp Thr Val Ile Glu Pro
385                 390                 395                 400

Val Val Gly Gly Glu Glu Pro Val Lys Gln Ala Asp Met Gly Ala Arg
                405                 410                 415

Lys Asn Ser Tyr Asp Asp Val Leu Gln Trp Leu Phe Arg Asp Gln Pro
                420                 425                 430

Ser Ser Pro Pro Pro Ala Arg Tyr Arg Ser Ala Asp Arg Phe Arg Thr
            435                 440                 445

Thr Glu Pro Ser Asn Phe Gly Ser Ala Leu Ala Ser Pro Asp Phe Met
    450                 455                 460

Asp Ser Ser Ser Arg Thr Ser Arg Pro Lys Thr Ser Tyr Gly Arg Arg
465                 470                 475                 480

Ala Gln Ser Gln Gly Ser Arg Thr Thr Gly Ser Ser Thr Ser Ala
                485                 490                 495

Ser Ala Thr Leu Pro His Ser Ala Asn Tyr Ser Pro Leu Ala Glu Gly
            500                 505                 510

Ile Ser Gln Cys Gly Leu Asn Ser Pro Ser Cys Ser Ile Lys Ser
    515                 520                 525

Gly Gln Val Val Tyr Gly Asp Ala Arg Ser Met Gly Arg Ser Cys Asp
530                 535                 540

Pro Ser Asp Ser Ser Arg Arg Phe Ser Ala Leu Ser Pro Ser Asp Thr
545                 550                 555                 560

Leu Asn Val Ser Ser Thr Arg Gly Ile Asn Pro Val Ile Gly Ser Asn
                565                 570                 575

Asp Val Phe Ser Thr Met Pro Phe Ala Asp Ser Ile Ala Ile Ala Glu
            580                 585                 590

Arg Ile Asp Ser Ser Pro Thr Leu Thr Ser Gly Glu Pro Ile Leu Cys
    595                 600                 605

Asp Asp Leu Gln Trp Glu Glu Pro Asp Leu Ser Cys Leu Ala Pro Phe
    610                 615                 620
```

```
Val Asp Thr Tyr Asp Met Met Gln Met Asp Glu Gly Leu Pro Pro Glu
625                 630                 635                 640

Leu Gln Ala Leu Tyr Asp Leu Pro Asp Phe Thr Pro Ala Val Pro Gln
                645                 650                 655

Ala Pro Ala Ala Arg Pro Val His Ile Asp Arg Ser Pro Pro Ala Lys
            660                 665                 670

Arg Met His Gln Ser Gly Pro Ser Asp Leu Asp Phe Met Tyr Thr Gln
        675                 680                 685

His Tyr Gln Pro Phe Gln Gln Asp Glu Thr Tyr Trp Gln Gly Gln Gln
    690                 695                 700

Gln Gln Asn Glu Gln Gln Pro Ser Ser Tyr Ser Pro Phe Pro Met Leu
705                 710                 715                 720

Ser

<210> SEQ ID NO 11
<211> LENGTH: 163
<212> TYPE: PRT
<213> ORGANISM: Homo sapiens

<400> SEQUENCE: 11

Phe Phe Leu Arg Met Lys Cys Thr Leu Thr Ser Arg Gly Arg Thr Met
1               5                   10                  15

Asn Ile Lys Ser Ala Thr Trp Lys Val Leu His Cys Thr Gly His Ile
            20                  25                  30

His Val Tyr Asp Thr Asn Ser Asn Gln Pro Gln Cys Gly Tyr Lys Lys
        35                  40                  45

Pro Pro Met Thr Cys Leu Val Leu Ile Cys Glu Pro Ile Pro His Pro
50                  55                  60

Ser Asn Ile Glu Ile Pro Leu Asp Ser Lys Thr Phe Leu Ser Arg His
65                  70                  75                  80

Ser Leu Asp Met Lys Phe Ser Tyr Cys Asp Glu Arg Ile Thr Glu Leu
                85                  90                  95

Met Gly Tyr Glu Pro Glu Glu Leu Leu Gly Arg Ser Ile Tyr Glu Tyr
            100                 105                 110

Tyr His Ala Leu Asp Ser Asp His Leu Thr Lys Thr His His Asp Met
        115                 120                 125

Phe Thr Lys Gly Gln Val Thr Thr Gly Gln Tyr Arg Met Leu Ala Lys
    130                 135                 140

Arg Gly Gly Tyr Val Trp Val Glu Thr Gln Ala Thr Val Ile Tyr Asn
145                 150                 155                 160

Thr Lys Asn

<210> SEQ ID NO 12
<211> LENGTH: 163
<212> TYPE: PRT
<213> ORGANISM: Pan troglodytes

<400> SEQUENCE: 12

Phe Phe Leu Arg Met Lys Cys Thr Leu Thr Ser Arg Gly Arg Thr Met
1               5                   10                  15

Asn Ile Lys Ser Ala Thr Trp Lys Val Leu His Cys Thr Gly His Ile
            20                  25                  30

His Val Tyr Asp Thr Asn Ser Asn Gln Pro Gln Cys Gly Tyr Lys Lys
        35                  40                  45

Pro Pro Met Thr Cys Leu Val Leu Ile Cys Glu Pro Ile Pro His Pro
50                  55                  60
```

```
Ser Asn Ile Glu Ile Pro Leu Asp Ser Lys Thr Phe Leu Ser Arg His
 65                  70                  75                  80

Ser Leu Asp Met Lys Phe Ser Tyr Cys Asp Glu Arg Ile Thr Glu Leu
                 85                  90                  95

Met Gly Tyr Glu Pro Glu Leu Leu Gly Arg Ser Ile Tyr Glu Tyr
            100                 105                 110

Tyr His Ala Leu Asp Ser Asp His Leu Thr Lys Thr His His Asp Met
            115                 120                 125

Phe Thr Lys Gly Gln Val Thr Thr Gly Gln Tyr Arg Met Leu Ala Lys
            130                 135                 140

Arg Gly Gly Tyr Val Trp Val Glu Thr Gln Ala Thr Val Ile Tyr Asn
145                 150                 155                 160

Thr Lys Asn

<210> SEQ ID NO 13
<211> LENGTH: 163
<212> TYPE: PRT
<213> ORGANISM: Macaca mulatta

<400> SEQUENCE: 13

Phe Phe Leu Arg Met Lys Cys Thr Leu Thr Ser Arg Gly Arg Thr Met
  1               5                  10                  15

Asn Ile Lys Ser Ala Thr Trp Lys Val Leu His Cys Thr Gly His Ile
                 20                  25                  30

His Val Tyr Asp Thr Asn Ser Asn Gln Pro Gln Cys Gly Tyr Lys Lys
             35                  40                  45

Pro Pro Met Thr Cys Leu Val Leu Ile Cys Glu Pro Ile Pro His Pro
         50                  55                  60

Ser Asn Ile Glu Ile Pro Leu Asp Ser Lys Thr Phe Leu Ser Arg His
 65                  70                  75                  80

Ser Leu Asp Met Lys Phe Ser Tyr Cys Asp Glu Arg Ile Thr Glu Leu
                 85                  90                  95

Met Gly Tyr Glu Pro Glu Leu Leu Gly Arg Ser Ile Tyr Glu Tyr
            100                 105                 110

Tyr His Ala Leu Asp Ser Asp His Leu Thr Lys Thr His His Asp Met
            115                 120                 125

Phe Thr Lys Gly Gln Val Thr Thr Gly Gln Tyr Arg Met Leu Ala Lys
            130                 135                 140

Arg Gly Gly Tyr Val Trp Val Glu Thr Gln Ala Thr Val Ile Tyr Asn
145                 150                 155                 160

Thr Lys Asn

<210> SEQ ID NO 14
<211> LENGTH: 163
<212> TYPE: PRT
<213> ORGANISM: Canis lupus familiaris

<400> SEQUENCE: 14

Phe Phe Leu Arg Met Lys Cys Thr Leu Thr Ser Arg Gly Arg Thr Met
  1               5                  10                  15

Asn Ile Lys Ser Ala Thr Trp Lys Val Leu His Cys Thr Gly His Ile
                 20                  25                  30

His Val Tyr Asp Thr Asn Ser Asn Gln Ser Gln Cys Gly Tyr Lys Lys
             35                  40                  45

Pro Pro Met Thr Cys Leu Val Leu Ile Cys Glu Pro Ile Pro His Pro
```

```
                 50                  55                  60
Ser Asn Ile Glu Ile Pro Leu Asp Ser Lys Thr Phe Leu Ser Arg His
 65                  70                  75                  80

Ser Leu Asp Met Lys Phe Ser Tyr Cys Asp Glu Arg Ile Thr Glu Leu
                 85                  90                  95

Met Gly Tyr Glu Pro Glu Leu Leu Gly Arg Ser Ile Tyr Glu Tyr
                100                 105                 110

Tyr His Ala Leu Asp Ser Asp His Leu Thr Lys Thr His His Asp Met
                115                 120                 125

Phe Thr Lys Gly Gln Val Thr Thr Gly Gln Tyr Arg Met Leu Ala Lys
                130                 135                 140

Arg Gly Gly Tyr Val Trp Val Glu Thr Gln Ala Thr Val Ile Tyr Asn
145                 150                 155                 160

Thr Lys Asn

<210> SEQ ID NO 15
<211> LENGTH: 163
<212> TYPE: PRT
<213> ORGANISM: Bos Taurus

<400> SEQUENCE: 15

Phe Phe Leu Arg Met Lys Cys Thr Leu Thr Ser Arg Gly Arg Thr Met
 1                5                  10                  15

Asn Ile Lys Ser Ala Thr Trp Lys Val Leu His Cys Thr Gly His Ile
                 20                  25                  30

His Val Tyr Asp Thr Asn Ser Asn Gln Ser Gln Cys Gly Tyr Lys Lys
                 35                  40                  45

Pro Pro Met Thr Cys Leu Val Leu Ile Cys Glu Pro Ile Pro His Pro
                 50                  55                  60

Ser Asn Ile Glu Ile Pro Leu Asp Ser Lys Thr Phe Leu Ser Arg His
 65                  70                  75                  80

Ser Leu Asp Met Lys Phe Ser Tyr Cys Asp Glu Arg Ile Thr Glu Leu
                 85                  90                  95

Met Gly Tyr Glu Pro Glu Leu Leu Gly Arg Ser Ile Tyr Glu Tyr
                100                 105                 110

Tyr His Ala Leu Asp Ser Asp His Leu Thr Lys Thr His His Asp Met
                115                 120                 125

Phe Thr Lys Gly Gln Val Thr Thr Gly Gln Tyr Arg Met Leu Ala Lys
                130                 135                 140

Arg Gly Gly Tyr Val Trp Ile Glu Thr Gln Ala Thr Val Ile Tyr Asn
145                 150                 155                 160

Thr Lys Asn

<210> SEQ ID NO 16
<211> LENGTH: 163
<212> TYPE: PRT
<213> ORGANISM: Mus musculus

<400> SEQUENCE: 16

Phe Phe Leu Arg Met Lys Cys Thr Leu Thr Ser Arg Gly Arg Thr Met
 1                5                  10                  15

Asn Ile Lys Ser Ala Thr Trp Lys Val Leu His Cys Thr Gly His Ile
                 20                  25                  30

His Val Tyr Asp Thr Asn Ser Asn Gln Pro Gln Cys Gly Tyr Lys Lys
                 35                  40                  45
```

```
Pro Pro Met Thr Cys Leu Val Leu Ile Cys Glu Pro Ile Pro His Pro
    50                  55                  60

Ser Asn Ile Glu Ile Pro Leu Asp Ser Lys Thr Phe Leu Ser Arg His
65                  70                  75                  80

Ser Leu Asp Met Lys Phe Ser Tyr Cys Asp Glu Arg Ile Thr Glu Leu
                85                  90                  95

Met Gly Tyr Glu Pro Glu Leu Leu Gly Arg Ser Ile Tyr Glu Tyr
                100                 105                 110

Tyr His Ala Leu Asp Ser Asp His Leu Thr Lys Thr His His Asp Met
            115                 120                 125

Phe Thr Lys Gly Gln Val Thr Thr Gly Gln Tyr Arg Met Leu Ala Lys
            130                 135                 140

Arg Gly Gly Tyr Val Trp Val Glu Thr Gln Ala Thr Val Ile Tyr Asn
145                 150                 155                 160

Thr Lys Asn

<210> SEQ ID NO 17
<211> LENGTH: 163
<212> TYPE: PRT
<213> ORGANISM: Rattus norvegicus

<400> SEQUENCE: 17

Phe Phe Leu Arg Met Lys Cys Thr Leu Thr Ser Arg Gly Arg Thr Met
1               5                   10                  15

Asn Ile Lys Ser Ala Thr Trp Lys Val Leu His Cys Thr Gly His Ile
                20                  25                  30

His Val Tyr Asp Thr Ser Ser Asn Gln Pro Gln Cys Gly Tyr Lys Lys
            35                  40                  45

Pro Pro Met Thr Cys Leu Val Leu Ile Cys Glu Pro Ile Pro His Pro
    50                  55                  60

Ser Asn Ile Glu Ile Pro Leu Asp Ser Lys Thr Phe Leu Ser Arg His
65                  70                  75                  80

Ser Leu Asp Met Lys Phe Ser Tyr Cys Asp Glu Arg Ile Thr Glu Leu
                85                  90                  95

Met Gly Tyr Glu Pro Glu Leu Leu Gly Arg Ser Ile Tyr Glu Tyr
                100                 105                 110

Tyr His Ala Leu Asp Ser Asp His Leu Thr Lys Thr His His Asp Met
            115                 120                 125

Phe Thr Lys Gly Gln Val Thr Thr Gly Gln Tyr Arg Met Leu Ala Lys
            130                 135                 140

Arg Gly Gly Tyr Val Trp Val Glu Thr Gln Ala Thr Val Ile Tyr Asn
145                 150                 155                 160

Thr Lys Asn

<210> SEQ ID NO 18
<211> LENGTH: 163
<212> TYPE: PRT
<213> ORGANISM: Gallus gallus

<400> SEQUENCE: 18

Phe Phe Leu Arg Met Lys Cys Thr Leu Thr Ser Arg Gly Arg Thr Val
1               5                   10                  15

Asn Ile Lys Ser Ala Thr Trp Lys Val Leu His Cys Thr Gly His Ile
                20                  25                  30

Arg Val Tyr Asp Thr Cys Asn Asn Gln Thr His Cys Gly Tyr Lys Lys
            35                  40                  45
```

```
Pro Pro Met Thr Cys Leu Val Leu Ile Cys Glu Pro Ile Pro His Pro
    50                  55                  60

Ser Asn Ile Glu Val Pro Leu Asp Ser Lys Thr Phe Leu Ser Arg His
65                  70                  75                  80

Ser Leu Asp Met Lys Phe Ser Tyr Cys Asp Glu Arg Ile Thr Glu Leu
                85                  90                  95

Met Gly Tyr Glu Pro Glu Glu Leu Leu Gly Arg Ser Ile Tyr Glu Tyr
            100                 105                 110

Tyr His Ala Leu Asp Ser Asp His Leu Thr Lys Thr His His Asp Met
            115                 120                 125

Phe Thr Lys Gly Gln Val Thr Thr Gly Gln Tyr Arg Met Leu Ala Lys
            130                 135                 140

Gln Gly Gly Tyr Val Trp Val Glu Thr Gln Ala Thr Val Ile Tyr Asn
145                 150                 155                 160

Thr Lys Asn

<210> SEQ ID NO 19
<211> LENGTH: 166
<212> TYPE: PRT
<213> ORGANISM: Danio rerio

<400> SEQUENCE: 19

Phe Phe Leu Arg Met Lys Cys Thr Leu Thr Ser Arg Gly Arg Thr Val
1               5                   10                  15

Asn Ile Lys Ser Ala Thr Trp Lys Val Leu His Cys Ala Gly His Val
            20                  25                  30

Arg Val His Glu Gly Ser Glu Ala Ser Glu Asp Ser Gly Phe Lys Glu
        35                  40                  45

Pro Pro Val Thr Tyr Leu Val Leu Ile Cys Glu Pro Ile Pro His Pro
    50                  55                  60

Ser Asn Ile Glu Val Pro Leu Asp Ser Lys Thr Phe Leu Ser Arg His
65                  70                  75                  80

Thr Leu Asp Met Lys Phe Ser Tyr Cys Asp Glu Arg Ile Thr Glu Leu
                85                  90                  95

Met Gly Tyr Glu Pro Asp Asp Leu Leu Asn Arg Ser Val Tyr Glu Tyr
            100                 105                 110

Tyr His Ala Leu Asp Ser Asp His Leu Thr Lys Thr His His Asn Leu
            115                 120                 125

Phe Ala Lys Gly Gln Ala Thr Thr Gly Gln Tyr Arg Met Leu Ala Lys
            130                 135                 140

Lys Gly Gly Phe Val Trp Val Glu Thr Gln Ala Thr Val Ile Tyr Asn
145                 150                 155                 160

Pro Lys Asn Ser Gln Pro
            165

<210> SEQ ID NO 20
<211> LENGTH: 161
<212> TYPE: PRT
<213> ORGANISM: Caenorhabditis elegans

<400> SEQUENCE: 20

Met Val Leu Arg Met Lys Thr Val Ile Ser Pro Arg Gly Arg Cys Leu
1               5                   10                  15

Asn Leu Lys Ser Ala Leu Tyr Lys Ser Val Ser Phe Leu Val His Ser
            20                  25                  30
```

Lys Val Ser Thr Gly Gly His Val Ser Phe Met Gln Gly Ile Thr Ile
            35                  40                  45

Pro Ala Gly Gln Gly Thr Thr Asn Ala Asn Ala Ser Ala Met Thr Lys
 50                  55                  60

Tyr Thr Glu Ser Pro Met Gly Ala Phe Thr Thr Arg His Thr Cys Asp
 65                  70                  75                  80

Met Arg Ile Thr Phe Val Ser Asp Lys Phe Asn Tyr Ile Leu Lys Ser
                    85                  90                  95

Glu Leu Lys Thr Leu Met Gly Thr Ser Phe Tyr Glu Leu Val His Pro
                100                 105                 110

Ala Asp Met Met Ile Val Ser Lys Ser Met Lys Glu Leu Phe Ala Lys
                115                 120                 125

Gly His Ile Arg Thr Pro Tyr Tyr Arg Leu Ile Ala Ala Asn Asp Thr
            130                 135                 140

Leu Ala Trp Ile Gln Thr Glu Ala Thr Thr Ile Thr His Thr Thr Lys
145                 150                 155                 160

Gly

<210> SEQ ID NO 21
<211> LENGTH: 453
<212> TYPE: PRT
<213> ORGANISM: Homo sapiens

<400> SEQUENCE: 21

Met Asp Phe Phe Arg Val Val Glu Asn Gln Gln Pro Pro Ala Thr Met
 1               5                  10                  15

Pro Leu Asn Val Ser Phe Thr Asn Arg Asn Tyr Asp Leu Asp Tyr Asp
                20                  25                  30

Ser Val Gln Pro Tyr Phe Tyr Cys Asp Glu Glu Glu Asn Phe Tyr Gln
            35                  40                  45

Gln Gln Gln Gln Ser Glu Leu Gln Pro Pro Ala Pro Ser Glu Asp Ile
 50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
                100                 105                 110

Gln Leu Glu Met Val Thr Glu Leu Leu Gly Gly Asp Met Val Asn Gln
            115                 120                 125

Ser Phe Ile Cys Asp Pro Asp Asp Glu Thr Phe Ile Lys Asn Ile Ile
 130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
                180                 185                 190

Leu Gln Asp Leu Ser Ala Ala Ala Ser Glu Cys Ile Asp Pro Ser Val
            195                 200                 205

Val Phe Pro Tyr Pro Leu Asn Asp Ser Ser Ser Pro Lys Ser Cys Ala
 210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
            245                 250                 255

Glu Glu Thr Pro Pro Thr Thr Ser Ser Asp Ser Glu Glu Glu Gln Glu
        260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
        290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
            355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
            435                 440                 445

Leu Arg Asn Ser Cys
    450

<210> SEQ ID NO 22
<211> LENGTH: 453
<212> TYPE: PRT
<213> ORGANISM: Pan troglodytes

<400> SEQUENCE: 22

Met Asp Phe Phe Arg Ile Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Lys Leu Val
145                 150                 155                 160

```
Ser Glu Lys Leu Ala Ser Tyr Gln Ala Ala Arg Lys Asp Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ser Glu Cys Ile Asp Pro Ser Val
        195                 200                 205

Val Phe Pro Tyr Pro Leu Asn Asp Ser Ser Pro Lys Ser Cys Pro
210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
        290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Asp Lys Arg Arg Thr His Asn Val Leu Glu Arg Gln Arg Arg Asn Glu
        370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg Asn Ser Cys
    450

<210> SEQ ID NO 23
<211> LENGTH: 438
<212> TYPE: PRT
<213> ORGANISM: Macaca mulatta

<400> SEQUENCE: 23

Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Glu Asn Phe Tyr
            20                  25                  30

Gln Gln Gln Gln Gln Ser Glu Leu Gln Pro Pro Ala Pro Ser Glu Asp
        35                  40                  45

Ile Trp Lys Lys Phe Glu Leu Leu Pro Thr Pro Pro Leu Ser Pro Ser
        50                  55                  60

Arg Arg Ser Gly Leu Cys Ser Pro Ser Tyr Val Ala Val Thr Pro Phe
```

```
            65                  70                  75                  80
    Ser Pro Arg Gly Asp Asn Asp Gly Gly Gly Ser Phe Ser Thr Ala
                    85                  90                  95

Asp Gln Leu Glu Met Val Thr Glu Leu Leu Gly Gly Asp Met Val Asn
                    100                 105                 110

Gln Ser Phe Ile Cys Asp Pro Asp Glu Thr Phe Ile Lys Asn Ile
                    115                 120                 125

Ile Ile Gln Asp Cys Met Trp Ser Gly Phe Ser Ala Ala Ala Lys Leu
            130                 135                 140

Val Ser Glu Lys Leu Ala Ser Tyr Gln Ala Ala Arg Lys Asp Ser Gly
    145                 150                 155                 160

Ser Pro Asn Pro Ala Arg Gly His Ser Val Cys Ser Thr Ser Ser Leu
                    165                 170                 175

Tyr Leu Gln Asp Leu Ser Ala Ala Ala Ser Glu Cys Ile Asp Pro Ser
                    180                 185                 190

Val Val Phe Pro Tyr Pro Leu Asn Asp Ser Ser Ser Pro Lys Ser Cys
                    195                 200                 205

Ala Ser Pro Asp Ser Ser Ala Phe Ser Pro Ser Ser Asp Ser Leu Leu
            210                 215                 220

Ser Ser Thr Glu Ser Ser Pro Gln Ala Ser Pro Glu Pro Leu Val Leu
    225                 230                 235                 240

His Glu Glu Thr Pro Pro Thr Thr Ser Ser Asp Ser Glu Glu Glu Gln
                    245                 250                 255

Glu Glu Glu Glu Glu Ile Asp Val Val Ser Val Glu Lys Arg Gln Ala
                    260                 265                 270

Pro Gly Lys Arg Ser Glu Ser Gly Ser Pro Ser Ala Gly Gly His Ser
                    275                 280                 285

Lys Pro Pro His Ser Pro Leu Val Leu Lys Arg Cys His Val Ser Thr
            290                 295                 300

His Gln His Asn Tyr Ala Ala Pro Pro Ser Thr Arg Lys Asp Tyr Pro
    305                 310                 315                 320

Ala Ala Lys Arg Val Lys Leu Asp Ser Val Arg Val Leu Arg Gln Ile
                    325                 330                 335

Ser Asn Asn Arg Lys Cys Thr Ser Pro Arg Ser Ser Asp Thr Glu Glu
                    340                 345                 350

Asn Asp Lys Arg Arg Thr His Asn Val Leu Glu Arg Gln Arg Arg Asn
                    355                 360                 365

Glu Leu Lys Arg Ser Phe Phe Ala Leu Arg Asp Gln Ile Pro Glu Leu
            370                 375                 380

Glu Asn Asn Glu Lys Ala Pro Lys Val Val Ile Leu Lys Lys Ala Thr
    385                 390                 395                 400

Ala Tyr Ile Leu Ser Val Gln Ala Glu Glu Gln Lys Leu Ile Ser Glu
                    405                 410                 415

Lys Asp Leu Leu Arg Lys Arg Arg Glu Gln Leu Lys His Lys Leu Glu
                    420                 425                 430

Gln Leu Arg Asn Ser Cys
            435

<210> SEQ ID NO 24
<211> LENGTH: 452
<212> TYPE: PRT
<213> ORGANISM: Canis lupus familiaris

<400> SEQUENCE: 24
```

-continued

Met Asp Leu Leu Arg Val Glu Thr Pro Ala Ala Met Pro Leu
1               5                   10                  15

Asn Val Ser Phe Ala Asn Arg Asn Tyr Asp Leu Asp Tyr Asp Ser Val
            20                  25                  30

Gln Pro Tyr Phe Tyr Cys Asp Glu Glu Asn Phe Tyr Gln Gln Gln
            35                  40                  45

Gln Gln Ser Glu Leu Gln Pro Pro Ala Pro Ser Glu Asp Ile Trp Lys
50                  55                  60

Lys Phe Glu Leu Leu Pro Thr Pro Pro Leu Ser Pro Arg Arg Ser
65                  70                  75                  80

Gly Leu Cys Ser Pro Ser Tyr Val Ala Val Ala Ser Phe Ser Pro Arg
                85                  90                  95

Gly Asp Asp Asp Gly Gly Gly Gly Ser Phe Ser Thr Ala Asp Gln Leu
            100                 105                 110

Glu Met Val Thr Glu Leu Leu Gly Gly Asp Met Val Asn Gln Ser Phe
            115                 120                 125

Ile Cys Asp Pro Asp Asp Glu Thr Phe Ile Lys Asn Ile Ile Ile Gln
    130                 135                 140

Asp Cys Met Trp Ser Gly Phe Ser Ala Ala Lys Leu Val Ser Glu
145                 150                 155                 160

Lys Leu Ala Ser Tyr Gln Ala Ala Arg Lys Asp Ser Gly Ser Pro Ser
                165                 170                 175

Pro Ala Arg Gly Pro Gly Gly Cys Ser Thr Ser Ser Leu Tyr Leu Gln
            180                 185                 190

Asp Leu Ser Ala Ala Ser Glu Cys Ile Asp Pro Ser Val Val Phe
            195                 200                 205

Pro Tyr Pro Leu Asn Asp Ser Ser Ser Pro Lys Pro Cys Ala Ser Pro
210                 215                 220

Asp Ser Ala Ala Phe Ser Pro Ser Ser Asp Ser Leu Leu Ser Ser Ala
225                 230                 235                 240

Glu Ser Ser Pro Arg Ala Ser Pro Glu Pro Leu Ala Leu His Glu Glu
                245                 250                 255

Thr Pro Pro Thr Thr Ser Ser Asp Ser Glu Glu Glu Gln Glu Asp Glu
            260                 265                 270

Glu Glu Ile Asp Val Val Ser Val Glu Lys Arg Gln Pro Pro Ala Lys
            275                 280                 285

Arg Ser Glu Ser Gly Ser Pro Ser Ala Gly Gly His Ser Lys Pro Pro
290                 295                 300

His Ser Pro Leu Val Leu Lys Arg Cys His Val Ser Thr His Gln His
305                 310                 315                 320

Asn Tyr Ala Ala Pro Pro Ser Thr Arg Lys Asp Tyr Pro Ala Ala Lys
                325                 330                 335

Arg Ala Arg Leu Asp Ser Gly Arg Val Leu Lys Gln Ile Ser Asn Asn
            340                 345                 350

Arg Lys Cys Ala Ser Pro Arg Ser Ser Asp Thr Glu Glu Asn Asp Lys
            355                 360                 365

Arg Arg Thr His Asn Val Leu Glu Arg Gln Arg Arg Asn Glu Leu Lys
            370                 375                 380

Arg Ser Phe Phe Ala Leu Arg Asp Gln Ile Pro Glu Leu Glu Asn Asn
385                 390                 395                 400

Glu Lys Ala Pro Lys Val Val Ile Leu Lys Lys Ala Thr Ala Tyr Ile
                405                 410                 415

Leu Ser Val Gln Ala Glu Glu Gln Lys Leu Leu Ser Glu Lys Asp Leu

```
                    420                 425                 430
Leu Arg Lys Arg Arg Glu Gln Leu Lys His Lys Leu Glu Gln Leu Arg
                435                 440                 445

Asn Ser Gly Ala
    450

<210> SEQ ID NO 25
<211> LENGTH: 439
<212> TYPE: PRT
<213> ORGANISM: Bos taurus

<400> SEQUENCE: 25

Met Pro Leu Asn Val Ser Phe Ala Asn Lys Asn Tyr Asp Leu Asp Tyr
1               5                   10                  15

Asp Ser Val Gln Pro Tyr Phe Tyr Cys Asp Glu Glu Glu Asn Phe Tyr
                20                  25                  30

His Gln Gln Gln Gln Ser Glu Leu Gln Pro Pro Ala Pro Ser Glu Asp
            35                  40                  45

Ile Trp Lys Lys Phe Glu Leu Leu Pro Thr Pro Pro Leu Ser Pro Ser
        50                  55                  60

Arg Arg Ser Gly Leu Cys Ser Pro Ser Tyr Val Ala Val Ala Ser Phe
65                  70                  75                  80

Ser Pro Arg Gly Asp Asp Asp Gly Gly Gly Gly Ser Phe Ser Ser Ala
                85                  90                  95

Asp Gln Leu Glu Met Val Thr Glu Leu Leu Gly Gly Asp Met Val Asn
                100                 105                 110

Gln Ser Phe Ile Cys Asp Pro Asp Asp Glu Thr Leu Ile Lys Asn Ile
            115                 120                 125

Ile Ile Gln Asp Cys Met Trp Ser Gly Phe Ser Ala Ala Ala Lys Leu
        130                 135                 140

Val Ser Glu Lys Leu Ala Ser Tyr Gln Ala Ala Arg Lys Asp Gly Gly
145                 150                 155                 160

Ser Pro Ser Pro Ala Arg Gly His Gly Gly Cys Ser Thr Ser Ser Leu
                165                 170                 175

Tyr Leu Gln Asp Leu Ser Ala Ala Ala Ser Glu Cys Ile Asp Pro Ser
                180                 185                 190

Val Val Phe Pro Tyr Pro Leu Asn Asp Ser Ser Ser Pro Lys Pro Cys
            195                 200                 205

Ala Ser Pro Asp Ser Thr Ala Phe Ser Pro Ser Ser Asp Ser Leu Leu
        210                 215                 220

Ser Ser Ala Glu Ser Ser Pro Arg Ala Ser Pro Glu Pro Leu Ala Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Pro
                260                 265                 270

Pro Ala Lys Arg Ser Glu Ser Gly Ser Pro Ser Ala Gly Ser His Ser
            275                 280                 285

Lys Pro Pro His Ser Pro Leu Val Leu Lys Arg Cys His Val Ser Thr
        290                 295                 300

His Gln His Asn Tyr Ala Ala Pro Pro Ser Thr Arg Lys Asp Tyr Pro
305                 310                 315                 320

Ala Ala Lys Arg Ala Lys Leu Asp Ser Gly Arg Val Leu Lys Gln Ile
                325                 330                 335
```

```
Ser Asn Asn Arg Lys Cys Ala Ser Pro Arg Ser Ser Asp Thr Glu Glu
            340                 345                 350

Asn Asp Lys Arg Thr His Asn Val Leu Glu Arg Gln Arg Arg Asn
        355                 360                 365

Glu Leu Lys Arg Ser Phe Phe Ala Leu Arg Asp Gln Ile Pro Glu Leu
    370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Gln Gln Lys Leu Lys Ser Glu
                405                 410                 415

Ile Asp Val Leu Gln Lys Arg Arg Glu Gln Leu Lys Lys Lys Leu Glu
            420                 425                 430

Gln Ile Arg Asn Ser Cys Ala
            435

<210> SEQ ID NO 26
<211> LENGTH: 454
<212> TYPE: PRT
<213> ORGANISM: Mus musculus

<400> SEQUENCE: 26

Met Asp Phe Leu Trp Ala Leu Glu Thr Pro Gln Thr Ala Thr Thr Met
1               5                   10                  15

Pro Leu Asn Val Asn Phe Thr Asn Arg Asn Tyr Asp Leu Asp Tyr Asp
            20                  25                  30

Ser Val Gln Pro Tyr Phe Ile Cys Asp Glu Glu Glu Asn Phe Tyr His
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Ala Thr Ser Phe
                85                  90                  95

Ser Pro Arg Glu Asp Asp Asp Gly Gly Gly Gly Asn Phe Ser Thr Ala
            100                 105                 110

Asp Gln Leu Glu Met Met Thr Glu Leu Leu Gly Gly Asp Met Val Asn
        115                 120                 125

Gln Ser Phe Ile Cys Asp Pro Asp Asp Glu Thr Phe Ile Lys Asn Ile
    130                 135                 140

Ile Ile Gln Asp Cys Met Trp Ser Gly Phe Ser Ala Ala Ala Lys Leu
145                 150                 155                 160

Val Ser Glu Lys Leu Ala Ser Tyr Gln Ala Ala Arg Lys Asp Ser Thr
                165                 170                 175

Ser Leu Ser Pro Ala Arg Gly His Ser Val Cys Ser Thr Ser Ser Leu
            180                 185                 190

Tyr Leu Gln Asp Leu Thr Ala Ala Ala Ser Glu Cys Ile Asp Pro Ser
        195                 200                 205

Val Val Phe Pro Tyr Pro Leu Asn Asp Ser Ser Ser Pro Lys Ser Cys
    210                 215                 220

Thr Ser Ser Asp Ser Thr Ala Phe Ser Pro Ser Ser Asp Ser Leu Leu
225                 230                 235                 240

Ser Ser Glu Ser Ser Pro Arg Ala Ser Pro Glu Pro Leu Val Leu His
                245                 250                 255

Glu Glu Thr Pro Pro Thr Thr Ser Ser Asp Ser Glu Glu Glu Gln Glu
            260                 265                 270
```

-continued

```
Asp Glu Glu Glu Ile Asp Val Ser Val Glu Lys Arg Gln Thr Pro
            275                 280                 285

Ala Lys Arg Ser Glu Ser Gly Ser Ser Pro Ser Arg Gly His Ser Lys
290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Ala Lys Leu Asp Ser Gly Arg Val Leu Lys Gln Ile Ser
            340                 345                 350

Asn Asn Arg Lys Cys Ser Ser Pro Arg Ser Ser Asp Thr Glu Glu Asn
            355                 360                 365

Asp Lys Arg Arg Thr His Asn Val Leu Glu Arg Gln Arg Arg Asn Glu
            370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Ile Gln Ala Asp Glu His Lys Leu Thr Ser Glu Lys
            420                 425                 430

Asp Leu Leu Arg Lys Arg Arg Glu Gln Leu Lys His Lys Leu Glu Gln
            435                 440                 445

Leu Arg Asn Ser Gly Ala
450

<210> SEQ ID NO 27
<211> LENGTH: 453
<212> TYPE: PRT
<213> ORGANISM: Rattus norvegicus

<400> SEQUENCE: 27

Met Asn Phe Leu Trp Glu Val Glu Asn Pro Thr Val Thr Thr Met Pro
1               5                   10                  15

Leu Asn Val Ser Phe Ala Asn Arg Asn Tyr Asp Leu Asp Tyr Asp Ser
            20                  25                  30

Val Gln Pro Tyr Phe Ile Cys Asp Glu Glu Glu Asn Phe Tyr His Gln
        35                  40                  45

Gln Gln Gln Ser Glu Leu Gln Pro Pro Ala Pro Ser Glu Asp Ile Trp
    50                  55                  60

Lys Lys Phe Glu Leu Leu Pro Thr Pro Pro Leu Ser Pro Ser Arg Arg
65                  70                  75                  80

Ser Gly Leu Cys Ser Pro Ser Tyr Val Ala Val Ala Thr Ser Phe Ser
                85                  90                  95

Pro Arg Glu Asp Asp Asp Gly Gly Gly Gly Asn Phe Ser Thr Ala Asp
            100                 105                 110

Gln Leu Glu Met Met Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Thr Ser
                165                 170                 175

Leu Ser Pro Ala Arg Gly His Ser Val Cys Ser Thr Ser Ser Leu Tyr
```

```
            180                 185                 190
Leu Gln Asp Leu Thr Ala Ala Ala Ser Glu Cys Ile Asp Pro Ser Val
            195                 200                 205

Val Phe Pro Tyr Pro Leu Asn Asp Ser Ser Pro Lys Ser Cys Thr
        210                 215                 220

Ser Ser Asp Ser Thr Ala Phe Ser Ser Ser Asp Ser Leu Leu Ser
225                 230                 235                 240

Ser Glu Ser Ser Pro Arg Ala Thr Pro Glu Pro Leu Val Leu His Glu
                245                 250                 255

Glu Thr Pro Pro Thr Thr Ser Ser Asp Ser Glu Glu Glu Gln Asp Asp
            260                 265                 270

Glu Glu Glu Ile Asp Val Val Ser Val Glu Lys Arg Gln Pro Pro Ala
        275                 280                 285

Lys Arg Ser Glu Ser Gly Ser Ser Pro Ser Arg Gly His Ser Lys Pro
    290                 295                 300

Pro His Ser Pro Leu Val Leu Lys Arg Cys His Val Ser Thr His Gln
305                 310                 315                 320

His Asn Tyr Ala Ala Pro Pro Ser Thr Arg Lys Asp Tyr Pro Ala Ala
                325                 330                 335

Lys Arg Ala Lys Leu Asp Ser Gly Arg Val Leu Lys Gln Ile Ser Asn
            340                 345                 350

Asn Arg Lys Cys Ser Ser Pro Arg Ser Ser Asp Thr Glu Glu Asn Asp
        355                 360                 365

Lys Arg Arg Thr His Asn Val Leu Glu Arg Gln Arg Arg Asn Glu Leu
    370                 375                 380

Lys Arg Ser Phe Phe Ala Leu Arg Asp Gln Ile Pro Glu Leu Glu Asn
385                 390                 395                 400

Asn Glu Lys Ala Pro Lys Val Val Ile Leu Lys Lys Ala Thr Ala Tyr
                405                 410                 415

Ile Leu Ser Val Gln Ala Asp Glu His Lys Leu Ile Ser Glu Lys Asp
            420                 425                 430

Leu Leu Arg Lys Arg Arg Glu Gln Leu Lys His Lys Leu Glu Gln Leu
        435                 440                 445

Arg Asn Ser Gly Ala
    450

<210> SEQ ID NO 28
<211> LENGTH: 416
<212> TYPE: PRT
<213> ORGANISM: Gallus gallus

<400> SEQUENCE: 28

Met Pro Leu Ser Ala Ser Leu Pro Ser Lys Asn Tyr Asp Tyr Asp Tyr
1               5                   10                  15

Asp Ser Val Gln Pro Tyr Phe Tyr Phe Glu Glu Glu Glu Asn Phe
            20                  25                  30

Tyr Leu Ala Ala Gln Gln Arg Gly Ser Glu Leu Gln Pro Pro Ala Pro
        35                  40                  45

Ser Glu Asp Ile Trp Lys Lys Phe Glu Leu Leu Pro Thr Pro Pro Leu
    50                  55                  60

Ser Pro Ser Arg Arg Ser Ser Leu Ala Ala Ala Ser Cys Phe Pro Ser
65                  70                  75                  80

Thr Ala Asp Gln Leu Glu Met Val Thr Glu Leu Leu Gly Gly Asp Met
                85                  90                  95
```

```
Val Asn Gln Ser Phe Ile Cys Asp Pro Asp Glu Ser Phe Val Lys
            100                 105                 110

Ser Ile Ile Ile Gln Asp Cys Met Trp Ser Gly Phe Ser Ala Ala
        115                 120                 125

Lys Leu Glu Lys Val Val Ser Glu Lys Leu Ala Thr Tyr Gln Ala Ser
130                 135                 140

Arg Arg Glu Gly Gly Pro Ala Ala Ser Arg Pro Gly Pro Pro
145                 150                 155                 160

Ser Gly Pro Pro Pro Pro Ala Gly Pro Ala Ser Ala Gly Leu
                165                 170                 175

Tyr Leu His Asp Leu Gly Ala Ala Ala Asp Cys Ile Asp Pro Ser
            180                 185                 190

Val Val Phe Pro Tyr Pro Leu Ser Glu Arg Ala Pro Arg Ala Pro
        195                 200                 205

Pro Gly Ala Asn Pro Ala Ala Leu Leu Gly Val Asp Thr Pro Pro Thr
210                 215                 220

Thr Ser Ser Asp Ser Glu Glu Gln Glu Glu Asp Glu Glu Ile Asp
225                 230                 235                 240

Val Val Thr Leu Ala Glu Ala Asn Glu Ser Glu Ser Ser Thr Glu Ser
                245                 250                 255

Ser Thr Glu Ala Ser Glu Glu His Cys Lys Pro His His Ser Pro Leu
            260                 265                 270

Val Leu Lys Arg Cys His Val Asn Ile His Gln His Asn Tyr Ala Ala
        275                 280                 285

Pro Pro Ser Thr Lys Val Glu Tyr Pro Ala Ala Lys Arg Leu Lys Leu
    290                 295                 300

Asp Ser Gly Arg Val Leu Lys Gln Ile Ser Asn Asn Arg Lys Cys Ser
305                 310                 315                 320

Ser Pro Arg Thr Ser Asp Ser Glu Glu Asn Asp Lys Arg Arg Thr His
                325                 330                 335

Asn Val Leu Glu Arg Gln Arg Arg Asn Glu Leu Lys Leu Ser Phe Phe
            340                 345                 350

Ala Leu Arg Asp Gln Ile Pro Glu Val Ala Asn Asn Glu Lys Ala Pro
        355                 360                 365

Lys Val Val Ile Leu Lys Lys Ala Thr Glu Tyr Val Leu Ser Ile Gln
370                 375                 380

Ser Asp Glu His Arg Leu Ile Ala Glu Lys Glu Gln Leu Arg Arg Arg
385                 390                 395                 400

Arg Glu Gln Leu Lys His Lys Leu Glu Gln Leu Arg Asn Ser Arg Ala
            405                 410                 415

<210> SEQ ID NO 29
<211> LENGTH: 419
<212> TYPE: PRT
<213> ORGANISM: Danio rerio

<400> SEQUENCE: 29

Met Glu Arg His Ser Leu Asn Thr Ser Val Lys Met Pro Val Ser Ala
1               5                   10                  15

Ser Leu Ala Cys Lys Asn Tyr Asp Tyr Asp Tyr Asp Ser Ile Gln Pro
            20                  25                  30

Tyr Phe Tyr Phe Asp Asn Asp Asp Glu Asp Phe Tyr His His Gln Gln
        35                  40                  45

Gly Gln Thr Gln Pro Ser Ala Pro Ser Glu Asp Ile Trp Lys Lys Phe
    50                  55                  60
```

Glu Leu Leu Pro Thr Pro Pro Leu Ser Pro Ser Arg Arg Gln Ser Leu
65                  70                  75                  80

Ser Thr Ala Glu Gln Leu Glu Met Val Ser Glu Phe Leu Gly Asp Asp
            85                  90                  95

Val Val Ser Gln Ser Phe Ile Cys Asp Asp Ala Asp Tyr Ser Gln Ser
            100                 105                 110

Phe Ile Lys Ser Ile Ile Ile Gln Asp Cys Met Trp Ser Gly Phe Ser
            115                 120                 125

Ala Ala Ala Lys Leu Glu Lys Val Val Ser Glu Arg Leu Ala Ser Leu
130                 135                 140

His Ala Glu Arg Lys Glu Leu Met Ser Asp Ser Asn Ser Asn Arg Leu
145                 150                 155                 160

Asn Ala Ser Tyr Leu Gln Asp Leu Ser Thr Ser Ala Ser Glu Cys Ile
            165                 170                 175

Asp Pro Ser Val Val Phe Pro Tyr Pro Leu Thr Glu Cys Gly Lys Ala
            180                 185                 190

Gly Lys Val Ala Ser Pro Gln Pro Met Leu Val Leu Asp Thr Pro Pro
            195                 200                 205

Asn Ser Ser Ser Ser Gly Ser Asp Ser Glu Asp Glu Glu Glu
210                 215                 220

Asp Glu Glu Glu Glu Glu Glu Glu Glu Glu Glu Glu Glu Glu Glu Glu
225                 230                 235                 240

Glu Glu Glu Ile Asp Val Val Thr Val Glu Lys Arg Gln Lys Arg His
            245                 250                 255

Glu Thr Asp Ala Ser Glu Ser Arg Tyr Pro Ser Pro Leu Val Leu Lys
            260                 265                 270

Arg Cys His Val Ser Thr His Gln His Asn Tyr Ala Ala His Pro Ser
            275                 280                 285

Thr Arg His Asp Gln Pro Ala Val Lys Arg Leu Arg Leu Glu Ala Ser
290                 295                 300

Asn Asn His Ser Ile Asn Ser Ser Ser Asn Arg His Val Lys Gln
305                 310                 315                 320

Arg Lys Cys Ala Ser Pro Arg Thr Ser Asp Ser Glu Asp Asn Asp Lys
            325                 330                 335

Arg Arg Thr His Asn Val Leu Glu Arg Gln Arg Arg Asn Glu Leu Lys
            340                 345                 350

Leu Ser Phe Phe Ala Leu Arg Asp Glu Ile Pro Glu Val Ala Asn Asn
            355                 360                 365

Glu Lys Ala Ala Lys Val Val Ile Leu Lys Lys Ala Thr Glu Cys Ile
            370                 375                 380

His Ser Met Gln Leu Asp Glu Gln Arg Leu Leu Ser Ile Lys Glu Gln
385                 390                 395                 400

Leu Arg Arg Lys Ser Glu Gln Leu Lys His Arg Leu Gln Gln Leu Arg
            405                 410                 415

Ser Ser His

<210> SEQ ID NO 30
<211> LENGTH: 396
<212> TYPE: PRT
<213> ORGANISM: Danio rerio

<400> SEQUENCE: 30

Met Pro Leu Asn Ser Ser Met Glu Cys Lys Asn Tyr Asp Tyr Asp Tyr
1               5                   10                  15

Asp Ser Tyr Gln Pro Tyr Phe Tyr Phe Asp Asn Glu Asp Glu Asp Phe
            20                  25                  30

Tyr Asn His Gln His Gly Gln Pro Ala Pro Ser Glu Asp Ile Trp
        35                  40                  45

Lys Lys Phe Glu Leu Leu Pro Thr Pro Pro Leu Ser Pro Ser Arg Arg
50                  55                  60

Pro Ser Leu Ser Asp Pro Phe Pro Ser Thr Ala Asp Lys Leu Glu Met
65                  70                  75                  80

Val Ser Glu Phe Leu Gly Asp Val Val Asn His Ser Ile Ile Cys
                85                  90                  95

Asp Ala Asp Tyr Ser Gln Ser Phe Leu Lys Ser Ile Ile Gln Asp
            100                 105                 110

Cys Met Trp Ser Gly Phe Ser Ala Ala Lys Leu Glu Lys Val Val
            115                 120                 125

Ser Glu Arg Leu Ala Ser Leu Gln Ala Ala Arg Lys Glu Ser Ser Arg
130                 135                 140

Thr Glu Ser Ala Asp Ile Cys Arg Ser Val Gly Phe Leu Gln Asp Met
145                 150                 155                 160

Ser Thr Pro Ala Ser Gln Cys Ile Asp Pro Ser Val Val Phe Pro Phe
            165                 170                 175

Pro Leu Thr Asp Ser Thr Lys Pro Cys Lys Pro Ala Pro Thr Pro Ala
            180                 185                 190

Ser Thr Thr Leu Pro Leu Asp Thr Pro Pro Asn Ser Gly Ser Ser Ser
            195                 200                 205

Ser Ser Ser Asp Ser Glu Ser Asp Asp Glu Asp Glu Asp Glu Glu
            210                 215                 220

Glu Glu Glu Glu Ile Asp Val Val Thr Val Glu Lys Arg Lys Ser Val
225                 230                 235                 240

Lys Lys Ser Asp Ala Asn Ala Thr His Gln Ser Pro Val Val Leu Lys
            245                 250                 255

Arg Cys His Val Asn Ile His Gln His Asn Tyr Ala Ala His Pro Ser
            260                 265                 270

Thr Arg Asn Glu Gln Pro Ala Val Lys Arg Ile Lys Phe Glu Ser His
            275                 280                 285

Ile Arg Val Phe Lys Gln Ile Ser His Asn Arg Lys Cys Ala Ser Pro
            290                 295                 300

Arg Thr Ser Asp Ser Glu Asp Asn Asp Lys Arg Arg Thr His Asn Val
305                 310                 315                 320

Leu Glu Arg Gln Arg Arg Asn Glu Leu Lys Leu Ser Phe Phe Ala Leu
            325                 330                 335

Arg Asp Val Ile Pro Asp Val Ala Asn Asn Glu Lys Ala Ala Lys Val
            340                 345                 350

Val Ile Leu Lys Lys Ala Thr Glu Cys Ile Ala Ser Met Gln Glu Asp
            355                 360                 365

Glu Gln Arg Leu Ile Ser Leu Lys Glu Gln Leu Arg Arg Lys Cys Glu
            370                 375                 380

His Leu Lys Gln Arg Leu Glu Gln Leu Ser Cys Ser
385                 390                 395

<210> SEQ ID NO 31
<211> LENGTH: 26
<212> TYPE: DNA
<213> ORGANISM: Artificial Sequence
<220> FEATURE:

<223> OTHER INFORMATION: Synthetic oligonucleotide

<400> SEQUENCE: 31
gccagcctga cccatagcca taatat                                          26

<210> SEQ ID NO 32
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 32
gagagatttt atgggtgtaa tgcgg                                           25

<210> SEQ ID NO 33
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 33
caccaaaccc acagaaaaca g                                               21

<210> SEQ ID NO 34
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 34
gggtcagagg aagagataaa gttg                                            24

<210> SEQ ID NO 35
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 35
aatgtccgca gtgatgtcc                                                  19

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
gcctgagttt gtgtttgctg                                                 20

<210> SEQ ID NO 37
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 37
tgaagttcgc attttgatgg c                                               21

```
<210> SEQ ID NO 38
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 38
ctttggtcct ggcatctcta c                                              21

<210> SEQ ID NO 39
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 39
cacccagatg caaaactttc ag                                             22

<210> SEQ ID NO 40
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 40
ctgctcttta tacttgctca cag                                            23

<210> SEQ ID NO 41
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 41
atagagccca agatcaagca g                                              21

<210> SEQ ID NO 42
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 42
tgtaacagcc ttccagtgc                                                 19

<210> SEQ ID NO 43
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 43
accaaaaccc atcccgtc                                                  18

<210> SEQ ID NO 44
<211> LENGTH: 21
<212> TYPE: DNA
<213> ORGANISM: Artificial Sequence
<220> FEATURE:
<223> OTHER INFORMATION: Synthetic oligonucleotide
```

```
<400> SEQUENCE: 44
tctgtaaggg ctccaaatgt g                                              21

<210> SEQ ID NO 45
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 45
gttcataggg tcagaggtca ag                                             22

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 46
tccattaaga tgtcctgtgc g                                              21

<210> SEQ ID NO 47
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 47
accccttctc tgtctaccg                                                 19

<210> SEQ ID NO 48
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 48
aatgctcgct tctccttgta g                                              21

<210> SEQ ID NO 49
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 49
atcaaggcac tgtccaagg                                                 19

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
tcattttcct gcatctcccg                                                20

<210> SEQ ID NO 51
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 51
accctaatct agtcccgtcc                                              20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
cagccaaaac cagatgacag                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
cattggtgat ggtattgcgc                                              20

<210> SEQ ID NO 54
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 54
tcccaaacac gacaactcc                                               19

<210> SEQ ID NO 55
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 55
ggaccgagtt ctgtatgtct tg                                           22

<210> SEQ ID NO 56
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 56
aaacccaaat tcgtcttcca tg                                           22

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
```
cttgaatccc tgctctgtgg                                             20

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
aaagctgaga gtgccaagag                                             20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 59
ttccagtgca gatgtccaag                                             20

<210> SEQ ID NO 60
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 60
ctgttgaagg acggtagaag g                                           21

<210> SEQ ID NO 61
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 61
gttcgttgcc taccctcac                                              19

<210> SEQ ID NO 62
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 62
tctctttact catcttcata gccg                                        24

<210> SEQ ID NO 63
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 63
ccgtgagggc aatgatttat ac                                          22

<210> SEQ ID NO 64
<211> LENGTH: 21
<212> TYPE: DNA
<213> ORGANISM: Artificial Sequence

```
<220> FEATURE:
<223> OTHER INFORMATION: Synthetic oligonucleotide

<400> SEQUENCE: 64
gtcaaaccag tcagagctac c                                              21

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
tgcacctacc ctatcactca                                                20

<210> SEQ ID NO 66
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 66
ggctcatcct gatcatagaa tgg                                            23

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
cccaccccat attaaacccg                                                20

<210> SEQ ID NO 68
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 68
gaggtatgaa ggaaaggtat aaggg                                          25

<210> SEQ ID NO 69
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 69
cccagatata gcattcccac g                                              21

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
actgttcatc ctgttcctgc                                                20
```

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 71
tcccaatcgt tgtagccatc                                               20

<210> SEQ ID NO 72
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 72
tgttggaaag aatggagtcg g                                             21

<210> SEQ ID NO 73
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 73
atactagcaa ttacttctat tttcataggg                                    30

<210> SEQ ID NO 74
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 74
gagggatggg ttgtaaggaa g                                             21

<210> SEQ ID NO 75
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 75
aagcaaatcc atatgaatgc gg                                            22

<210> SEQ ID NO 76
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 76
gctcatggta gtggaagtag aag                                           23

<210> SEQ ID NO 77
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 77
catcactcct attctgccta gc                                              22

<210> SEQ ID NO 78
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 78
ccaactccat aagctccata cc                                              22

<210> SEQ ID NO 79
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 79
ccaactccat aagctccata cc                                              22

<210> SEQ ID NO 80
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 80
gattttggac gtaatctgtt ccg                                             23

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 81
acgaaaatga cccagacctc                                                 20

<210> SEQ ID NO 82
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 82
gagatgacaa atcctgcaaa gatg                                            24

<210> SEQ ID NO 83
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 83
tgttggagtt atgttggaag gag                                             23

<210> SEQ ID NO 84

```
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 84
caaagatcac ccagctacta cc                                                22

<210> SEQ ID NO 85
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 85
agttgataac cgagtcgttc tg                                                22

<210> SEQ ID NO 86
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 86
ctgttgcttg atttagtcgg c                                                 21

<210> SEQ ID NO 87
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 87
cgtgaaggaa cctaccaagg                                                   20

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 88
cgctcagaag aatcctgcaa                                                   20

<210> SEQ ID NO 89
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 89
gccacaacta gatacatcaa catg                                              24

<210> SEQ ID NO 90
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 90
```
tggttgttag tgattttggt gaag        24

<210> SEQ ID NO 91
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 91
gaacatcaag tcagcaacgt g        21

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 92
tttgacggat gaggaatggg        20

<210> SEQ ID NO 93
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 93
cgagaatggc tgtggatgag        20

<210> SEQ ID NO 94
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 94
ggatggtgtt ggacagtgta g        21

<210> SEQ ID NO 95
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 95
gctccccaga acaagattac ag        22

<210> SEQ ID NO 96
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 96
tcgcccttga gtttgtcttc        20

<210> SEQ ID NO 97
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 97
tcaaagagaa caagggcgag                                                 20

<210> SEQ ID NO 98
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 98
aggaagcgga catcacaatc                                                 20

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99
tgcagcccaa ggatctctct                                                 20

<210> SEQ ID NO 100
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 100
cggcttgccc gagatct                                                    17

<210> SEQ ID NO 101
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 101
ccattctcta ccgtcctgtt g                                               21

<210> SEQ ID NO 102
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 102
tccatgtaag cgttgtccag                                                 20

<210> SEQ ID NO 103
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 103
ggcagcttga gttaaacgaa c                                               21
```

<210> SEQ ID NO 104
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 104
tggtgacatg gttaatcggt c                                              21

<210> SEQ ID NO 105
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 105
gactgtgaag atgagtgacc g                                              21

<210> SEQ ID NO 106
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 106
caatccgtaa ccaaacccag                                                20

<210> SEQ ID NO 107
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 107
aacctccgct ttcatgtaga g                                              21

<210> SEQ ID NO 108
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 108
gacatctcct agtttggaca gtg                                            23

<210> SEQ ID NO 109
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 109
gatggctttg agggtctgg                                                 19

<210> SEQ ID NO 110
<211> LENGTH: 22
<212> TYPE: DNA
<213> ORGANISM: Artificial Sequence
<220> FEATURE:

```
<223> OTHER INFORMATION: Synthetic oligonucleotide

<400> SEQUENCE: 110
cttggttatg ttggcactga tc                                              22

<210> SEQ ID NO 111
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 111
tgtgttaggg gactggtgga ca                                              22

<210> SEQ ID NO 112
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 112
catcacccac ttacccccaa aa                                              22

<210> SEQ ID NO 113
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 113
ataaccgagt cgttctgcca at                                              22

<210> SEQ ID NO 114
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 114
tttcagagca ttggccatag aa                                              22
```

NAD BIOSYNTHESIS AND PRECURSORS FOR THE TREATMENT AND PREVENTION OF CANCER AND PROLIFERATION

This application is a national stage filing under 35 U.S.C. § 371 of international application PCT/US2013/064154, filed Oct. 9, 2013, entitled "NAD Biosynthesis and Precursors for the Treatment and Prevention of Cancer and Proliferation," which claims the benefit under 35 U.S.C. § 119(e) of U.S. Provisional Application Ser. No. 61/711,552, entitled "Treatment of Age-Related and Mitochondrial Diseases by Inhibition of HIF-1α Function," filed on Oct. 9, 2012, U.S. Provisional Application Ser. No. 61/832,414, entitled "NAD Biosynthesis and NAD Precursors for the Treatment of Disease," filed on Jun. 7, 2013, and U.S. Provisional Application Ser. No. 61/832,203, entitled "NAD Biosynthesis and Precursors for the Treatment and Prevention of Cancer and Proliferation," filed on Jun. 7, 2013, the entire contents of each of which are herein incorporated by reference in their entireties.

GOVERNMENT INTEREST

This invention was made with Government support under National Institutes of Health Grant AG028730. The Government has certain rights in this invention.

FIELD OF THE INVENTION

The invention relates to methods for treatment and prevention of diseases or disorders associated with mitochondrial dysfunction by administering inhibitors of HIF1-α and/or agents that increase levels of NAD+. The invention relates to methods for treatment and prevention of cancer by administering agents that increase levels of NAD+.

BACKGROUND

Aging is characterized by a progressive decline in cellular and tissue homeostasis leading to a variety of age-related diseases that limit lifespan. Although improvements in sanitation, diet and medicines over the past 100 years have produced dramatic improvements in human health, maximum human lifespan has not changed. The inability to impact the maximal lifespan is due, in large part, to a limited understanding of why aging occurs and what genes control these processes.

Mitochondria are highly dynamic organelles that move throughout the cell and undergo structural transitions, changing the length, morphology, shape and size. Moreover, mitochondria are continuously eliminated and regenerated in a process known as mitochondrial biogenesis. Over the past 2 billion years, since eukaryotes subsumed the α-proteobacterial ancestor of mitochondria, most mitochondrial genes have been transferred to the nuclear genome, where regulation is better integrated. However, the mitochondrial genome still encodes rRNAs, tRNAs, and 13 subunits of the electron transport chain (ETC). Functional communication between the nuclear and mitochondrial genomes is therefore essential for mitochondrial biogenesis, efficient oxidative phosphorylation, and normal health. Failure to maintain the stoichiometry of ETC complexes is exemplified by mitochondrial disorders such as Leber's hereditary optic neuropathy (LHON), mitochondrial encephalomyopathy, lactic acidosis and stroke like episode syndrome (MELAS), myoclonic epilepsy with ragged red fibers (MERRF), and Leigh Syndrome.

One of the most conserved and robust phenomena in biology, in organisms as diverse as yeast and humans, is a progressive decline in mitochondrial function with age leading to a loss of cellular homeostasis and organismal health. In mammals, there is a large body of evidence implicating mitochondrial decline in aging and age-related diseases, including type II diabetes, Parkinson's disease, Alzheimer's disease, sarcopenia, lethargy, frailty, hepatic steatosis and obesity. For example, mice with mutations that impair the proofreading capacity of the mitochondrial DNA polymerase gamma (Poly) exhibit a premature aging phenotype. Conversely, targeting peroxisomal catalase to mitochondria (mCAT) extends mouse lifespan. Recently, telomere erosion in mice was found to disrupt mitochondrial function but the underlying mechanism has not yet been established. Despite the apparent importance of mitochondrial decline in aging and disease, there is considerable debate about its underlying causes.

Deregulation of mitochondrial homeostasis is one of the hallmarks of aging and disease in diverse species such as yeast and humans. In mammals, disruption of mitochondrial homeostasis is believed to be an underlying cause of aging and the etiology of numerous age-related diseases (de Moura et al., 2010; Figueiredo et al., 2009; Sahin et al., 2011; Schulz et al., 2007; Wallace et al., 2010). Despite its importance, there is still a great deal of controversy as to why age induces the disruption of mitochondrial homeostasis and how this process might be slowed or reversed.

In light of the foregoing, there is great need for novel compositions and methods for improving metabolism and mitochondrial function in aging tissues. Such compositions and methods would be useful for the treatment of age related and mitochondrial diseases, as well as for increasing stress resistance, improving resistance to hypoxia and extending the lifespan of organisms and cells.

NAD+ is an essential co-factor for several important enzymes (Canto and Auwerx, 2011). In mammals, NAD+ is generated from nicotinamide in a salvage pathway wherein nicotinamide phosphoribosyltransferase (NAMPT) converts nicotinamide to nicotinamide mononucleotide (NMN) which is then converted to NAD+ by nicotinamide mononucleotide adenylyltransferase (NMNAT) (Canto and Auwerx, 2011).

SUMMARY

As described herein, Hypoxia-Inducible Factor 1α (HIF-1α) interacts with the transcription factor c-Myc to inhibit c-Myc activity, causing genome asynchrony and the decline in mitochondrial function during aging. Reducing the ability of HIF-1α to inhibit c-Myc activity, such as by disrupting the formation of the complex containing HIF-1α and c-Myc, therefore conveys beneficial effects on metabolism, cellular fitness, survival (e.g., survival under hypoxic conditions) and mitochondrial function in aged tissues. Thus, agents that reduce inhibition of c-Myc activity by HIF-1α and/or disrupt the formation of a complex between HIF-1α and c-Myc (e.g., anti-HIF-1α antibodies, HIF-1α decoy proteins, small molecules), are useful for the treatment of age-related and mitochondrial diseases, including Alzheimer's disease, diabetes mellitus, heart disease, obesity, osteoporosis, Parkinson's disease and stroke. Such agents are also therefore useful for extending the life span, increasing the stress resistance and improving resistance to hypoxia of a subject (e.g., a human, a non-human animal and/or a plant) or a cell.

In certain embodiments, the instant invention relates to a method of treating or preventing an age-related disease and/or a mitochondrial disease by administration of an agent that reduces inhibition of c-Myc activity by HIF-1α. In some embodiments, the agent inhibits the formation of a complex between HIF-1α and c-Myc. In some embodiments, the agent induces a conformational change in HIF-1α or c-Myc that abrogates their interaction and/or alters the ability of HIF-1α to affect c-Myc activity, protein levels or cell localization. In certain embodiments the age-related disease is Alzheimer's disease, amniotropic lateral sclerosis, arthritis, atherosclerosis, cachexia, cancer, cardiac hypertrophy, cardiac failure, cardiac hypertrophy, cardiovascular disease, cataracts, colitis, chronic obstructive pulmonary disease, dementia, diabetes mellitus, frailty, heart disease, hepatic steatosis, high blood cholesterol, high blood pressure, Huntington's disease, hyperglycemia, hypertension, infertility, inflammatory bowel disease, insulin resistance disorder, lethargy, metabolic syndrome, muscular dystrophy, multiple sclerosis, neuropathy, nephropathy, obesity, osteoporosis, Parkinson's disease, psoriasis, retinal degeneration, sarcopenia, sleep disorders, sepsis and/or stroke. In some embodiments the mitochondrial disease is mitochondrial myopathy, diabetes mellitus and deafness (DAD), Leber's hereditary optic neuropathy (LHON), Leigh syndrome, neuropathy, ataxia, retinitis pigmentosa and petosis (NARP), myoclonic epilepsy with ragged red fibers (MERRF), myoneurogenic gastrointestinal encephalopathy (MNGIE), mitochondrial myopathy, encephalomyopathy, lactic acidosis, stroke-like symptoms (MELAS), Kearns-Sayre syndrome (KSS), chronic progressive external opthalmoplegia (CPEO) and/or mtDNA depletion.

In certain embodiments, the instant invention relates to a method of increasing the life span and/or increasing the stress resistance of a subject by administration of an agent that reduces inhibition of c-Myc activity by HIF-1α. In some embodiments the agent inhibits the formation of a complex between HIF-1α and c-Myc. In some embodiments, the agent induces a conformational change in HIF-1α or c-Myc that abrogates their interaction and/or alters the ability of HIF-1α to affect c-Myc activity, protein levels or cell localization. For example, in some embodiments, administration of the agent increases the resistance of cells in the organism against stress (e.g., heat shock, osmotic stress, DNA damaging agents and inadequate nitrogen levels). In certain embodiments, the invention relates to extending the life span or increasing the stress resistance of a cell by contacting the cell with an agent that inhibits the formation of a complex between HIF-1α and c-Myc.

In some embodiments, the present invention relates to a method of improving the survival of a cell, organ and/or tissue under hypoxic conditions. In certain embodiments the method includes contacting the cell, organ and/or tissue with an agent that reduces inhibition of c-Myc activity by HIF-1α. In some embodiments the agent inhibits the formation of a complex between HIF-1α and c-Myc. In some embodiments, the agent induces a conformational change in HIF-1α or c-Myc that abrogates their interaction and/or alters the ability of HIF-1α to affect c-Myc activity, protein levels or cell localization. In some embodiments, the cell, organ and/or tissue has been exposed to a hypoxic environment. In certain embodiments the cell, organ and/or tissue is within a subject (e.g., a subject suffering from ischemia, cardiovascular diseases, myocardial infarction, congestive heart disease, cardiomyopathy, myocarditis, macrovascular disease, peripheral vascular disease, reperfusion or stroke) who is administered the agent. In some embodiments, the cell is being cultured in vitro. In some embodiments the cell is a neuron, a cardiac myocyte, a skeletal myocyte, an iPS cell, blood cell, germ cell or germ cell precursor.

In certain embodiments, the present invention relates to a method of treating or preventing damage to a tissue or organ that has been exposed to hypoxia in a subject by administering an agent described herein to the subject. In some embodiments the subject is suffering from or has suffered from ischemia, cardiovascular diseases, myocardial infarction, congestive heart disease, cardiomyopathy, myocarditis, macrovascular disease, peripheral vascular disease reperfusion or a stroke.

In certain embodiments, the agent is an isolated antibody or antigen binding fragment thereof that specifically binds to a domain in HIF-1α that contributes to complex formation with c-Myc. For example, in certain embodiments the antibody or antigen binding fragment thereof binds to an epitope of human HIF-1α located within amino acids 167-329 of the HIF-1α protein. In some embodiments the antibody or antigen binding fragment thereof can be monoclonal, polyclonal, chimeric, humanized and/or human. In certain embodiments, the antibody or antigen binding fragment thereof is a full length immunoglobulin molecule; an scFv; a Fab fragment; an Fab' fragment; an F(ab')2; an Fv; a NANOBODY®; or a disulfide linked Fv. In some embodiments the antibody or antigen binding fragment thereof binds to HIF-1α with a dissociation constant of no greater than about $10^{-6}$ M, $10^{-7}$ M, $10^{-8}$ M or $10^{-9}$ M. In certain embodiments the antibody or antigen binding fragment thereof inhibits the formation of a complex between HIF-1α and c-Myc.

In certain embodiments, the agent is an isolated soluble polypeptide that includes at least 5, 6, 7, 8, 9, 10, 11, 12, 13, 14, 15, 20, 25, 30, 35, 40, 45, 50, 75, or 100 consecutive amino acids of the HIF-1α domain that contributes to complex formation with c-Myc. For example, in some embodiments the isolated soluble polypeptide includes at least 5, 6, 7, 8, 9, 10, 11, 12, 13, 14, 15, 20, 25, 30, 35, 40, 45, 50, 75, or 100 consecutive amino acids of one of SEQ ID NO: 11-20. In some embodiments, the polypeptide comprises one of SEQ ID NO: 11-20. In certain embodiments the polypeptide also includes an immunoglobulin constant domain (e.g., a human immunoglobulin constant domain). In some embodiments the polypeptide binds to c-Myc with a dissociation constant of no greater than about $10^{-6}$ M, $10^{-7}$ M, $10^{-8}$ M or $10^{-9}$ M.

In certain embodiments, the agent is a small molecule. In some embodiments the small molecule binds the HIF-1α domain that contributes to complex formation with c-Myc. In some embodiments the small molecule binds to human HIF-1α at a location within amino acids 167-329 of the HIF-1α protein. In some embodiments, the small molecule is attached to an antibody, protein or a peptide.

In some embodiments, the instant invention relates to a method of determining whether a test agent is a candidate therapeutic agent for the treatment of an age-related disease, for the treatment of a mitochondrial disease, for increasing life span, for improving resistance to hypoxia and/or for increasing stress resistance. In certain embodiments, the method comprises forming a test reaction mixture that includes a HIF-1α polypeptide or fragment thereof, an c-Myc polypeptide or fragment thereof and a test agent. In some embodiments the method includes the step of incubating the test reaction mixture under conditions conducive for the formation of a complex between the HIF-1α polypeptide or fragment thereof and the c-Myc polypeptide or fragment thereof. In certain embodiments, the test reaction includes a cell lysate. In some embodiments, the method includes the step of determining the amount of the complex in the test reaction mixture. In some embodiments, a test agent that reduces the amount of the complex in the test reaction mixture compared to the amount of the complex in a control reaction mixture is a candidate therapeutic agent for the treatment of an age-related disease, for the treatment of a mitochondrial disease, for increasing life span, for improving resistance to hypoxia and/or for increasing stress resistance. In some embodiments, the HIF-1α polypeptide or fragment thereof comprises an amino acid sequence of one of SEQ ID NO: 11-20. In some embodiments the test agent is an antibody, a protein, a peptide or a small molecule. In certain embodiments the test agent is a member of a library of test agents.

In some embodiments, the control reaction mixture is substantially identical to the test reaction mixture except that the control reaction mixture does not comprise a test agent. In certain embodiments the control reaction mixture is substantially identical to the test reaction mixture except that the control reaction mixture comprises a placebo agent instead of a test agent.

In some embodiments, the test reaction mixture is formed by adding the test agent to a mixture comprising the HIF-1α polypeptide or fragment thereof and the c-Myc polypeptide or fragment thereof. In certain embodiments the test reaction mixture is formed by adding the HIF-1α polypeptide or fragment thereof to a mixture comprising the test agent and the c-Myc polypeptide or fragment thereof. In certain embodiments the test reaction mixture is formed by adding the c-Myc polypeptide or fragment thereof to a mixture comprising the test agent and the HIF-1α polypeptide or fragment thereof.

In certain embodiments, the HIF-1α polypeptide or fragment thereof is anchored to a solid support in the test reaction mixture. In some embodiments the test reaction mixture is incubated under conditions conducive to the binding of the c-Myc polypeptide or fragment thereof to the anchored HIF-1α polypeptide or fragment thereof. In some embodiments, the method also includes the step of isolating c-Myc polypeptide or fragment thereof bound to the HIF-1α polypeptide or fragment thereof from c-Myc polypeptide or fragment thereof not bound to the HIF-1α polypeptide or fragment thereof. In certain embodiments, the amount of complex in the test reaction mixture is determined by detecting the amount of c-Myc polypeptide or fragment thereof bound to the HIF-1α polypeptide or fragment thereof. In some embodiments the c-Myc polypeptide or fragment thereof is linked (e.g. bound either directly or indirectly) to a detectable moiety (e.g., a fluorescent moiety, a luminescent moiety, a radioactive moiety, etc.).

In some embodiments, the c-Myc polypeptide or fragment thereof is anchored to a solid support in the test reaction mixture. In some embodiments the test reaction mixture is incubated under conditions conducive to the binding of the HIF-1α polypeptide or fragment thereof to the anchored c-Myc polypeptide or fragment thereof. In certain embodiments the method also includes the step of isolating HIF-1α polypeptide or fragment thereof bound to the c-Myc polypeptide or fragment thereof from HIF-1α polypeptide or fragment thereof not bound to the c-Myc polypeptide or fragment thereof. In some embodiments the amount of complex in the test reaction mixture is determined by detecting the amount of HIF-1α polypeptide or fragment thereof bound to the c-Myc polypeptide or fragment thereof. In certain embodiments the HIF-1α polypeptide or fragment thereof is linked (e.g. bound either directly or indirectly) to a detectable moiety (e.g., a fluorescent moiety, a luminescent moiety, a radioactive moiety, etc.).

In some embodiments, the instant invention relates to a method of determining whether a test agent is a candidate therapeutic agent for the treatment of an age-related disease, for the treatment of a mitochondrial disease, for increasing life span, for improving resistance to hypoxia and/or for increasing stress resistance that includes contacting a polypeptide comprising a sequence of one of SEQ ID NO: 11-20 with a test agent and determining whether the test agent binds to the epitope; wherein a test agent that binds to the epitope is a candidate therapeutic agent for the treatment of an age-related disease, for the treatment of a mitochondrial disease, for increasing life span, for improving resistance to hypoxia and/or for increasing stress resistance. In some embodiments the test agent is an antibody, a protein, a peptide or a small molecule. In certain embodiments the test agent is a member of a library of test agents. In some embodiments the test agent is a small molecule.

In some embodiments the polypeptide is attached to a solid substrate. In some embodiments, the method also includes the step of isolating test agent that is bound to the epitope from test agent that is not bound to the epitope. In some embodiments the test agent is linked to a detectable moiety.

In some embodiments the test agent is attached to a solid substrate. In certain embodiments the method also includes the step of isolating polypeptide that is bound to the test agent from polypeptide that is not bound to the test agent. In some embodiments the polypeptide is linked to a detectable moiety. In certain embodiments the test agent is a member of a library of test agents. In some embodiments the test agent is a small molecule.

In some embodiments, the instant invention relates to a method of determining whether a test agent is a candidate therapeutic agent for the treatment of an age-related disease, for the treatment of a mitochondrial disease, for increasing life span, for improving resistance to hypoxia and/or for increasing stress resistance, wherein the method includes the steps of contacting a cell that expresses HIF-1α and c-Myc with a test agent, and detecting the expression of a reporter gene that is transcriptionally regulated by c-Myc. In some embodiments, the reporter gene is a gene that controls mitochondrial function, such as TFAM, ND1, ND2, ND3, ND4, ND4I, ND5, ND6, CYTB, COX1, COX2, COX3, ATP6 or ATP8. In some embodiments, a test agent that increases expression of the reporter gene in the cell as compared to a cell that has not been contacted with the test agent is a candidate therapeutic agent for the treatment of an age-related disease, for the treatment of a mitochondrial disease, for increasing life span, for improving resistance to hypoxia and/or for increasing stress resistance.

In some embodiments, the reporter gene is operably linked to the promoter of c-Myc target gene, such as the promoter of TFAM, ND1, ND2, ND3, ND4, ND4I, ND5, ND6, CYTB, COX1, COX2, COX3, ATP6 or ATP8. In some embodiments expression of the reporter gene is detected by detecting the presence and/or amount of reporter gene mRNA (e.g., by RT PCR, northern blot, a nucleic acid probe hybridization assay and/or a gene expression array). In certain embodiments expression of the reporter gene is detected by detecting the presence and/or amount of reporter gene encoded protein (e.g., by western blot, ELISA, an antibody hybridization assay, etc.). In some embodiments, the cell is a mammalian cell (e.g., a C2C12 cell). In certain embodiments, the cell is in an organism. In some embodiments, the cell is a transgenic cell that recombinantly expresses the reporter gene. In certain embodiments the reporter gene encodes a detectable moiety, such as a fluorescent protein (e.g., GFP, RFP, YFP, etc.), or an enzyme that catalyzes a reaction that produces a change in luminescence, opacity or color. In certain embodiments the test agent is a member of a library of test agents. In some embodiments the agent is a small molecule.

Aspects of the present disclosure relate to the surprising discovery that HIF-1α is increased during aging and mitochondrial disorders and that NAD$^+$ precursors and NAD$^+$ biosynthetic genes (e.g., NMNAT-1 and NAMPT) counteract HIF-1α activity. Accordingly, provided herein are methods and compositions for the treatment of diseases or disorders associated with mitochondrial dysfunction.

Thus, in one embodiment, a method for treating or preventing a disease associated with deregulation of mitochondrial homeostasis in a subject in need thereof is provided. The method comprises administering to the subject an effective amount of a HIF-1α inhibitor. In some aspects, the disease associated with deregulation of mitochondrial homeostasis is aging, an aging-related disease, a mitochondrial disease, metabolic disorder, cardiovascular disease, stroke, pulmonary hypertension, ischemia, cachexia, sarcopenia, a neurodegenerative disease, dementia, lipodystrophy, liver steatosis, hepatitis, cirrhosis, kidney failure, preeclampsia, male infertility, diabetes, muscle wasting, or combinations thereof. In some aspects, the HIF-1α inhibitor is a small molecule, siRNA, or antisense oligonucleotide. In some aspects, the small molecule is chrysin (5,7-dihydroxyflavone), methyl 3-(2-(4-(adamantan-1-yl)phenoxy)acetamido)-4-hydroxybenzoate, P3155, NSC 644221, S-2-amino-3-[4'-N,N,-bis(chloroethyl)amino]phenyl propionic acid N-oxide dihydrochloride, dimethyl-bisphenol A, vincristine, apigenin, 2-methoxyestradiol, chetomin, or echinomycin.

In some embodiments, the method further comprises administering to the subject an effective amount of an agent that increases the level of NAD$^+$ in the subject. In some aspects, the agent is an NAD$^+$ precursor, such as NMN or a salt thereof, or an NMN prodrug. In some aspects, the agent is administered at a dose of between 0.5-5 grams per day. In some embodiments, the agent is an enzyme involved in NAD$^+$ biosynthesis, or an enzymatically active fragment thereof, or a nucleic acid encoding an enzyme involved in NAD$^+$ biosynthesis, or an enzymatically active fragment thereof. In some aspects, the enzyme is NMNAT-1 or NAMPT.

In another embodiment, a method for treating or preventing a disease associated with deregulation of mitochondrial homeostasis in a subject in need thereof is provided, comprising administering to the subject an effective amount of an agent that increases the level of NAD$^+$ in the subject. In some aspects, the disease associated with deregulation of mitochondrial homeostasis is aging, an aging-related disease, a mitochondrial disease, metabolic disorder, cardiovascular disease, stroke, pulmonary hypertension, ischemia, cachexia, sarcopenia, a neurodegenerative disease, dementia, lipodystrophy, liver steatosis, hepatitis, cirrhosis, kidney failure, preeclampsia, male infertility, or combinations thereof. In some aspects, the agent is an NAD$^+$ precursor, such as NMN or a salt thereof, or an NMN prodrug. In some aspects, the agent is administered at a dose of between 0.5-5 grams per day. In some embodiments, the agent is an enzyme involved in NAD+ biosynthesis, or an enzymatically active fragment thereof, or a nucleic acid encoding an enzyme involved in NAD+ biosynthesis, or an enzymatically active fragment thereof. In some aspects, the enzyme is NMNAT-1 or NAMPT.

In another embodiment, a screening method for identifying a HIF-1α inhibitor is provided. The method comprises (a) contacting a eukaryotic cell with a candidate compound; (b) determining the level of expression of one or more mitochondrial genes; (c) comparing the level of expression determined in (b) to a reference level of expression, wherein the reference level is determined in the absence of the candidate compound; and (d) identifying the compound as a HIF-1α inhibitor if a significantly decreased level of mitochondrial gene expression is determined in (b), as compared to the reference level in (c). In some aspects, the one or more mitochondrial genes is selected from cytochrome b, cytochrome oxidase, NADH dehydrogenase, and ATP synthase.

Aspects of the invention relate to methods for treating or preventing cancer in a subject in need thereof comprising administering to the subject an effective amount of an agent that increases the level of NAD+ in the subject. In some embodiments, the agent is an NAD+ precursor. In some embodiments, the NAD+ precursor is NMN or a salt thereof, or a prodrug thereof. In some embodiments, the agent is administered at a dose of between 0.5-5 grams per day.

In some embodiments, the agent is an enzyme involved in NAD+ biosynthesis, or an enzymatically active fragment thereof, or a nucleic acid encoding an enzyme involved in NAD+ biosynthesis, or an enzymatically active fragment thereof. In some embodiments, the enzyme is NMNAT-1 or NAMPT. In some embodiments, the subject is a human.

Further aspects of the invention relate to methods for modulating cell proliferation in a subject in need thereof comprising administering to the subject an effective amount of an agent that increases the level of NAD+ in the subject. In some embodiments, the agent is an NAD+ precursor. In some embodiments, the NAD+ precursor is NMN or a salt thereof, or a prodrug thereof. In some embodiments, the agent is administered at a dose of between 0.5-5 grams per day.

In some embodiments, the agent is an enzyme involved in NAD+ biosynthesis, or an enzymatically active fragment thereof, or a nucleic acid encoding an enzyme involved in NAD+ biosynthesis, or an enzymatically active fragment thereof. In some embodiments, the enzyme is NMNAT-1 or NAMPT. In some embodiments, the subject is a human.

These and other aspects of the invention, as well as various embodiments thereof, will become more apparent in reference to the drawings and detailed description of the invention. Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. in the drawings:

FIG. 1 provides exemplary HIF-1α amino acid sequences (SEQ ID NOs: 1-10).

FIG. 2 provides exemplary amino acid sequences of the domain of the HIF-1α protein that is required for complex formation with c-Myc (SEQ ID NOs: 11-20).

FIG. 3 provides exemplary c-Myc amino acid sequences (SEQ ID NOs: 21-30).

FIG. 6 shows loss of SIRT1 disrupts mitochondrial homeostasis through PGC-1α-independent regulation of mitochonrially-encoded ETC subunits driven by HIF-1α stabilization. (A) ND1, CYTB, COX1 and ATP6 mRNA analyzed by qPCR in WT and PGC-1α/β knockout myotubes treated with adenovirus overexpressing SIRT1 or empty vector. Relative expression values were normalized to WT control cells (n=4 experiments, $*p<0.05$ versus WT empty vector, #p<0.05 versus PGC-1α/β KO empty vector). (B) TFAM mRNA analyzed by qPCR in gastrocnemius of WT and SIRT1 KO animals. Relative expression values were normalized to WT mice (n=4, $*p<0.05$ versus WT). (C) TFAM promoter activity measured by luciferase assay in primary myoblasts extracted from WT and SIRT1 KO mice. Relative luciferase values were normalized to WT (n=6, $*p<0.05$ versus control). (D) Representative immunoblot for SIRT1, TFAM and tubulin in C2C12 cells infected with nontargeting or SIRT1 shRNA with or without TFAM overexpression. (E) ND1, CYTB, COX1 and ATP6 mRNA analyzed by qPCR in C2C12 cells infected with nontargeting or SIRT1 shRNA with or without TFAM overexpression. Relative expression values were normalized to control cells (n=4, $*p<0.05$ versus shCtl, #p<0.05 versus shSIRT1). (F) Mitochondrial DNA content analyzed by qPCR in C2C12 cells infected with nontargeting or SIRT1 shRNA with or without TFAM overexpression. Relative amount was normalized to control cells (n=4, $*p<0.05$ versus shCtl, #p<0.05 versus shSIRT1). (G) ATP content in C2C12 cells infected with nontargeting or SIRT1 shRNA with or without TFAM overexpression (n=4, $*p<0.05$ versus shCtl, #p<0.05 versus shSIRT1). (H) HK2, PKM, and PFKM mRNA analyzed by qPCR in gastrocnemius of WT and SIRT1 KO mice. Relative expression values were normalized to WT mice (n=5, $*p<0.05$ versus WT). (I) LDHA mRNA analyzed by qPCR in gastrocnemius of WT and SIRT1 KO mice. Relative expression values were normalized to WT mice (n=5, $*p<0.05$ versus WT). (J) Representative immunoblot for HIF1α and tubulin in gastrocnemius of WT and SIRT1 KO mice. (K) PGK-1, Glut1, PKD1, and VEGFa mRNA analyzed by qPCR in gastrocnemius of WT and SIRT1 KO mice. Relative expression values were normalized to WT mice (n=4, $*p<0.05$ versus WT). (L) Hypoxia response element activity in primary myoblasts isolated from WT and SIRT1 KO mice and treated with or without DMOG. Relative luciferase activity was normalized to WT cells (n=6, $*p<0.05$ versus WT). (M) ND1, CYTB, COX1 and ATP6 mRNA analyzed by qPCR in PGC-1α/β KO myotubes treated with adenovirus overexpressing SIRT1 or empty vector as well as treatment with DMSO or with HIF stabilizing compounds DMOG and DFO. Relative expression values were normalized to control cells (n=5, $*p<0.05$ versus empty vector, #p<0.05 versus SIRT1 OE). Values are expressed as mean±SEM.

FIG. 7 shows HIF-1α, but not HIF-2α, controls oxidative phosphorylation by regulating mitochondrially-encoded ETC components in response to SIRT1. (A) Representative immunoblot for HA-tag and tubulin in control C2C12 cells and cells overexpressing either HIF-1α or HIF-2a with the proline residues mutated (HIF-1α DPA; HIF-2α DPA). (B) Expression of nuclear (NDUFS8, SDHb, Uqcrc1, COX5b, ATP5a1) versus mitochondrially-encoded genes (ND1, CYTB, COX1, ATP6) analyzed by qPCR in control, HIF-1α DPA or HIF-2a DPA C2C12 cells. Relative expression values were normalized to control cells (n=6, $*p<0.05$ versus empty vector). (C) Mitochondrial DNA content analyzed by qPCR in control, HIF-1α DPA or HIF-2a DPA C2C12 cells treated with adenovirus overexpressing SIRT1 or empty vector. Relative amount was normalized to control cells (n=5, $*p<0.05$ versus empty vector, #p<0.05 versus SIRT1 OE). (D) ND1, CYTB, COX1 and ATP6 mRNA analyzed by qPCR in control, HIF-1α DPA or HIF-2a DPA C2C12 cells treated with adenovirus overexpressing SIRT1 or empty vector. Relative expression values were normalized to control cells (n=4, $*p<0.05$ versus empty vector, #p<0.05 versus SIRT1 OE). (E) HIF-1α mRNA analyzed by qPCR in C2C12 cells infected with HIF-1α or nontargeting shRNA. Relative expression values were normalized to control cells (n=4, $*p<0.05$ versus control). (F) Mitochondrial DNA content analyzed by qPCR in C2C12 cells infected with HIF-1α or nontargeting shRNA treated with EX-527. Relative amount was normalized to control cells (n=6, *p<0.05 versus control, #p<0.05 versus control EX-527). (G) ND1, CYTB, COX1 and ATP6 mRNA analyzed by qPCR in C2C12 cells infected with HIF-1α or nontargeting shRNA treated with EX-527. Relative expression values were normalized to control cells (n=6, *p<0.05 versus control, #p<0.05 versus control EX-527). (H) Representative images of mitochondrial membrane potential in C2C12 cells infected with HIF-1α or nontargeting shRNA treated with EX-527 and analyzed by fluorescence microscopy. (I) ATP content in C2C12 cells infected with HIF-1α or nontargeting shRNA treated with EX-527 (n=4, *p<0.05 versus control, #p<0.05 versus control EX-527).

FIG. 8 shows HIF1-α regulates genome synchrony by modulation of TFAM promoter through c-Myc in response to changes in SIRT1 activity. (A) c-Myc activity in primary myoblasts extracted from WT and SIRT1 KO animals. Relative luciferase values were normalized to WT cells (n=3, *p<0.05 versus control). (B) Representative immunoblot for c-Myc and tubulin in C2C12 cells infected with c-Myc or nontargeting shRNA. (C) Mitochondrial DNA content analyzed by qPCR in C2C12 cells infected with c-Myc or nontargeting shRNA and treated with adenovirus overexpressing SIRT1 or empty vector. Relative amount was normalized to control cells (n=5, *p<0.05 versus empty vector, #p<0.05 versus SIRT1 OE). (D) TFAM promoter activity in C2C12 cells infected with c-Myc or nontargeting shRNA and treated with adenovirus overexpressing SIRT1 or empty vector (n=4, *p<0.05 versus empty vector, #p<0.05 versus SIRT1 OE). (E) ND1, CYTB, COX1 and ATP6 mRNA analyzed by qPCR in C2C12 cells infected with c-Myc or nontargeting shRNA and treated with adenovirus overexpressing SIRT1 or empty vector. Relative expression values were normalized to control cells (n=6, *p<0.05 versus empty vector, #p<0.05 versus SIRT1 OE). (F) Representative immunoblot for c-Myc and tubulin in C2C12 cells overexpressing c-Myc. (G) Mitochondrial DNA content analyzed by qPCR in C2C12 cells overexpressing c-Myc. Relative amount was normalized to control cells (n=5, *p<0.05 versus empty vector, #p<0.05 versus c-Myc OE). (H) ND1, CYTB, COX1 and ATP6 mRNA analyzed by qPCR in C2C12 cells overexpressing c-Myc. Relative expression values were normalized to control cells (n=6, *p<0.05 versus empty vector, #p<0.05 versus c-Myc OE). (I) TFAM promoter activity in in C2C12 cells overexpressing c-Myc. (n=6, *p<0.05 versus empty vector, #p<0.05 versus c-Myc OE). (J) ATP content in C2C12 cells overexpressing c-Myc. (n=6, *p<0.05 versus empty vector, #p<0.05 versus c-Myc OE). (K) TFAM promoter activity in control or HIF-1α DPA C2C12 cells treated with adenovirus overexpressing SIRT1 or empty vector (n=6, *p<0.05 versus empty vector #p<0.05 versus SIRT1 OE). (L) TFAM promoter activity in C2C12 cells infected with HIF-1α or nontargeting shRNA treated with EX-527 and c-Myc siRNA (n=6, *p<0.05 versus DMSO, #p<0.05 versus Ex-527, +*p<0.05 versus HIF-1α KD). Values are expressed as mean±SEM.

FIG. 9 shows Caloric restriction protects from age-related mitochondrial dysfunction in skeletal muscle by preventing HIF-1α stabilization and loss of mitochondrial-encoded ETC genes. (A) NAD levels in gastrocnemius of 6- and 22-month AL and 22-month old CR mice (n=5, *p<0.05 versus 6-month-old animals #p<0.05 versus 22-month-old AL mice). (B) Mitochondrial membrane potential of isolated mitochondria from skeletal muscle of 6- and 22-month AL and 22-month old CR mice (n=5, *p<0.05 versus 6-month-old animals #p<0.05 versus 22-month-old AL mice). (C) ATP content in skeletal muscle of 6- and 22-month AL and 22-month old CR mice (n=5, *p<0.05 versus 6 month old animals #p<0.05 versus 22 month old AL mice). (D) Cytochrome c Oxidase Activity (Cox) activity in skeletal muscle of 6- and 22-month AL and 22-month old CR mice (n=4, *p<0.05 versus 6-month-old animals #p<0.05 versus 22-month-old AL mice). (E) Mitochondrial DNA content analyzed by qPCR in gastrocnemius of 6- and 22-month AL and 22-month old CR mice. Relative amount was normalized to 6-month-old mice (n=5, *p<0.05 versus 6-month-old animals #p<0.05 versus 22-month-old AL mice). (F) ND1, CYTB, COX1 and ATP6 mRNA analyzed by qPCR in gastrocnemius of 6- and 22-month AL and 22-month old CR mice. Relative expression values were normalized to 6-month-old mice (n=5, *p<0.05 versus 6-month-old animals #p<0.05 versus 22-month-old AL mice). (G) Representative immunoblot for COX2, COX4, and tubulin in gastrocnemius of 22-month-old AL and CR mice. (H) Representative immunoblot for HIF1α, and tubulin in gastrocnemius of 6- and 22-month AL and 22-month old CR mice. (I) PGK-1, Glut1, PKD1, and VEGFa mRNA analyzed by qPCR in gastrocnemius o6- and 22-month AL and 22-month old CR mice. Relative expression values were normalized to 6-month-old mice. (n=5, *p<0.05 versus 6-month-old animals #p<0.05 versus 22-month-old AL mice). Values are expressed as mean±SEM.

FIG. 10 shows increasing NAD+ rescues age-related mitochondrial dysfunction and genome asynchrony in skeletal muscle through a SIRT1-HIF-1α pathway. (A) NAD levels in gastrocnemius of 3- and 24-month-old mice treated with either the vehicle (PBS) or NMN (n=5, *p<0.05 versus 3-month-old PBS animals, #p<0.05 versus 24-month-old PBS animals). (B) Mitochondrial membrane potential of isolated mitochondria from skeletal muscle of 3- and 24-month-old mice treated with either the vehicle (PBS) or NMN (n=4, *p<0.05 versus 3-month-old PBS animals, #p<0.05 versus 24-months-old PBS animals). (C) ATP content in skeletal muscle of 3- and 24-month-old mice treated with either the vehicle (PBS) or NMN (n=5, *p<0.05 versus 3-month-old PBS animals, #p<0.05 versus 24-month-old PBS animals). (D) Cytochrome c Oxidase (Cox) activity in skeletal muscle of 3- and 24-month-old mice treated with either the vehicle (PBS) or NMN (n=4, *p<0.05 versus 3-month-old animals, #p<0.05 versus 24-month-old PBS animals). (E) Representative immunoblot for HIF1α, and tubulin in gastrocnemius of 3- and 24-month-old mice treated with either the vehicle (PBS) or NMN. (F) PGK-1, Glut1, PKD1, and VEGFa mRNA analyzed by qPCR in gastrocnemius of 3- and 24-month-old mice treated with either the vehicle (PBS) or NMN. Relative expression values were normalized to 3 month old PBS animals. (n=5, *p<0.05 versus 3-month-old PBS animals, #p<0.05 versus 24-month-old PBS animals). (G) ND1, CYTB, COX1 and ATP6 mRNA analyzed by qPCR in PGC-1α/β KO myotubes treated with PBS or NMN as well as treatment with DMSO or with DMOG or DFO. Relative expression values were normalized to PBS treated cells. (n=6, *p<0.05 versus PBS, #p<0.05 versus NMN). (H) ND1, CYTB, COX1 and ATP6 mRNA analyzed by qPCR in gastrocnemius of WT and SIRT1 KO mice treated with either the vehicle (PBS) or NMN (n=4, *p<0.05 versus WT untreated animals). (I) Mitochondrial membrane potential of isolated mitochondria from skeletal muscle of WT and SIRT1 KO mice treated with either the vehicle (PBS) or NMN (n=4, *p<0.05 versus WT PBS animals). (J) Model for age-related mitochondrial dysfunction caused by genome asynchrony. A decline in $NAD^+$ with age leads to HIF-1α-mediated inhibition of nuclear-mitochondrial communication and a deficiency of mitochondrially-encoded electron transport chain (ETC) subunits. Values are expressed as mean±SEM.

FIG. 11 reveals that aging leads to a specific decline in mitochondrial-encoded genes and impairment in mitochondrial homeostasis through decline in nuclear NAD levels. FIG. 11A depicts ATP content from gastrocnemius of 6-, 22-, and 30-month-old mice (n=5, *p<0.05 versus 6-month-old animals). FIG. 11B depicts mitochondrial DNA content analyzed by qPCR in gastrocnemius of 6-, 22-, and 30-month-old mice. Relative amount was normalized to 6-month-old mice (n=5). FIG. 11C depicts mitochondrial DNA integrity in gastrocnemius of 6-, 22-, and 30-month-old mice. Relative amount was normalized to 6-month-old mice (n=5, *p<0.05 versus 6-month-old animals). FIG. 11D depicts expression of nuclear (NDUFS8, SDHb, Uqcrc1, COX5b, ATP5a1) versus mitochondrial-encoded genes (ND1, Cytb, COX1, ATP6) analysed by qPCR in gastrocnemius of 6-, 22-, and 30-month-old mice. Relative expression values were normalized to 6-month-old mice (n=5, *p<0.05 versus 6-month-old animals). FIG. 11E depicts a representative immunoblot for COX2 and COX4 in gastrocnemius of 6-, 22-, and 30-month-old mice. FIG. 11F depicts $NAD^+$ levels in gastrocnemius of 6-, 22-, and 30-month-old mice (n=5, *p<0.05 versus 6-month-old animals). FIG. 11G depicts expression of nuclear (NDUFS8, SDHb, Uqcrc1, COX5b, ATP5a1) versus mitochondrial-encoded genes (ND1, Cytb, COX1, ATP6) analysed by qPCR in primary myoblasts WT cells infected with NMNAT1 or nontargeting shRNA. Relative amount was normalized to control cells (n=4, *p<0.05 versus control). FIG. 11H depicts expression of nuclear (NDUFS8, SDHb, Uqcrc1, COX5b, ATP5a1) versus mitochondrial-encoded genes (ND1, Cytb, COX1, ATP6) analysed by qPCR in primary myoblasts WT cells infected with NMNAT2 or nontargeting shRNA. Relative amount was normalized to control cells (n=4, *p<0.05 versus control). FIG. 11I depicts expression of nuclear (NDUFS8, SDHb, Uqcrc1, COX5b, ATP5a1) versus mitochondrial-encoded genes (ND1, Cytb, COX1, ATP6) analysed by qPCR in primary myoblasts WT cells infected with NMNAT3 or nontargeting shRNA. Relative amount was normalized to control cells (n=4, *p<0.05 versus control). FIG. 11J depicts mitochondrial DNA content analyzed by qPCR in primary myoblasts WT cells infected with NMNAT1 or nontargeting shRNA. Relative amount was normalized to control cells (n=4, *p<0.05 versus control). FIG. 11K depicts ATP content in primary myoblasts WT cells infected with NMNAT1 or nontargeting shRNA. Relative amount was normalized to control cells (n=4, *p<0.05 versus control). Values are expressed as mean±SEM.

FIG. 12 reveals that loss of SIRT1 resembles the specific decrease in the expression of mitochondrial-encoded genes that occurs with aging and resulting in disruption mitochondrial metabolism and impaired muscle health. FIG. 12A depicts ATP content from gastrocnemius of WT and SIRT1 KO mice (n=5). FIG. 12B depicts mitochondrial DNA content analyzed by qPCR in gastrocnemius of WT and SIRT1 KO mice Relative amount was normalized to WT mice (n=5). FIG. 12C depicts electronic microscopy analysis of gastrocnemius from WT and SIRT1 KO mice and the respective mitochondrial area quantification (n=4). FIG. 12D depicts expression of nuclear (NDUFS8, NDUFAS, SDHb, SDHd, Uqcrc1, Uqcrc2, COX5b, Cox6a1, ATP5a1, ATPc1) versus mitochondrial-encoded genes (ND1, ND2, ND3, ND4, ND41, ND5, ND6, Cytb, COX1, COX2, COX3, ATP6 and ATP8) analyzed by qPCR in gastrocnemius of WT and SIRT1 KO mice. Relative expression values were normalized to WT mice (n=5). FIG. 12E depicts a representative immunoblot for COX2 and COX4 in gastrocnemius of WT and SIRT1 KO mice. FIG. 12F depicts expression of mitochondrial-encoded genes (ND1, Cytb, COX1, ATP6) analysed by qPCR in SIRT1 flox/flox Cre-ERT2 primary myoblasts treated with vehicle, or OHT to induce SIRT1 excision infected with NMNAT1 or nontargeting shRNA. Relative amount was normalized to control cells (n=4, *p<0.05 versus control). FIG. 12G depicts representative immunoblot for MyHCHIIa, MyHCIIb and Tubulin in gastrocnemius of WT and SIRT1 KO mice. FIG. 12H depicts a representative immunoblot for Atrogin-1, MuRF1 and Tubulin in gastrocnemius of WT and SIRT1 KO mice. FIG. 12I depicts a representative immunoblot for p-AKT, Total AKT, p-IRS-1 and Total IRS-1 in soleus of WT and SIRT1 KO mice under basal conditions and upon insulin stimulation. Values are expressed as mean±SEM (*p<0.05 versus WT animals).

FIG. 13 reveals that SIRT1 regulates mitochondrial homeostasis through energy sensitive PGC-1α-dependent and—independent mechanisms. FIG. 13A depicts expression of nuclear (NDUFS8, SDHb, Uqcrc1, COX5b, ATP5a1) versus mitochondrial-encoded genes (ND1, Cytb, COX1, ATP6) analysed by qPCR in WT and PGC-1α/β knockout myotubes treated with adenovirus overexpressing SIRT1 or empty vector. Relative expression values were normalized to WT control cells (n=4 experiments). FIG. 13B depicts expression of nuclear (NDUFS8, SDHb, Uqcrc1, COX5b, ATP5a1) versus mitochondrial-encoded genes (ND1, Cytb, COX1, ATP6) analysed by qPCR in SIRT1 flox/flox Cre-ERT2 primary myoblasts treated with vehicle, or OHT to induce SIRT1 excision for 6, 12, 24 and 48 hours. Relative expression values were normalized to control cells (n=4). FIG. 13C depicts mitochondrial mass measured by staining of the cells with NAO in SIRT1 flox/flox Cre-ERT2 primary myoblasts treated with vehicle, or OHT to induce SIRT1 excision for 6, 12, 24 and 48 hours. FIG. 13D depicts a representative immunoblot for p-AMPK (Thr172) and AMPK in SIRT1 flox/flox Cre-ERT2 primary myoblasts treated with vehicle, or OHT to induce SIRT1 excision for 6, 12, 24 and 48 hours. FIG. 13E depicts expression of nuclear (NDUFS8, SDHb, Uqcrc1, COX5b, ATP5a1) versus mitochondrial-encoded genes (ND1, Cytb, COX1, ATP6) analysed by qPCR in PGC-1α/β knockout myotubes infected with adenovirus expressing a flag-PGC-1α WT, PGC-1α T177A/S538A mutant or empty and treated with vehicle (DMSO) or EX-527 for 48 h. Relative expression values were normalized to control cells (n=4). FIG. 13F depicts a representative immunoblot for p-ACC (Ser79) and ACC in SIRT1 flox/flox Cre-ERT2 primary myoblasts treated with vehicle, or OHT to induce SIRT1 excision for 48 h and infected with empty or AMPK-DN adenovirus for the same period of time. FIG. 13G depicts expression of nuclear (NDUFS8, SDHb, Uqcrc1, COX5b, ATP5a1) versus mitochondrial-encoded genes (ND1, Cytb, COX1, ATP6) analysed by qPCR in SIRT1 flox/flox Cre-ERT2 primary myoblasts treated with vehicle, or OHT to induce SIRT1 excision for 48 h and infected with empty or AMPK-DN adenovirus for the same period of time. Relative expression values were normalized to control cells (n=4). FIG. 13H depicts TFAM mRNA analyzed by qPCR in gastrocnemius of WT and SIRT1 KO animals. Relative expression values were normalized to WT mice (n=5, *p<0.05 versus WT). FIG. 13I depicts TFAM promoter activity measured by luciferase assay in primary myoblasts extracted from WT and SIRT1 KO mice. Relative luciferase values were normalized to WT cells (n=6, *p<0.05 versus control). FIG. 13J depicts a representative immunoblot for SIRT1, TFAM ant Tubulin in SIRT1 flox/flox Cre-ERT2 primary myoblasts treated with vehicle, or OHT to induce SIRT1 excision for 24 h after which the cells were added back TFAM by infection with a TFAM adenovirus, or for 48 h hours and infected with empty or TFAM adenovirus for the same period of time. FIG. 13K depicts expression of nuclear (NDUFS8, SDHb, Uqcrc1, COX5b, ATP5a1) versus mitochondrial-encoded genes (ND1, Cytb, COX1, ATP6) analysed by qPCR in SIRT1 flox/flox Cre-ERT2 primary myoblasts treated with vehicle, or OHT to induce SIRT1 excision for 24 h after which the cells were added back TFAM by infection with a TFAM adenovirus, or for 48 h hours and infected with empty or TFAM adenovirus for the same period of time. Relative expression values were normalized to control cells (n=4). FIG. 13L depicts ATP content in SIRT1 flox/flox Cre-ERT2 primary myoblasts treated with vehicle, or OHT to induce SIRT1 excision for 24 h after which the cells were added back TFAM by infection with a TFAM adenovirus, or for 48 h hours and infected with empty or TFAM adenovirus for the same period of time (n=4). FIG. 13M depicts a representative immunoblot for p-AMPK (Thr172) and AMPK in SIRT1 flox/flox Cre-ERT2 primary myoblasts treated with vehicle, or OHT to induce SIRT1 excision for 24 h after which the cells were added back TFAM by infection with a TFAM adenovirus, or for 48 h hours and infected with empty or TFAM adenovirus for the same period of time.

FIG. 14 reveals that loss of SIRT1 induces a psedohypoxic state that disrupts mitochondrial-encoded genes and mitochondrial homeostasis. FIG. 14A depicts HK2, PKM, and PFKM mRNA analyzed by qPCR in gastrocnemius of WT and SIRT1 KO mice. Relative expression values were normalized to WT mice (n=5, $*p<0.05$ versus WT). FIG. 14B depicts LDHA mRNA analyzed by qPCR in gastrocnemius of WT and SIRT1 KO mice. Relative expression values were normalized to WT mice (n=5, $*p<0.05$ versus WT). FIG. 14C depicts lactate levels measured in gastrocnemius of WT and SIRT1 KO mice (n=5, $*p<0.05$ versus WT). FIG. 14D depicts a representative immunoblot for HIF-1α and Tubulin in gastrocnemius of WT and SIRT1 KO mice and in SIRT1 flox/flox Cre-ERT2 primary myoblasts treated with vehicle, or OHT to induce SIRT1 excision for 24 h. FIG. 14E depicts a representative immunoblot for HIF-1α and Tubulin in gastrocnemius of WT and Egln1 KO mice. FIG. 14F depicts expression of nuclear (NDUFS8, SDHb, Uqcrc1, COX5b, ATP5a1) versus mitochondrial-encoded genes (ND1, Cytb, COX1, ATP6) analysed by qPCR in gastrocnemius of WT and Egln1 KO mice (n=5). FIG. 14G depicts mitochondrial DNA content analyzed by qPCR in gastrocnemius of WT and Egln1 KO mice. Relative amount was normalized to WT mice (n=5). FIG. 14H depicts expression of mitochondrial-encoded genes (ND1, Cytb, COX1 and ATP6) analyzed by qPCR in PGC-1α/β KO myotubes treated with adenovirus overexpressing SIRT1 or empty vector as well as treatment with DMSO or with HIF stabilizing compound DMOG. Relative expression values were normalized to control cells (n=4). FIG. 14I depicts a representative immunoblot for HA-tag and tubulin in control C2C12 cells and cells overexpressing either HIF-1α or HIF-2a with the proline residues mutated (HIF-1α DPA; HIF-2a DPA). FIG. 14J depicts expression of nuclear (NDUFS8, SDHb, Uqcrc1, COX5b, ATP5a1) versus mitochondrial-encoded genes (ND1, Cytb, COX1, ATP6) analyzed by qPCR in control, HIF-1α DPA or HIF-2a DPA C2C12 cells. Relative expression values were normalized to control cells (n=6, $*p<0.05$ versus empty vector). FIG. 14K depicts expression of mitochondrial-encoded genes (ND1, Cytb, COX1 and ATP6) analyzed by qPCR in control, HIF-1α DPA or HIF-2a DPA C2C12 cells treated with adenovirus overexpressing SIRT1 or empty vector. Relative expression values were normalized to control cells (n=4). FIG. 14L depicts a representative immunoblot for HIF-1α and Tubulin in SIRT1 flox/flox Cre-ERT2 primary myoblasts treated with vehicle, or OHT to induce SIRT1 excision infected with HIF-1α or nontargeting shRNA and DMOG to promote HIF-1α stabilization. FIG. 14M depicts mitochondrial DNA content analyzed by qPCR in SIRT1 flox/flox Cre-ERT2 primary myoblasts treated with vehicle, or OHT to induce SIRT1 excision infected with HIF-1α or nontargeting shRNA. Relative amount was normalized to control cells (n=4). FIG. 14N depicts ATP content in gastrocnemius of in SIRT1 flox/flox Cre-ERT2 primary myoblasts treated with vehicle, or OHT to induce SIRT1 excision infected with HIF-1α or nontargeting shRNA. Relative amount was normalized to control cells (n=5). Values are expressed as mean±SEM.

FIG. 15 reveals that SIRT1 regulates HIF-1α stabilization in the skeletal muscle through regulation of VHL expression. FIG. 15A depicts a representative immunoblot for VHL and Tubulin in gastrocnemius of WT and SIRT1 KO mice. FIG. 15B depicts a representative immunoblot for VHL and Tubulin is gastrocnemius of WT and SIRT1-Tg overexpressing mice. FIG. 15C depicts VHL mRNA analyzed by qPCR in gastrocnemius of WT and SIRT1 KO mice. Relative expression values were normalized to control WT mice (n=5). FIG. 15D depicts VHL mRNA analyzed by qPCR in gastrocnemius of WT and SIRT1-Tg mice. Relative expression values were normalized to control WT mice (n=5). FIG. 15E depicts VHL promoter activity measured by luciferase assay in SIRT1 flox/flox Cre-ERT2 primary myoblasts treated with vehicle, or OHT for 24 h to induce SIRT1 excision. Relative luciferase values were normalized to vehicle. Relative luciferase values were normalized to control cells (n=5, $*p<0.05$ versus control). FIG. 15F depicts VHL promoter activity measured by luciferase assay in primary myoblasts infected with adenovirus expressing SIRT1 or empty vector. Relative luciferase values were normalized to empty vector (n=5, $*p<0.05$ versus control). FIG. 15G depicts a representative immunoblot for VHL, HIF-1α and Tubulin in primary myoblasts WT cells infected with NMNAT1 or nontargeting shRNA. FIG. 15H depicts VHL mRNA analyzed by qPCR in primary WT myoblasts infected with NMNAT1 or nontargeting shRNA. Relative expression values were normalized to control cells (n=4). FIG. 15I depicts a representative immunoblot for VHL, HIF-1α and Tubulin in gastrocnemius of 6-, 22-, and 30-month-old mice. FIG. 15J depicts a representative immunoblot for VHL, HIF-1α, TFAM and Tubulin in SIRT1 flox/flox Cre-ERT2 primary myoblasts treated with vehicle, or OHT to induce SIRT1 excision for 6, 12, 24 hours and in cells treated with OHT for 24 h after which SIRT1 was added back by infection with an adenovirus. FIG. 15K depicts a representative immunoblot for VHL and Tubulin in SIRT1 flox/flox Cre-ERT2 primary myoblasts infected with VHL or nontargeting shRNA. FIG. 15L depicts a representative immunoblot for VHL and Tubulin in SIRT1 flox/flox Cre-ERT2 primary myoblasts infected with VHL or nontargeting shRNA and treated with OHT for 24 h after which SIRT1 was added back by infection with an adenovirus. FIG. 15M depicts TFAM promoter activity measured by luciferase assay in SIRT1 flox/flox Cre-ERT2 primary myoblasts infected with VHL or nontargeting shRNA and treated with OHT for 24 h after which SIRT1 was added back by infection with an adenovirus. Relative luciferase values were normalized to control cells (n=4). FIG. 15N depicts expression of mitochondrial-encoded genes (ND1, Cytb, COX1 and ATP6) analyzed by qPCR in primary WT myoblasts infected with VHL or nontargeting shRNA and treated with adenovirus expressing SIRT1 or empty vector. Relative expression values were normalized to control cells (n=5). Values are expressed as mean±SEM.

FIG. 16 reveals that HIF-1α regulates mitochondrial homeostasis by modulation of TFAM promoter through c-Myc in response to changes in SIRT1 activity. FIG. 16A depicts c-Myc activity in SIRT1 flox/flox Cre-ERT2 primary myoblasts and treated with vehicle, or OHT to induce SIRT1 excision for 6, 12, 24 hours. Relative luciferase values were normalized to control cells (n=4). FIG. 16B depicts a representative immunoblot for c-Myc and tubulin in C2C12 cells infected with c-Myc or nontargeting shRNA. FIG. 16C depicts mitochondrial DNA content analyzed by qPCR in C2C12 cells infected with c-Myc or nontargeting shRNA and treated with adenovirus overexpressing SIRT1 or empty vector. Relative amount was normalized to control cells (n=5, *$p<0.05$ versus empty vector, #$p<0.05$ versus SIRT1 OE). FIG. 16D depicts ND1, Cytb, COX1 and ATP6 mRNA analyzed by qPCR in C2C12 cells infected with c-Myc or nontargeting shRNA and treated with adenovirus overexpressing SIRT1 or empty vector. Relative expression values were normalized to control cells (n=6, *$p<0.05$ versus empty vector, #$p<0.05$ versus SIRT1 OE). FIG. 16E depicts TFAM promoter activity measured by luciferase assay in primary WT myoblasts infected with c-Myc or nontargeting shRNA. Relative luciferase values were normalized to control cells (n=4). FIG. 16F depicts TFAM promoter activity full length or c-Myc consensus sequence mutation measured by luciferase assay in primary WT myoblasts infected with c-Myc or empty vector. Relative luciferase values were normalized to control cells (n=4). FIG. 16G depicts TFAM promoter activity full length or c-Myc consensus sequence mutation measured by luciferase assay in primary WT myoblasts infected with adenovirus expressing PGC-1α or empty vector. Relative luciferase values were normalized to control cells (n=4). FIG. 16H depicts TFAM promoter activity full length or c-Myc consensus sequence mutation measured by luciferase assay in primary WT myoblasts infected with adenovirus expressing SIRT1 or empty vector. Relative luciferase values were normalized to control cells (n=4). FIGS. 16I and 16J depict chromatin immunoprecipitation (I) and respective quantification by qPCR (J) of c-Myc and HIF-1α to the TFAM promoter in SIRT1 flox/flox Cre-ERT2 primary myoblasts treated with vehicle, or OHT to induce SIRT1 excision for 24 hours. FIG. 16K depicts chromatin immunoprecipitation of c-Myc to the TFAM promoter in SIRT1 flox/flox Cre-ERT2 primary myoblasts treated with vehicle, or OHT to induce SIRT1 excision for 24 hours infected with HIF-1α or nontargeting shRNA. FIG. 16L depicts TFAM promoter activity measured by luciferase assay in SIRT1 flox/flox Cre-ERT2 primary myoblasts treated with vehicle, or OHT to induce SIRT1 excision for 24 hours infected with HIF-1α or nontargeting shRNA. Relative luciferase values were normalized to control cells (n=4). Values are expressed as mean±SEM.

FIG. 17 reveals that increasing NAD levels rescues age-related mitochondrial and muscle dysfunction through a SIRT1-HIF-1α pathway. FIG. 17A depicts NAD levels in gastrocnemius of 3- and 24-month-old mice treated with either the vehicle (PBS) or NMN (n=5, *$p<0.05$ versus 3-month-old PBS animals, #$p<0.05$ versus 24-month-old PBS animals). FIG. 17B depicts ATP content in gastrocnemius of 6- and 22-month-old mice treated with either the vehicle (PBS) or NMN (n=6). FIG. 17C depicts expression of mitochondrial-encoded genes (ND1, Cytb, COX1 and ATP6) analyzed by qPCR in in gastrocnemius of 6- and 22-month-old mice treated with either the vehicle (PBS) or NMN. Relative expression values were normalized to 6-months old PBS mice (n=6). FIG. 17D depicts a representative immunoblot for VHL, HIF-1α and Tubulin in gastrocnemius of b- and 22-month-old mice treated with either the vehicle (PBS) or NMN. FIG. 17E depicts lactate levels in gastrocnemius of 6- and 22-month-old mice treated with either the vehicle. (PBS) or NMN (n=6). FIG. 17F depicts expression of mitochondrial-encoded genes (ND1, Cytb, COX1 and ATP6) analyzed by qPCR in gastrocnemius of WT and Egln1 KO mice treated with either the vehicle (PBS) or NMN. Relative expression values were normalized to WT PBS mice (n=5). Egln1 encodes the HIF-1 prolyl-hydroxylase that targets HIF-1 for degradation. FIG. 17G depicts ATP content in gastrocnemius of WT and Egln1 KO mice treated with either the vehicle (PBS) or NMN (n=5). FIG. 17H depicts expression of mitochondrial-enoded genes (ND1, Cytb, COX1 and ATP6) analyzed by qPCR in primary myoblasts WT cells infected with NMNAT1 or nontargeting shRNA treated with either the vehicle (PBS) or NMN. Relative expression values were normalized to control cells (n=4). FIG. 17I depicts expression of mitochondrial-encoded genes (ND1, Cytb, COX1 and ATP6) analyzed by qPCR in gastrocnemius of WT and SIRT1 KO mice treated with either the vehicle (PBS) or NMN. Relative expression values were normalized to WT PBS mice (n=4). FIG. 17J depicts a representative immunoblot for Atrogin-2, MuRF1 and Tubulin in gastrocnemius of 6- and 22-month-old mice treated with either the vehicle (PBS) or NMN. FIG. 17K depicts a representative immunoblot for p-AKT, AKT, p-IRS-1, IRS-1 in gastrocnemius of 6- and 22-month-old mice treated with either the vehicle (PBS) or NMN.

FIG. 8 provides additional data related to the content of FIG. 11. FIG. 18A depicts a representative immunoblot for NMNAT1 and Tubulin in primary myoblasts WT cells infected with NMNAT1 or nontargeting shRNA. Relative amount was normalized to control cells. FIG. 18B depicts a representative immunoblot for NMNAT2 and Tubulin in primary myoblasts WT cells infected with NMNAT2 or nontargeting shRNA. Relative amount was normalized to control cells. FIG. 18C depicts a representative immunoblot for NMNAT3 and Tubulin in primary myoblasts WT cells infected with NMNAT3 or nontargeting shRNA. Relative amount was normalized to control cells. FIG. 18D depicts ATP content in primary myoblasts WT cells infected with NMNAT2 or nontargeting shRNA (n=4). FIG. 18E depicts ATP content in primary myoblasts WT cells infected with NMNAT3 or nontargeting shRNA (n=4). FIG. 18F depicts SIRT1 mRNA analyzed by qPCR in gastrocnemius of 6-, 22-, and 30-month-old mice. Relative expression values were normalized to 6-month-old mice (n=5, *$p<0.05$ versus 6-month-old animals). FIG. 18G depicts a representative immunoblot for SIRT1 and tubulin in gastrocnemius of 6-, 22-, and 30-month-old mice. Values are expressed as mean±SEM.

FIG. 19 provides additional data related to the content of FIG. 12. FIG. 19A depicts Cytochrome c Oxidase (COX) activity in gastrocnemius of WT and SIRT1 KO mice (n=5). FIG. 19B depicts Succinate Dehydrogenase (SDH) activity in gastrocnemius of WT and SIRT1 KO mice (n=5). FIG. 19C depicts mitochondrial ribosomal rRNA expression analyzed by qPCR in gastrocnemius of WT and SIRT1 KO mice. Relative expression values were normalized to WT mice (n=5). FIG. 19D depicts expression of nuclear (NDUFS8, SDHb, Uqcrc1, COX5b, ATP5a1) versus mitochondrial-encoded genes (ND1, Cytb, COX1, ATP6) analyzed by qPCR in liver of WT and SIRT1 KO mice. Relative expression values were normalized to WT mice (n=4, *p<0.05 versus control). FIG. 19E depicts expression of nuclear (NDUFS8, SDHb, Uqcrc1, COX5b, ATP5a1) versus mitochondrial-encoded genes (ND1, Cytb, COX1, ATP6) analyzed by qPCR in white adipose tissue of WT and SIRT1 KO mice. Relative expression values were normalized to WT mice (n=5). FIG. 19F depicts expression of nuclear (NDUFS8, SDHb, Uqcrc1, COX5b, ATP5a1) versus mitochondrial-encoded genes (ND1, Cytb, COX1, ATP6) analyzed by qPCR in brain of WT and SIRT1 KO mice. Relative expression values were normalized to WT mice (n=5). FIG. 19G depicts expression of nuclear (NDUFS8, SDHb, Uqcrc1, COX5b, ATP5a1) versus mitochondrial-encoded genes (ND1, Cytb, COX1, ATP6) analyzed by qPCR in heart of WT and SIRT1 KO mice. Relative expression values were normalized to WT mice (n=5). FIG. 19H depicts expression of inflammatory markers (TNF-α, IL-6, IL-18 and Nlrp3) analyzed by qPCR in gastrocnemius of WT and SIRT1 KO mice. Relative expression values were normalized to WT mice (n=5). Values are expressed as mean±SEM.

FIG. 20 provides additional data related to the content of FIG. 13. FIG. 20A depicts expression of nuclear (NDUFS8, SDHb, Uqcrc1, COX5b, ATP5a1) versus mitochondrial-encoded genes (ND1, Cytb, COX1, ATP6) analyzed by qPCR in gastrocnemius of WT and SIRT1 KO mice under fed and fasted conditions. Relative expression values were normalized to WT Fed mice (n=5). FIG. 20B depicts mitochondrial DNA content analyzed by qPCR in SIRT1 flox/flox Cre-ERT2 primary myoblasts treated with vehicle, or OHT to induce SIRT1 excision for 6, 12, 24 and 48 hours. Relative amount was normalized to control cells (n=5). FIG. 20C depicts mitochondrial membrane potential analyzed by TMRM fluorescence in SIRT1 flox/flox Cre-ERT2 primary myoblasts treated with vehicle, or OHT to induce SIRT1 excision for 6, 12, 24 and 48 hours (n=5). FIG. 20D depicts a representative immunoblot for Flag and Tubulin in PGC-1α/β knockout myotubes infected with adenovirus expressing a flag-PGC-1α WT, PGC-1α T177A/S538A mutant or empty vector. FIG. 20E depicts a representative immunoblot for p-AMPK (Thr172) and AMPK in gastrocnemius of WT and SIRT1 KO mice under fed and fasted conditions. FIG. 20F depicts a representative immunoblot for p-AMPK (Thr172) and AMPK in gastrocnemius of 6- and 22-months-old mice. FIG. 20G depicts PGC-1α, PGC-1β, NRF-1, NRF-2m TFB1M, TFB2M, POLMRT and Twinkle expression in gastrocnemius of WT and SIRT1 KO mice. Relative expression values were normalized to WT mice (n=5). FIG. 20H depicts a representative immunoblot for TFAm and Tubulin in primary WT myoblasts infected with adenovirus expressing TFAM or empty vector. FIG. 20I depicts expression of nuclear (NDUFS8, SDHb, Uqcrc1, COX5b, ATP5a1) versus mitochondrial-encoded genes (ND1, Cytb, COX1, ATP6) analyzed by qPCR in primary WT myoblasts infected with adenovirus expressing TFAM or empty vector. Relative expression values were normalized to control cells (n=4). FIG. 20J depicts mitochondrial DNA content analyzed by qPCR in primary WT myoblasts infected with adenovirus expressing TFAM or empty vector. Relative amount was normalized to control cells (n=4). FIG. 20K depicts ATP content in primary WT myoblasts infected with adenovirus expressing TFAM or empty vector (n=4). Values are expressed as mean±SEM.

FIG. 21 provides additional data related to the content of FIG. 14. FIG. 21A depicts HIF-1α target genes (PGK-1, Glut1, PDK1 and Vegfa) expression in gastrocnemius of WT and SIRT1 KO mice. Relative expression values were normalized to WT mice (n=5). FIG. 21B depicts hypoxia response element activity in primary myoblasts isolated from WT and SIRT1 KO mice and treated with or without DMOG. Relative luciferase activity was normalized to WT cells (n=6, *p<0.05 versus WT). FIG. 21C depicts a representative immunoblot of HIF-1α and Tubulin in PGC-1α/β KO myotubes treated with adenovirus overexpressing SIRT1 or empty vector as well as treatment with DMSO or with HIF stabilizing compound DMOG. FIG. 21D depicts NAD+/NADH ration measured in primary WT myoblasts treated with either 10 mM pyruvate, 10 mM lactate or vehicle for 24 h (n=4). FIG. 21E depicts a representative immunoblot of HIF-1α and Tubulin in primary WT myoblasts treated with 10 mM pyruvate, 10 mM lactate or vehicle for 24 h. FIG. 21F depicts expression of mitochondrial-encoded genes (ND1, Cytb, COX1 and ATP6) in PGC-1α/β KO myotubes treated with 10 mM pyruvate, 10 mM lactate or vehicle for 24 h in the presence or absence of DMOG. Relative expression values were normalized to control cells (n=4). FIG. 21G depicts a representative immunoblot for SIRT1, HIF-1α and Tubulin in gastrocnemius of WT and SIRT1-tg mice treated with vehicle (PBS) or DMOG. FIG. 21H depicts expression of mitochondrial-encoded genes (ND1, Cytb, COX1 and ATP6) in gastrocnemius of WT and SIRT1-tg mice treated with vehicle (PBS) or DMOG. Relative expression values were normalized to WT PBS mice (n=5). FIG. 21I depicts ATP content in gastrocnemius of WT and SIRT1-tg mice treated with vehicle (PBS) or DMOG (n=5). FIG. 21J depicts mitochondrial DNA content analyzed by qPCR in control, HIF-1α DPA or HIF-2α DPA C2C12 cells treated with adenovirus overexpressing SIRT1 or empty vector. Relative amount was normalized to control cells (n=5, *p<0.05 versus empty vector, #p<0.05 versus SIRT1 OE). FIG. 21K depicts ARNT mRNA analyzed by qPCR in C2C12 cells infected with ARNT or nontargeting shRNA. Relative expression values were normalized to control cells (n=4, *p<0.05 versus control). FIG. 21L depicts mitochondrial DNA content analyzed by qPCR in C2C12 cells infected with ARNT or nontargeting shRNA. Relative amount was normalized to control cells (n=5, *p<0.05 versus control). FIG. 21M depicts ND1, Cytb, COX1 and ATP6 mRNA analyzed by qPCR in C2C12 cells infected with ARNT or nontargeting shRNA. Relative levels were normalized to control cells (n=6, *p<0.05 versus control). FIG. 21N depicts ATP content in C2C12 cells infected with ARNT or nontargeting shRNA. Relative expression values were normalized to control cells (n=4, *p<0.05 versus control). Values are expressed as mean±SEM.

FIG. 22 provides additional data related to the content of FIG. 15. FIG. 22A depicts a representative immunoblot for COX2, SIRT1, HIF1-α, VHL, TFAM and Tubulin in parental or rho0 cells derived from SIRT1 flox/flox Cre-ERT2 primary myoblasts treated with vehicle, or OHT for 24 h to induce SIRT1 excision. FIG. 22B depicts ROS levels, measured by DHE fluorescence intensity, in SIRT1 flox/flox Cre-ERT2 primary myoblasts treated with vehicle, or OHT for 6, 12, 24 and 48 hours to induce SIRT1 excision. Relative expression values were normalized to control cells (n=4). FIG. 22C depicts a representative immunoblot for HA and Tubulin in SIRT1 flox/flox Cre-ERT2 primary myoblasts treated with vehicle, or OHT for 24 h to induce SIRT1 excision and infected with HA-HIF-1α, the Q and R mutants of the K709 and Q mutant of K674. FIG. 22D depicts a representative immunoblot for HIF-1α-OH, HIF-1α and Tubulin in SIRT1 flox/flox Cre-ERT2 primary myoblasts treated with vehicle, or OHT for 24 h to induce SIRT1 excision in the presence and absence of the proteasome inhibitor, MG-132. FIG. 22E depicts a representative immunoblot for HIF-2α and Tubulin in gastrocnemius of WT and SIRT1 KO mice and in SIRT1 flox/flox Cre-ERT2 primary myoblasts treated with vehicle, or OHT for 24 h to induce SIRT1 excision or treated with DMOG to stabilize HIFα. FIG. 22F depicts HIF-2α target genes (Epo, Cacna1a, Angpt2 and Ptplz1) expression in gastrocnemius of WT and SIRT1 KO mice. Relative expression values were normalized to WT mice (n=5).

FIG. 23 provides additional data related to the content of FIG. 16. FIG. 23A depicts a representative immunoblot for c-Myc and tubulin in C2C12 cells overexpressing c-Myc. FIG. 23B depicts mitochondrial DNA content analyzed by qPCR in C2C12 cells overexpressing c-Myc. Relative amount was normalized to control cells (n=5, *p<0.05 versus empty vector, #p<0.05 versus c-Myc OE). FIG. 23C depicts ND1, Cytb, COX1 and ATP6 mRNA analyzed by qPCR in C2C12 cells overexpressing c-Myc. Relative expression values were normalized to control cells (n=6, *p<0.05 versus empty vector, #p<0.05 versus c-Myc OE). FIG. 23D depicts ATP content in C2C12 cells overexpressing c-Myc. (n=6, *p<0.05 versus empty vector, #p<0.05 versus c-Myc OE). FIG. 23E depicts TFAM promoter activity full length or c-Myc consensus sequence mutation measured by luciferase assay in primary WT myoblasts treated with vehicle (DMSO) or DMOG. Relative luciferase values were normalized to control cells (n=4). FIG. 23F depicts TFAM promoter activity full length or c-Myc consensus sequence mutation measured by luciferase assay in SIRT1 flox/flox Cre-ERT2 primary myoblasts treated with vehicle, or OHT for 24 h to induce SIRT1 excision. Relative luciferase values were normalized to control cells (n=4). FIGS. 23G and 23H depict chromatin immunoprecipitation (G) and respective quantification by qPCR (H) of HIF-1α to the LDHA gene in SIRT1 flox/flox Cre-ERT2 primary myoblasts treated with vehicle, or OHT to induce SIRT1 excision for 24 hours.

FIG. 24 provides additional data related to the content of FIG. 17. FIG. 24A depicts NAD+ levels in gastrocnemius of 6- and 22-month AL and 22-month old CR mice (n=5, *p<0.05 versus 6-month-old animals #p<0.05 versus 22-month-old AL mice). FIG. 24B depicts ATP content in skeletal muscle of 6- and 22-month AL and 22-month old CR mice (n=5, *p<0.05 versus 6 month old animals #p<0.05 versus 22 month old AL mice). FIG. 24C depicts Cytochrome c Oxidase Activity (Cox) activity in skeletal muscle of 6- and 22-month AL and 22-month old CR mice (n=4, *p<0.05 versus 6-month-old animals #p<0.05 versus 22-month-old AL mice). FIG. 24D depicts mitochondrial DNA content analyzed by qPCR in gastrocnemius of 6- and 22-month AL and 22-month old CR mice. Relative amount was normalized to 6-month-old mice (n=5, *p<0.05 versus 6-month-old animals #p<0.05 versus 22-month-old AL mice). FIG. 24E depicts ND1, Cytb, COX1 and ATP6 mRNA analyzed by qPCR in gastrocnemius of 6- and 22-month AL and 22-month old CR mice. Relative expression values were normalized to 6-month-old mice (n=5, *p<0.05 versus 6-month-old animals #p<0.05 versus 22-month-old AL mice). FIG. 24F depicts a representative immunoblot for COX2, COX4, and tubulin in gastrocnemius of 22-month-old AL and CR mice. FIG. 24G depicts a representative immunoblot for HIF1α, and tubulin in gastrocnemius of 6- and 22-month AL and 22-month old CR mice. FIG. 24H depicts Cytochrome c Oxidase Activity (Cox) activity in gastrocnemius of 3- and 24-month-old mice treated with either the vehicle (PBS) or NMN (n=5, *p<0.05 versus 3-month-old PBS animals, #p<0.05 versus 24-month-old PBS animals). FIG. 24I depicts mitochondrial DNA content in in gastrocnemius of 6- and 22-month-old mice treated with either the vehicle (PBS) or NMN. Relative amount was normalized to 6-months-old PBS mice (n=6). FIG. 24J depicts expression of inflammatory markers (TNF-α, IL-6 and IL-18) in gastrocnemius of 6- and 22-month-old mice treated with either the vehicle (PBS) or NMN. Relative expression levels were normalized to 6-months-old PBS mice (n=6).

FIG. 26 depicts HIF-1alpha levels and shows that that the downstream effects on metabolism promote cancer proliferation via the Warburg effect. FIG. 26A reveals that HIF-1alpha is regulated at the protein levels by prolylhydroxylation and proteasome degradation. EGNL1=prolylhydroxylase of HIF-1, hydroxylated form of HIF-1 is recognized by VHL, an E3 ubiquitin ligase. FIG. 26B reveals that HIF-1alpha stabilization promotes cancer by activating angiogenesis and cell survival gene expression programs, and that HIF-1alpha stabilization promotes cell proliferation by inducing a metabolic reprogramming, the Warburg effect, diverting the carbons away from oxidation by the mitochondrial electron transport chain (ETC) and promoting glycolysis. FIG. 26C demonstrates NAD+ levels in gastrocnemius of 3- and 24-month-old mice treated with either the vehicle (PBS) or NMN (n=5, *p<0.05 versus 3-month-old PBS animals, #p<0.05 versus 24-month-old PBS animals). FIG. 26D demonstrates ATP content in gastrocnemius of 3- and 24-month-old mice treated with either the vehicle (PBS) or NMN (n=6). FIG. 26E demonstrates expression of mitochondrial-encoded ETC genes (ND1, Cytb, COX1 and ATP6) analyzed by qPCR in in gastrocnemius of 6- and 22-month-old mice treated with either the vehicle (PBS) or NMN. Relative expression values were normalized to 6-months old PBS mice (n=6). FIG. 26F demonstrates representative immunoblot for VHL, HIF-1α and Tubulin in gastrocnemius of 6- and 22-month-old mice treated with either the vehicle (PBS) or NMN. FIG. 26G demonstrates expression of HIF-1α target genes (PGK-1, Glut1, PDK1 and Vegfa) analyzed by qPCR in in gastrocnemius of 3- and 24-month-old mice treated with either the vehicle (PBS) or NMN. Relative expression values were normalized to 6-months old PBS mice (n=5). FIG. 26H demonstrates lactate levels in gastrocnemius of 6- and 22-month-old mice treated with either the vehicle (PBS) or NMN (n=6). FIG. 26I demonstrates expression of mitochondrial-encoded genes (ND1, Cytb, COX1 and ATP6) analyzed by qPCR in gastrocnemius of WT and Egln1 KO mice treated with either the vehicle (PBS) or NMN. Relative expression values were normalized to WT PBS mice (n=5). FIG. 26J demonstrates ATP content in gastrocnemius of WT and Egln1 KO mice treated with either the vehicle (PBS) or NMN (n=5). FIG. 26K demonstrates expression of mitochondrial-encoded ETC genes (ND1, Cytb, COX1 and ATP6) analyzed by qPCR in gastrocnemius of WT and SIRT1 KO mice treated with either the vehicle (PBS) or NMN. Relative expression values were normalized to WT PBS mice (n=4). NMN treatment consisted of IP injections of 500 mg/kg/day for 7 consecutive days in C57BL6J mice.

FIGS. 27A and B demonstrate that HIF-1alpha stabilization and target genes are modulated by NAD biosynthesis (NMNAT-1 and NAMPT). The NAD+ biosynthetic pathway in mammals is depicted. There are 3 NMNAT paralogs—NMNAT-1 is the nuclear form. NMNAT-1, a nuclear adenylyltransferase, converts NaMN and NMN to NAAD and NAD+. FIG. 27C provides a representative immunoblot for NMNAT1 and Tubulin in primary WT myoblasts infected with NMNAT1 or nontargeting shRNA. FIG. 27D demonstrates that VHL is a prolyhydroxylase that modified HIF-1 so it can be recognized by VHL mRNA analyzed by qPCR in primary WT myoblasts infected with NMNAT1 or nontargeting shRNA. Relative expression values were normalized to control cells (n=4). FIG. 27E demonstrates a representative immunoblot for VHL, HIF-1α and Tubulin in primary myoblasts WT cells infected with NMNAT-1 or nontargeting shRNA. FIG. 27F demonstrates expression of HIF-1alpha target genes (PGK-1, Glut1, PDK1 and Vegfa) analyzed by qPCR in primary WT myoblasts infected with NMNAT1 or nontargeting shRNA. Relative expression values were normalized to control cells (n=4). FIG. 27G demonstrates NAMPT mRNA analyzed by qPCR in C2C12 myoblasts infected with NAMPT or nontargeting shRNA. Relative expression values were normalized to control cells (n=4). FIG. 27H demonstrates hypoxia response element activity in C2C23 myoblasts infected with NAMPT or nontargeting shRNA. Relative luciferase activity was normalized to control cells (n=4). In some embodiments, NaMN, NMN and/or NR (nicotinamide riboside) are used as a starting material to raise NAD+.

FIG. 28 demonstrates that caloric restriction, a known intervention that suppresses most cancers, maintains NAD+ levels and shows the same effects as NMN on VHL/HIF1. FIG. 28A demonstrates NAD+ levels in gastrocnemius of 6- and 22-month AL and 22-month old CR mice (n=5, *p<0.05 versus 6-month-old animals #p<0.05 versus 22-month-old AL mice). FIG. 28B demonstrates a representative immunoblot for HIF1α, and tubulin in gastrocnemius of 6- and 22-month AL and 22-month old CR mice. FIG. 28C demonstrates HIF-1 gene targets, PGK-1, Glut1, PKD1, and VEGFa mRNA analyzed by qPCR in gastrocnemius 6- and 22-month AL and 22-month old CR mice. Relative expression values were normalized to 6-month-old mice. (n=5, *p<0.05 versus 6-month-old animals #p<0.05 versus 22-month-old AL mice).

DETAILED DESCRIPTION OF THE INVENTION

Figure 4D:
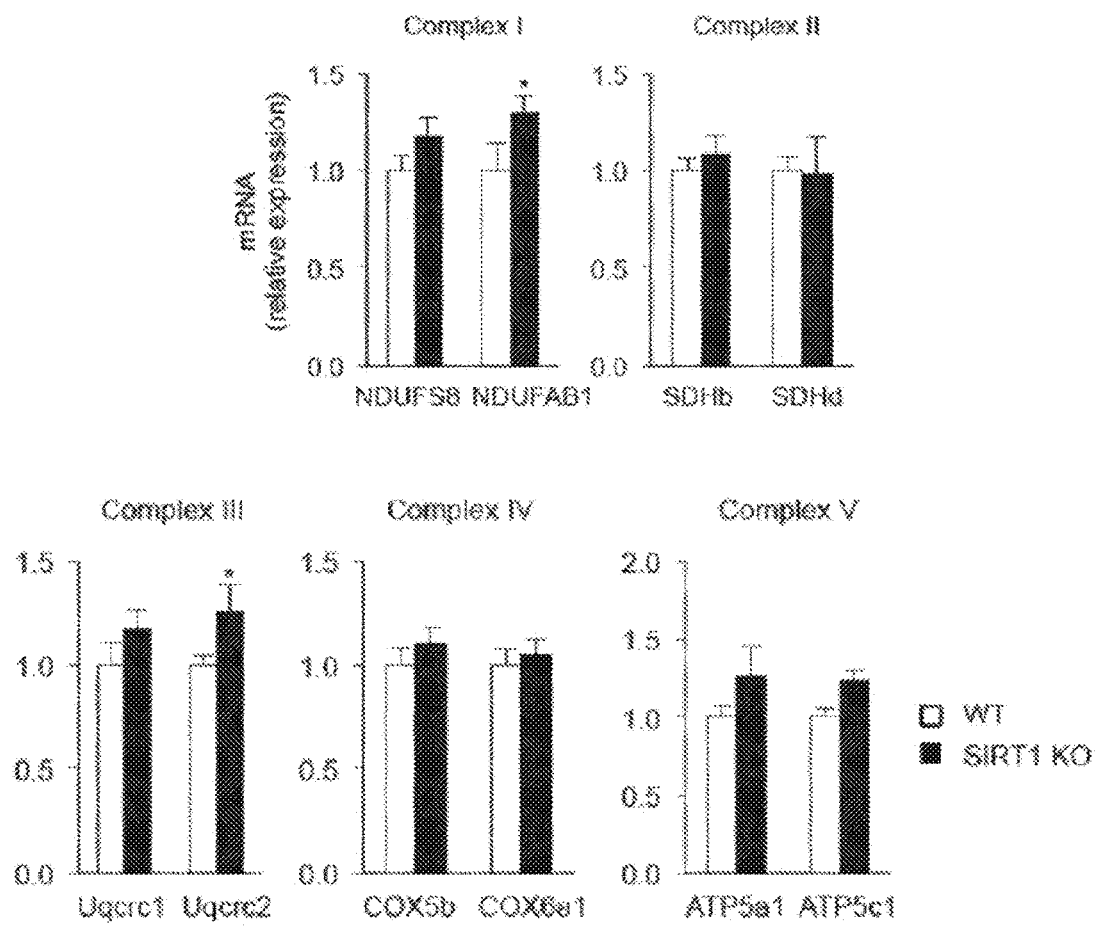
FIG. 4 shows loss of SIRT1 causes a specific decrease in the expression of mitochondrially-encoded genes resulting in genome asynchrony and mitochondrial dysfunction. (A) Mitochondrial membrane potential of isolated mitochondria from skeletal muscle of WT and SIRT1 KO mice (n=4). (B) ATP content from gastrocnemius of WT and SIRT1 KO mice (n=4). (C) Electronic microscopy analysis of gastrocnemius from WT and SIRT1 KO mice and the respective mitochondrial area quantification (n=4). (D-E) NDUFS8, NDUFAS, SDHb, SDHd, Uqcrc1, Uqcrc2, COX5b, Cox6a1, ATP5a1, ATPb1 (D), ND1, ND2, ND3, ND4, ND41, ND5, ND6, CYTB, COX1, COX2, COX3, ATP6 and ATP8 (E) mRNA analyzed by qPCR in gastrocnemius of WT and SIRT1 KO mice. Relative expression values were normalized to WT mice (n=4). (F) Representative immunoblot for COX2 and COX4 in gastrocnemius of WT and SIRT1 KO mice. (G) Cytochrome c Oxidase (COX) activity in gastrocnemius of WT and SIRT1 KO mice (n=5). (H) Succinate Dehydrogenase (SDH) activity in gastrocnemius of WT and SIRT1 KO mice (n=5). (I) Mitochondrial DNA content analyzed by qPCR in gastrocnemius of WT and SIRT1 KO mice Relative amount was normalized to WT mice (n=4). Values are expressed as mean±SEM ($*p<0.05$ versus WT animals).
Figure 4E:
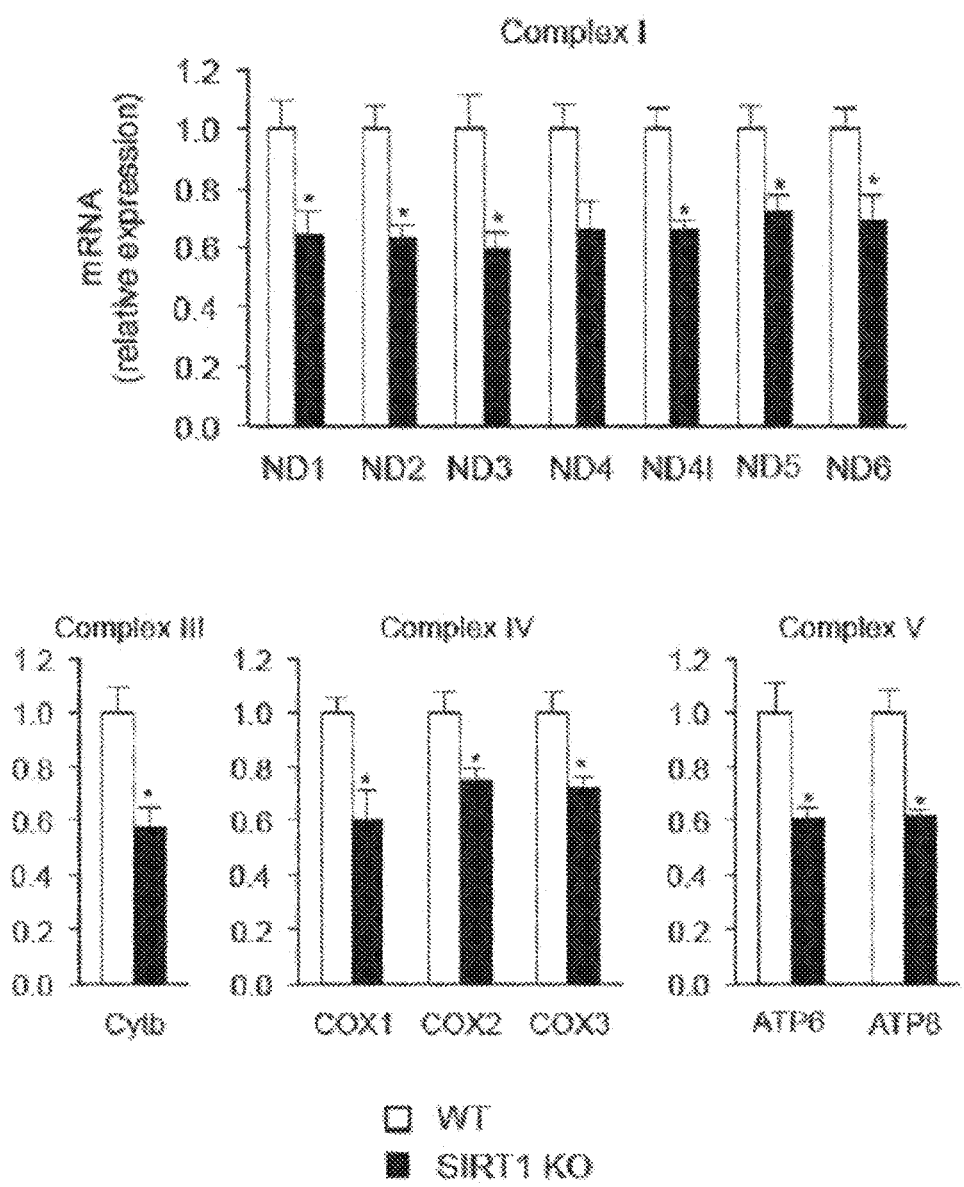

Disclosed herein are novel compositions and methods for the treatment of age-related diseases, the treatment of mitochondrial diseases, the improvement of stress resistance, the improvement of resistance to hypoxia and the extension of life span. Also described herein are methods for the identification of agents useful in the foregoing methods.

As disclosed herein, the instant inventors discovered that HIF-1α interacts with c-Myc to inhibit c-Myc activity, which results in mitochondrial dysfunction during the aging process. Agents that reduce HIF-1α's ability to inhibit c-Myc, including, for example, agents that inhibit the formation of a complex between HIF-1α and c-Myc, convey beneficial effects on metabolism and mitochondrial function in aging tissues. Such agents can, for example, inhibit complex formation by targeting the domain of HIF-1α that is required for formation of a complex with c-Myc (e.g., amino acids 167-329 of the human HIF-1α protein). Such agents may also, for example, prevent HIF-1α from altering c-Myc activity, abundance and/or its localization within the cell.

Thus, in certain embodiments, the instant invention relates to compositions and/or methods for the treatment of age-related diseases, the treatment of mitochondrial diseases, the improvement of the stress response, the improvement of hypoxia resistance and/or the improvement of life span by administering an agent that reduces HIF-1α's inhibition of c-Myc. In some embodiments, the agent reduces HIF-1α's inhibition of c-Myc by acting to inhibit of the formation of a HIF-1α/c-Myc complex. In some embodiments, the agent induces a conformational change in HIF-1α or c-Myc that abrogates their interaction and/or alters the ability of HIF-1α to affect c-Myc activity, protein levels or cell localization. In some embodiments the agent is an antibody, an antigen binding fragment thereof, a small molecule and/or a polypeptide that binds to HIF-1α or c-Myc. For example, in some embodiments the agents described herein bind to the HIF-1α domain required for c-Myc complex formation.

Definitions

For convenience, certain terms employed in the specification, examples, and appended claims are collected here.

As used herein, the term "administering" means providing a pharmaceutical agent or composition to a subject, and includes, but is not limited to, administering by a medical professional and self-administering.

The term "agent" is used herein to denote a chemical compound, a small molecule, a mixture of chemical compounds and/or a biological macromolecule (such as a nucleic acid, an antibody, an antibody fragment, a protein or a peptide). Agents may be identified as having a particular activity by screening assays described herein below. The activity of such agents may render them suitable as a "therapeutic agent" which is a biologically, physiologically, or pharmacologically active substance (or substances) that acts locally or systemically in a subject.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

As used herein, the term "antibody" may refer to both an intact antibody and an antigen binding fragment thereof. Intact antibodies are glycoproteins that include at least two heavy (H) chains and two light (L) chains inter-connected by disulfide bonds. Each heavy chain includes a heavy chain variable region (abbreviated herein as $V_H$) and a heavy chain constant region. Each light chain includes a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" includes, for example, monoclonal antibodies, polyclonal antibodies, chimeric antibodies, humanized antibodies, human antibodies, multispecific antibodies (e.g., bispecific antibodies), single-chain antibodies and antigen-binding antibody fragments. An "isolated antibody," as used herein, refers to an antibody which is substantially free of other antibodies having different antigenic specificities. An isolated antibody may, however, have some cross-reactivity to other, related antigens.

The terms "antigen binding fragment" and "antigen-binding portion" of an antibody, as used herein, refers to one or more fragments of an antibody that retain the ability to bind to an antigen. Examples of binding fragments encompassed within the term "antigen-binding fragment" of an antibody include Fab, Fab', F(ab')$_2$, Fv, scFv, disulfide linked Fv, Fd, diabodies, single-chain antibodies, NANOBODIES®, isolated CDRH3, and other antibody fragments that retain at least a portion of the variable region of an intact antibody. These antibody fragments can be obtained using conventional recombinant and/or enzymatic techniques and can be screened for antigen binding in the same manner as intact antibodies.

As used herein, the term "c-Myc" refers to the c-Myc transcription factor originally identified as an oncogene in Burkett's lymphoma patients. c-Myc is a highly conserved transcriptional regulator present in many organisms. Exemplary c-Myc amino acid sequences are provided in FIG. 3.

The terms "CDR", and its plural "CDRs", refer to a complementarity determining region (CDR) of an antibody or antibody fragment, which determine the binding character of an antibody or antibody fragment. In most instances, three CDRs are present in a light chain variable region (CDRL1, CDRL2 and CDRL3) and three CDRs are present in a heavy chain variable region (CDRH1, CDRH2 and CDRH3). CDRs contribute to the functional activity of an antibody molecule and are separated by amino acid sequences that comprise scaffolding or framework regions. Among the various CDRs, the CDR3 sequences, and particularly CDRH3, are the most diverse and therefore have the strongest contribution to antibody specificity. There are at least two techniques for determining CDRs: (1) an approach based on cross-species sequence variability (i.e., Kabat et al., Sequences of Proteins of Immunological Interest (National Institute of Health, Bethesda, Md. (1987), incorporated by reference in its entirety); and (2) an approach based on crystallographic studies of antigen-antibody complexes (Chothia et al., Nature, 342:877 (1989), incorporated by reference in its entirety).

"Diabetes" refers to high blood sugar or ketoacidosis, as well as chronic, general metabolic abnormalities arising from a prolonged high blood sugar status or a decrease in glucose tolerance. "Diabetes" encompasses both the type I and type II (Non-Insulin Dependent Diabetes Mellitus or NIDDM) forms of the disease. The risk factors for diabetes include the following factors: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

The term "epitope" means a protein determinant capable of specific binding to an antibody. Epitopes usually consist of chemically active surface groupings of molecules such as amino acids or sugar side chains. Certain epitopes can be defined by a particular sequence of amino acids to which an antibody is capable of binding, such as, for example, the interaction domain sequences provided in FIG. 2.

As used herein, the term "HIF-1α" refers to the Hypoxia-Inducible Factor 1, alpha subunit protein. HIF-1α is a highly conserved protein present in most, if not all, metazoa. Exemplary HIF-1α amino acid sequences are provided in FIG. 1. Under certain conditions, HIF-1α forms a complex with c-Myc. A specific interaction domain of the HIF-1α protein is required for this complex formation. Exemplary interaction domain sequences are provided in FIG. 2.

As used herein, the term "humanized antibody" refers to an antibody that has at least one CDR derived from a mammal other than a human, and a FR region and the constant region of a human antibody. A humanized antibody is useful as an effective component in a therapeutic agent according to the present invention since antigenicity of the humanized antibody in human body is lowered.

An "insulin resistance disorder," as discussed herein, refers to any disease or condition that is caused by or contributed to by insulin resistance. Examples include: diabetes, gestational diabetes, obesity, metabolic syndrome, insulin-resistance syndromes, syndrome X, insulin resistance, high blood pressure, hypertension, high blood cholesterol, dyslipidemia, hyperlipidemia, dyslipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive nephrosclerosis some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related disorders, such as gallstones, cholescystitis and cholelithiasis, gout, obstructive sleep apnea and respiratory problems, osteoarthritis, and prevention and treatment of bone loss, e.g. osteoporosis.

The term "isolated polypeptide" refers to a polypeptide, in certain embodiments prepared from recombinant DNA or RNA, or of synthetic origin, or some combination thereof, which (1) is not associated with proteins that it is normally found with in nature, (2) is isolated from the cell in which it normally occurs, (3) is isolated free of other proteins from the same cellular source, (4) is expressed by a cell from a different species, or (5) does not occur in nature.

As used herein, the term "monoclonal antibody" refers to an antibody obtained from a population of substantially homogeneous antibodies that specifically bind to the same epitope, i.e., the individual antibodies comprising the population are identical except for possible naturally occurring mutations that may be present in minor amounts. The modifier "monoclonal" indicates the character of the antibody as being obtained from a substantially homogeneous population of antibodies, and is not to be construed as requiring production of the antibody by any particular method.

"Obese" individuals or individuals suffering from obesity are generally individuals having a body mass index (BMI) of at least 25 or greater. Obesity may or may not be associated with insulin resistance.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body "Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon-containing) or inorganic molecules. Many pharmaceutical companies have extensive libraries of chemical and/or biological mixtures, often fungal, bacterial, or algal extracts, which can be screened with any of the assays described herein.

"Stress" refers to any non-optimal condition for growth, development or reproduction. A "stress condition" can be exposure to heatshock; osmotic stress; a DNA damaging agent; inadequate salt level; inadequate nitrogen levels; inadequate nutrient level; radiation or a toxic compound, e.g., a toxin or chemical warfare agent (such as dirty bombs and other weapons that may be used in bioterrorism). "Inadequate levels" refer to levels that result in non-optimal condition for growth, development or reproduction.

As used herein, "specific binding" refers to the ability of an antibody to bind to a predetermined antigen or the ability of a polypeptide to bind to its predetermined binding partner. Typically, an antibody or polypeptide specifically binds to its predetermined antigen or binding partner with an affinity corresponding to a $K_D$ of about $10^{-7}$ M or less, and binds to the predetermined antigen/binding partner with an affinity (as expressed by $K_D$) that is at least 10 fold less, at least 100 fold less or at least 1000 fold less than its affinity for binding to a non-specific and unrelated antigen/binding partner (e.g., BSA, casein).

As used herein, the term "subject" means a human or non-human animal selected for treatment or therapy.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

Anti-HIF-1α Antibodies

In certain embodiments, the present invention relates to antibodies and antigen binding fragments thereof that bind specifically to HIF-1α and uses thereof. In some embodiments, the antibodies bind to a domain of HIF-1α required for complex formation with c-Myc. In some embodiments, the HIF-1α domain has an amino acid sequence selected from SEQ ID NOs 11-20. Accordingly, in certain embodiments the antibodies described herein are able to inhibit complex formation between HIF-1α and c-Myc. Such antibodies can be polyclonal or monoclonal and can be, for example, murine, chimeric, humanized or fully human.

Polyclonal antibodies can be prepared by immunizing a suitable subject (e.g. a mouse) with a polypeptide immunogen (e.g., a polypeptide having an amino acid sequence selected from SEQ ID NOs 11-20). The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography to obtain the IgG fraction.

At an appropriate time after immunization, e.g., when the antibody titers are highest, antibody-producing cells can be obtained from the subject and used to prepare monoclonal antibodies using standard techniques, such as the hybridoma technique originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

As an alternative to preparing monoclonal antibody-secreting hybridomas, a monoclonal specific for HIF-1α and/or a polypeptide having an amino acid sequence selected from SEQ ID NOs 11-20 can be identified and isolated by screening a recombinant combinatorial immunoglobulin library (e.g., an antibody phage display library or an antibody yeast display library) with the appropriate polypeptide (e.g. a polypeptide having an amino acid sequence selected from SEQ ID NOs 11-20) to thereby isolate immunoglobulin library members that bind the polypeptide.

Additionally, recombinant antibodies specific for HIF-1α and/or a polypeptide having an amino acid sequence selected from SEQ ID NOs 11-20, such as chimeric or humanized monoclonal antibodies, can be made using standard recombinant DNA techniques. Such chimeric and humanized monoclonal antibodies can be produced by recombinant DNA techniques known in the art, for example using methods described in U.S. Pat. No. 4,816,567; U.S. Pat. No. 5,565,332; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229: 1202-1207; Oi et al. (1986) *Biotechniques* 4:214; Winter U.S. Pat. No. 5,225,539; Jones et al. (1986) *Nature* 321:

552-525; Verhoeyan et al. (1988) *Science* 239:1534; and Beidler et al. (1988) *J. Immunol.* 141:4053-4060.

Human monoclonal antibodies specific for HIF-1α and/or a polypeptide having an amino acid sequence selected from SEQ ID NOs 11-20 can be generated using transgenic or transchromosomal mice carrying parts of the human immune system rather than the mouse system. For example, "HuMAb mice" which contain a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) Nature 368(6474): 856 859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) Handbook of Experimental Pharmacology 113:49 101; Lonberg, N. and Huszar, D. (1995) Intern. Rev. Immunol. Vol. 13: 65 93, and Harding, F. and Lonberg, N. (1995) Ann. N. Y Acad. Sci 764:536 546). The preparation of HuMAb mice is described in Taylor, L. et al. (1992) Nucleic Acids Research 20:6287 6295; Chen, J. et al. (1993) International Immunology 5: 647 656; Tuaillon et al. (1993) Proc. Natl. Acad. Sci USA 90:3720 3724; Choi et al. (1993) Nature Genetics 4:117 123; Chen, J. et al. (1993) EMBO J. 12: 821 830; Tuaillon et al. (1994) J. Immunol. 152:2912 2920; Lonberg et al., (1994) Nature 368(6474): 856 859; Lonberg, N. (1994) Handbook of Experimental Pharmacology 113:49 101; Taylor, L. et al. (1994) International Immunology 6: 579 591; Lonberg, N. and Huszar, D. (1995) Intern. Rev. Immunol. Vol. 13: 65 93; Harding, F. and Lonberg, N. (1995) Ann. N.Y. Acad. Sci 764:536 546; Fishwild, D. et al. (1996) Nature Biotechnology 14: 845 851. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807.

In certain embodiments, the antibodies of the instant invention are able to bind to an epitope of HIF-1α in a domain required for complex formation with c-Myc (e.g., a domain having an amino acid sequence selected from SEQ ID NOs 11-20) with a dissociation constant of no greater than $10^{-6}$, $10^{-7}$, $10^{-8}$ or $10^{-9}$ M. Standard assays to evaluate the binding ability of the antibodies are known in the art, including for example, ELISAs, Western blots and RIAs. The binding kinetics (e.g., binding affinity) of the antibodies also can be assessed by standard assays known in the art, such as by Biacore analysis. In some embodiments, the binding of the antibody to HIF-1α substantially inhibits the ability of c-Myc to form a complex with HIF-1α. As used herein, an antibody substantially inhibits the ability of c-Myc to form a complex with HIF-1α when an excess of antibody reduces the quantity of complex formed to by at least about 20%, 40%, 60% or 80%, 85% or 90% (as measured in an in vitro competitive binding assay).

Soluble HIF-1α Polypeptides

In certain embodiments, the invention relates to isolated polypeptides comprising a HIF-1α domain or fraction thereof required for c-Myc to form a complex with HIF-1α (i.e., comprising a portion of an amino acid sequence selected from SEQ ID NO: 11-20). Such polypeptides can be useful, for example, for inhibiting the ability of c-Myc to form a complex with HIF-1α and for identifying and/or generating antibodies that specifically bind to the c-Myc interaction domain of HIF-1α. In some embodiments, the polypeptide comprises at least 5, 6, 7, 8, 9, 10, 11, 12, 13, 14, 15, 16, 17, 18, 19, 20, 25, 30, 35, 40, 45, 50, 60, 70, 80, 90 or 100 consecutive amino acids of an amino acid sequence selected from SEQ ID NO: 11-20. In some embodiments the polypeptide of the invention comprises less than 100, 90, 80, 70, 60, 50, 40, 30, 25 or 20 consecutive amino acids of the natural HIF-1α protein (e.g., a protein having an amino acid sequence selected from SEQ ID NO: 1-10). In some embodiments, the polypeptide of the invention comprises an amino acid sequence selected from SEQ ID NO: 11-20.

In some embodiments, the polypeptide of the instant invention is able to bind to c-Myc. In some embodiments, the polypeptide binds to c-Myc with a dissociation constant of no greater than $10^{-5}$ M, $10^{-6}$ M, $10^{-7}$ M, $10^{-8}$ M or $10^{-9}$ M. Standard assays to evaluate the binding ability of the polypeptides are known in the art, including for example, ELISAs, Western blots and RIAs and suitable assays are described in the Examples. The binding kinetics (e.g., binding affinity) of the polypeptides also can be assessed by standard assays known in the art, such as by Biacore analysis. In some embodiments, the binding of the polypeptide to c-Myc substantially inhibits the ability of c-Myc to bind to HIF-1α. As used herein, a polypeptide substantially inhibits adhesion of c-Myc to HIF-1α when an excess of polypeptide reduces the quantity of c-Myc bound to HIF-1α by at least about 20%, 40%, 60% or 80%, 85% or 90% (as measured in an in vitro competitive binding assay).

In some embodiments, the polypeptides of the present invention can be isolated from cells or tissue sources by an appropriate purification scheme using standard protein purification techniques. In another embodiment, polypeptides of the present invention are produced by recombinant DNA techniques. Alternatively, polypeptides of the present invention can be chemically synthesized using standard peptide synthesis techniques.

In some embodiments, polypeptides of the present invention comprise an amino acid sequence substantially identical to a sequence selected from SEQ ID NO: 11-20, or a fragment thereof. Accordingly, in another embodiment, the polypeptides of the present invention comprises an amino acid sequence at least about 80%, 85%, 90%, 91%, 92%, 93%, 94%, 95%, 96%, 97%, 98%, 99% or more identical to a sequence selected from SEQ ID NO: 11-20, or a fragment thereof.

In certain embodiments, the polypeptides of the present invention comprise an amino acid identical to a sequence selected from SEQ ID NO: 11-20, or a fragment thereof except for 1 or more (e.g., 1, 2, 3, 4, 5, 6, 7, 8, 9, 10 or more) conservative sequence modifications. As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues of the polypeptides described herein can be replaced with other amino acid residues from the same side chain family and the altered antibody can be tested for retained function using the functional assays described herein.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The invention also provides chimeric or fusion proteins. As used herein, a "chimeric protein" or "fusion protein" comprises a polypeptide(s) of the present invention (e.g., those comprising a sequence selected from SEQ ID NO: 11-20, or a fragment thereof) linked to a distinct polypeptide to which it is not linked in nature. For example, the distinct polypeptide can be fused to the N-terminus or C-terminus of the polypeptide either directly, through a peptide bond, or indirectly through a chemical linker. In some embodiments, the peptide of the instant invention is linked to an immunoglobulin constant domain (e.g., an IgG constant domain, such as a human IgG constant domain).

A chimeric or fusion polypeptide of the present invention can be produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, Ausubel et al., eds., John Wiley & Sons: 1992). Moreover, many expression vectors are commercially available that already encode a fusion moiety.

The polypeptides described herein can be produced in prokaryotic or eukaryotic host cells by expression of polynucleotides encoding a polypeptide(s) of the present invention. Alternatively, such peptides can be synthesized by chemical methods. Methods for expression of heterologous polypeptides in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:501; Chaiken I. M. (1981) CRC Crit. Rev. Biochem. 11:255; Kaiser et al. (1989) Science 243:187; Merrifield, B. (1986) Science 232:342; Kent, S. B. H. (1988) Annu. Rev. Biochem. 57:957; and Offord, R. E. (1980) Semisynthetic Proteins, Wiley Publishing, which are incorporated herein by reference.

Other Inhibitors of HIF-1α/c-Myc Complex Formation

Certain embodiments of the present invention relate to methods of treating age-related and mitochondrial diseases, enhancing stress response, improving resistance to hypoxia and/or increasing life span. These methods include administering that reduces HIF-1α' a ability to inhibit c-Myc function. For example, in certain embodiments the agent inhibits complex formation between HIF-1α and c-Myc. In some embodiments, the agents induce a conformational change in HIF-1α or c-Myc that abrogates their interaction and/or alters the ability of HIF-1α to affect c-Myc activity, protein levels or cell localization.

In some embodiments, any agent that reduces inhibition of c-Myc by HIF-1α can be used to practice the methods of the invention. In some embodiments, the agent inhibits complex formation between HIF-1α and c-Myc. Such agents can be those described herein or those identified through routine screening assays (e.g. the screening assays described herein).

In some embodiments, assays used to identify agents useful in the methods of the present invention include a reaction between a polypeptide comprising a sequence selected from SEQ ID NO: 11-20 or a fragment thereof and one or more assay components. The other components may be either a test compound (e.g. the potential agent), or a combination of test compounds and a c-Myc protein or fragment thereof. Agents identified via such assays, may be useful, for example, for preventing or treating age-related and mitochondrial diseases, enhancing stress response and/or improving life span.

Agents useful in the methods of the present invention may be obtained from any available source, including systematic libraries of natural and/or synthetic compounds. Agents may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of agents may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

Agents useful in the methods of the present invention may be identified, for example, using assays for screening candidate or test compounds which inhibit complex formation between c-Myc and HIF-1α.

The basic principle of the assay systems used to identify compounds that inhibit complex formation between c-Myc and HIF-1α involves preparing a reaction mixture containing a HIF-1α protein or fragment thereof and a c-Myc protein or fragment thereof under conditions and for a time sufficient to allow the HIF-1α protein or fragment thereof to form a complex with the c-Myc protein or fragment thereof. In order to test an agent for modulatory activity, the reaction mixture is prepared in the presence and absence of the test compound. The test compound can be initially included in the reaction mixture, or can be added at a time subsequent to the addition of the HIF-1α protein or fragment thereof and the c-Myc protein or fragment thereof. Control reaction mixtures are incubated without the test compound or with a placebo. The formation of any complexes between the HIF-1α protein or fragment thereof and the c-Myc protein or fragment thereof is then detected. The formation of a complex in the control reaction, but less or no such formation in the reaction mixture containing the test compound, indicates that the compound interferes with the interaction of the HIF-1α protein or fragment thereof and the c-Myc protein or fragment thereof.

The assay for compounds that modulate the interaction of the HIF-1α protein or fragment thereof and the c-Myc protein or fragment thereof may be conducted in a heterogeneous or homogeneous format. Heterogeneous assays involve anchoring either the HIF-1α protein or fragment thereof or the c-Myc protein or fragment thereof onto a solid phase and detecting complexes anchored to the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the HIF-1α protein or fragment thereof and the c-Myc protein or fragment thereof (e.g., by competition) can be identified by conducting the reaction in the presence of the test substance, i.e., by adding the test substance to the reaction mixture prior to or simultaneously with the HIF-1α protein or fragment thereof and the c-Myc protein or fragment thereof. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the HIF-1α protein or fragment thereof or the c-Myc protein or fragment thereof is anchored onto a solid surface or matrix, while the other corresponding non-anchored component may be labeled, either directly or indirectly. In practice, microtitre plates are often utilized for this approach. The anchored species can be immobilized by a number of methods, either non-covalent or covalent, that are typically well known to one who practices the art. Non-covalent attachment can often be accomplished simply by coating the solid surface with a solution of the HIF-1α protein or fragment thereof or the c-Myc protein or fragment thereof and drying. Alternatively, an immobilized antibody specific for the assay component to be anchored can be used for this purpose.

In related assays, a fusion protein can be provided which adds a domain that allows one or both of the assay components to be anchored to a matrix. For example, glutathione-S-transferase/marker fusion proteins or glutathione-S-transferase/binding partner can be adsorbed onto glutathione sepharose beads (Sigma Chemical, St. Louis, Mo.) or glutathione derivatized microtiter plates, which are then combined with the test compound or the test compound and either the non-adsorbed the HIF-1α protein or fragment thereof or the c-Myc protein or fragment thereof, and the mixture incubated under conditions conducive to complex formation (e.g., physiological conditions). Following incubation, the beads or microtiter plate wells are washed to remove any unbound assay components, the immobilized complex assessed either directly or indirectly, for example, as described above.

A homogeneous assay may also be used to identify inhibitors of complex formation. This is typically a reaction, analogous to those mentioned above, which is conducted in a liquid phase in the presence or absence of the test compound. The formed complexes are then separated from unreacted components, and the amount of complex formed is determined. As mentioned for heterogeneous assay systems, the order of addition of reactants to the liquid phase can yield information about which test compounds modulate (inhibit or enhance) complex formation and which disrupt preformed complexes.

In such a homogeneous assay, the reaction products may be separated from unreacted assay components by any of a number of standard techniques, including but not limited to: differential centrifugation, chromatography, electrophoresis and immunoprecipitation. In differential centrifugation, complexes of molecules may be separated from uncomplexed molecules through a series of centrifugal steps, due to the different sedimentation equilibria of complexes based on their different sizes and densities (see, for example, Rivas, G., and Minton, A. P., *Trends Biochem Sci* 1993 August; 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the complex as compared to the uncomplexed molecules may be exploited to differentially separate the complex from the remaining individual reactants, for example through the use of ion-exchange chromatography resins. Such resins and chromatographic techniques are well known to one skilled in the art (see, e.g., Heegaard, 1998, *J Mol. Recognit.* 11:141-148; Hage and Tweed, 1997, *J. Chromatogr. B. Biomed. Sci. Appl.,* 699:499-525). Gel electrophoresis may also be employed to separate complexed molecules from unbound species (see, e.g., Ausubel et al (eds.), In: *Current Protocols in Molecular Biology*, J. Wiley & Sons, New York. 1999). In this technique, protein or nucleic acid complexes are separated based on size or charge, for example. In order to maintain the binding interaction during the electrophoretic process, nondenaturing gels in the absence of reducing agent are typically preferred, but conditions appropriate to the particular interactants will be well known to one skilled in the art. Immunoprecipitation is another common technique utilized for the isolation of a protein-protein complex from solution (see, e.g., Ausubel et al (eds.), In: *Current Protocols in Molecular Biology*, J. Wiley & Sons, New York. 1999). In this technique, all proteins binding to an antibody specific to one of the binding molecules are precipitated from solution by conjugating the antibody to a polymer bead that may be readily collected by centrifugation. The bound assay components are released from the beads (through a specific proteolysis event or other technique well known in the art which will not disturb the protein-protein interaction in the complex), and a second immunoprecipitation step is performed, this time utilizing antibodies specific for the correspondingly different interacting assay component. In this manner, only formed complexes should remain attached to the beads. Variations in complex formation in both the presence and the absence of a test compound can be compared, thus offering information about the ability of the compound to modulate interactions between the HIF-1α protein or fragment thereof and the c-Myc protein or fragment thereof.

Agents useful in the methods described herein may also be identified, for example, using methods wherein a cell (e.g., a cell that expresses c-Myc and HIF-1α, such as a mammalian cell) is contacted with a test compound, and the expression level of a c-Myc target gene or a reporter gene under the transcriptional control of the promoter of a c-Myc target gene is determined (collectively referred to as c-Myc reporter genes). As used herein, the term "c-Myc target gene" refers to a gene whose expression increases in the presence of c-Myc. Examples of c-Myc target genes are well known in the art and include, for example, TFAM, ND1, ND2, ND3, ND4, ND4I, ND5, ND6, CYTB, COX1, COX2, COX3, ATP6 and ATP8. In some embodiments, the c-Myc reporter gene encodes a readily detectable protein (e.g., a fluorescent protein or a protein catalyzes a reaction that produces a change in color, luminescence and/or opacity). In some embodiments, the level of expression of the reporter gene in the presence of the test compound is compared to the level of expression of mRNA or protein in the absence of the candidate compound. If the expression of the mRNA or protein increases in the presence of the test compound, the test compound an agent useful in the methods described herein.

Pharmaceutical Compositions

In certain embodiments the instant invention relates to a composition, e.g., a pharmaceutical composition, containing at least one agent described herein together with a pharmaceutically acceptable carrier. In one embodiment, the composition includes a combination of multiple (e.g., two or more) agents of the invention.

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; or (2) parenteral administration, for example, by subcutaneous, intramuscular, intravenous or epidural injection as, for example, a sterile solution or suspension, or sustained-release formulation.

Methods of preparing these formulations or compositions include the step of bringing into association an agent described herein with the carrier and, optionally, one or more accessory ingredients. In general, the formulations are prepared by uniformly and intimately bringing into association an agent described herein with liquid carriers, or finely divided solid carriers, or both, and then, if necessary, shaping the product.

Pharmaceutical compositions of this invention suitable for parenteral administration comprise one or more agents described herein in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Regardless of the route of administration selected, the agents of the present invention, which may be used in a suitable hydrated form, and/or the pharmaceutical compositions of the present invention, are formulated into pharmaceutically-acceptable dosage forms by conventional methods known to those of skill in the art.

Therapeutic Methods

Disclosed herein are novel methods of treating age-related and mitochondrial diseases, enhancing stress response, improving resistance to hypoxia and/or increasing life span. In certain embodiments the agents described herein are administered to a subject (e.g., a subject in need thereof). In some embodiments, the agents are used to enhance stress response, improve hypoxia resistance or increase the life span of a cell. In such embodiments, the agent is contacted to the cell either in vitro or in vivo.

In some embodiments, the present invention provides therapeutic methods of treating an age-related disease. Age-related diseases include, but are not limited to, Alzheimer's disease, amniotropic lateral sclerosis, arthritis, atherosclerosis, cachexia, cancer, cardiac hypertrophy, cardiac failure, cardiac hypertrophy, cardiovascular disease, cataracts, colitis, chronic obstructive pulmonary disease, dementia, diabetes mellitus, frailty, heart disease, hepatic steatosis, high blood cholesterol, high blood pressure, Huntington's disease, hyperglycemia, hypertension, infertility, inflammatory bowel disease, insulin resistance disorder, lethargy, metabolic syndrome, muscular dystrophy, multiple sclerosis, neuropathy, nephropathy, obesity, osteoporosis, Parkinson's disease, psoriasis, retinal degeneration, sarcopenia, sleep disorders, sepsis and/or stroke.

In some embodiments, the present invention provides therapeutic methods of treating a mitochondrial disease. Mitochondrial diseases include, but are not limited to, mitochondrial myopathy, diabetes mellitus and deafness (DAD), Leber's hereditary optic neuropathy (LHON), Leigh syndrome, neuropathy, ataxia, retinitis pigmentosa and petosis (NARP), myoclonic epilepsy with ragged red fibers (MERRF), myoneurogenic gastrointestinal encephalopathy (MNGIE), mitochondrial myopathy, encephalomyopathy, lactic acidosis, stroke-like symptoms (MELAS), Kearns-Sayre syndrome (KSS), chromic progressive external opthalmoplegia (CPEO) and/or mtDNA depletion.

In certain embodiments, the methods described herein are useful for increasing the life span of a cell or organism. All animals typically go through a period of growth and maturation followed by a period of progressive and irreversible physiological decline ending in death. The length of time from birth to death is known as the life span of an organism, and each organism has a characteristic average life span. Aging is a physical manifestation of the changes underlying the passage of time as measured by percent of average life span.

In some cases, characteristics of aging can be quite obvious. For example, characteristics of older humans include skin wrinkling, graying of the hair, baldness, and cataracts, as well as hypermelanosis, osteoporosis, altered adiposity, cerebral cortical atrophy, lymphoid depletion, memory loss, thymic atrophy, increased incidence of diabetes type II, atherosclerosis, cancer, muscle loss, bone loss, and heart disease. Nehlin et al. (2000), Annals NY Acad Sci 980:176-79. Other aspects of mammalian aging include weight loss, lordokyphosis (hunchback spine), absence of vigor, lymphoid atrophy, decreased bone density, dermal thickening and subcutaneous adipose tissue, decreased ability to tolerate stress (including heat or cold, wounding, anesthesia, and hematopoietic precursor cell ablation), liver pathology, atrophy of intestinal villi, skin ulceration, amyloid deposits, and joint diseases. Tyner et al. (2002), Nature 415:45-53.

Careful observation reveals characteristics of aging in other eukaryotes, including invertebrates. For example, characteristics of aging in the model organism *C. elegans* include slow movement, flaccidity, yolk accumulation, intestinal autofluorescence (lipofuscin), loss of ability to eat food or dispel waste, necrotic cavities in tissues, and germ cell appearance.

Those skilled in the art will recognize that the aging process is also manifested at the cellular level, as well as in mitochondria. Cellular aging is manifested in reduced mitochondrial function, loss of doubling capacity, increased levels of apoptosis, changes in differentiated phenotype, and changes in metabolism, e.g., decreased fatty acid oxidation, respiration, and protein synthesis and turnover.

Given the programmed nature of cellular and organismal aging, it is possible to evaluate the "biological age" of a cell or organism by means of phenotypic characteristics that are correlated with aging. For example, biological age can be deduced from patterns of gene expression, resistance to stress (e.g., oxidative or genotoxic stress), rate of cellular proliferation, and the metabolic characteristics of cells (e.g., rates of protein synthesis and turnover, mitochondrial function, ubiquinone biosynthesis, cholesterol biosynthesis, ATP levels within the cell, levels of a Krebs cycle intermediate in the cell, glucose metabolism, nucleic acid metabolism, ribosomal translation rates, etc.). As used herein, "biological age" is a measure of the age of a cell or organism based upon the molecular characteristics of the cell or organism. Biological age is distinct from "temporal age," which refers to the age of a cell or organism as measured by days, months, and years.

The rate of aging of an organism, e.g., an invertebrate (e.g., a worm or a fly) or a vertebrate (e.g., a rodent, e.g., a mouse) can be determined by a variety of methods, e.g., by one or more of: a) assessing the life span of the cell or the organism; (b) assessing the presence or abundance of a gene transcript or gene product in the cell or organism that has a biological age-dependent expression pattern; (c) evaluating resistance of the cell or organism to stress, e.g., genotoxic stress (e.g., etopocide, UV irradition, exposure to a mutagen, and so forth) or oxidative stress; (d) evaluating one or more metabolic parameters of the cell or organism; (e) evaluating the proliferative capacity of the cell or a set of cells present in the organism; and (f) evaluating physical appearance or behavior of the cell or organism. In one example, evaluating the rate of aging includes directly measuring the average life span of a group of animals (e.g., a group of genetically matched animals) and comparing the resulting average to the average life span of a control group of animals (e.g., a group of animals that did not receive the test compound but are genetically matched to the group of animals that did receive the test compound). Alternatively, the rate of aging of an organism can be determined by measuring an age-related parameter. Examples of age-related parameters include: appearance, e.g., visible signs of age; the expression of one or more genes or proteins (e.g., genes or proteins that have an age-related expression pattern); resistance to oxidative stress; metabolic parameters (e.g., protein synthesis or degradation, ubiquinone biosynthesis, cholesterol biosynthesis, ATP levels, glucose metabolism, nucleic acid metabolism, ribosomal translation rates, etc.); and cellular proliferation (e.g., of retinal cells, bone cells, white blood cells, etc.).

In certain embodiments, the methods described herein relate to increasing the life span of cells and/or protecting cells against at least certain stresses in vitro. For example, cells in culture can be treated as described herein, such as to keep them proliferating longer. This is particularly useful for primary cell cultures (i.e., cells obtained from an organism, e.g., a human), which are known to have only a limited life span in culture. Treating such cells according to methods of the invention (e.g., by contacting the cells with an agent that inhibits complex formation between HIF-1α and c-Myc or the ability of HIF-1α to inhibit c-Myc activity, levels or cell localization) will result in increasing the amount of time that the cells are kept alive in culture. Embryonic stem (ES) cells and pluripotent cells, and cells differentiated therefrom, can also be modified according to the methods of the invention such as to keep the cells or progeny thereof in culture for longer periods of time. Primary cultures of cells, ES cells, pluripotent cells and progeny thereof can be used, e.g., to identify compounds having particular biological effects on the cells or for testing the toxicity of compounds on the cells (i.e., cytotoxicity assays).

In other embodiments, cells that are intended to be preserved for long periods of time are treated as described herein. The cells can be cells in suspension, e.g., blood cells, stem cells, iPS cells, germ cells, germ cell precursors, or tissues or organs. For example, blood collected from an individual for administering to an individual can be treated according to the invention, such as to preserve the blood cells or stem cells for longer periods of time. Other cells that one may treat for extending their lifespan and/or protect them against certain types of stresses include cells for consumption, e.g., cells from non-human mammals (such as meat), or plant cells (such as vegetables). Cells may also be treated prior to implantation or genetic or physical manipulation.

In another embodiment, cells obtained from a subject, e.g., a human or other mammal, are treated according to the methods of the invention and then administered to the same or a different subject. Accordingly, cells or tissues obtained from a donor for use as a graft can be treated as described herein prior to administering to the recipient of the graft. For example, bone marrow cells can be obtained from a subject, treated ex vivo to extend their life span and protect the cells against certain types of stresses and then administered to a recipient. The graft can be an organ, a tissue or loose cells.

In yet other embodiments, cells are treated in vivo to increase their life span and/or protect them against certain types of stresses. For example, skin can be protected from aging, e.g., developing wrinkles, by treating skin, e.g., epithelial cells, as described herein. In an exemplary embodiment, skin is contacted with a pharmaceutical or cosmetic composition comprising an agent described herein.

In addition to applying the methods of the invention in humans and non-human animals, the methods can also be applied to plants and plant cells. Accordingly, the invention also provides methods for extending the life span of plants and plant cells and for rendering the plant and plant cells more resistant to stress, e.g., excessive salt conditions. This can be achieved, e.g., by inhibiting complex formation of proteins in the plant cells that are essentially homologous to the proteins described herein in the animal systems (i.e., HIF-1α and c-Myc) in order to increase the life span and/or the stress resistance of cells.

Agents, such as those described herein, that extend the life span of cells and protect them from stress can also be administered to subjects for treatment of diseases, e.g., chronic diseases, associated with cell death, such as to protect the cells from cell death, e.g., diseases associated with neural cell death or muscular cell death. In particular, the methods may be used to prevent or alleviate neurodegeneration and peripheral neuropathies associated with chemotherapy, such as cancer chemotherapy (e.g., taxol or cisplatin treatment). Neurodegenerative diseases include Parkinson's disease, Alzheimer's disease, multiple sclerosis, amniotropic lateral sclerosis (ALS), retinal degeneration, macular degeneration, Huntington's disease and muscular dystrophy. Thus, the agents may be used as neuroprotective agents. The agent may be administered in the tissue or organ likely to encounter cell death.

In certain embodiments, the methods described herein relate to improving the survival of a cell that has been exposed to hypoxia. In some embodiments, the method includes contacting the cell with an that reduces inhibition of c-Myc activity by HIF-1α. In some embodiments, the cell has been exposed to a hypoxic environment. In certain embodiments the cell is a neuron, a cardiac myocyte, a skeletal myocyte, an iPS cell, blood cell, germ cell or germ cell precursor. In some embodiments, the cell is being cultured in vitro. In certain embodiments the cell is a part of a tissue or organ of a subject who is administered the agent (e.g., a subject suffering from ischemia, cardiovascular diseases, myocardial infarction, congestive heart disease, cardiomyopathy, myocarditis, macrovascular disease, peripheral vascular disease or stroke).

In certain embodiments, the present invention relates to a method of treating or preventing damage to a tissue or organ that has been exposed to hypoxia in a subject by administering an agent described herein to the subject. Tissues and organs are often exposed to hypoxic conditions during a stroke, a myocardial infarction or a peripheral vascular disease. Thus, in some embodiments the methods the subject that may be treated include patients suffering from a cardiac disease, e.g., ischemia, cardiovascular diseases, myocardial infarction, congestive heart disease. Cardiovascular diseases that can be treated or prevented include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to the retinal arterioles, the glomerular arterioles, the vasa nervorum, cardiac arterioles, and associated capillary beds of the eye, the kidney, the heart, and the central and peripheral nervous systems. The methods may also be used for increasing HDL levels in plasma of an individual.

The pharmaceutical compositions of the present invention may be delivered by any suitable route of administration, including orally, nasally, as by, for example, a spray, rectally, intravaginally, parenterally, intracisternally and topically, as by powders, ointments or drops, including buccally and sublingually. In certain embodiments the pharmaceutical compositions are delivered generally (e.g., via oral or parenteral administration).

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the compounds of the invention employed in the pharmaceutical composition at levels lower than that required in order to achieve the desired therapeutic effect and gradually increase the dosage until the desired effect is achieved.

Conserved amongst organisms as diverse as yeast and humans is a progressive decline in mitochondrial function with age, leading to a loss of cellular homeostasis and organismal health (Figueiredo et al., 2008; Figueiredo et al., 2009; Hartmann et al., 2011; Lanza and Nair, 2010). Mitochondria are highly dynamic organelles that are continuously eliminated and regenerated in a process known as mitochondrial biogenesis (Michel et al., 2012). Over the past 2 billion years, since eukaryotes subsumed the α-proteobacterial ancestor of mitochondria, most mitochondrial genes have been transferred to the nuclear genome, where regulation is better integrated. However, the mitochondrial genome still encodes rRNAs, tRNAs, and 13 subunits of the electron transport chain (ETC) (Falkenberg et al., 2007; Larsson, 2010). Functional communication between the nuclear and mitochondrial genomes is therefore essential for mitochondrial biogenesis and homeostasis, efficient oxidative phosphorylation, and normal health (Scarpulla, 2011b). The major known regulatory pathway of mitochondrial biogenesis involves the peroxisome proliferator-activated receptor-γ coactivators alpha and beta (PGC-1α and PGC1-1β), which induce Nuclear Respiratory Factors 1 and 2 (NRF-1 and -2) (Evans and Scarpulla, 1990). NRF-1/-2 binds to and promotes transcription of nuclear genes encoding ETC components and the protein machinery needed to replicate, transcribe, and translate mitochondrial DNA (mtDNA). One of the key proteins that enable this coordination between the nucleus and mitochondria is TFAM (mitochondrial transcription factor A), a nuclear-encoded protein that promotes transcription of mitochondrial-encoded genes and the replication of mtDNA (Parisi and Clayton, 1991; Scarpulla, 2011a).

In mammals, there is a large body of evidence implicating mitochondrial decline in aging, age-related diseases, and many other diseases, disorders, or conditions. For example, mice with mutations that impair the proofreading capacity of the mitochondrial DNA polymerase gamma (Polγ) exhibit a premature aging phenotype (Trifunovic et al., 2005; Trifunovic et al., 2004; Vermulst et al., 2008). Conversely, targeting peroxisomal catalase to mitochondria (mCAT) extends mouse lifespan (Schriner et al., 2005). Recently, telomere erosion in mice was found to disrupt mitochondrial function but the underlying mechanism has not yet been established (Sahin et al., 2011). Despite the apparent importance of mitochondrial decline in aging and disease, there is considerable debate about its underlying causes (Dutta et al., 2012; Moslehi et al., 2012; Peterson et al., 2012). The original idea of Harman (Harman, 1972), that reactive oxygen species (ROS) from mitochondria are a primary cause of disruption of mitochondrial homeostasis, has been challenged (Andziak and Buffenstein, 2006; Andziak et al., 2006; Howes, 2006) (Lapointe and Hekimi, 2010), leaving the primary causes of mitochondrial disturbances during the aging process unresolved.

Mammalian sirtuins (SIRT1-7) are a conserved family of $NAD^+$-dependent lysine-modifying enzymes that modulate the physiological response to dietary changes and can protect against several age-related diseases (Haigis and Sinclair, 2010). The expression of SIRT1, an $NAD^+$-dependent protein deacetylase, is elevated in a number of tissues following restriction of caloric intake (CR) by 30-40% (Cohen et al., 2004), one intervention generally accepted to extend lifespan. Overexpression or pharmacological activation of SIRT1 reproduces many of the health benefits of CR, including protection from metabolic decline (Banks et al., 2008; Baur et al., 2006; Bordone et al., 2007; Lagouge et al., 2006; Minor et al., 2011; Pfluger et al., 2008), cardiovascular disease (Zhang et al., 2008), cancer (Herranz et al., 2010; Oberdoerffer et al., 2008) and neurodegeneration (de Oliveira et al., 2010; Donmez et al., 2010; Qin et al., 2006). Studies have linked the health benefits of CR to increased mitochondrial biogenesis (Cerqueira et al., 2011; Choi et al., 2011; Civitarese et al., 2007; Lopez-Lluch et al., 2006) and delayed mitochondrial decline (Niemann et al., 2010) mediated by the deacetylation and activation of PGC-1α by SIRT1 (Baur et al., 2006; Gerhart-Hines et al., 2007; Lagouge et al., 2006; Minor et al., 2011; Rodgers et al., 2005).

While oxidative metabolism is critical for the health of metazoans, in the case of cancer the opposite is true. Cancer cells typically undergo a shift away from oxidative phosphorylation towards anaerobic glycolysis, allowing them to generate substrates for biomass, even in the presence of oxygen. This metabolic reprogramming, known as the Warburg effect (Warburg, 1956), is driven by several different pathways including the mTOR pathway, the oncogene c-Myc, and hypoxia-inducible factor 1 (HIF-1α), to induce a survival response in low oxygen conditions (Cadenas et al., 2010). Interestingly, both SIRT1 and SIRT3 regulate HIF-1α. SIRT1 regulates HIF-1α transcriptional activity under hypoxic conditions (Lim et al., 2010) while SIRT3 regulates HIF-1α protein stability (Bell et al., 2011; Finley et al., 2011). In *C. elegans*, the Hif-1 gene regulates lifespan and may also mediate the effects of CR (Chen et al., 2009; Leiser and Kaeberlein, 2010), however, a role for HIF-1α in mammalian aging has not been explored.

The present disclosure provides evidence that a cause of the disruption in mitochondrial homeostasis during aging is a pseudohypoxic response that disrupts the coordination between the nuclear and mitochondrial genomes, eliciting a specific decline in mitochondrial-encoded genes. The cause was traced to a decline in nuclear NAD and SIRT1 activity with age, which triggers the accumulation of HIF-1α that suppresses the ability of c-Myc to regulate TFAM, independently of the canonical PGC-1α pathway. The result is an imbalance between nuclear- and mitochondrial-encoded ETC components and loss of oxidative phosphorylation (OXPHOS) capacity, leading to mitochondrial dysfunction and thus loss of cell health (which in turn results in e.g., aging, age-related diseases, and other diseases or disorders described herein).

Accordingly, provided herein are methods and compositions for treating or preventing diseases or disorders associated with mitochondrial dysfunction (e.g., resulting from the deregulation of mitochondrial homeostasis). In some embodiments, "mitochondrial dysfunction" or "deregulation of mitochondrial homeostasis" means that one or more mitochondrial component (e.g., ETC component) is depleted, for example by a decrease in mitochondrial gene expression or mitochondrial DNA content, resulting in compromised mitochondrial function (e.g., loss of or decreased oxidative phosphorylation (OXPHOS) capacity). Examples of diseases, disorders, or conditions associated with mitochondrial dysfunction include, but are not limited to, aging, aging-related diseases, mitochondrial diseases (e.g., Alper's disease, Barth syndrome, beta-oxidation defects, carnitine-acyl-carnitine deficiency, carnitine deficiency, creatine deficiency syndromes, co-enzyme Q10 deficiency, complex I deficiency, complex II deficiency, complex III deficiency, complex IV deficiency/COX deficiency, complex V deficiency, chronic progressive external ophthalmoplegia syndrome, CPT I deficiency, CPT II deficiency, Kearns-Sayre syndrome, lactic acidosis, long-chain acyl-CoA dehydrongenase deficiency, Leigh disease, Luft disease, glutaric aciduria type II, mitochondrial cytopathy, mitochondrial DNA depletion, mitochondrial encephalopathy, mitochondrial myopathy, and Pearson syndrome), metabolic diseases and disorders (e.g., amino acid deficiency), diseases resulting from mitochondrial and energy deficiency, lethargy, heart disorders, cardiovascular disease, stroke, infarction, pulmonary hypertension, ischemia, cachexia, sarcopenia, neurodegenerative diseases (e.g., Alzherimer's disease, Parkinson's disease, Huntington's disease), dementia, lipodystrophy, liver steatosis, hepatitis, cirrhosis, kidney failure, preeclampsia, male infertility, obesity, diabetes (e.g., diabetes type I), muscle disorders, and muscle wasting. In some aspects, methods and compositions provided herein are useful for promoting cell viability (in various species), vascular remodeling, wound healing and healing in general (e.g., treating wounds resulting from cuts, scrapes, surgery, bodily insults, trauma, burns, abrasions, sunburns, etc.). In some aspects, the methods and compositions are useful for promoting iron homeostasis and/or erythropoiesis. In some aspects, methods and compositions provided herein are useful to promote successful organ and tissue transplantation, or to promote recovery from organ and tissue transplantation. In some aspects, provided methods and compositions are useful for preserving cells and organs. In some aspects, methods and compositions provided herein have cosmetic applications, for example for treating conditions associated with mitochondrial dysfunction which relate to the skin or scalp/hair, such as skin aging (e.g., loss in volume and elasticity, discoloration, liver spots (lentigo senislis)), wrinkles, baldness, and loss of hair pigmentation. In some embodiments, agents or compositions described herein are useful for products or methods relating to cosmetics, energy drinks, and/or animal industries.

In some embodiments, the methods include administering to the subject an effective amount of an agent that inhibits HIF-1α. HIF-1α inhibitors can inhibit activity of the protein including its binding to hypoxia-responsive elements, promote degradation of HIF-1α, reduce HIF-1α protein stability, or inhibit HIF-1α protein synthesis. Small molecule HIF-1α inhibitors include: chrysin (5,7-dihydroxyflavone); methyl 3-(2-(4-(adamantan-1-yl)phenoxy)acetamido)-4-hydroxybenzoate (LW6; see Biochem Pharmacol. 2010 Oct. 1; 80(7):982-9); P3155 (see BMC Cancer 2011, 11:338); NSC 644221 (see Clin Cancer Res. 2007 Feb. 1; 13(3):1010-8); S-2-amino-3-[4'-N,N,-bis(chloroethyl)amino]phenyl propionic acid N-oxide dihydrochloride (PX-478, see Mol Cancer Ther. 2008 January; 7(1):90-100); dimethyl-bisphenol A; vincristine; apigenin (see Mol Carcinog. 2008 September; 47(9):686-700); 2-methoxyestradiol; chetomin; and echinomycin. HIF-1α inhibitors also can include siRNA molecules (see BMC Cancer 2010, 10:605; U.S. Ser. No. 13/555,589) or antisense oligonucleotides (e.g., EZN-2968—see Mol Cancer Ther. 2008 November; 7(11):3598-608). The subject is typically a subject having, or suspected of having a disease, disorder, or condition associated with mitochondrial dysfunction (e.g., as described herein).

In some embodiments, the methods further comprise administering to the subject an effective amount of an agent that increases the levels of nicotinamide adenine dinucleotide (NAD+; which may also be referred to herein as NAD) in the subject. Examples of such agents include $NAD^+$ precursor, such as nicotinic acid, nicotinamide, nicotinamide mononucleotide (NMN), nicotinamide riboside (NR), or a salt thereof or prodrug thereof. In some embodiments, such an agent is administered at a dose of between 0.5-5 grams per day. In some embodiments, NMN is orally administered in doses of between 250 mg-5 grams per day. $NAD^+$ levels also can be increased by increasing the activity of enzymes (or enzymatically active fragments thereof) involved in $NAD^+$ biosynthesis (de novo synthesis or salvage pathways). Enzymes involved in $NAD^+$ biosynthesis such as nicotinate phosphoribosyl transferase 1 (NPT1), pyrazinamidase/nicotinamidase 1 (PNC1), nicotinic acid mononucleotide adenylyltransferase 1 (NMA1), nicotinic acid mononucleotide adenylyltransferase 2 (NMA2), nicotinamide N-methyltransferase (NNMT), nicotinamide phosphoribosyl transferase (NAMPT or NAMPRT), nicotinate/nicotinamide mononucleotide adenylyl transferase 1 (NMNAT-1), and nicotinamide mononucleotide adenylyl transferase 2 (NMNAT-2); are described in U.S. Pat. No. 7,977,049, which is incorporated by reference herein. The HIF-1α inhibitor and agent that increases the levels of $NAD^+$ can be administered simultaneously (e.g., as a single formulation) or sequentially (e.g., as separate formulations).

In some embodiments, the methods include administering to a subject an effective amount of an agent that increases the levels of NAD+, without administering an inhibitor of HIF-1α.

Aspects of the invention thus relate to compositions of matter including $NAD^+$ precursors, such as NMN or a salt thereof or prodrug thereof. Further aspects of the invention relate to compositions of matter including an enzyme involved in NAD+ biosynthesis, such as NMNAT-1 or NAMPT, or an enzymatically active fragment thereof, or a nucleic acid encoding an enzyme involved in $NAD^+$ biosynthesis, or an enzymatically active fragment thereof. In some embodiments, compositions include conjugates of agents described herein, such as fish oil conjugates.

As used herein, the term "prodrug" means a derivative of a compound that can hydrolyze, oxidize, or otherwise react under biological conditions (in vitro or in vivo) to provide a compound described herein as useful in the methods of the invention. While prodrugs typically are designed to provide active compound upon reaction under biological conditions, prodrugs may have similar activity as a prodrug.

The references by Goodman and Gilman (The Pharmacological Basis of Therapeutics, 8th Ed, McGraw-Hill, Int. Ed. 1992, "Biotransformation of Drugs", p 13-15); T. Higuchi and V. Stella (Pro-drugs as Novel Delivery Systems, Vol. 14 of the A.C.S. Symposium Series); and Bioreversible Carriers in Drug Design (E. B. Roche, ed., American Pharmaceutical Association and Pergamon Press, 1987) describing pro-drugs generally are hereby incorporated by reference. Prodrugs of the compounds described herein can be prepared by modifying functional groups present in said component in such a way that the modifications are cleaved, either in routine manipulation or in vivo, to the parent component. Typical examples of prodrugs are described for instance in WO 99/33795, WO 99/33815, WO 99/33793 and WO 99/33792, each of which is incorporated herein by reference for these teachings. Prodrugs can be characterized by increased bio-availability and are readily metabolized into the active inhibitors in vivo.

Examples of prodrugs include, but are not limited to, analogs or derivatives of the compounds described herein, further comprising biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of the compounds described herein that comprise —NO, —$NO_2$, —ONO, or —$ONO_2$ moieties. Prodrugs are prepared using methods known to those of skill in the art, such as those described by BURGER'S MEDICINAL CHEMISTRY AND DRUG DISCOVERY (1995) 172-178, 949-982 (Manfred E. Wolff ed., $5^{th}$ ed), the entire teachings of which are incorporated herein by reference.

As used herein, the terms "biohydrolyzable amide," "biohydrolyzable ester," "biohydrolyzable carbamate," "biohydrolyzable carbonate," "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

Prodrugs can include fatty acids or lipids linked to the compounds described herein by the moieties described herein. Exemplary fatty acids include the omega-3 fatty acids eicosapentaenoic acid (EPA) and docosahexaenoic acid (DHA). Such prodrugs and the preparation thereof will be clear to the skilled person; reference is for instance made to the prodrug types and preparations described in U.S. Pat. No. 5,994,392, U.S. Pat. No. 4,933,324 and U.S. Pat. No. 5,284,876.

As used herein, the term "salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+$ $(C_{1-4}alkyl)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate, and aryl sulfonate.

As used herein, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. No. 6,372,778, U.S. Pat. No. 6,369,086, U.S. Pat. No. 6,369,087 and U.S. Pat. No. 6,372,733.

Thus, the invention includes methods for delivering agents to a subject. As used herein, the term "subject" refers to a human or non-human mammal. Non-human mammals include livestock animals, companion animals, laboratory animals, and non-human primates. Non-human subjects also specifically include, without limitation, chickens, horses, cows, pigs, goats, dogs, cats, guinea pigs, hamsters, mink, and rabbits. In some embodiments the subject is a patient. As used herein, a "patient" refers to a subject who is under the care of a physician, dentist, or other health care worker, including someone who has consulted with, received advice from or received a prescription or other recommendation from a physician or other health care worker. A patient is typically a subject having or at risk of having a disorder associated with mitochondrial dysfunction.

Pharmaceutical Compositions

In some embodiments, pharmaceutical compositions comprising one or more HIF-1α inhibitors and/or one or more agents that increase the level of $NAD^+$ in a subject are provided. In some aspects, the HIF-1α inhibitors and additional agents are collectively referred to as the "agents" or "active ingredient"s of the pharmaceutical compositions provided herein. The compositions comprising the agents can be mixed with a pharmaceutically acceptable carrier, either taken alone or in combination with the one or more additional therapeutic agents described above, to form pharmaceutical compositions. A pharmaceutically acceptable carrier is compatible with the active ingredient(s) of the composition (and preferably, capable of stabilizing it). Such compositions are delivered or administered in effective amounts to treat an individual, such as a human having a disease or disorder resulting from a nonsense mutation, for example those described herein. To "treat" a disease, means to reduce or eliminate a sign or symptom of the disease, to stabilize the disease, and/or to reduce or slow further progression of the disease. In some embodiments, "treat", "treatment" or "treating" is intended to include prophylaxis, amelioration, prevention or cure from the disease.

Actual dosage levels of active ingredients in the pharmaceutical compositions of the invention can be varied to obtain an amount of the active HIF-1α inhibitor(s) and/or other agent(s) that is effective to achieve the desired therapeutic response for a particular patient, combination, and mode of administration. The selected dosage level depends upon the activity of the particular HIF-1α inhibitors and other agent(s), the route of administration, the severity of the condition being treated, the condition, and prior medical history of the patient being treated. However, it is within the skill of one in the art to start doses of the compositions described herein at levels lower than required to achieve the desired therapeutic effort and to gradually increase the dosage until the desired effect is achieved. A "therapeutically effective amount," as used herein, refers to an amount of a compound and/or an additional therapeutic agent, or a composition thereof that results in improvement (complete or partial) of a disease or disorder caused by mitochondrial dysfunction (e.g., mitochondrial homeostasis deregulation). A therapeutically effective amount also refers to an amount that prevents or delays the onset of a disease or disorder caused by mitochondrial dysfunction. The therapeutically effective amount will vary with the particular condition being treated, the age and physical condition of the subject being treated, the severity of the condition, the duration of the treatment, the nature of the concurrent therapy (if any), the specific route of administration, and like factors are within the knowledge and expertise of the health practitioner. For example, an effective amount can depend upon the duration the subject has had the disease. In some aspects, an effective amount of a composition described herein when administered to a subject results in e.g., increased muscle strength, increased motility, restoration of muscle function or phenotype, decreased fatigue, decreased difficulty with motor skills, decreased dementia, etc. In some aspects, the desired therapeutic or clinical effect resulting from administration of an effective amount of a composition described herein, may be measured or monitored by methods known to those of ordinary skill in the art e.g., by routine physical examination.

In the combination therapies, an effective amount can refer to each individual agent or to the combination as a whole, wherein the amounts of all agents administered are together effective, but wherein the component agent of the combination may not be present individually in an effective amount.

The pharmaceutical compositions described herein (e.g., those containing HIF-1α inhibitors and/or agents that increase $NAD^+$ levels), can be administered to a subject by any suitable route. For example, compositions can be administered orally, including sublingually, rectally, parenterally, intracisternally, intravaginally, intraperitoneally, topically and transdermally (as by powders, ointments, or drops), bucally, or nasally. The term "parenteral" administration as used herein refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation also is contemplated, including, for example, embedding a composition of the disclosure in the body such as, for example, in the brain, in the abdominal cavity, under the splenic capsule, brain, or in the cornea.

The pharmaceutical compositions described herein can also be administered in the form of liposomes. As is known in the art, liposomes generally are derived from phospholipids or other lipid substances. Liposomes are formed by mono- or multi-lamellar hydrated liquid crystals that are dispersed in an aqueous medium. Any nontoxic, physiologically acceptable, and metabolizable lipid capable of forming liposomes can be used. The present compositions in liposome form can contain, in addition to an agent of the present disclosure, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33, et seq.

Dosage forms for topical administration of the pharmaceutical compositions described herein include powders, sprays, ointments, and inhalants as described herein. The active agent(s) is mixed under sterile conditions with a pharmaceutically acceptable carrier and any needed preservatives, buffers, or propellants which may be required. Ophthalmic formulations, eye ointments, powders, and solutions also are contemplated as being within the scope of this disclosure.

Pharmaceutical compositions (e.g., those containing HIF-1α inhibitors and/or agents that increase $NAD^+$ levels) for parenteral injection comprise pharmaceutically acceptable sterile aqueous or non-aqueous solutions, dispersions, suspensions, or emulsions, as well as sterile powders for reconstitution into sterile injectable solutions or dispersions just prior to use. Examples of suitable aqueous and non-aqueous carriers, diluents, solvents, or vehicles include water ethanol, polyols (such as, glycerol, propylene glycol, polyethylene glycol, and the like), and suitable mixtures thereof, vegetable oils (such, as olive oil), and injectable organic esters such as ethyl oleate. Proper fluidity can be maintained, for example, by the use of coating materials such as lecithin, by the maintenance of the required particle size in the case of dispersions, and by the use of surfactants.

Compositions also can contain adjuvants such as preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It also may be desirable to include isotonic agents such as sugars, sodium chloride, and the like. Prolonged absorption of the injectable pharmaceutical form can be brought about by the inclusion of agents which delay absorption, such as aluminum monostearate and gelatin.

In some cases, in order to prolong the effect of the pharmaceutical compositions described herein (e.g., those containing HIF-1α inhibitors and/or agents that increase $NAD^+$ levels), it is desirable to slow the absorption of the drug from subcutaneous or intramuscular injection. This result can be accomplished by the use of a liquid suspension of crystalline or amorphous materials with poor water solubility. The rate of absorption of the active agent(s) then depends upon its rate of dissolution which, in turn, may depend upon crystal size and crystalline form. Alternatively, delayed absorption of a parenterally administered active agent(s) is accomplished by dissolving or suspending the agent(s) in an oil vehicle.

Injectable depot forms are made by forming microencapsule matrices of the agent(s) in biodegradable polymers such a polylactide-polyglycolide. Depending upon the ratio of agent(s) to polymer and the nature of the particular polymer employed, the rate of agent(s) release can be controlled. Examples of other biodegradable polymers include poly (orthoesters) and poly(anhydrides). Depot injectable formulations also are prepared by entrapping the agent(s) in liposomes or microemulsions which are compatible with body tissue.

The injectable formulations can be sterilized, for example, by filtration through a bacterial- or viral-retaining filter, or by incorporating sterilizing agents in the form of sterile solid compositions which can be dissolved or dispersed in sterile water or other sterile injectable medium just prior to use.

Also described here are methods for oral administration of the pharmaceutical compositions described herein. Oral solid dosage forms are described generally in Remington's Pharmaceutical Sciences, 18th Ed., 1990 (Mack Publishing Co. Easton Pa. 18042) at Chapter 89. Solid dosage forms for oral administration include capsules, tablets, pills, powders, troches or lozenges, cachets, pellets, and granules. Also, liposomal or proteinoid encapsulation can be used to formulate the present compositions (as, for example, proteinoid microspheres reported in U.S. Pat. No. 4,925,673). Liposomal encapsulation may include liposomes that are derivatized with various polymers (e.g., U.S. Pat. No. 5,013,556). In general, the formulation includes the agent(s) and inert ingredients which protect against degradation in the stomach and which permit release of the biologically active material in the intestine. In some embodiments, agents that increase levels of $NAD^+$, for example NMN, can be orally administered in dosages from 250 mg to 5 grams per day.

In such solid dosage forms, the agent(s) is mixed with, or chemically modified to include, a least one inert, pharmaceutically acceptable excipient or carrier. The excipient or carrier preferably permits (a) inhibition of proteolysis and/or nucleic acid degradation, and (b) uptake into the blood stream from the stomach or intestine. In a most preferred embodiment, the excipient or carrier increases uptake of the agent(s), overall stability of the agent(s) and/or circulation time of the agent(s) in the body. Excipients and carriers include, for example, sodium citrate or dicalcium phosphate and/or (a) fillers or extenders such as starches, lactose, sucrose, glucose, cellulose, modified dextrans, mannitol, and silicic acid, as well as inorganic salts such as calcium triphosphate, magnesium carbonate and sodium chloride, and commercially available diluents such as FAST-FLO®, EMDEX®, STA-RX 1500®, EMCOMPRESS® and AVICEL®, (b) binders such as, for example, methylcellulose ethylcellulose, hydroxypropyhnethyl cellulose, carboxymethylcellulose, gums (e.g., alginates, *acacia*), gelatin, polyvinylpyrrolidone, and sucrose, (c) humectants, such as glycerol, (d) disintegrating agents, such as agar-agar, calcium carbonate, potato or tapioca starch, alginic acid, certain silicates, sodium carbonate, starch including the commercial disintegrant based on starch, EXPLOTAB®, sodium starch glycolate, AMBERLITE®, sodium carboxymethylcellulose, ultramylopectin, gelatin, orange peel, carboxymethyl cellulose, natural sponge, bentonite, insoluble cationic exchange resins, and powdered gums such as agar, karaya or tragacanth; (e) solution retarding agents such a paraffin, (f) absorption accelerators, such as quaternary ammonium compounds and fatty acids including oleic acid, linoleic acid, and linolenic acid (g) wetting agents, such as, for example, cetyl alcohol and glycerol monosterate, anionic detergent surfactants including sodium lauryl sulfate, dioctyl sodium sulfosuccinate, and dioctyl sodium sulfonate, cationic detergents, such as benzalkonium chloride or benzethonium chloride, nonionic detergents including lauromacrogol 400, polyoxyl 40 stearate, polyoxyethylene hydrogenated castor oil 10, 50 and 60, glycerol monostearate, polysorbate 40, 60, 65, and 80, sucrose fatty acid ester, methyl cellulose and carboxymethyl cellulose; (h) absorbents, such as kaolin and bentonite clay, (i) lubricants, such as talc, calcium sterate, magnesium stearate, solid polyethylene glycols, sodium lauryl sulfate, polytetrafluoroethylene (PTFE), liquid paraffin, vegetable oils, waxes, CARBOWAX® 4000, CARBOWAX® 6000, magnesium lauryl sulfate, and mixtures thereof; (j) glidants that improve the flow properties of the drug during formulation and aid rearrangement during compression that include starch, talc, pyrogenic silica, and hydrated silicoaluminate. In the case of capsules, tablets, and pills, the dosage form also can comprise buffering agents.

Solid compositions of a similar type also can be employed as fillers in soft and hard-filled gelatin capsules, using such excipients as lactose or milk sugar, as well as high molecular weight polyethylene glycols and the like.

The solid dosage forms of tablets, dragees, capsules, pills, and granules can be prepared with coatings and shells, such as enteric coatings and other coatings well known in the pharmaceutical formulating art. They optionally can contain opacifying agents and also can be of a composition that they release the active ingredients(s) only, or preferentially, in a part of the intestinal tract, optionally, in a delayed manner. Exemplary materials include polymers having pH sensitive solubility, such as the materials available as EUDRAGIT® Examples of embedding compositions which can be used include polymeric substances and waxes.

The agent(s) also can be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active ingredient(s), the liquid dosage forms can contain inert diluents commonly used in the art, such as, for example, water or other solvents, solubilizing agents and emulsifiers, such as ethyl alcohol, isopropyl alcohol ethyl carbonate ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydroflirfuryl alcohol, polyethylene glycols, fatty acid esters of sorbitan, and mixtures thereof.

Besides inert diluents, the oral compositions also can include adjuvants, such as wetting agents, emulsifying and suspending agents, sweetening, coloring, flavoring, and perfuming agents. Oral compositions can be formulated and further contain an edible product, such as a beverage. Oral composition can also be administered by oral gavage.

Suspensions, in addition to the active ingredient(s), can contain suspending agents such as, for example ethoxylated isostearyl alcohols, polyoxyethylene sorbitol and sorbitan esters, microcrystalline cellulose, aluminum metahydroxide, bentonite, agar-agar, tragacanth, and mixtures thereof.

Also contemplated herein is pulmonary delivery of the HIF-1α inhibitors and/or agents that increase NAD$^+$ levels. The agents are delivered to the lungs of a mammal while inhaling, thereby promoting the traversal of the lung epithelial lining to the blood stream. See, Adjei et al., Pharmaceutical Research 7:565-569 (1990); Adjei et al., International Journal of Pharmaceutics 63:135-144 (1990) (leuprolide acetate); Braquet et al., Journal of Cardiovascular Pharmacology 13 (suppl.5): s.143-146 (1989)(endothelin-1); Hubbard et al., Annals of Internal Medicine 3:206-212 (1989)(α1-antitrypsin); Smith et al., J. Clin. Invest. 84:1145-1146 (1989) (α1-proteinase); Oswein et al., "Aerosolization of Proteins," Proceedings of Symposium on Respiratory Drug Delivery II, Keystone, Colo., March, 1990 (recombinant human growth hormone); Debs et al., The Journal of Immunology 140:3482-3488 (1988) (interferon-γ and tumor necrosis factor α) and Platz et al., U.S. Pat. No. 5,284,656 (granulocyte colony stimulating factor).

Contemplated for use in the practice of this invention are a wide range of mechanical devices designed for pulmonary delivery of therapeutic products, including, but not limited to, nebulizers, metered dose inhalers, and powder inhalers, all of which are familiar to those skilled in the art.

Some specific examples of commercially available devices suitable for the practice of the invention are the ULTRAVENT® nebulizer, manufactured by Mallinckrodt, Inc., St. Louis, Mo.; the ACORN II® nebulizer, manufactured by Marquest Medical Products, Englewood, Colo.; the VENTOL® metered dose inhaler, manufactured by Glaxo Inc., Research Triangle Park, N.C.; and the SPINHALER® powder inhaler, manufactured by Fisons Corp., Bedford, Mass.

All such devices require the use of formulations suitable for the dispensing of the agent(s) described herein. Typically, each formulation is specific to the type of device employed and can involve the use of an appropriate propellant material, in addition to diluents, adjuvants, and/or carriers useful in therapy.

The composition is prepared in particulate form, preferably with an average particle size of less than 10 μm, and most preferably 0.5 to 5 μm, for most effective delivery to the distal lung.

Carriers include carbohydrates such as trehalose, mannitol, xylitol, sucrose, lactose, and sorbitol. Other ingredients for use in formulations may include lipids, such as DPPC, DOPE, DSPC and DOPC, natural or synthetic surfactants, polyethylene glycol (even apart from its use in derivatizing the inhibitor itself), dextrans, such as cyclodextran, bile salts, and other related enhancers, cellulose and cellulose derivatives, and amino acids.

Also, the use of liposomes, microcapsules or microspheres, inclusion complexes, or other types of carriers is contemplated.

Formulations suitable for use with a nebulizer, either jet or ultrasonic, typically comprise an agent of the invention dissolved in water at a concentration of about 0.1 to 25 mg of biologically active protein per mL of solution. The formulation also can include a buffer and a simple sugar (e.g., for protein stabilization and regulation of osmotic pressure). The nebulizer formulation also can contain a surfactant to reduce or prevent surface-induced aggregation of the inhibitor composition caused by atomization of the solution in forming the aerosol.

Formulations for use with a metered-dose inhaler device generally comprise a finely divided powder containing the agent suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid also can be useful as a surfactant.

Formulations for dispensing from a powder inhaler device comprise a finely divided dry powder containing the agent(s) and also can include a bulking agent, such as lactose, sorbitol, sucrose, mannitol, trehalose, or xylitol, in amounts which facilitate dispersal of the powder from the device, e.g., 50 to 90% by weight of the formulation.

Nasal delivery of the agent(s) and compositions of the invention also are contemplated. Nasal delivery allows the passage of the agent(s) or composition to the blood stream directly after administering the therapeutic product to the nose, without the necessity for deposition of the product in the lung. Formulations for nasal delivery include those with dextran or cyclodextran. Delivery via transport across other mucous membranes also is contemplated.

Compositions for rectal or vaginal administration are preferably suppositories which can be prepared by mixing the agent(s) with suitable nonirritating excipients or carriers, such as cocoa butter, polyethylene glycol, or suppository wax, which are solid at room temperature, but liquid at body temperature, and therefore melt in the rectum or vaginal cavity and release the active agent.

In order to facilitate delivery of agent(s) across cell and/or nuclear membranes, compositions of relatively high hydrophobicity are preferred. Agent(s) can be modified in a manner which increases hydrophobicity, or the agents can be encapsulated in hydrophobic carriers or solutions which result in increased hydrophobicity.

In one aspect, the invention provides kits comprising a pharmaceutical composition comprising a therapeutically effective amount of one or more HIF-1α inhibitors and/or a therapeutically effective amount of one or more agents that increase $NAD^+$ levels and instructions for administration of the pharmaceutical composition. In some aspects of the invention, the kit can include a pharmaceutical preparation vial, a pharmaceutical preparation diluent vial, and the HIF-1α inhibitors(s) and additional agent(s). The diluent vial contains a diluent such as physiological saline for diluting what could be a concentrated solution or lyophilized powder of the agent of the invention. In some embodiments, the instructions include instructions for mixing a particular amount of the diluent with a particular amount of the concentrated pharmaceutical preparation, whereby a final formulation for injection or infusion is prepared. In some embodiments, the instructions include instructions for use in a syringe or other administration device. In some embodiments, the instructions include instructions for treating a patient with an effective amount of the HIF-1α inhibitors(s) and optional additional agent(s). It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

In another embodiment, methods for screening for inhibitors of HIF-1α are provided. As described herein, increased HIF-1α activity or levels is causative of mitochondrial dysfunction. Such dysfunction can be measured according to standard methods, for example any of those described in the Examples section. In one example, a readout of mitochondrial dysfunction (e.g., resulting from increased levels or activity of HIF-1α) is a decrease in mitochondrial gene expression. Thus, in some aspects a screening method for identifying a HIF-1α inhibitors comprises (a) contacting a eukaryotic cell with a candidate compound; (b) determining the level of expression of one or more mitochondrial genes; (c) comparing the level of expression determined in (b) to a reference level of expression, wherein the reference level is determined in the absence of the candidate compound; and (d) identifying the compound as a HIF-1α inhibitor if a significantly decreased level of mitochondrial gene expression is determined in (b), as compared to the reference level in (c). In some aspects, the reference level is a predetermined level, for example the wild type level, or the level in a mutant cell. In some aspects, the one or more mitochondrial genes is selected from any of the 13 genes encoding protein in the mitochondrial genome, for example cytochrome b, cytochrome oxidase, NADH dehydrogenase, or ATP synthase. In some aspects, the eukaryotic cell is any of the cells described in the Examples section, including those genetically modified. For example, the cell may comprise a knockout of SIRT1, which as described herein has an accumulation of HIF1-α, and thus mitochondrial dysfunction. Thus, in this example, the method would comprise contacting the cell with a candidate compound and identifying the compound as a HIF-1α inhibitor if the candidate compound increases mitochondrial gene expression, or otherwise improves or restores mitochondrial function or homeostasis.

In some embodiments, the readout of mitochondrial dysfunction (e.g., resulting from increased levels or activity of HIF-1α) is a loss or depletion of mitochondrial DNA content. Thus, in some aspects, the method comprises (a) contacting a eukaryotic cell with a candidate compound; (b) determining the amount of mitochondrial DNA in the cell; (c) comparing the amount determined in (b) to a reference amount, wherein the reference level is determined in the absence of the candidate compound; and (d) identifying the compound as a HIF-1α inhibitor if a significantly decreased amount of mitochondrial DNA is determined in (b), as compared to the reference level in (c). In some aspects, the reference level is a predetermined level, for example the wild type level, or the level in a mutant cell. In some aspects, the eukaryotic cell is any of the cells described in the Examples section, including those genetically modified. For example, the cell may comprise a knockout of SIRT1, which as described herein has an accumulation of HIF1-α, and thus mitochondrial dysfunction (and depletion or loss of mitochondrial DNA). Thus, in this example, the method would comprise contacting the cell with a candidate compound and identifying the compound as a HIF-1α inhibitor if the candidate compound increases the amount of mitochondrial DNA in the cell.

Described herein are methods for rapidly reversing Warburg metabolism that is known to drive tumorigenesis and tumor growth. Methods can include administering a safe pharmacological agent, such as NMN, or a salt or prodrug thereof. One of the main drivers of cellular proliferation is HIF-1α, a hypoxia responsive transcription factor. It was observed that HIF-1α is increased during aging and that NAD precursors and NAD biosynthetic genes (e.g., NMNAT-1 and NAMPT) counteract HIF1 activity. It was also observed that this is mediated, in part, by the repression of VHL, an E3 ubiquitin ligase that promotes degradation of HIF-1 via the proteasome. Demonstrated herein are methods for modulating gene expression and metabolism of cells that would be beneficial in cancer treatment and/or prevention. Thus, compounds and genes that raise NAD will be beneficial for the prevention and treatment of cancer and modulating cellular proliferation.

Aspects of the invention relate to administering compounds such as NMN and NR, two precursors of NAD to treat most cancer types. In some embodiments, the dose is in the range of 0.5-5 grams per day.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Provided herein are methods for treating or preventing cancer in a subject in need thereof. The methods include administering to the subject an effective amount of an agent that increases the level of NAD+ in the subject. Examples of such agents include NAD+ precursors, such as NMN or a salt thereof or prodrug thereof. In some embodiments, such an agent is administered at a dose of between 0.5-5 grams per day. Other examples of agents include an enzyme involved in NAD+ biosynthesis, such as NMNAT-1 or NAMPT, or an enzymatically active fragment thereof, or a nucleic acid encoding an enzyme involved in NAD+ biosynthesis, or an enzymatically active fragment thereof. In some embodiments the subject is a human or non-human mammal.

Agents that increase levels of nicotinamide adenine dinucleotide (NAD+; which may also be referred to herein as NAD) include NAD+ precursors, such as nicotinic acid, nicotinamide, nicotinamide mononucleotide (NMN) and nicotinamide riboside (NR).

NAD+ levels also can be increased by increasing the activity of enzymes involved in NAD+ biosynthesis (de novo synthesis or salvage pathways). Enzymes involved in NAD+ biosynthesis such as nicotinate phosphoribosyl transferase 1 (NPT1), pyrazinamidase/nicotinamidase 1 (PNC1), nicotinic acid mononucleotide adenylyltransferase 1 (NMA1), nicotinic acid mononucleotide adenylyltransferase 2 (NMA2), nicotinamide N-methyltransferase (NNMT), nicotinamide phosphoribosyl transferase (NAMPT or NAMPRT), nicotinate/nicotinamide mononucleotide adenylyl transferase 1 (NMNAT-1), and nicotinamide mononucleotide adenylyl transferase 2 (NMNAT-2); are described in U.S. Pat. No. 7,977,049, which is incorporated by reference herein.

As used herein, the term "prodrug" means a derivative of a compound that can hydrolyze, oxidize, or otherwise react under biological conditions (in vitro or in vivo) to provide a compound described herein as useful in the methods of the invention. While prodrugs typically are designed to provide active compound upon reaction under biological conditions, prodrugs may have similar activity as a prodrug.

The references by Goodman and Gilman (The Pharmacological Basis of Therapeutics, 8th Ed, McGraw-Hill, Int. Ed. 1992, "Biotransformation of Drugs", p 13-15); T. Higuchi and V. Stella (Pro-drugs as Novel Delivery Systems, Vol. 14 of the A.C.S. Symposium Series); and Bioreversible Carriers in Drug Design (E. B. Roche, ed., American Pharmaceutical Association and Pergamon Press, 1987) describing pro-drugs generally are hereby incorporated by reference. Prodrugs of the compounds described herein can be prepared by modifying functional groups present in said component in such a way that the modifications are cleaved, either in routine manipulation or in vivo, to the parent component. Typical examples of prodrugs are described for instance in WO 99/33795, WO 99/33815, WO 99/33793 and WO 99/33792, each of which is incorporated herein by reference for these teachings. Prodrugs can be characterized by increased bio-availability and are readily metabolized into the active inhibitors in vivo.

Examples of prodrugs include, but are not limited to, analogs or derivatives of the compounds described herein, further comprising biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of the compounds described herein that comprise —NO, —NO$_2$, —ONO, or —ONO$_2$ moieties. Prodrugs are prepared using methods known to those of skill in the art, such as those described by BURGER'S MEDICINAL CHEMISTRY AND DRUG DISCOVERY (1995) 172-178, 949-982 (Manfred E. Wolff ed., 5$^{th}$ ed), the entire teachings of which are incorporated herein by reference.

As used herein, the terms "biohydrolyzable amide," "biohydrolyzable ester," "biohydrolyzable carbamate," "biohydrolyzable carbonate," "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

Prodrugs can include fatty acids or lipids linked to the compounds described herein by the moieties described herein. Exemplary fatty acids include the omega-3 fatty acids eicosapentaenoic acid (EPA) and docosahexaenoic acid (DHA). Such prodrugs and the preparation thereof will be clear to the skilled person; reference is for instance made to the prodrug types and preparations described in U.S. Pat. No. 5,994,392, U.S. Pat. No. 4,933,324 and U.S. Pat. No. 5,284,876.

As used herein, the term "salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+$ $(C_{1-4}alkyl)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate, and aryl sulfonate.

As used herein, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. No. 6,372,778, U.S. Pat. No. 6,369,086, U.S. Pat. No. 6,369,087 and U.S. Pat. No. 6,372,733.

Aspects of the invention relate to compositions of matter including NAD+ precursors, such as NMN or a salt thereof or prodrug thereof. Further aspects of the invention relate to compositions of matter including an enzyme involved in NAD+ biosynthesis, such as NMNAT-1 or NAMPT, or an enzymatically active fragment thereof, or a nucleic acid encoding an enzyme involved in NAD+ biosynthesis, or an enzymatically active fragment thereof. In some embodiments, compositions include conjugates of agents described herein, such as fish oil conjugates.

Aspects of the invention relate to treatment and/or prevention of disorders associated with cell proliferation. Non-limiting examples of disorders associated with cell proliferation include cancer, bacterial infection, immune rejection response of organ transplant, solid tumors, viral infection, autoimmune disorders (such as arthritis, lupus, inflammatory bowel disease, Sjogrens syndrome, multiple sclerosis) and aplastic conditions.

As used herein, "cancer" refers to a diverse class of diseases characterized by an abnormal proliferation of the diseased cells. In the case of cancer, the therapeutically effective amount of an agent may reduce the number of cancer cells; reduce the tumor size; inhibit cancer cell infiltration into peripheral organs; inhibit tumor metastasis; inhibit, to some extent, tumor growth; and/or relieve to some extent one or more of the symptoms associated with the disorder. Several non-limiting examples of cancer include: carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

It should be appreciated that agents described herein can be used in combination with other agents known in the art to treat or prevent cancer or other disorders associated will cell proliferation. For example, agents described herein could be combined with any anti-neoplastic agent or chemotherapeutic agent known in the art. Non-limiting examples of anti-neoplastic agents and chemotherapeutic agents are described in, and incorporated by reference from, US Patent Publication No. 20130028862.

Thus, the invention includes methods for delivering agents to a subject. As used herein, the term "subject" refers to a human or non-human mammal. Non-human mammals include livestock animals, companion animals, laboratory animals, and non-human primates. Non-human subjects also specifically include, without limitation, chickens, horses, cows, pigs, goats, dogs, cats, guinea pigs, hamsters, mink, and rabbits. In some embodiments the subject is a patient. As used herein, a "patient" refers to a subject who is under the care of a physician, dentist, or other health care worker, including someone who has consulted with, received advice from or received a prescription or other recommendation from a physician or other health care worker. A patient is typically a subject having or at risk of having a disorder associated with cancer.

As used herein, the term treat, treated, or treating when used with respect to an disorder such as cancer refers to a prophylactic treatment which increases the resistance of a subject to development of the disease or, in other words, decreases the likelihood that the subject will develop the disease as well as a treatment after the subject has developed the disease in order to fight the disease or prevent the disease from becoming worse.

The term "effective amount" of an agent of the invention refers to the amount necessary or sufficient to realize a desired biologic effect. For example, an effective amount of an agent for treating cancer is that amount sufficient to prevent an increase in one or more symptoms of cancer or that amount necessary to decrease one or more symptoms of cancer in the subject that would otherwise occur in the absence of the agent. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular composition being administered, the size of the subject, or the severity of the disease or condition. One of ordinary skill in the art can empirically determine the effective amount of a particular composition of the invention without necessitating undue experimentation.

The agents of the invention may be delivered to the subject on an as needed or desired basis. For instance a subject may self-administer the agents as desired or a physician may administer the agents. Additionally a physician or other health care worker may select a delivery schedule. In other embodiments of the invention, the agents are administered on a routine schedule. A "routine schedule" as used herein, refers to a predetermined designated period of time. The routine schedule may encompass periods of time which are identical or which differ in length, as long as the schedule is predetermined. For instance, the routine schedule may involve administration of the composition on a daily basis, every two days, every three days, every four days, every five days, every six days, a weekly basis, a monthly basis or any set number of days or weeks therebetween, every two months, three months, four months, five months, six months, seven months, eight months, nine months, ten months, eleven months, twelve months, etc. Alternatively, the predetermined routine schedule may involve, for example, administration of the composition on a daily basis for the first week, followed by a monthly basis for several months, and then every three months after that. Any particular combination would be covered by the routine schedule as long as it is determined ahead of time that the appropriate schedule involves administration on a certain day.

The agents may be administered alone or in any appropriate pharmaceutical carrier, such as a liquid, for example saline, or a powder, for administration in vivo. They can also be co-delivered with larger carrier particle or within administration devices. The agents may be formulated. The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the agents can be administered to a subject by any mode. Administering a pharmaceutical composition of the present invention may be accomplished by any means known to the skilled artisan. Routes of administration include but are not limited to oral, parenteral, intramuscular, intravenous, subcutaneous, mucosal, intranasal, sublingual, intratracheal, inhalation, ocular, vaginal, dermal, rectal, and by direct injection.

It is well known to those skilled in the art that agents may be administered to patients using a full range of routes of administration. As an example, agents may be blended with direct compression or wet compression tableting excipients using standard formulation methods. The resulting granulated masses may then be compressed in molds or dies to form tablets and subsequently administered via the oral route of administration. Alternately particle granulates may be extruded, spheronized and administered orally as the contents of capsules and caplets. Tablets, capsules and caplets may be film coated to alter dissolution of the delivery system (enteric coating) or target delivery of the particle to different regions of the gastrointestinal tract. Additionally, particles may be orally administered as suspensions in aqueous fluids or sugar solutions (syrups) or hydroalcoholic solutions (elixirs) or oils. The particles may also be administered directly by the oral route without any further processing.

The agents of the invention may be systemically administered in combination with a pharmaceutically acceptable vehicle such as an inert diluent or an assimilable edible carrier. They may be enclosed in hard or soft shell gelatin capsules or compressed into tablets. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of an active compound, e.g., calcium. The percentage of the compositions and preparations may, of course, be varied and may conveniently be between about 2 to about 60% of the weight of a given unit dosage form. The amount of active compound in such therapeutically useful compositions is such that an effective dosage level will be obtained. In some embodiments, agents described herein, such as NMN or a salt or prodrug thereof, are administered at a dosage of 250 mg-5 grams per day, by an oral route.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed.

To ensure full gastric resistance a coating impermeable to at least pH 5.0 can be helpful. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic, e.g., powder; for liquid forms, a soft gelatin shell may be used. The shell material of cachets could be thick starch or other edible paper. For pills, lozenges, molded tablets or tablet triturates, moist massing techniques can be used.

The agents of the invention may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In some embodiments the compositions of the invention are not encapsulated or formulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

For topical administration, the agents of the invention will generally be administered as compositions or formulations, in combination with a dermatologically acceptable carrier, which may be a solid or a liquid. Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

The compositions of the inventions may include a physiologically or pharmaceutically acceptable carrier, excipient, or stabilizer mixed with the particles. The term "pharmaceutically acceptable" means a non-toxic material that does not interfere with the effectiveness of the biological activity of the active ingredients. The term "pharmaceutically-acceptable carrier" means one or more compatible solid or liquid filler, diluants or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency. A pharmaceutical preparation is a composition suitable for administration to a subject. Such preparations are usually sterile and prepared according to GMP standards, particularly if they are to be used in human subjects. In general, a pharmaceutical composition or preparation comprises the particles, and optionally agents of the invention and a pharmaceutically-acceptable carrier, wherein the agents are generally provided in effective amounts.

Agents may also be suspended in non-viscous fluids and nebulized or atomized for administration of the dosage form to nasal membranes. Agents may also be delivered parenterally by either intravenous, subcutaneous, intramuscular, intrathecal, intravitreal or intradermal routes as sterile suspensions in isotonic fluids.

Finally, agents may be nebulized and delivered as dry powders in metered-dose inhalers for purposes of inhalation delivery. For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of for use in an inhaler or insufflator may be formulated containing the microparticle and optionally a suitable base such as lactose or starch. Those of skill in the art can readily determine the various parameters and conditions for producing aerosols without resort to undue experimentation. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Techniques for preparing aerosol delivery systems are well known to those of skill in the art. Generally, such systems should utilize components which will not significantly impair the biological properties of the agent in the nanoparticle or microparticle (see, for example, Sciarra and Cutie, "Aerosols," in Remington's Pharmaceutical Sciences, 18th edition, 1990, pp. 1694-1712; incorporated by reference).

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

Agents, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Further aspects of the invention relate to kits comprising a pharmaceutical composition comprising a therapeutically effective amount of one or more agents that increase NAD+ levels and instructions for administration of the pharmaceutical composition. In some aspects of the invention, the kit can include a pharmaceutical preparation vial, a pharmaceutical preparation diluent vial, and the agent(s). The diluent vial can contain a diluent such as physiological saline for diluting what could be a concentrated solution or lyophilized powder of the agent of the invention. In some embodiments, the instructions include instructions for mixing a particular amount of the diluent with a particular amount of the concentrated pharmaceutical preparation, whereby a final formulation for injection or infusion is prepared. In some embodiments, the instructions include instructions for use in a syringe or other administration device. In some embodiments, the instructions include instructions for treating a patient with an effective amount of an agent. It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

The present invention is further illustrated by the following Examples, which in no way should be construed as further limiting. The entire contents of all of the references (including literature references, issued patents, published patent applications, and co-pending patent applications) cited throughout this application are hereby expressly incorporated herein by reference.

EXAMPLES

The present invention will be more specifically illustrated by the following Examples. However, it should be understood that the present invention is not limited by these examples in any manner.

Experimental Procedures

Generation of a Whole Body Adult-Inducible SIRT1 Knockout Mouse

Whole body adult-inducible SIRT1 knockout mice were treated with tamoxifen for 5 weeks and the efficiency of deletion in DNA from tail samples was determined by PCR. Animals were then maintained on regular diet for 4 months. For the fasting experiments, mice were fasted for 16 hrs prior to sacrifice. All animal care followed the guidelines and was approved by the Institutional Animal Care and Use Committees (IACUCs) at Harvard Medical School.

Aging Cohorts

C57BL/6J mice of 3, 6, 22, 24, or 30 months of age were obtained from the National Institutes of Aging mouse aging colony. Mice were acclimated for at least one-week prior to sacrifice. 3, and 24-month-old mice were given interperitoneal (IP) injections of 500 mg NMN/kg body weight per day or the equivalent volume of PBS for 7 consecutive days at 5:00 pm and 7:00 am on day 8 and sacrificed 4 hr after last injection. All animal studies followed the guidelines of and were approved by the Harvard Institutional Animal Care and Use Committee C2C12 Cell Cultures Treatments, Adenoviral Infections and SIRT1 Gene Silencing Methods for cell culture treatments, adenoviral infections, and gene silencing in C2C12 cells can be found in the supplemental information.

Mitochondrial Function

Skeletal muscle mitochondria were isolated as described previously (Frezza et al., *Nat. Protoc.* 2:287-295 (2007)). Mitochondrial membrane potential, cytochrome c activity and succinate dehydrogenase were determined as described (Brautigan et al., *Methods Enzymol.* 53:128-164 (1978); Rolo et al., *Biochim. Biophys. Acta.* 1637:127-132 (s003); Singer, T. P., *Methods Biochem. Anal.* 22:123-175 (1974)). ATP content was measured with a commercial kit according to the manufacturer's instructions (Roche).

TFAM Promoter, HRE and c-Myc Activity

TFAM promoter, HRE and c-Myc activity were determined using a luciferase-based system. Luciferase activity was measured using the Dual-Luciferase Reporter Assay System (Promega) with *Renilla* as the reference.

$NAD^+$ Measurement $NAD^+$ from C2C12 cells and skeletal muscle was quantified with a commercially available kit (BioVision) according to the manufacturer's instructions and as described before (Gomes et al., *Biochim. Biophys. Acta.* 1822:185-195 (2012)).

Statistical Analysis

Data were analyzed by a two-tailed Student's t-test. All data are reported as mean±SEM. Statistical analysis was performed using Excel software.

Example 1: Knockout of SIRT1 in Adult Mice Causes an Imbalance Between Nuclear and Mitochondrially-Encoded ETC Subunits The biological importance of SIRT1 has limited the type and interpretation of experiments that are possible in complex organisms. One of the main obstacles to studying the role of this enzyme in mammals is the fact that inbred SIRT1 knockout mice die in utero or exhibit developmental abnormalities. In the case of tissue-specific knockouts, which are viable, one cannot rule out the possibility that artifacts have been introduced during the selection pressures of development. To circumvent this obstacle, an adult-inducible whole body SIRT1 knockout mouse strain (SIRT1 KO) was developed that allows the testing of the effect of deleting SIRT1 in adult animals.

At 6-8 weeks of age, male SIRT1 KO mice (C57BL/6J Cre-ERT2×SIRT1$^{floxΔE4/floxΔE4}$) and "wildtype" (WT) controls (Cre-ERT2 or SIRT1$^{floxΔE4/floxΔE4}$) were placed on a tamoxifen diet for 5 weeks, resulting in deletion of SIRT1 from major tissues in the SIRT1 KO mice but not in controls. In contrast to the germline knockout mice, deletion of SIRT1 in the adult did not affect mortality and the SIRT1 KO mice appeared outwardly normal. Upon closer examination of the muscle, however, a metabolic defect was apparent. Mitochondria isolated from gastrocnemius muscle of SIRT1 KO animals had significantly lower mitochondrial membrane potential (FIG. 4A) and cellular ATP levels (FIG. 4B).

There was no difference in mitochondrial mass between SIRT1 KO and wildtype animals, as indicated by comparing the cross-sectional area and number of mitochondria in electron micrographs (FIG. 4C). Quantitative PCR was performed to determine the mRNA levels of ETC subunits encoded by either the nuclear and mitochondrial genome. The mRNA levels of all 13 mitochondrially-encoded ETC genes were reduced in the SIRT1 KO mice compared to wildtype controls, but there was no decrease in the expression of any of the nuclear-encoded components tested (FIGS. 4D and E). Consistent with this, protein levels of the mitochondrially-encoded COX2 (cytochrome c oxidase subunit II) subunit were significantly decreased but the nuclear-encoded COX4 (Cytochrome c oxidase subunit IV) was unaltered (FIG. 4F). The specific loss of mitochondrial subunits predicts that Complex II of the ETC, which is comprised of only nuclear-encoded subunits, should be less affected by the SIRT1 deletion than other ETC complexes. The activity of Complex II (SDH) in the KO mouse was not significantly different from the wildtype, whereas the activity of Complex IV (COX) was significantly decreased (FIGS. 4G and H). In addition, mtDNA content was also reduced in the SIRT1 KO muscle relative to wildtype (FIG. 4I) despite no difference in mitochondrial mass (see FIG. 4C). To simplify discussion, the discord between nuclear and mitochondrial ETC components is referred to herein as "genome asynchrony."

Example 2: Age-Related Mitochondrial Dysfunction Resembles Genome Asynchrony in SIRT1 KO Mice It was tested whether genome asynchrony caused by the loss of SIRT1 was relevant to normal aging. A progressive, age-dependent decline in mitochondrial function with age was observed in our C57BL/6J mice. By 22 months of age, mitochondrial membrane potential, ATP content and COX activity were all decreased, a trend that was extended even further by 30 months of age (FIG. 5A-C), while there was an equal decrease in mtDNA content at both ages (FIG. 5D). The integrity of mitochondrial DNA in skeletal muscle of 6, 22 and 30 month old mice was quantified using a long-range PCR-mediated detection method. mtDNA integrity at 30 months of age was considerably lower than at 6 months. mtDNA integrity was not significantly reduced in the 22-month-olds. (FIG. 5E). These data, indicate that an alternative mechanism may be primarily responsible for the mitochondrial dysfunction observed in 22-month-old animals.

Figure 5H:
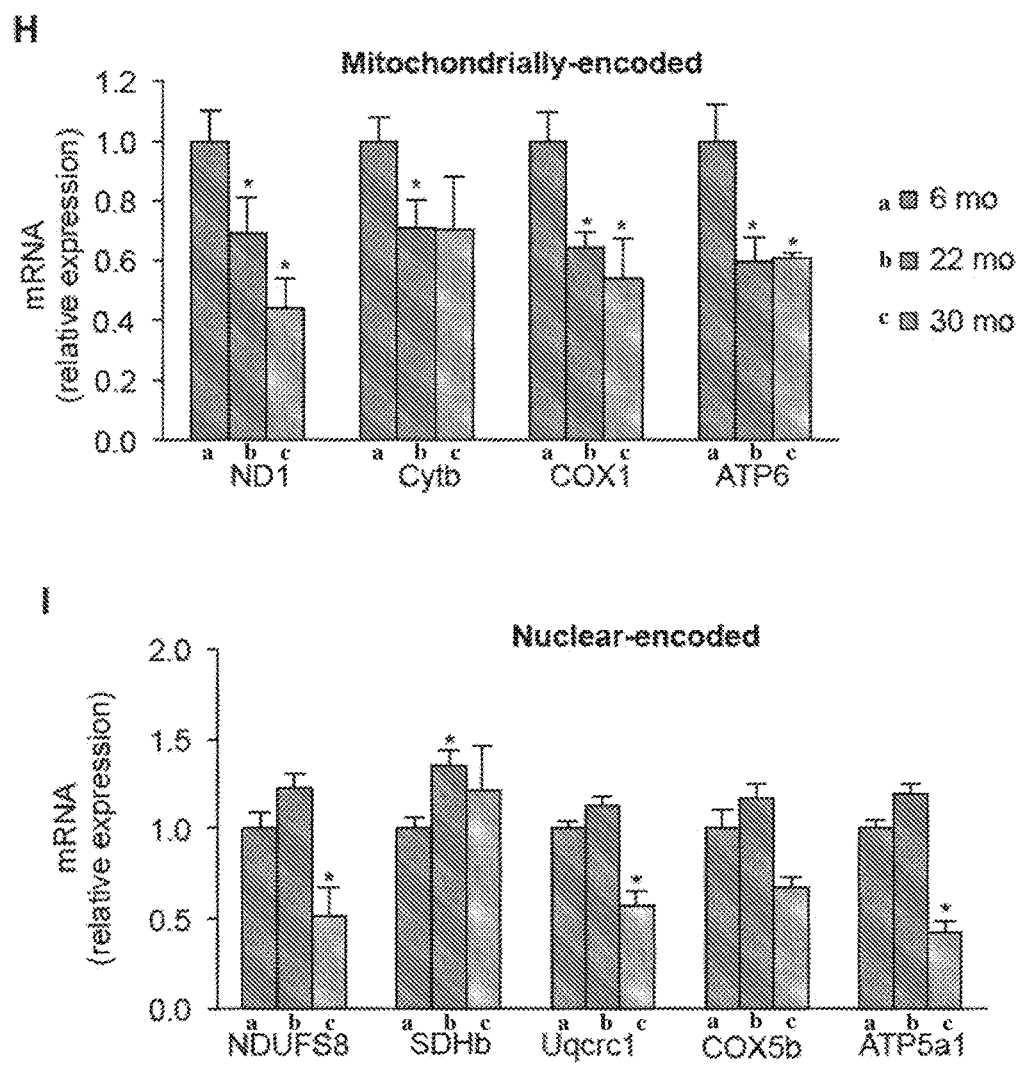
FIG. 5 shows aging leads to genome asynchrony and impaired mitochondrial function. (A) Mitochondrial membrane potential of isolated mitochondria from skeletal muscle of 6-, 22-, and 30-month-old mice (n=4). (B) ATP content from gastrocnemius of 6-, 22-, and 30-month-old mice (n=5). (C) Cytochrome c Oxidase (COX) activity in gastrocnemius of 6-, 22-, and 30-month-old mice (n=4). (D) Mitochondrial DNA content analyzed by qPCR in gastrocnemius of 6-, 22-, and 30-month-old mice. Relative amount was normalized to 6 month old mice (n=5). (E) Mitochondrial DNA integrity in gastrocnemius of 6-, 22-, and 30-month-old mice. Relative amount was normalized to 6 month old mice (n=5). (F) SIRT1 mRNA analyzed by qPCR in gastrocnemius of 6-, 22-, and 30-month-old mice. Relative expression values were normalized to 6 month old mice (n=5). (G) NAD$^+$ levels in gastrocnemius of 6-, 22-, and 30-month-old mice (n=5). (H-I) ND1, CYTB, COX1, and ATP6 (H), NDUFS8, SDHb, Uqcrc1, COX5b, ATP5a1 (I) mRNA analyzed by qPCR in gastrocnemius of 6-, 22-, and 30-month-old mice. Relative expression values were normalized to 6-month-old mice (n=5). (J) Expression of nuclear (NDUFS8, SDHb, Uqcrc1, COX5b, ATP5a1) versus mitochondrially-encoded genes (ND1, CYTB, COX1, ATP6) analysed by qPCR in gastrocnemius of 6-, 22-, and 30-month-old mice. Relative expression values were normalized to 6-month-old mice (N=5). (K) Representative immunoblot for COX2 and COX4 in gastrocnemius of 6-, 22-, and 30-month-old mice. Values are expressed as mean±SEM ($*p<0.05$ versus 6-month-old animals).

Whether the mitochondrial dysfunction in 22-month-old mice was related to the phenomenon observed in SIRT1 KO mice was tested. This possibility was supported by the fact that $NAD^+$ levels and SIRT1 activity decline with aging in a variety of tissues. While SIRT1 expression was not altered under these experimental conditions, $NAD^+$ levels were reduced in skeletal muscle of elderly mice (FIGS. 5F and 5G), indicating that SIRT1 activity may be impaired. A comparison between the skeletal muscle of 22-month- and 6-month-old mice showed that ETC genes encoded by the mitochondrial genome (ND1, CYTB, COX1, ATP6) were all significantly lower at 22 months, whereas ETC components encoded by the nuclear genome (NDUFS8, SDHb, Uqcrc1, COX5, ATP5a) were not (FIGS. 5H and I). By 30 months, however, both the nuclear and the mitochondrial ETC subunit mRNAs were lower relative to the 6-month-olds, with the exception of SDHb, which did not decline during aging (FIGS. 5I and J). Mirroring the SIRT1 KO mice, levels of the mitochondrially-encoded COX2 protein were decreased at 22 months but COX4, a nuclear-encoded protein, was only slightly lower. By 30 months however, both proteins were equally reduced relative to the young mice (FIG. 5K).

Example 3: SIRT1 Regulates Mitochondrial Homeostasis Through PGC-1α-Dependent and Independent Mechanisms The adaptation of metabolic tissues to fasting involves upregulation of SIRT1 and the targeted deacetylation of the transcriptional co-activator PGC-1α. Consistent with this, both the young SIRT1 KO and 22-month-old wildtype animals failed to upregulate ETC genes in response to fasting. Hence, it was possible that the phenotypes observed in the SIRT1 KO mice and the aged mice were a defect in the SIRT1-PGC-1α pathway of mitochondrial biogenesis. To test this, the expression of nuclear- and mitochondrially-encoded ETC genes in primary myotubes from PGC-1α/β KO mice and the effect of SIRT1 in this context was examined. The ability of SIRT1 to induce nuclear-encoded ETC genes was absent in the PGC-1α/β KO myotubes. However, overexpression of SIRT1 induced the mitochondrial ETC genes even in the absence of PGC-1α and PGC-1β (FIG. 6A). Moreover, genome asynchrony was not a phenotype of the PGC-1α/β KO myotubes under basal conditions, as both the mitochondrial and nuclear encoded components of the ETC were similarly affected by the knockout. Together, these observations revealed that SIRT1 can regulate mitochondrial gene expression independently of the canonical PGC-1α pathway and raised the possibility that genome asynchrony was due to an alternative mechanism.

To provide additional clues about the molecular basis of genome asynchrony, the gene expression patterns of skeletal muscle of SIRT1 KO mice was analyzed. Out of the mitochondrial biogenesis genes that were analyzed, only TFAM was decreased (FIG. 6B). Consistent with the in vivo findings, TFAM promoter activity was 50% lower in primary myoblasts isolated from SIRT1 KO mice than from wildtype littermates (FIG. 6C). If genome asynchrony in cells lacking SIRT1 is caused by a decrease in TFAM, restoring the expression levels of TFAM should correct genome asynchrony, along with mtDNA content and ATP levels. The restoration of TFAM levels in SIRT1 knockdown cells (FIG. 3D) was sufficient to correct genome asynchrony, mtDNA content, and ATP levels (FIG. 6E-G). This provided strong evidence that TFAM is a limiting factor that is depleted in SIRT1 KO mice causing genome asynchrony and decreased mitochondrial function.

Example 4: SIRT1 Regulates Mitochondrial Homeostasis Through HIF-1α

How SIRT1 regulates TFAM independently of PGC-1α/β was next examined. Expression analysis of gastrocnemius tissue showed that genes involved in glycolysis are more expressed in the SIRT1 KO animals, including hexokinase 2 (HK2), pyruvate kinase (PKM), phosphofructokinase (PFKM) and lactate dehydrogenase A (LDHA) (FIGS. 6H and I), reminiscent of Warburg remodeling of metabolism in cancer cells.

To test whether genome asynchrony and the resulting mitochondrial dysfunction in the muscle might be due to ectopic HIF-1α stabilization and the induction of a pseudo-hypoxic response, protein levels of HIF-1α were examined by Western blotting in skeletal muscle of SIRT1 KO mice. As shown in FIG. 6J, the levels of HIF-1α were considerably higher in the KO tissue, demonstrating that loss of SIRT1 leads to HIF-1α accumulation. The SIRT1 KO animals exhibited a gene expression pattern reminiscent of a shift towards non-oxidative metabolism, including upregulation of HIF-1α target genes PGK-1, Glut1, PDK1 and VEGFa (FIG. 6K). Consistently, primary myoblasts isolated from SIRT1 KO animals showed increased activity of the hypoxia response element (HRE), despite being cultured in normoxic conditions (FIG. 6L).

To test if the normal hypoxic response reproduces the effect of a SIRT1 deletion by causing genome asynchrony, C2C12 myoblasts were grown under hypoxic conditions (1% oxygen) or treated with dimethyloxaloylglycine (DMOG), a HIFα prolyl hydroxylase inhibitor that stabilizes HIF. Both treatments resulted in a specific decline in mtDNA content and the expression of mitochondrially-encoded ETC genes but not the nuclear-encoded components, paralleling the effect of a SIRT1 deletion.

Next whether the ability of SIRT1 to regulate mitochondrial function independently of PGC-1α/β is mediated by HIF-1α was tested. Overexpression of SIRT1 in PGC-1α/β knockout myocytes induced the expression of mitochondrial ETC genes (as shown above) but the induction was completely blocked by the HIF-1α-stabilizing compounds DMOG and desferrioxamine (DFO) (FIG. 6M). Furthermore, cells expressing a mutant allele of HIF-1α that is constitutively stabilized due to the replacement of the two hydroxylated prolines with alanines (DPA) (FIG. 7A), caused genome asynchrony similar to hypoxia and treatment with DMOG (FIG. 7B). The stabilized HIF-1α also prevented SIRT1 from increasing the expression of mitochondrially-encoded ETC subunits or mtDNA content (FIGS. 7C and 7D). Importantly, cells expressing a mutant allele of the related factor HIF-2α (stabilized by mutation of prolines 405 and 531 to alanine) did not induce genome asynchrony and had no effect on the ability of SIRT1 to promote the expression of mitochondrial ETC genes or mtDNA content. (FIG. 7A-D), indicating that this effect of SIRT1 is specific to HIF-1α.

Having shown that HIF-1α stabilization was sufficient to induce genome asynchrony, it was next tested whether it was necessary. Genome asynchrony was induced using the specific SIRT1 inhibitor EX-527 and HIF-1α was knocked down using an shRNA against HIF-1α (FIG. 7E). Knockdown of HIF-1α in C2C12 cells treated with the SIRT1 inhibitor EX-527 prevented genome asynchrony and decline in mitochondrial function, as evidenced by the maintenance of mtDNA content (FIG. 7F), mitochondrial ETC gene expression (FIG. 7G), mitochondrial membrane potential (FIG. 7G) and ATP levels (FIG. 7I). Impairment of the transcriptional activity of the HIF complex by knockdown of ARNT did not impair the effects of SIRT1 inhibition with EX-527, indicating that the effect of HIF-1α on mitochondrial homeostasis in response to SIRT1 is not mediated through changes in the HIF-1α/ARNT transcription complex but rather HIF-1α's ability to regulate the activity of other transcriptional mediators.

Example 5: c-Myc Links SIRT1 and HIF-1α to Genome Asynchrony

Under certain circumstances, HIF-1α regulates c-Myc independently of its transcriptional activity (Koshiji et al., *EMBO J.* 23:1949-1956 (2004); Koshiji et al., *Mol. Cell.* 17:793-803 (2005), each of which is hereby incorporated by reference in its entirety). It was tested whether c-Myc was the factor linking SIRT1 and HIF-1α to genome asynchrony. Myoblasts from the SIRT1 KO mice were about half as active as wildtype cells in a c-Myc reporter assay (FIG. 8A). Additionally, knockdown of c-Myc (FIG. 8B) completely blocked the ability of SIRT1 to increase mtDNA content, the expression of mitochondrially-encoded ETC genes, and TFAM promoter activity in C2C12 myoblasts (FIG. 8C-E). Conversely, in C2C12 myoblasts treated with EX-527, overexpression of c-Myc (FIG. 8F) restored the level of mtDNA content, mitochondrial ETC mRNA, TFAM promoter activity, and increased cellular ATP levels (FIG. 8G-J). A stabilized form of HIF-1α (DPA) inhibited c-Myc reporter activity in C2C12 myoblasts and prevented the increase in TFAM promoter caused by SIRT1 overexpression (FIG. 8K). Furthermore, the ability of HIF-1α knockdown to prevent the loss of TFAM promoter activity was completely prevented by c-Myc knockdown (FIG. 8L). Together these data show that HIF-1α inhibits TFAM by interfering with c-Myc, providing a link between HIF-1α and the regulation of mitochondrially-encoded ETC subunits The data also demonstrate that SIRT1 can regulate mitochondrial function via a PGC-1α/β-independent mechanism that involves Hif-1α and c-Myc.

Example 6: CR Delays Age-Related Mitochondrial Dysfunction by Preventing HIF-1α-Induced Genome Asynchrony In male C57BL/6 mice, instituting a 30-40% reduction in caloric intake from 6 weeks to 22 months of age prevents an age-associated decline in NAD$^+$ levels (FIG. 9A) mitochondrial membrane potential (FIG. 9B), ATP levels (FIG. 9C) and COX activity (FIG. 9D). CR also prevented the decrease in mtDNA content (FIG. 9E) and mitochondrially-encoded ETC components (FIG. 9F) while maintaining levels of COX subunits 2 and 4 (FIG. 9G).

If the SIRT1 KO mouse is a mimic of normal mitochondrial decline, then muscle from old mice should also contain higher levels of HIF-1α and CR should counteract this. As shown in FIG. 9H, HIF-1α levels in the muscle of 22-month-old mice were considerably higher than young controls, and CR prevented this increase (FIG. 9H). CR also suppressed the increased expression of key target genes downstream of HIF-1α that promote the shift towards non-oxidative metabolism, paralleling the effects of SIRT1 KO (FIG. 9I).

Example 7: NMN Induces NAD Levels in Skeletal Muscle and Reverses Age-Induced Genome Asynchrony and Mitochondrial Dysfunction To test whether a decline in NAD$^+$ availability, invokes a pseudohypoxic response in muscle that inhibits mitochondrial function, we treated 3- and 24-month-old C57BL/6J mice for one week by intraperitoneal injection of nicotinamide mononucleotide (NMN) (500 mg/kg body weight), a compound that increases NAD$^+$ levels in a variety of tissues. After the treatment, levels of cellular NAD$^+$ in both the young and old mice were approximately 2-fold higher, such that the treated 24-month-old mice resembled the untreated 3-month-olds (FIG. 10A). In the treated old mice a restoration of mitochondrial membrane potential to the levels of the young mice (FIG. 10B), concomitant with increases in ATP levels and COX activity (FIGS. 10C and D) were observed. Moreover, NMN treatment reversed the age-induced increase in HIF-1α in muscle and suppressed the expression of HIF-1α target genes (FIGS. 10E and 10F).

As a functional test of whether NMN reverses genome asynchrony by depleting cells of HIF-1α, primary PGC- 1α/β KO myotubes were incubated with NMN in the presence and absence of the HIF stabilizing compounds DMOG and DFO. As shown in FIG. 10K, NMN induced expression of mitochondrially-encoded ETC genes (ND1, CYTB, COX1, ATP6) but this effect was completely abolished by DMOG and DFO, indicating that, under these conditions, NMN improves mitochondrial function independently of PGC-1α/β by depleting HIF-1α (FIG. 10G).

The inducible SIRT1 KO mouse allowed the testing of the involvement of SIRT1 in the effects of NMN in vivo. The ability of NMN treatment to induce mitochondrially-encoded genes and improve mitochondrial function was lost in animals lacking SIRT1 (FIGS. 10H and 10I). Taken together, this result demonstrates that restoring NAD levels in old animals is sufficient to restore mitochondrial function and that the mechanism involves the SIRT1-mediated suppression of a pseudohypoxic response that disrupts nuclear-mitochondrial communication.

Example 8: Aging Leads to a Specific Decline in Mitochondrial-Encoded Genes Through Decreased Nuclear NAD Levels Materials and Methods
Aging Cohorts, SIRT1 KO, EGLN1 KO and SIRT1 OE Mice and NMNAT1 Electroporation C57BL/6J mice of 6, 22, or 30 months of age were obtained from the National Institutes of Aging mouse aging colony. Additionally 22 months old caloric restricted mice were also obtained from the National Institutes of Aging mouse aging colony. EGLN1 KO, SIRT1 KO and SIRT1 OE mice were generated as previously described (Minamishima et al., 2008; Price et al., 2012). Mice were acclimated for at least one-week prior to sacrifice. 3, 6, 22 and 24-month-old mice were given interperitoneal (IP) injections of 500 mg NMN/kg body weight per day or the equivalent volume of PBS for 7 consecutive days at 5:00 pm and 7:00 am on day 8 and sacrificed 4 hr after last injection.

Whole body SIRT1 overexpressor (SIRT1-tg) mice of 6 months of age were given interperitoneal (IP) injections of 300 mg DMOG/kg body weight per day or the equivalent volume of PBS for 5 consecutive days.

Whole body adult-inducible Egln1 knockout mice (Minamishima et al, 2007) were treated with IP injection of tamoxifen for 3 days after which they were allowed to rest. The mice were given interperitoneal (IP) injections of 500 mg NMN/kg body weight per day or the equivalent volume of PBS for 7 consecutive days at 5:00 pm and 7:00 am on day 8 and sacrificed 4 hr after last injection. All animal studies followed the guidelines of and were approved by the Harvard Institutional Animal Care and Use Committee.

All animal care followed the guidelines and was approved by the Institutional Animal Care and Use Committees (IACUCs) at Harvard Medical School.
Adenovirus Generation and Mutagenesis C2C12 cell line (ATCC) was cultured in low glucose Dulbecco's modified eagle medium (DMEM) (Invitrogen) supplemented with 10% FBS (Invitrogen) and a mix of antibiotic and antimycotic (Invitrogen). To inhibit SIRT1, cells were treated the vehicle (0.001% DMSO) or 10 μM EX-527 (Tocris) for 12 h. C2C12 myoblasts were infected with an empty or SIRT1 adenovirus as described before (Gerhart-Hines et al., 2007) and the media was replaced with fresh DMEM for additional 48 h, after that the cells were treated as described before. To test the effects of hypoxia and HIFα stabilization in genome asynchrony, C2C12 myoblasts were exposed to 1% oxygen for 16 h or treated with the vehicle (0.001% DMSO) or DMOG (Cayman) for the same period of time.

Generation of Primary Myoblasts, Rho0 Cells, Cell Culture Treatments, Adenoviral Infections and Gene Silencing Primary myoblasts cells were isolated from WT, SIRT1 KO (Price et al., 2012) and PGC-1α/β KO (Zechner et al., 2010) mice as previously described (Price et al., 2012). WT and PGC-1α/β KO primary myoblasts were plated and allowed to differentiate into myotubes by replacing the media with low glucose DMEM supplemented with 2% horse serum (Sigma-Aldrich) for 4 days. After the differentiation the cells were infected with empty vector or flag-SIRT1 adenovirus as described before (Gerhart-Hines et al., 2007). Media was replaced with fresh DMEM supplemented with 2% horse serum (Sigma-Aldrich) for an additional 48 hr and, after that the cells were harvested for the different assays as described. To investigate the role of HIF-1α in genome asynchrony, PGC-1α/β KO primary myotubes were treated for 12 hours with 1 mM DMOG (Sigma) or 10 μM DFO (Sigma), 24 h after infection with empty vector of flag-SIRT1 adenovirus or after 12 h treatment with 500 mM NMN (Sigma).
Mitochondrial Function Mitochondrial membrane potential was evaluated by fluorescence of the potential dependent TMRM probe. Briefly, cells were incubated with 100 nM TMRM for 15 minutes in the dark, after which the media was replaced and the fluorescence was measure by flow cytometry.

ROS and mitochondrial mass were evaluated by flow cytometry using the fluorescent probes DHE and NAO respectively as described before (Bell et a, 2011; Gomes et al, 2012).

Cytochrome c oxidase activity was polarographically determined based on the O2 consumption upon cytochrome c oxidation, as previously described (Brautigan et al., 1978). The reaction was carried out at 25° C. in 1.3 mL of standard respiratory medium (as in mitochondrial respiration) supplemented with 2 μM rotenone, 10 μM oxidized cytochrome c, 0.3 mg TritonX-100. Following addition of the sample, the reaction was initiated by adding 5 mM ascorbate plus 0.25 mM tetramethylphenylene-diamine (TMPD).

Succinate dehydrogenase activity was polarographically determined based on the 02 consumption using phenazine metasulphate (PMS) as an artificial electron acceptor, as previously described (Singer, 1974). The reaction was carried out at 25° C. in 1.3 mL of standard respiratory medium (as in mitochondrial respiration) supplemented with 5 mM succinate, 2 μM rotenone, 0.1 μg antimycin A, 1 mM KCN and 0.3 mg Triton X-100. After the addition of the sample, the reaction was initiated with 1 mM PMS.

ATP content was measured with a commercial kit according to the manufacturer's instructions (Roche).
Electron Microscopy Skeletal muscle from mice were fixed in 2.5% glutaraldehyde and 2.5% paraformaldehyde in cacodylate buffer (Electron Microscopy Sciences) then were removed, put directly into fixative, then were embedded and photographed with an electron microscope (Tecnai G2 Spirit BioTWIN) and mitochondrial area quantified with Image J software.
Gene Expression and mtDNA Analysis RNA from skeletal muscle tissue and C2C12 cells were extracted with RNeasy mini kit (Qiagen) according to the instructions and quantified using the NanoDrop 1000 spectrophotometer (Thermo Scientific). cDNA was synthesized with the iSCRIP cDNA synthesis kit (BioRad) using 600 ng of RNA. Quantitative RT-PCR reactions were performed using 1 µM of primers and LightCycler® 480 SYBR Green Master (Roche) on an LightCycler® 480 detection system (Roche). Calculations were performed by a comparative method (2-ΔCT) using 18S as an internal control. For mtDNA analysis, total DNA was extracted with DNeasy blood and tissue kit (Qiagen). mtDNA was amplified using primers specific for the mitochondrial cytochrome c oxidase subunit 2 (COX2) gene and normalized to genomic DNA by amplification of the ribosomal protein s18 (rps18) nuclear gene. Primers were designed using the IDT software (IDT) and the primer sequences can be found in Table 1.

Total DNA was extracted with DNeasy blood and tissue kit (Qiagen). Integrity of mtDNA was assessed using the long range PCR mediated detection method as described previously (Santos et al., 2006), using the following primer sequences:

Fwd: GCCAGCCTGACCCATAGCCATAATAT (SEQ ID NO: 31)

Rev: GAGAGATTTTATGGGTGTAATGCGG (SEQ ID NO: 32)

Chromatin Immunoprecipitation and Immunoblots

Protein extracts from tissue or C2C12 cells were obtained by lysis in ice-cold lysis buffer (150 mM NaCl, 10 mM Tris HCl (pH 7.4), 1 mM EDTA, 1 mM EGTA, 1% Triton X-100, 0.5% NP-40) supplemented with a cocktail of protease and phosphatase inhibitors (Roche). Protein content was determined by the Bradford protein assay (Biorad), and 50 µg proteins were run on SDS-PAGE under reducing conditions. The separated proteins were then electrophoretically transferred to a polyvinylidene difluoride membrane (Perkin-Elmer). Proteins of interest were revealed with specific antibodies: anti-TFAM (Aviva biosciences), anti-COX2, anti-COX4 (Mitosciences), anti-SIRT1, anti-β-tubulin (Sigma-Aldrich), anti-HIF1α (Cayman), anti-HA (Covance) and anti-c-Myc (Cell Signaling) overnight at 4° C. The immunostaining was detected using horseradish peroxidase-conjugated anti-rabbit or anti-mouse immunoglobulin for 1 h at room temperature. Bands were revealed using Amersham ECL detection system (GE Healthcare).

Chromatin immunoprecipitation was performed using a commercial available kit (Millipore) according to the manufacturer's instructions and using anti-HIF1α (Cayman) and anti-c-Myc (Cell Signaling) antibodies.

TFAM Promoter, VHL Promoter, HRE and c-Myc Activity

TFAM promoter, VHL promoter, HRE and c-Myc activity were determined using a luciferase-based system. Luciferase activity was measured using the Dual-Luciferase Reporter Assay System (Promega) with *Renilla* as the reference.

TFAM promoter activity was evaluated using a TFAM promotes-luc plasmid. A fragment of the mouse Tfam promoter (1.4 kb upstream of the coding sequence) was cloned into a pGL4.15 vector (Promega). Luciferase activity was measured using the Dual-Luciferase Reporter Assay System (Promega) with *Renilla* as the reference 48 h after transfection.

HIF-mediated transcriptional activity was measured using an HRE-luciferase plasmid (Bell et al., 2011). VHL promoter activity was measured using a commercially available luciferase plasmid (Affymetrix). c-Myc-mediated transcriptional activity was measured using a luciferase plasmid containing CDK4 Myc binding sites (Addgene plasmid 16564) and a mutated version as a negative control (Addgene plasmid 16565). The plasmids were transfected using X-tremeGENE HP (Roche) in accordance with the manufacturer's protocol. Luciferase activity was measured using the Dual-Luciferase Reporter Assay System (Promega) with *Renilla* as the reference 48 h after transfection.

SIRT1, c-Myc, HF1α and ARNT Gene Silencing in C2C12 Cells

SIRT1 knockdown cells were produced as described before (Gomes et al., 2012). ShMyc#1 (TRCN0000042517; Open Biosystems) ShMyc#2 (TRCN0000054885; Open Biosystems), shHIF1α (TRCN0000054450; Open Biosystems), shARNT#1 and shANRT#2 (TRCN0000079930 and TRCN0000079931, respectively; Open Biosystems) and control shGFP lentivirus were produced by co-transfection of 293T cells with plasmids encoding psPAX2 (Addgene plasmid 12260), pMD2.G (Addgene plasmid 12259) using X-tremeGENE HP (Roche) in accordance with the manufacturer's protocol. Media was changed 24 hours post-transfection and the virus harvested after 48 hours, was filtered and used to infect C2C12 cells in the presence of 5 µg/mL polybrene (Sigma-Aldrich) via spin infection (2500 rpm, 30 minutes). Selection of resistant colonies was initiated 24 hours later using 2 µg/mL puromycin (Invivogen).

c-Myc Overexpression and HIF1α and HIF2α DPA in C2C12 Cells pMXsc-Myc (Addgene plasmid 13375) and empty as well as pBabe empty (Addgene plasmid 1764), HIF1α DPA (Addgene plasmid 19005), and HIF2α DPA (Addgene plasmid 19006) retrovirus were produced by co-transfection of 293T cells with plasmids encoding gagpol (Addgene plasmid 14887) and vsvg (Addgene plasmid 8454) using X-tremeGENE HP (Roche) in accordance with the manufacturer's protocol. Media was changed 24 hours post-transfection and the virus harvested after 48 hours, was filtered and used to infect C2C12 cells in the presence of 5 µg/mL polybrene (Sigma-Aldrich) via spin infection (2500 rpm, 30 minutes). Selection of resistant colonies was initiated 24 hours later using 2 µg/mL puromycin (Invivogen). For silencing c-Myc in HIF1α knockdown cells, non-target or RNAi targeting c-Myc (Dharmacon) was transfected using Lipofectamine RNAiMAX (Invitrogen) according to the manufacturer's instructions. 24 hours after the first transfection, the transfection was repeated, to enhance the knockdown, and after 24 h hours the media was replaced and the cells treated as described previously.

TFAM Overexpression in C2C12 Cells Lacking SIRT1

To increase expression of TFAM in C2C12 cells lacking SIRT1, mouse TFAM cDNA cloned into the pIRES2-EGFP (Clontech) backbone with the EGFP cassette replaced with a hygromycin resistance cassette, was transfected using Fugene HD (Roche) in accordance with the manufacturer's instructions. Media was changed 24 h post-transfection and the selection of resistant colonies was initiated 48 h post-transfection using 100 µg/mL hygromycin as well as 2 µg/mL puromycin to maintain SIRT1 silenced. After selection the cells were maintained and treated as described before with the addition of hygromycin and puromycin to the media.

$NAD^+$ Measurement $NAD^+$ from skeletal muscle was quantified with a commercially available kit (BioVision) according to the manufacturer's instructions and as described before (Gomes et al., 2012).

Statistical Analysis

Data were analyzed by a two-tailed Student's t-test. All data are reported as mean±SEM. Statistical analysis was performed using Excel software.

TABLE 1

Mouse primers used for PCR analysis (SEQ ID NOs: 33-114)

| Gene | | Primer Sequence | Ta(°C.) |
|---|---|---|---|
| PGC-1α | Forward | CACCAAACCCACAGAAAACAG | 60 |
| | Reverse | GGGTCAGAGGAAGAGATAAAGTTG | |
| NRF-1 | Forward | AATGTCCGCAGTGATGTCC | 60 |
| | Reverse | GCCTGAGTTTGTGTTTGCTG | |
| NRF-2 | Forward | TGAAGTTCGCATTTTGATGGC | 60 |
| | Reverse | CTTTGGTCCTGGCATCTCTAC | |
| TFAM | Forward | CACCCAGATGCAAAACTTTCAG | 60 |
| | Reverse | CTGCTCTTTATACTTGCTCACAG | |
| TFB1M | Forward | ATAGAGCCCAAGATCAAGCAG | 60 |
| | Reverse | TGTAACAGCCTTCCAGTGC | |
| TFB2M | Forward | ACCAAAACCCATCCCGTC | 60 |
| | Reverse | TCTGTAAGGGCTCCAAATGTG | |
| NDUFS8 | Forward | GTTCATAGGGTCAGAGGTCAAG | 60 |
| | Reverse | TCCATTAAGATGTCCTGTGCG | |
| SDHb | Forward | ACCCCTTCTCTGTCTACCG | 60 |
| | Reverse | AATGCTCGCTTCTCCTTGTAG | |
| Uqcrc1 | Forward | ATCAAGGCACTGTCCAAGG | 60 |
| | Reverse | TCATTTTCCTGCATCTCCCG | |
| COX5b | Forward | ACCCTAATCTAGTCCCGTCC | 60 |
| | Reverse | CAGCCAAAACCAGATGACAG | |
| ATP5a1 | Forward | CATTGGTGATGGTATTGCGC | 60 |
| | Reverse | TCCCAAACACGACAACTCC | |
| NDUFAB1 | Forward | GGACCGAGTTCTGTATGTCTTG | 60 |
| | Reverse | AAACCCAAATTCGTCTTCCATG | |
| SDHd | Forward | CTTGAATCCCTGCTCTGTGG | 60 |
| | Reverse | AAAGCTGAGAGTGCCAAGAG | |
| Uqcrc2 | Forward | TTCCAGTGCAGATGTCCAAG | 60 |
| | Reverse | CTGTTGAAGGACGGTAGAAGG | |
| COX6a1 | Forward | GTTCGTTGCCTACCCTCAC | 60 |
| | Reverse | TCTCTTTACTCATCTTCATAGCCG | |
| ATP5b1 | Forward | CCGTGAGGGCAATGATTTATAC | 60 |
| | Reverse | GTCAAACCAGTCAGAGCTACC | |
| ND1 | Forward | TGCACCTACCCTATCACTCA | 60 |
| | Reverse | GGCTCATCCTGATCATAGAATGG | |
| Ctyb | Forward | CCCACCCCATATTAAACCCG | 60 |
| | Reverse | GAGGTATGAAGGAAAGGTATAAGGG | |
| COX1 | Forward | CCCAGATATAGCATTCCCACG | 60 |
| | Reverse | ACTGTTCATCCTGTTCCTGC | |
| ATP6 | Forward | TCCCAATCGTTGTAGCCATC | 60 |
| | Reverse | TGTTGGAAAGAATGGAGTCGG | |
| ND2 | Forward | ATACTAGCAATTACTTCTATTTTCATAGGG | 60 |
| | Reverse | GAGGGATGGGTTGTAAGGAAG | |
| ND3 | Forward | AAGCAAATCCATATGAATGCGG | 60 |
| | Reverse | GCTCATGGTAGTGGAAGTAGAAG | |
| ND4 | Forward | CATCACTCCTATTCTGCCTAGC | 60 |
| | Reverse | CCAACTCCATAAGCTCCATACC | |
| ND4l | Forward | CCAACTCCATAAGCTCCATACC | 60 |
| | Reverse | GATTTTGGACGTAATCTGTTCCG | |
| ND5 | Forward | ACGAAAATGACCCAGACCTC | 60 |
| | Reverse | GAGATGACAAATCCTGCAAAGATG | |

TABLE 1-continued

Mouse primers used for PCR analysis (SEQ ID NOs: 33-114)

| Gene | | Primer Sequence | Ta(°C.) |
|---|---|---|---|
| ND6 | Forward | TGTTGGAGTTATGTTGGAAGGAG | 60 |
| | Reverse | CAAAGATCACCCAGCTACTACC | |
| COX2 | Forward | AGTTGATAACCGAGTCGTTCTG | 60 |
| | Reverse | CTGTTGCTTGATTTAGTCGGC | |
| COX3 | Forward | CGTGAAGGAACCTACCAAGG | 60 |
| | Reverse | CGCTCAGAAGAATCCTGCAA | |
| ATP8 | Forward | GCCACAACTAGATACATCAACATG | 60 |
| | Reverse | TGGTTGTTAGTGATTTTGGTGAAG | |
| HIF1α | Forward | GAACATCAAGTCAGCAACGTG | 60 |
| | Reverse | TTTGACGGATGAGGAATGGG | |
| ARNT | Forward | CGAGAATGGCTGTGGATGAG | 60 |
| | Reverse | GGATGGTGTTGGACAGTGTAG | |
| LDHA | Forward | GCTCCCCAGAACAAGATTACAG | 60 |
| | Reverse | TCGCCCTTGAGTTTGTCTTC | |
| HK2 | Forward | TCAAAGAGAACAAGGGCGAG | 60 |
| | Reverse | AGGAAGCGGACATCACAATC | |
| Glut1 | Forward | TGCAGCCCAAGGATCTCTCT | 60 |
| | Reverse | CGGCTTGCCCGAGATCT | |
| PKM | Forward | CCATTCTCTACCGTCCTGTTG | 60 |
| | Reverse | TCCATGTAAGCGTTGTCCAG | |
| VEGFa | Forward | GGCAGCTTGAGTTAAACGAAC | 60 |
| | Reverse | TGGTGACATGGTTAATCGGTC | |
| PDK1 | Forward | GACTGTGAAGATGAGTGACCG | 60 |
| | Reverse | CAATCCGTAACCAAACCCAG | |
| PGK-1 | Forward | AACCTCCGCTTTCATGTAGAG | 60 |
| | Reverse | GACATCTCCTAGTTTGGACAGTG | |
| PFKM | Forward | GATGGCTTTGAGGGTCTGG | 60 |
| | Reverse | CTTGGTTATGTTGGCACTGATC | |
| mtDNA (RSP18) | Forward | TGTGTTAGGGGACTGGTGGACA | 60 |
| | Reverse | CATCACCCACTTACCCCAAAA | |
| mtDNA (COX2) | Forward | ATAACCGAGTCGTTCTGCCAAT | 60 |
| | Reverse | TTTCAGAGCATTGGCCATAGAA | |

Aging is associated with a decline in mitochondrial homeostasis (Figueiredo et al., 2008; Figueiredo et al., 2009; Hartmann et al., 2011; Lanza and Nair, 2010; Osiewacz, 2011) and consistent with previous reports (Peterson et al., 2012), a progressive, age-dependent decline in OXPHOS efficiency with age in the C57BL/6J mice was observed. By 22 months of age, ATP content was decreased, a trend that was extended even further by 30 months of age (FIG. 11A), while there was an equal decrease in mtDNA content at both ages (FIG. 11B). The integrity of mitochondrial DNA in skeletal muscle of 6, 22 and 30 month old mice was quantified using a long-range PCR-mediated detection method (Santos et al., 2006). As expected, mtDNA integrity at 30 months of age was considerably lower than at 6 months, consistent with the mtDNA damage hypothesis of aging. Surprisingly, mtDNA integrity was not significantly reduced in the 22-month-old mice. (FIG. 11C). This data, together with previous reports (Andziak and Buffenstein, 2006; Andziak et al., 2006; Howes, 2006; Lapointe et al., 2009), suggests that there is a mechanism that is independent of oxidative damage to mtDNA which may be responsible for the decline in OXPHOS observed in 22-month-old animals.

It has been previously shown that there is a correlation with age and a decline in the activity of the OXPHOS complexes, except for complex II, (Boffoli et al., 1994; Bowling et al., 1993; Kwong and Sohal, 2000) which is the only complex of the ETC chain that is composed of only nuclear-encoded subunits (Falkenberg et al., 2007). As a decline in mtDNA content was observed, it was reasoned that the impairment in OXHPOS observed in 22-month-old mice could be due to a specific decline in mitochondrial-encoded ETC complex subunits. A comparison between the skeletal muscle of 22-month- and 6-month-old mice showed that ETC genes encoded by the mitochondrial genome (ND1, Cytb, COX1, ATP6) were all significantly lower at 22 months, whereas those encoded by the nuclear genome (NDUFS8, SDHb, Uqcrc1, COX5, ATP5a) remained unchanged (FIG. 11D). By 30 months, however, both the nuclear and the mitochondrial-encoded ETC subunit mRNAs were lower relative to the 6-month-old mice (FIG. 11D). Mirroring the effects at the mRNA level, protein levels of the mitochondrial-encoded COX2 gene (cytochrome c oxidase subunit II) was decreased at 22 months but COX4 (Cytochrome c oxidase subunit IV), a nuclear-encoded protein was only slightly lower. By 30 months however, both proteins were equally reduced relative to the young mice (FIG. 11E).

$NAD^+$ levels decline with aging in a variety of tissues (Braidy et al., 2011; Massudi et al., 2012), and since $NAD^+$ is an essential co-factor for several important enzymes (Canto and Auwerx, 2011) it was next determined whether the specific decline in mitochondrial-encoded genes observed in 22-month-old mice was related with $NAD^+$ levels. Consistent with other reports (Braidy et al., 2011; Massudi et al., 2012) observed a decline in $NAD^+$ levels was observed in the skeletal muscle of elderly mice (FIG. 11F). In mammals $NAD^+$ is generated from nicotinamide in a salvage pathway where nicotinamide phosphoribosyltransferase (NAMPT) converts nicotinamide to nicotinamide mononucleotide (NMN) which is then converted to $NAD^+$ by nicotinamide mononucleotide adenylyltransferase (NMNAT) (Canto and Auwerx, 2011). Interestingly, there are three NMNAT isoforms in mammals, each with a specific subcellular localization: NMNAT1 in the nucleus; NMNAT2 in the Golgi apparatus and cytosol; and NMNAT3 in the mitochondria (Jayaram et al., 2011). The different localizations of the NMNATs allows for the differential regulation of $NAD^+$ levels in different cellular compartments (Falk et al., 2012; Zhang et al., 2009; Zhang et al., 2012). To determine whether changes in compartmentalized $NAD^+$ levels are responsible for the generation of the imbalance between nuclear- and mitochondrial-encoded genes the different NMNATs were targeted with shRNA in primary myoblasts. A decline in mitochondrial-encoded genes was observed when NMNAT1 was knocked down, but not NMNAT2 or NMNAT3 (FIG. 11G-I and FIG. 18A-C). The specific knockdown of NMNAT1 also resulted in decline in mtDNA content (FIG. 11J) as well as ATP levels (FIG. 11K) mirroring the effects observed in 22-old-mice. Together, these data indicate that age-associated impairment in mitochondrial homeostasis is caused, at least in part, by a specific decline in mitochondrial-encoded subunits of the ETC that is driven by decreased nuclear $NAD^+$ levels.

Example 9: Knockout of SIRT1 in Adult Mice Causes a Specific Decline in Mitochondrial-Encoded Genes Similar to Aging SIRT1 is an $NAD^+$-dependent deacetylase present in the nucleus and known to be tightly regulated by nuclear energetics (Canto and Auwerx, 2012; Yang and Sauve, 2006), and plays an essential role in maintenance of cellular homeostasis (Haigis and Sinclair, 2010). Both SIRT1 mRNA and protein levels were not altered in 22-month-old mice (FIGS. 18F and 18G), but since a specific decline in mitochondrial-encoded genes was observed which could be driven by modulation of nuclear NAD levels, it was hypothesized that this effect could be mediated by alterations in SIRT1 activity. To test this an adult-inducible whole body SIRT1 knockout mouse strain was utilized (SIRT1 KO; Price et al., 2012), circumventing the developmental abnormalities of germline SIRT1 KO mice (Cheng et al., 2003; McBurney et al., 2003; Sequeira et al., 2008). Interestingly, SIRT1 KO mice have a decline in cellular ATP levels (FIG. 12A) as well as a decline in mtDNA content (FIG. 12B), similar to what was observed in the skeletal muscle of 22-month-old mice (FIG. 11). Surprisingly, there was no difference in mitochondrial mass between SIRT1 KO and wild-type animals, as indicated by comparing the cross-sectional area and number of mitochondria in electron micrographs (FIG. 12C). Given that SIRT1 regulates PGC-1α activity, a master regulator of the mitochondrial biogenesis program, a general decrease in the expression of ETC components in the SIRT1 KO mice was expected. However, the mRNA levels of all 13 mitochondrial-encoded ETC genes, as well as the 2 rRNAs encoded by the mitochondrial genome, were reduced in the SIRT1 KO mice compared to wild-type controls (FIG. 12D and FIG. 19C) without a decrease in the expression of any of the nuclear-encoded components (FIG. 12D). Consistent with this, protein levels of the mitochondrial-encoded COX2 subunit were significantly decreased but the nuclear-encoded COX4 was unaltered (FIG. 12E). The specific loss of mitochondrial subunits without a change in nuclear encoded subunits suggests that Complex II of the ETC, should be less affected by SIRT1 deletion than other ETC complexes. Indeed, the activity of Complex II (SDH) in the KO mouse was not significantly different from the wild-type, whereas the activity of Complex IV (COX) was significantly decreased (FIGS. 19A and 19B). This defect is not restricted to skeletal muscle as a specific decline in mitochondrial-encoded genes was also observed in the heart of SIRT1 KO mice (FIG. 19G). However, this effect of SIRT1 does not seem to be systematic, as there was not this difference in WAT and brain, but rather a general decline in both nuclear- and mitochondrial-encoded genes in these tissues (FIG. 19D-F). Overexpression of the nuclear specific NMNAT1 induces mitochondrial-encoded genes in a SIRT1-dependent manner, as shown by the inability of NMNAT1 to induce the expression of mitochondrial-encoded genes in primary myoblasts lacking SIRT1. These data suggest that the regulation of mitochondrial homeostasis via nuclear energetics seen in aging may occur through SIRT1 (FIG. 12F).

Maintenance of mitochondrial function plays a critical role in maintenance of cellular homeostasis and muscle health (Johnson et al., 2013; Powers et al., 2012). As SIRT1 KO animals present with altered mitochondrial homeostasis it was next determined whether muscle physiology was also altered. In line with the impairment in OXPHOS capacity, a reduction in markers of slow twitch oxidative muscle fiber marker MyHCIIa was also observed, as was a concomitant increase in fast twitch glycolytic fibers as evidenced by increase in MyHCIIb content in the gastrocnemius of the SIRT1 KO mice (FIG. 12G). In addition, the SIRT1 KO mice had a striking increase in the muscle atrophy markers, (Atrogin-1 and MuRF1) (FIG. 12H), (Gumucio and Mendias, 2013), as well as, increased expression of inflammatory markers (IL-6, IL-18 and Nlrp3) (FIG. 19H). A decline in insulin signaling pathway in the soleus of SIRT1 KO animals under basal conditions was also observed, as shown by a pronounced decline in phosphorylation of AKT and IRS1. Similarly to what was observed under basal conditions, the soleus from SIRT1 KO mice demonstrated decreased phosphorylation of both AKT and IRS1 in response to insulin as compared to WT mice (FIG. 12I).

Together, these data demonstrate that loss of SIRT1 minors the specific decline in mitochondrial-encoded genes, disruption of mitochondrial homeostasis and negatively impacts muscle health similar to what occurs with age.

Example 10: SIRT1 Regulates Mitochondrial Homeostasis Through PGC-1α-Dependent and Independent Mechanisms SIRT1 has been previously shown to regulate mitochondrial homeostasis under low energy conditions, by de-acetylating the transcriptional co-activator PGC-1α to activate mitochondrial biogenesis (Gerhart-Hines et al., 2007; Rodgers et al., 2005). Consistent with this, it was observed that SIRT1 KO animals failed to upregulate ETC genes in response to fasting (FIG. 20A). However, as shown in FIG. 12, under basal conditions a general effect of SIRT1 in the mitochondrial biogenesis program and mitochondrial mass was not observed, but rather a specific decline in mitochondrial-encoded genes only, suggesting that SIRT1 might regulate mitochondrial-encoded genes independently of PGC-1α. To test this, the expression of nuclear- and mitochondrial-encoded ETC genes in primary myotubes from PGC-1α/β KO mice and the effect of SIRT1 in this context was examined. As expected, the ability of SIRT1 to induce nuclear-encoded ETC genes was absent in the PGC-1α/β KO myotubes (FIG. 13A). However, overexpression of SIRT1 induced the mitochondrial ETC genes even in the absence of PGC-1α and PGC-1β (FIG. 13A), demonstrating, for the first time, that SIRT1 can regulate mitochondrial gene expression independently of the canonical PGC-1α pathway.

Using myotubes isolated from the inducible SIRT1 KO mice (Hubbard et al., 2013), time course experiments to determine when mitochondrial homeostasis is disrupted were performed. The results demonstrated that a specific decline in mitochondrial-encoded genes (FIG. 13B), mtDNA content (FIG. 20B) and a decrease in mitochondrial membrane potential occurs as early as 12 h after excision of SIRT1 by the addition of 2-Hydroxytamoxifen (OHT) (FIG. 20C). These defects occurred without having any effect on either nuclear-encoded genes (FIG. 13B) or mitochondrial mass (FIG. 13C), resembling the effects observed in the skeletal muscle of SIRT1 KO mice under basal conditions (FIG. 12). Interestingly, 48 hr after excision there was a decline in both nuclear- and mitochondrial-encoded genes, mitochondrial mass and a more pronounced decrease in mitochondrial membrane potential (FIG. 13B-C and FIG. 20B-C) This data suggests that loss of SIRT1 results in a biphasic disruption of mitochondrial homeostasis, possibly via two distinct mechanisms.

Regulation of PGC-1α activity is complex and depends on many factors (Fernandez-Marcos and Auwerx, 2011). SIRT1 regulates PGC-1α acetylation status in conditions of low energy when there is a need for increased mitochondrial metabolism, while under basal conditions PGC-1α acetylation status is primarily regulated by GCN5 (Dominy et al., 2012; Fernandez-Marcos and Auwerx, 2011). Phosphorylation of PGC-1α by AMPK-activated kinase (AMPK) can also play an important role in regulating its activity. AMPK phosphorylation of PGC-1α on T177 and S538 (Jager et al., 2007) is required for SIRT1-mediated deacetylation and activation of PGC-1α (Canto et al., 2009). This raises the interesting possibility that the biphasic disruption in mitochondrial homeostasis upon SIRT1 deletion is mediated by AMPK activity. Consistent with this idea AMPK activity (measured by T172 phosphorylation) was not altered up to 24 h of OHT treatment (FIG. 13D). However, at 48 h of treatment with OHT, the time point where SIRT1 effects on mitochondrial biogenesis were observed (FIGS. 13B and 13C), AMPK phosphorylation was markedly increased (FIG. 13D). Similarly, AMPK activity was unchanged in the skeletal muscle of SIRT1KO mice under fed conditions and in 22-month-old mice, but markedly increased by fasting (FIGS. 20D and 20E). These experiments suggest that AMPK activity might be what causes the biphasic response between one pathway versus the other in response to SIRT1 loss To further explore this idea, AMPK activity was blocked with an AMPK dominant negative adenovirus (AMPK-DN), which efficiently inhibited phosphorylation of the AMPK target ACC, (FIG. 13F). AMPK-DN blocked the decrease in nuclear-encoded genes observed 48 h after treatment with OHT, but not the decline in mitochondrial-encoded genes (FIG. 13G). In order to determine if this AMPK affect is through PGC-1α PGC-1α/β KO myotubes were reconstituted with either a WT PGC-1α or an AMPK insensitive version of PGC-1α (PGC-1α T177A/S538A) (FIG. 20F). Reconstitution with either WT or the mutant version of PGC-1α increased both nuclear- and mitochondrial-encoded genes (FIG. 13E). Inhibition of SIRT1 function for 48 h with the specific inhibitor EX-527 decreased both nuclear- and mitochondrial-encoded genes in the presence of WT PGC-1α while only the mitochondrial-encoded genes decreased in the presence of the PGC-1α mutant (FIG. 13E). Together, these results demonstrate that AMPK determines whether SIRT1 utilizes a PGC-1α-dependent or independent mechanism to impact mitochondrial homeostasis To provide additional clues about the molecular basis of this novel PGC-1α-independent regulation of mitochondrial-encoded genes by SIRT1, gene expression patterns were analyzed from skeletal muscle of SIRT1 KO mice. The only gene that changed which is involved in the mtDNA transcription was TFAM (FIG. 13H and FIG. 20G). Consistent with the in vivo findings, TFAM promoter activity was 50% lower in primary myoblasts isolated from SIRT1 KO mice than from wild-type littermates (FIG. 13I). TFAM is necessary for mtDNA stability, replication, and transcription (Falkenberg et al., 2007), thus it was reasoned that if the specific decline in mitochondrial-encoded genes in cells lacking SIRT1 is caused by a decrease in TFAM, restoring the expression levels of TFAM should correct this effect and restore mitochondrial homeostasis. Restoring TFAM levels in primary myoblasts previously treated with OHT for 24 h to induce SIRT1KO (FIG. 13J), was sufficient to rescue mitochondrial-gene expression levels (FIG. 13K) and ATP levels (FIG. 13L). In addition, the decline in mitochondrial biogenesis caused by prolonged loss of SIRT1 (48 h of treatment with OHT) was completely absent in cells where TFAM levels where maintained for that period of time (FIGS. 13K and 13L) and accordingly, AMPK activity was also not induced (FIG. 13M). Interestingly, a 2-3 fold overexpression of TFAM in primary myoblasts (FIG. 20H), not only lead to the predictable increase in the expression of mitochondrial-encoded genes and mtDNA content (FIGS. 20I and 20J) but also to a similar increase in nuclear-encoded genes (FIG. 20I) and as a result a global increase in OXPHOS activity and ATP production (FIG. 20K). Together, these results show that TFAM is the limiting factor that is depleted in SIRT1 KO mice causing a specific decline in mitochondrially-encoded genes and, as a consequence, impairing mitochondrial homeostasis.

Example 11: SIRT1 Regulates Mitochondrial Homeostasis Through HIF-1α

Next, experiments were performed to better understand how SIRT1 regulates TFAM independently of PGC-1α/β. The skeletal muscle in SIRT1 KO animals have increased type II glycolytic fibers (FIG. 12G) and expectedly gene expression analysis demonstrated increased levels of genes involved in glycolysis, including hexokinase 2 (HK2), pyruvate kinase (PKM), phosphofructokinase (PFKM) and lactate dehydrogenase A (LDHA) (FIGS. 14A and 14B). Accordingly, SIRT1 KO mice also presented increased lactate levels in the skeletal muscle (FIG. 14C), reminiscent of Warburg remodeling of metabolism in cancer cells.

The metabolic remodeling characteristic of cancer cells is in part mediated by the stabilization of the transcription factor HIF-1α (Majmundar et al., 2010). The similarity between the gene expression of muscle from the SIRT1 KO mice and of cancer cells prompted testing as to whether the specific decline in mitochondrial-encoded genes and consequent disruption of OXPHOS functionality might be due to a pseudohypoxic response and HIF-1α stabilization. As shown in FIG. 14D, the levels of HIF-1α were considerably higher in the KO tissue, demonstrating that loss of SIRT1 leads to HIF-1α accumulation. Moreover, the SIRT1 KO animals exhibited a gene expression pattern reminiscent of cancer cells, including upregulation of HIF-1α target genes PGK-1, Glut1, PDK1 and VEGFa (FIG. 21A). Moreover, primary myoblasts also demonstrated increased HIF-1α protein levels (FIG. 14D), as well as the activity of the hypoxia response element (HRE), despite being cultured in normoxic conditions (FIG. 21B). Consistent with the idea that manipulation of cellular energetics by decreasing NAD$^+$/NADH ratio with lactate treatment also induces HIF-1α protein stabilization in primary myoblasts (FIGS. 21D and 21E).

To test if stabilization of HIF-1α is sufficient to induce the observed decline in mitochondrial-encoded ETC genes similar to the effect of SIRT1 deletion in the skeletal muscle, Egln1 KO (PHD2) inducible-whole body KO mouse were used (Minamishima et al., 2008). As expected, upon induction of Egln1 deletion HIF-1α was stabilized in the skeletal muscle (FIG. 14E). Strikingly, Egln1 deletion and consequent HIF-1α stabilization resulted in a specific decline in mtDNA content and decreased expression of mitochondrial-encoded ETC genes but not the nuclear-encoded components, paralleling the effect of SIRT1 deletion in the skeletal muscle (FIGS. 14F and 14G). Moreover, treatment of PGC-1α/β knockout myotubes with dimethyloxaloylglycine (DMOG), a HIFα prolyl hydroxylase inhibitor that stabilizes HIF-1α protein (FIG. 21C), induced a decline in the expression of mitochondrial-encoded genes compared to vehicle control (FIG. 14H). Overexpression of SIRT1 in PGC-1α/β knockout myotubes induced the expression of mitochondrial ETC genes (as shown above) but the induction was completely blocked by DMOG (FIG. 14H). Furthermore, increasing NAD levels by supplementation with pyruvate in the PGC-1α/β KO cells increased mitochondrial-encoded genes (FIG. 21F). Interestingly, the NAD mediated increases in mitochondrial-encoded genes can be inhibited by stabilizing HIF-1α with DMOG (FIG. 14I and FIG. 21F). SIRT1 overexpression in vivo induces an increase in OXPHOS capacity in the skeletal muscle by increasing the mitochondrial biogenesis program (Price et al., 2012). Therefore, it was next determined whether HIF-1α stabilization in the whole body SIRT1 overexpressing mice (SIRT1-tg) (Price et al., 2012) would prevent this increase. SIRT1-tg mice were treated with vehicle or DMOG to increase HIF-1α (FIG. 21G) and this abolished the increase in the expression of mitochondrial-encoded genes, as well as, the increase in ATP levels observed in SIRT1-tg mice (FIGS. 21H and 21I).

To dissect which one of the HIFα proteins was responsible for this increase, constitutively stabilized HIF-1α or HIF-2a (DPA) were introduced into C2C12 myoblasts (FIG. 14I). Expression of the HIF-1α mutant caused a specific decline in the expression of mitochondrial-encoded genes similar to Egln1 KO and treatment with DMOG (FIG. 14J) and also prevented SIRT1 overexpression from increasing the expression of mitochondrial-encoded ETC subunits and mtDNA (FIG. 14K and FIG. 21J). Importantly, cells expressing a mutant allele of the related factor HIF-2a did not alter the gene expression pattern of both nuclear and mitochondrial-encoded ETC genes and had no effect on the ability of SIRT1 to promote the expression of mitochondrial ETC genes or mtDNA (FIG. 14L-K and FIG. 21J), indicating that this effect of SIRT1 is specific to HIF-1α.

Since HIF-1α stabilization was sufficient to induce a specific decline in mitochondrial-encoded genes, it was next determined whether it was also necessary. Knockdown of HIF-1α in primary myoblasts lacking SIRT1 (FIG. 14L) prevented the disruption of mitochondrial homeostasis, as evidenced by the maintenance of mtDNA content (FIG. 14O) and ATP levels (FIG. 14P). In addition, impairment of the transcriptional activity of the HIF complex by knockdown of ARNT did not impair the effects of SIRT1 inhibition with EX-527 (FIG. 21K-N) indicating that the effect of HIF-1α on mitochondrial homeostasis in response to SIRT1 is not mediated through changes in the HIF-1α/ARNT transcription complex, but rather HIF-1α's ability to regulate the activity of other transcriptional mediators. These data combined demonstrate that the effects of SIRT1 in the specific regulation of mitochondrial-encoded genes and maintenance of mitochondrial homeostasis are mediated by HIF-1α both in vitro and in vivo.

Example 12: HIF-1α Stabilization Induced by Loss of SIRT1 is Independent of Retrograde Signaling and HIF-1α Deacetylation and Mediated by Regulation of VHL Levels SIRT1 has been implicated in the regulation of HIF-1α transcriptional activity (Lim et al., 2010), but not protein stabilization. Mitochondrial homeostasis plays an important role in the regulation of HIF-1α protein stability through generation of ROS from complex III (Bell et al., 2007; Chandel et al., 2000) therefore it was determined whether ROS and retrograde signaling were the cause of HIF-1α stabilization in response to loss of SIRT1. Time course experiments demonstrate that ROS levels are only upregulated 24 h after SIRT1 deletion by OHT (FIG. 22B), while the impairment in mitochondrial homeostasis was observed at 12 h (FIG. 13A and FIG. 20B-C) and HIF-1α stabilization at 6 h (FIG. 15J). This data indicates that increased ROS upon SIRT1 deletion are not the cause of HIF-1α stabilization but rather a consequence of impaired mitochondrial homeostasis. Further supporting this idea, primary myoblasts depleted of mitochondrial DNA (rho0), which are unable to produce ROS and signal to the nucleus (Chandel and Schumacker, 1999), showed the same effects upon loss of SIRT1 as their parental control cells, indicating that the effects observed are also not due to retrograde signaling (FIG. 22A).

HIF-1α stability was also previously reported to be regulated by acetylation, particularly acetylation of the lysine 709 (Geng et al., 2011). Since SIRT1 is a deacetylase it is possible that it may regulate HIF-1α protein stability via K709 deacetylation. To explore this possibility we K709 was mutated to glutamine (acetylation mimetic) or arginine (non acetylated form), as well as, K674. The latter mutations serve as a positive control since this residue is deacetylated by SIRT1 but does not affect HIF-1α stability (Lim et al., 2010). Under control conditions, stabilization of HIF-1α in any of the mutants was not detected. Moreover, SIRT1 deletion did not affect the mutants (FIG. 22C), suggesting that SIRT1 does not regulate HIF-1α protein stability acetylation.

HIFα protein abundance is tightly regulated by an oxygen-dependent proteasomal degradation mechanism, involving the Von Hippel-Lindau protein (VHL) E3 ubiquitin ligase recognizing hydroxylated proline residues. (Kaelin, 2008). To determine whether SIRT1 deletion impacts HIF-1α stability through proline hydroxylation an antibody specific for HIF-1α proline hydroxylation was used. When HIF-1α protein was stabilized with MG132 no differences in hydroxylation were found between control cells and cells lacking SIRT1 (FIG. 22D), indicating that SIRT1 does not regulate HIF-1α hydroxylation. Interestingly, both VHL protein and mRNA levels were reduced by 50% in the skeletal muscle of SIRT1 KO mice (FIGS. 15A and 15C). Conversely, in the skeletal muscle of SIRT1-tg mice VHL protein and mRNA levels were increased (FIGS. 15B and 15D), demonstrating that SIRT1 regulates VHL abundance in the skeletal muscle. Consistent with HIF-1α stabilization being caused by decreased VHL in the absence of SIRT1, HIF-2a was also stabilized in both skeletal muscle and primary myoblasts upon SIRT1 deletion (FIG. 22E). However HIF-2a target genes were not upregulated (FIG. 22F), suggesting that under these conditions HIF-2a is not transcriptionally active. Interestingly, an effect on VHL promoter activity upon SIRT1 deletion was not observed, suggesting that the differences in VHL mRNA are independent of transcription (FIGS. 15E and 15F).

Consistent with the data demonstrating that decreased NAD+ during aging drives a pseudohypoxic response by inducing HIF-1α stabilization, knockdown of NMNAT1 in primary myoblasts lead to a decline in VHL mRNA and protein levels (FIGS. 15G and 15H) and consequent HIF-1α stabilization. VHL is also decreased in the skeletal muscle of 22-month-old mice but not 6 month-old mice. To determine causality, time course experiments were performed. As shown in FIG. 15J, VHL protein levels decline as earlier as 6 h upon SIRT1 deletion, coinciding with the accumulation of HIF-1α. In addition, TFAM levels decrease 12 h after SIRT1 deletion (FIG. 15J), further strengthening the idea that loss of SIRT1 causes a decrease in TFAM and a specific decline in mitochondrial-encoded genes due to HIF-1α stabilization.

As VHL levels were correlated with HIF-1α stabilization in several of the systems and animal models utilized, next it was determined whether decreasing VHL levels is necessary for SIRT1 to induce HIF-1α stabilization. VHL was knocked down in primary myoblasts with and without SIRT1 (FIG. 15K). SIRT1 rescue in the SIRT1KO cells no longer reversed HIF-1α accumulation as in cells with VHL (FIG. 15L). Accordingly, knockdown of VHL significantly reduces the ability of SIRT1 to induce TFAM promoter activity and consequently the expression of mitochondrial-encoded genes (FIGS. 15M and N). Together, these results show that SIRT1 regulates VHL to impact HIF-1α protein stability.

Example 13: c-Myc Links SIRT1 and HIF-1α to the Specific Decline in Mitochondrial-Encoded Gene Expression A major transcriptional mediator that has been shown to aid cancer cells to proliferate under hypoxic conditions is the oncogene c-Myc (Gordan et al., 2007). This is partially due to a crosstalk between HIF-1α and c-Myc, which together fine-tune the adaptive responses to the hypoxic environment. Interestingly, some reports suggest that c-Myc controls mitochondrial biogenesis (Kim et al., 2008; Li et al., 2005) and that primary hepatocytes from c-Myc knockout mice have reduced mitochondrial mass (Li et al., 2005). Despite these reports suggesting the role of c-Myc in the regulation of mitochondrial biogenesis, the relevance of c-Myc aging or in the development of aging-related diseases, other than cancer, remains unknown.

Based on the fact that HIF-1α regulates c-Myc independently of its transcriptional activity (Koshiji et al., 2004; Koshiji et al., 2005), it was postulated that c-Myc might be the factor linking SIRT1 and HIF-1α to the specific regulation of mitochondrial-encoded ETC genes. Consistent with this, loss of SIRT1 in primary myoblasts lead to a 50% decrease in c-Myc reporter activity, as early as 6 h after the deletion was induced (FIG. 16A). Additionally, knockdown of c-Myc (FIG. 16B) completely blocked the ability of SIRT1 to increase mtDNA, the expression of mitochondrial-encoded ETC genes (FIGS. 16C and 16D). Conversely, in C2C12 myoblasts treated with EX-527, overexpression of c-Myc (FIG. 23A) restored the level of mtDNA, mitochondrial ETC mRNA, and increased cellular ATP levels (FIG. 23B-D).

c-Myc was previously shown to directly bind to the TFAM promoter in cancer cells (Li et al., 2005) and consistent with this report, it was observed that knockdown of c-Myc in primary myoblasts leads to decreased TFAM promoter activity (FIG. 16E). Mutation of the c-Myc consensus sequence, CACGTG, present in the TFAM promoter decreased the promoter activity by about half of the full length promoter (FIG. 16F). Importantly, mutation of c-Myc binding site blocks the effect of c-Myc in the TFAM promoter and does not disrupt the activity of the TFAM promoter in response to PGC-1α overexpression (FIGS. 16F and 16G). Next it was tested whether c-Myc binding site was required for SIRT1's ability to induce TFAM promoter activity. Overexpression of SIRT1 in primary myoblasts lead to an increase in the full length TFAM promoter activity, however disruption of c-Myc binding site was sufficient to completely prevent the ability of SIRT1 to induce TFAM promoter activity (FIG. 16H). Furthermore, chromatin immunoprecipitation experiments showed that c-Myc binds to the TFAM promoter in primary myoblasts and that this binding is markedly reduced upon loss of SIRT1 induced by OHT (FIGS. 16I and 1J). Interestingly, stabilization of HIF-1α with DMOG in primary myoblasts reduces the full length TFAM promoter activity (FIG. 23E) and does not have an additive effect in the absence of the c-Myc binding site (FIGS. 23E and 23F). Chromatin immunoprecipitation experiments demonstrate that HIF-1α does not bind to the TFAM promoter (FIGS. 16I and 16J), however it can bind to its known target LDHA upon SIRT1 loss (FIGS. 23G and 23H). These data suggests that HIF-1α regulates c-Myc binding to the TFAM promoter, to mediate SIRT1 regulation of mitochondrial homeostasis independently of PGC-1α. To test if indeed SIRT1's effects on the activity of the TFAM promoter require HIF-1α/c-Myc, we used primary myoblasts where HIF-1α was knockdown (FIG. 14O). Similarly to what was observed before (as described above), c-Myc binds to the TFAM promoter and its binding is dramatically decreased upon SIRT1 deletion with OHT, which also correlated with a decrease in promoter activity (FIGS. 16K and 16L). However, in cells lacking HIF-1α loss of SIRT1 does not lead to a reduction in c-Myc binding to the TFAM promoter and consequently no alteration in the TFAM promoter activity was observed (FIGS. 16K and 16L).

Together these data demonstrate that HIF-1α inhibits TFAM transcription by interfering with c-Myc, providing the first clear link between HIF-1α and the regulation of mitochondrial-encoded ETC subunits. The data also demonstrate, for the first time, that SIRT1 can regulate mitochondrial homeostasis via a PGC-1α/β-independent mechanism that involves Hif-1α and c-Myc.

Example 14: Caloric Restriction (CR) and NAD$^+$ Supplementation Protects Against Pseudohypoxic Induced Decline in Mitochondrial Homeostasis and Muscle Health During Aging There are conflicting reports about the relationship between CR and mitochondrial homeostasis (Boily et al., 2008; Civitarese et al., 2007; Cohen et al., 2004; Hancock et al., 2011; Kaeberlein et al., 2005; Lopez-Lluch et al., 2006). In male C57BL/6 mice, it was found that instituting a 30-40% reduction in caloric intake from 6 weeks to 22 months of age prevents an age-associated decline in NAD$^+$ levels, ATP levels and COX activity (FIG. 24A-C). CR also prevented the decrease in mtDNA and mitochondrial-encoded ETC components (FIG. 23D-F). CR was also able to prevent the decline in VHL protein levels and consequent increase in HIF-1α protein levels in the muscle of 22-month-old mice (FIG. 24G), suggesting that aging induces a pseudohypoxic state that can be reversed by an intervention that activates SIRT1.

It was shown above that decreased levels of NAD$^+$ associated with age invokes a SIRT1 dependent pseudohypoxic response that disrupts mitochondrial homeostasis. Therefore, artificially boosting NAD$^+$ levels in old mice should restore mitochondrial homeostasis by reducing HIF-1α levels and restoring the expression of mitochondrial-encoded ETC components. Administration of NMN, a compound recently shown to increase NAD$^+$ levels in a variety of tissues (Yoshino et al., 2011), to 6- and 22-month-old C57BL/6J mice for one week increased levels of cellular NAD$^+$ in both the young and old mice were by 2-fold. The boost in the treated 22-month-old mice resembled the untreated 6-month-olds (FIG. 17A). NMN treatment restored oxidative phosphorylation capacity as demonstrated by an increase in ATP levels and COX activity (FIG. 17B and FIG. 24H), as well as the expression of mitochondrial-encoded genes in old mice (FIG. 17C). Moreover, NMN treatment also reversed the age-induced decline in VHL and consequent accumulation of HIF-1α (FIG. 17D), as well as suppressed the increase in lactate levels in the skeletal muscle (FIG. 17E). Interestingly, in Egln1 KO mice treated with NMN did not restore mitochondrial-encoded genes and ATP levels in the skeletal muscle when compared to WT controls, indicating that HIF-1α protein stabilization inhibits the effects of NMN (FIGS. 17F and 17G). Coming full circle, if the effects that were observed with NMN are due to increase in NAD$^+$ specific to the nucleus and reestablishment of proper nuclear energetics as our initial experiments suggested (FIG. 11), then impairment of NAD$^+$ production from NMN specifically in the nucleus should prevent NMN effects on mitochondria. In primary myoblasts, knockdown of NMNAT1 completely abolishes the ability of NMN to induce the expression of mitochondrial-encoded genes (FIG. 17H), demonstrating that indeed these effects are mediated by changes in nuclear energetics. In line with this, treatment of the inducible SIRT1 KO mouse with NMN showed that the ability of NMN to increase mitochondrial-encoded genes in the skeletal muscle is lost in animals lacking SIRT1 (FIG. 17I), demonstrating that SIRT1 is the mediator between changes in nuclear energetics and consequent alterations in mitochondrial homeostasis.

Figure 17L:
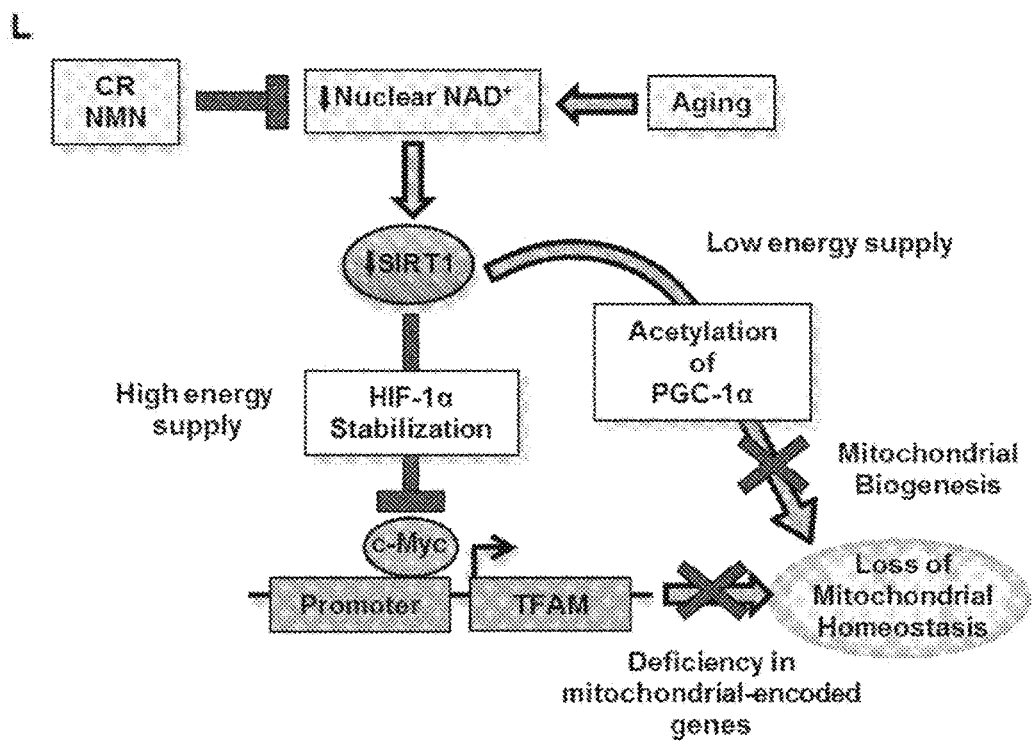
FIG. 17L depicts a schematic which reveals that the decline in nuclear NAD$^+$ during aging elicits a biphasic response mediated by SIRT1 to regulate mitochondrial homeostasis. In normal energy supply condition SIRT1 regulates specifically mitochondrial-encoded genes trough regulation of the TFAM promoter by regulating HIF-1α stabilization and c-Myc activity. Under conditions of low energy supply, like fasting or prolonged OXPHOS inhibition, SIRT1 regulates mitochondrial biogenesis through deacetylation of PGC-1α. Values are expressed as mean±SEM.

As a functional test of whether the effects of NMN in mitochondrial homeostasis were also relevant for global muscle health, several markers were evaluated. Muscle wasting and inflammation are markers of muscle aging and, as expected an increase in the muscle wasting markers Atrogin-1 and MuRF1 (FIG. 17J) and in the expression of inflammation markers in the skeletal muscle of old mice were observed (FIG. 24J). Strikingly, NMN treatment completely reversed these markers (FIG. 17J and FIG. 24K), indicating that restoring NAD levels can improve age-related muscle wasting and inflammation. In addition, NMN was also able to reverse age-induced insulin resistance in the skeletal muscle, as shown by its ability to restore insulin signaling in the soleus of old mice treated with NMN via the increasing the phosphorylation of two important downstream targets of the insulin receptor, AKT and IRS-1 (FIG. 17L).

Taken together, these results provides convincing evidence that restoring NAD levels in old animals is sufficient to restore mitochondrial homeostasis in the skeletal muscle through restoration of nuclear energetics and consequent SIRT1-mediated suppression of a pseudohypoxic, as well as to improve global muscle health.

DISCUSSION

Deregulation of mitochondrial homeostasis is one of the hallmarks of aging in diverse species such as yeast and humans. In mammals, disruption of mitochondrial homeostasis is believed to be an underlying cause of aging and the etiology of numerous age-related diseases (Coskun et al., 2011; de Moura et al., 2010; Figueiredo et al., 2009; Finsterer, 2004; Sahin et al., 2011; Schulz et al., 2007; Wallace et al., 2010). Despite its importance, there is still a great deal of controversy as to why age induces the disruption of mitochondrial homeostasis and how this process might be slowed or reversed.

One of the more surprising findings in described herein was that SIRT1 can regulate mitochondrial function independently of the canonical PGC-1α/β pathway. The data demonstrates that SIRT1 regulates mitochondrial homeostasis through two distinct pathways that are activated in distinct energetic states, and suggests that SIRT1 is involved in fine-tuning mitochondrial metabolism to maintain cellular homeostasis. Under normal cellular energetic conditions, SIRT1 regulates mitochondrial homeostasis through the PGC-1α/β-independent regulation of specifically mitochondrial-encoded genes driven by HIF-1α/c-Myc. However, under conditions of low energy, such as fasting and prolonged ETC decline, SIRT1 deacetylates and activates PGC-1α to induce fatty acid oxidation and promote mitochondrial biogenesis (Gerhart-Hines et al., 2007) (FIG. 17M). Mechanistically, the ability of SIRT1 to induce one pathway versus the other is related to AMPK activity and its ability to phosphorylate PGC-1α (Canto et al., 2009). Indeed, it was found that in conditions of energetic decline AMPK is active and signals PGC-1α to be deacetylated by SIRT1 through phosphorylation, thus activating the mitochondrial biogenesis program. However, under normal energetic conditions the phosphorylation signal is not present as AMPK is not active, thus SIRT1's effects on mitochondria are mainly mediated by the PGC-1α/β-independent pathway.

The ability of SIRT1 to regulate mitochondrial homeostasis independently of PGC-1α/β in SIRT1 KO and elderly mice was traced to an accumulation of HIF-1α in the skeletal muscle. This seems to occur in aerobic conditions, and it was demonstrated that this accumulation impairs OXPHOS and mitochondrial homeostasis in vitro and in vivo. Both CR and NMN reduced the level of HIF-1α in muscle, coincident with improvements in mitochondrial homeostasis. Conversely, stabilization of HIF-1α by genetic or pharmacological means induced an imbalance between nuclear- and mitochondrial-encoded ETC genes, and prevented the ability of SIRT1 to induce expression of mitochondrial-encoded genes. Different studies have previously linked SIRT1 to the hypoxic regulation of HIF-1α. One study demonstrated that inhibition of SIRT1 increases acetylation of HIF-1α, thereby increasing its transcriptional activity (Lim et al., 2010), while another study, has reported that SIRT1 inhibition reduces the accumulation and transcriptional activity of HIF-1α protein in hypoxic conditions (Laemmle et al., 2012). Importantly, it was shown herein that deletion of SIRT1 in vivo leads to an increase in HIF-1α protein levels in skeletal muscle under normal oxygen conditions, indicating that under normal physiological conditions SIRT1 acts as a negative regulator of HIF-1α protein stability. Interestingly it was demonstrated that the regulation of HIF-1α protein levels goes awry during aging. This occurs through the ability of SIRT1 to regulate mRNA of the E3 ubiquitin ligase VHL that is responsible for tagging HIF-1α for degradation. The data provided herein indicates that SIRT1 does not alter VHL promoter activity, thus suggesting that this change likely due to regulation of mRNA stability. However, further studies will be necessary to determine how SIRT1 regulates VHL mRNA levels in the skeletal muscle. Moreover, VHL also targets to proteasomal degration HIF-2a in a similar manner to HIF-1α. Interestingly, in addition to regulating HIF-1α (Lim et al., 2010), SIRT1 has also previously reported to regulate HIF-2a (Dioum et al., 2009). The expression of HIF-2a (but not HIF-1α) is regulated by PGC-1α and plays an important role in fiber type switching of skeletal muscle (Rasbach et al., 2010). The metabolic and fiber type changes that were observed are seemingly distinct from this pathway because the ability of SIRT1 to increase expression of mitochondrial genes or mtDNA content does not require PGC-1α, nor is it affected by stabilization of HIF-2a.

HIF-1α was previously associated with changes in mitochondrial biogenesis under conditions of obesity. High fat diet feeding induced the expression of HIF1α as well as levels of mtDNA in liver (Carabelli et al., 2011). HIF-1α was also reported to be stabilized in white adipose tissue in animal models of obesity, but upregulation of HIF-1α was found to be correlated with a decline in mitochondrial related genes in this tissue (Krishnan et al., 2012). Moreover, in the liver and macrophages of the long lived Mclk+/− mouse HIF-1α was found to be upregulated (Wang et al., 2010). The results herein also demonstrated that different tissues have different responses, suggesting that the role of HIF-1α in the regulation of mitochondrial homeostasis is tissue specific, possibly acting in accordance to the metabolic specificities of each tissue.

This metabolic state in the muscle of the SIRT1 KO and 22-month-old mice is referred to herein as pseudohypoxia, in part because the pattern of gene expression is similar to the effects of hypoxia and both involve HIF-1α and c-Myc. The other compelling reason is that the increase in HIF-1α and the shift towards non-oxidative pathways of the myoblasts occurs and persists even in the presence of normal levels of oxygen, similar to what has been described previously as a pseudohypoxic state (Sanders, 2012; Williamson et al., 1993). As far as the inventors are aware, this is the first report to suggest that pseudohypoxia-induced metabolic reprogramming is triggered in post-mitotic cells during aging and is responsible for the age-related disruption in mitochondrial homeostasis and raises the possibility that this mechanism might also be relevant to the metabolic reprogramming characteristic of cancer cells.

The finding that aging leads to a pseudohypoxic response driven by decline in nuclear energetics is particularly interesting since numerous studies have examined the role of HIF-1α in the regulation of life span in C. elegans. Although these studies clearly point to HIF-1α as a player in the aging process, its role is still a matter of debate with different lifespan outcomes being reported (Leiser and Kaeberlein, 2010). The data herein indicate that one possible explanation for the disparity is that moderate Hif-1 overexpression induces mitochondrial dysfunction, which, under certain conditions, has been shown to promote lifespan in the worm (Dillin et al., 2002; Felkai et al., 1999; Feng et al., 2001; Gallo et al., 2011).

In this study a series of genetic and pharmacological experiments are presented that point to HIF-1α-mediated inhibition of c-Myc as a cause of the specific decline in mitochondrial-encoded genes in the skeletal muscle. Together these findings clearly show that in addition to SIRT1's ability to regulate PGC-1α, it also regulates mitochondrial homeostasis by preventing the HIF-1α-mediated inhibition of c-Myc and TFAM expression, thereby providing the first link between HIF-1α/c-Myc and the disruption of mitochondrial homeostasis in the skeletal muscle during aging. Recent reports have shown that c-Myc and SIRT1 regulate each other via feedback loops, whether these are positive or negative loops is still a question of debate as different groups have reached different conclusions (Mao et al., 2011; Marshall et al., 2011; Menssen et al., 2012; Yuan et al., 2009). SIRT1 is known to directly regulate c-Myc transcriptional activity in cancer cells, either by deacetylation of c-Myc (Menssen et al., 2012) or by binding c-Myc and promoting its association with Max (Mao et al., 2011). However, under these conditions the effect of c-Myc on the TFAM promoter driven by SIRT1 requires HIF-1α, but a direct effect of SIRT1 on c-Myc under different condition cannot be excluded and as such additional studies will be required to elucidate how these feedback loops affect the regulation of mitochondrial-encoded genes.

These observations beg the question: why does aging produce a pseudohypoxic response that causes a selective loss of mitochondrial-encoded genes? On one hand, the fact that two different genomes encode different subunits of critical multi-protein complexes certainly demands tight coordination between the two genomes (Wallace et al., 2010), as such one can speculate that increased survival at advanced ages is simply beyond the force of natural selection, so that aged organisms simply succumb to entropy. On the other hand, a more nuanced explanation is based on the concept of antagonistic pleiotropy, the idea that adaptations that help young individuals survive can be deleterious later in life (Williams and Day, 2003). In this scenario, the SIRT1-HIF-1α-Myc-TFAM pathway evolved to ensure optimal mitochondrial function in response to nuclear energetics and oxygen content. In later life, however, the chronic activation of a pseudohypoxic response and the resulting disruption of normal metabolism, may result in accelerating age-related diseases. In line with this concept, disturbance in mitochondrial homeostasis during development in *C. elegans* extends lifespan (Dillin et al., 2002; Durieux et al., 2011). Moreover, mitochondrial homeostasis at old age is protected in the long lived Mclk1+/− mouse, however mitochondrial homeostasis was found to be disturbed in young ages (Wang et al., 2009) and more recently, it was shown that a mitonuclear protein imbalance can act as a conserved longevity pathway by inducing mtUPR (Houtkooper et al., 2013). While it cannot be excluded that when acutely induced this pseudohypoxia pathway might elicit mtUPR and thus be beneficial, it can be concluded that chronic induction of this pathway does not illicit mtUPR in both SIRT1 KO and in 22-months-old mice.

Together, the work described herein lead the following model, declining NAD specifically in the nucleus elicits a pseudohypoxic state driven by loss of SIRT1 activity, which induces an imbalance between nuclear- and mitochondrial-encoded genes and consequently disrupts the stoichiometric OXPHOS complexes, thus suggesting that a decline in nuclear energetics is, at least in part one, of the causes of age-related disruption of mitochondrial homeostasis and one of the means by which CR confers its beneficial health effects. Moreover, the current dogma is that aging is irreversible, but the data herein show that one week of treatment with a compound that boosts $NAD^+$ levels was sufficient to restore the mitochondrial function, as well as global muscle health of 22-month-old mice to levels similar to 6-month-olds. This study also suggests that compounds that prevent HIF-1α stabilization, or promote its degradation may also induce a similar beneficial effect on metabolism and mitochondrial homeostasis in aged tissues. In summary, these findings provide evidence for a new pathway that drives the changes in carbon utilization and the disruption in mitochondrial homeostasis that characterize aging, a pathway that is rapidly reversible and potentially amenable to treatment of a variety of age-related diseases.

REFERENCES

Andziak, B., and Buffenstein, R. (2006). Disparate patterns of age-related changes in lipid peroxidation in long-lived naked mole-rats and shorter-lived mice. Aging cell 5, 525-532.

Andziak, B., O'Connor, T. P., Qi, W., DeWaal, E. M., Pierce, A., Chaudhuri, A. R., Van Remmen, H., and Buffenstein, R. (2006). High oxidative damage levels in the longest-living rodent, the naked mole-rat. Aging Cell 5, 463-471.

Banks, A. S., Kon, N., Knight, C., Matsumoto, M., Gutierrez-Juarez, R., Rossetti, L., Gu, W., and Accili, D. (2008). SirT1 gain of function increases energy efficiency and prevents diabetes in mice. Cell metabolism 8, 333-341.

Baur, J. A., Pearson, K. J., Price, N. L., Jamieson, H. A., Lerin, C., Kalra, A., Prabhu, V. V., Allard, J. S., Lopez-Lluch, G., Lewis, K., et al. (2006). Resveratrol improves health and survival of mice on a high-calorie diet. Nature 444, 337-342.

Bell, E. L., Emerling, B. M., Ricoult, S. J., and Guarente, L. (2011). SirT3 suppresses hypoxia inducible factor 1alpha and tumor growth by inhibiting mitochondrial ROS production. Oncogene 30, 2986-2996.

Bell, E. L., Klimova, T. A., Eisenbart, J., Moraes, C. T., Murphy, M. P., Budinger, G. R., and Chandel, N. S. (2007). The Qo site of the mitochondrial complex III is required for the transduction of hypoxic signaling via reactive oxygen species production. The Journal of cell biology 177, 1029-1036.

Boffoli, D., Scacco, S. C., Vergari, R., Solarino, G., Santacroce, G., and Papa, S. (1994). Decline with age of the respiratory chain activity in human skeletal muscle. Biochimica et biophysica acta 1226, 73-82.

Boily, G., Seifert, E. L., Bevilacqua, L., He, X. H., Sabourin, G., Estey, C., Moffat, C., Crawford, S., Saliba, S., Jardine, K., et al. (2008). SirT1 regulates energy metabolism and response to caloric restriction in mice. PLoS One 3, e1759.

Bordone, L., Cohen, D., Robinson, A., Motta, M. C., van Veen, E., Czopik, A., Steele, A. D., Crowe, H., Marmor, S., Luo, J., et al. (2007). SIRT1 transgenic mice show phenotypes resembling calorie restriction. Aging Cell 6, 759-767.

Bowling, A. C., Mutisya, E. M., Walker, L. C., Price, D. L., Cork, L. C., and Beal, M. F. (1993). Age-dependent impairment of mitochondrial function in primate brain. Journal of neurochemistry 60, 1964-1967.

Braidy, N., Guillemin, G. J., Mansour, H., Chan-Ling, T., Poljak, A., and Grant, R. (2011). Age related changes in NAD+ metabolism oxidative stress and Sirt1 activity in wistar rats. PLoS One 6, e19194.

Cadenas, S., Aragones, J., and Landazuri, M. O. (2010). Mitochondrial reprogramming through cardiac oxygen sensors in ischaemic heart disease. Cardiovasc Res 88, 219-228.

Canto, C., and Auwerx, J. (2011). NAD+ as a signaling molecule modulating metabolism. Cold Spring Harbor symposia on quantitative biology 76, 291-298.

Canto, C., and Auwerx, J. (2012). Targeting sirtuin 1 to improve metabolism: all you need is NAD(+)? Pharmacological reviews 64, 166-187.

Canto, C., Gerhart-Hines, Z., Feige, J. N., Lagouge, M., Noriega, L., Milne, J. C., Elliott, P. J., Puigserver, P., and Auwerx, J. (2009). AMPK regulates energy expenditure by modulating NAD+ metabolism and SIRT1 activity. Nature 458, 1056-1060.

Carabelli, J., Burgueno, A. L., Rosselli, M. S., Gianotti, T. F., Lago, N. R., Pirola, C. J., and Sookoian, S. (2011). High fat diet-induced liver steatosis promotes an increase in liver mitochondrial biogenesis in response to hypoxia. Journal of cellular and molecular medicine 15, 1329-1338.

Cerqueira, F. M., da Cunha, F. M., Caldeira da Silva, C. C., Chausse, B., Romano, R. L., Garcia, C. C., Colepicolo, P., Medeiros, M. H., and Kowaltowski, A. J. (2011). Long-term intermittent feeding, but not caloric restriction, leads to redox imbalance, insulin receptor nitration, and glucose intolerance. Free Radic Biol Med 51, 1454-1460.

Chandel, N. S., McClintock, D. S., Feliciano, C. E., Wood, T. M., Melendez, J. A., Rodriguez, A. M., and Schumacker, P. T. (2000). Reactive oxygen species generated at mitochondrial complex III stabilize hypoxia-inducible factor-1alpha during hypoxia: a mechanism of O2 sensing. The Journal of biological chemistry 275, 25130-25138.

Chandel, N. S., and Schumacker, P. T. (1999). Cells depleted of mitochondrial DNA (rho0) yield insight into physiological mechanisms. FEBS letters 454, 173-176.

Chen, D., Thomas, E. L., and Kapahi, P. (2009). HIF-1 modulates dietary restriction-mediated lifespan extension via IRE-1 in Caenorhabditis elegans. PLoS Genet 5, e1000486.

Cheng, H. L., Mostoslaysky, R., Saito, S., Manis, J. P., Gu, Y., Patel, P., Bronson, R., Appella, E., Alt, F. W., and Chua, K. F. (2003). Developmental defects and p53 hyperacetylation in Sir2 homolog (SIRT1)-deficient mice. Proceedings of the National Academy of Sciences of the United States of America 100, 10794-10799.

Choi, J. S., Choi, K. M., and Lee, C. K. (2011). Caloric restriction improves efficiency and capacity of the mitochondrial electron transport chain in Saccharomyces cerevisiae. Biochemical and biophysical research communications 409, 308-314.

Civitarese, A. E., Carling, S., Heilbronn, L. K., Hulver, M. H., Ukropcova, B., Deutsch, W. A., Smith, S. R., and Ravussin, E. (2007). Calorie restriction increases muscle mitochondrial biogenesis in healthy humans. PLoS medicine 4, e76.

Cohen, H. Y., Miller, C., Bitterman, K. J., Wall, N. R., Hekking, B., Kessler, B., Howitz, K. T., Gorospe, M., de Cabo, R., and Sinclair, D. A. (2004). Calorie restriction promotes mammalian cell survival by inducing the SIRT1 deacetylase. Science 305, 390-392.

Coskun, P., Wyrembak, J., Schriner, S., Chen, H. W., Marciniack, C., Laferla, F., and Wallace, D. C. (2011). A mitochondrial etiology of Alzheimer and Parkinson disease. Biochimica et biophysica acta.

de Moura, M. B., dos Santos, L. S., and Van Houten, B. (2010). Mitochondrial dysfunction in neurodegenerative diseases and cancer. Environmental and molecular mutagenesis 51, 391-405.

de Oliveira, R. M., Pais, T. F., and Outeiro, T. F. (2010). Sirtuins: common targets in aging and in neurodegeneration. Curr Drug Targets 11, 1270-1280.

Dillin, A., Hsu, A. L., Arantes-Oliveira, N., Lehrer-Graiwer, J., Hsin, H., Fraser, A. G., Kamath, R. S., Ahringer, J., and Kenyon, C. (2002). Rates of behavior and aging specified by mitochondrial function during development. Science 298, 2398-2401.

Dioum, E. M., Chen, R., Alexander, M. S., Zhang, Q., Hogg, R. T., Gerard, R. D., and Garcia, J. A. (2009). Regulation of hypoxia-inducible factor 2alpha signaling by the stress-responsive deacetylase sirtuin 1. Science 324, 1289-1293.

Dominy, J. E., Jr., Lee, Y., Jedrychowski, M. P., Chim, H., Jurczak, M. J., Camporez, J. P., Ruan, H. B., Feldman, J., Pierce, K., Mostoslaysky, R., et al. (2012). The deacetylase Sirt6 activates the acetyltransferase GCN5 and suppresses hepatic gluconeogenesis. Molecular cell 48, 900-913.

Donmez, G., Wang, D., Cohen, D. E., and Guarente, L. (2010). SIRT1 suppresses beta-amyloid production by activating the alpha-secretase gene ADAM10. Cell 142, 320-332.

Durieux, J., Wolff, S., and Dillin, A. (2011). The cell-non-autonomous nature of electron transport chain-mediated longevity. Cell 144, 79-91.

Dutta, D., Calvani, R., Bernabei, R., Leeuwenburgh, C., and Marzetti, E. (2012). Contribution of impaired mitochondrial autophagy to cardiac aging: mechanisms and therapeutic opportunities. Circ Res 110, 1125-1138.

Evans, M. J., and Scarpulla, R. C. (1990). NRF-1: a trans-activator of nuclear-encoded respiratory genes in animal cells. Genes & development 4, 1023-1034.

Falk, M. J., Zhang, Q., Nakamaru-Ogiso, E., Kannabiran, C., Fonseca-Kelly, Z., Chakarova, C., Audo, I., Mackay, D. S., Zeitz, C., Borman, A. D., et al. (2012). NMNAT1 mutations cause Leber congenital amaurosis. Nature genetics 44, 1040-1045.

Falkenberg, M., Larsson, N. G., and Gustafsson, C. M. (2007). DNA replication and transcription in mammalian mitochondria. Annual review of biochemistry 76, 679-699.

Felkai, S., Ewbank, J. J., Lemieux, J., Labbe, J. C., Brown, G. G., and Hekimi, S. (1999). CLK-1 controls respiration, behavior and aging in the nematode Caenorhabditis elegans. Embo J 18, 1783-1792.

Feng, J., Bussiere, F., and Hekimi, S. (2001). Mitochondrial electron transport is a key determinant of life span in Caenorhabditis elegans. Dev Cell 1, 633-644.

Fernandez-Marcos, P. J., and Auwerx, J. (2011). Regulation of PGC-1alpha, a nodal regulator of mitochondrial biogenesis. The American journal of clinical nutrition 93, 884S-890.

Figueiredo, P. A., Mota, M. P., Appell, H. J., and Duarte, J. A. (2008). The role of mitochondria in aging of skeletal muscle. Biogerontology 9, 67-84.

Figueiredo, P. A., Powers, S. K., Ferreira, R. M., Appell, H. J., and Duarte, J. A. (2009). Aging impairs skeletal muscle mitochondrial bioenergetic function. The journals of gerontology Series A, Biological sciences and medical sciences 64, 21-33.

Finley, L. W., Carracedo, A., Lee, J., Souza, A., Egia, A., Zhang, J., Teruya-Feldstein, J., Moreira, P. I., Cardoso, S. M., Clish, C. B., et al. (2011). SIRT3 opposes reprogramming of cancer cell metabolism through HIF1alpha destabilization. Cancer Cell 19, 416-428.

Finsterer, J. (2004). Mitochondriopathies. European journal of neurology: the official journal of the European Federation of Neurological Societies 11, 163-186.

Gallo, M., Park, D., and Riddle, D. L. (2011). Increased longevity of some C. elegans mitochondrial mutants explained by activation of an alternative energy-producing pathway. Mech Ageing Dev 132, 515-518.

Geng, H., Harvey, C. T., Pittsenbarger, J., Liu, Q., Beer, T. M., Xue, C., and Qian, D. Z. (2011). HDAC4 protein regulates HIF1alpha protein lysine acetylation and cancer cell response to hypoxia. The Journal of biological chemistry 286, 38095-38102.

Gerhart-Hines, Z., Rodgers, J. T., Bare, O., Lerin, C., Kim, S. H., Mostoslaysky, R., Alt, F. W., Wu, Z., and Puigserver, P. (2007). Metabolic control of muscle mitochondrial function and fatty acid oxidation through SIRT1/PGC-1 alpha. The EMBO journal 26, 1913-1923.

Gomes, A. P., Duarte, F. V., Nunes, P., Hubbard, B. P., Teodoro, J. S., Varela, A. T., Jones, J. G., Sinclair, D. A., Palmeira, C. M., and Rolo, A. P. (2012). Berberine protects against high fat diet-induced dysfunction in muscle mitochondria by inducing SIRT1-dependent mitochondrial biogenesis. Biochim Biophys Acta 1822, 185-195.

Gordan, J. D., Thompson, C. B., and Simon, M. C. (2007). HIF and c-Myc: sibling rivals for control of cancer cell metabolism and proliferation. Cancer Cell 12, 108-113.

Gumucio, J. P., and Mendias, C. L. (2013). Atrogin-1, MuRF-1, and sarcopenia. Endocrine 43, 12-21.

Haigis, M. C., and Sinclair, D. A. (2010). Mammalian sirtuins: biological insights and disease relevance. Annual review of pathology 5, 253-295.

Hancock, C. R., Han, D. H., Higashida, K., Kim, S. H., and Holloszy, J. O. (2011). Does calorie restriction induce mitochondrial biogenesis? A reevaluation. FASEB journal: official publication of the Federation of American Societies for Experimental Biology 25, 785-791.

Harman, D. (1972). The biologic clock: the mitochondria? J Am Geriatr Soc 20, 145-147.

Hartmann, N., Reichwald, K., Wittig, I., Drose, S., Schmeisser, S., Luck, C., Hahn, C., Graf, M., Gausmann, U., Terzibasi, E., et al. (2011). Mitochondrial DNA copy number and function decrease with age in the short-lived fish Nothobranchius furzeri. Aging cell 10, 824-831.

Herranz, D., Munoz-Martin, M., Canamero, M., Mulero, F., Martinez-Pastor, B., Fernandez-Capetillo, O., and Serrano, M. (2010). Sirt1 improves healthy ageing and protects from metabolic syndrome-associated cancer. Nat Commun 1, 3.

Houtkooper, R. H., Mouchiroud, L., Ryu, D., Moullan, N., Katsyuba, E., Knott, G., Williams, R. W., and Auwerx, J. (2013). Mitonuclear protein imbalance as a conserved longevity mechanism. Nature 497, 451-457.

Howes, R. M. (2006). The free radical fantasy: a panoply of paradoxes. Ann N Y Acad Sci 1067, 22-26.

Hubbard, B. P., Gomes, A. P., Dai, H., Li, J., Case, A. W., Considine, T., Riera, T. V., Lee, J. E., E, S. Y., Lamming, D. W., et al. (2013). Evidence for a common mechanism of SIRT1 regulation by allosteric activators. Science 339, 1216-1219.

Jager, S., Handschin, C., St-Pierre, J., and Spiegelman, B. M. (2007). AMP-activated protein kinase (AMPK) action in skeletal muscle via direct phosphorylation of PGC-1alpha. Proceedings of the National Academy of Sciences of the United States of America 104, 12017-12022.

Jayaram, H. N., Kusumanchi, P., and Yalowitz, J. A. (2011). NMNAT expression and its relation to NAD metabolism. Current medicinal chemistry 18, 1962-1972.

Johnson, M. L., Robinson, M. M., and Nair, K. S. (2013). Skeletal muscle aging and the mitochondrion. Trends in endocrinology and metabolism: TEM 24, 247-256.

Kaeberlein, M., Hu, D., Kerr, E., Tsuchiya, M., Westman, E., Dang, N., Fields, S., and Kennedy, B. (2005). Increased life span due to calorie restriction in respiratory-deficient yeast. PLoS Genet 1.

Kaelin, W. G., Jr. (2008). The von Hippel-Lindau tumour suppressor protein: O2 sensing and cancer. Nature reviews Cancer 8, 865-873.

Kim, J., Lee, J. H., and Iyer, V. R. (2008). Global identification of Myc target genes reveals its direct role in mitochondrial biogenesis and its E-box usage in vivo. PloS one 3, e1798.

Koshiji, M., Kageyama, Y., Pete, E. A., Horikawa, I., Barrett, J. C., and Huang, L. E. (2004). HIF-1alpha induces cell cycle arrest by functionally counteracting Myc. Embo J 23, 1949-1956.

Koshiji, M., To, K. K., Hammer, S., Kumamoto, K., Harris, A. L., Modrich, P., and Huang, L. E. (2005). HIF-1alpha induces genetic instability by transcriptionally downregulating MutSalpha expression. Mol Cell 17, 793-803.

Krishnan, J., Danzer, C., Simka, T., Ukropec, J., Walter, K. M., Kumpf, S., Mirtschink, P., Ukropcova, B., Gasperikova, D., Pedrazzini, T., et al. (2012). Dietary obesity-associated Hif1alpha activation in adipocytes restricts fatty acid oxidation and energy expenditure via suppression of the Sirt2-NAD+ system. Genes & development 26, 259-270.

Kwong, L. K., and Sohal, R. S. (2000). Age-related changes in activities of mitochondrial electron transport complexes in various tissues of the mouse. Archives of biochemistry and biophysics 373, 16-22.

Laemmle, A., Lechleiter, A., Roh, V., Schwarz, C., Portmann, S., Furer, C., Keogh, A., Tschan, M. P., Candinas, D., Vorburger, S. A., et al. (2012). Inhibition of SIRT1 impairs the accumulation and transcriptional activity of HIF-1alpha protein under hypoxic conditions. PLoS One 7, e33433.

Lagouge, M., Argmann, C., Gerhart-Hines, Z., Meziane, H., Lerin, C., Daussin, F., Messadeq, N., Milne, J., Lambert, P., Elliott, P., et al. (2006). Resveratrol improves mitochondrial function and protects against metabolic disease by activating SIRT1 and PGC-1alpha. Cell 127, 1109-1122.

Lanza, I. R., and Nair, K. S. (2010). Mitochondrial function as a determinant of life span. Pflugers Archiv: European journal of physiology 459, 277-289.

Lapointe, J., and Hekimi, S. (2010). When a theory of aging ages badly. Cell Mol Life Sci 67, 1-8.

Lapointe, J., Stepanyan, Z., Bigras, E., and Hekimi, S. (2009). Reversal of the mitochondrial phenotype and slow development of oxidative biomarkers of aging in long-lived Mclk1+/− mice. The Journal of biological chemistry 284, 20364-20374.

Larsson, N. G. (2010). Somatic mitochondrial DNA mutations in mammalian aging. Annual review of biochemistry 79, 683-706.

Leiser, S. F., and Kaeberlein, M. (2010). The hypoxia-inducible factor HIF-1 functions as both a positive and negative modulator of aging. Biol Chem 391, 1131-1137.

Li, F., Wang, Y., Zeller, K. I., Potter, J. J., Wonsey, D. R., O'Donnell, K. A., Kim, J. W., Yustein, J. T., Lee, L. A., and Dang, C. V. (2005). Myc stimulates nuclearly encoded mitochondrial genes and mitochondrial biogenesis. Mol Cell Biol 25, 6225-6234.

Lim, J. H., Lee, Y. M., Chun, Y. S., Chen, J., Kim, J. E., and Park, J. W. (2010). Sirtuin 1 modulates cellular responses to hypoxia by deacetylating hypoxia-inducible factor 1alpha. Molecular cell 38, 864-878.

Lopez-Lluch, G., Hunt, N., Jones, B., Zhu, M., Jamieson, H., Hilmer, S., Cascajo, M. V., Allard, J., Ingram, D. K., Navas, P., et al. (2006). Calorie restriction induces mitochondrial biogenesis and bioenergetic efficiency. Proc Natl Acad Sci USA 103, 1768-1773.

Majmundar, A. J., Wong, W. J., and Simon, M. C. (2010). Hypoxia-inducible factors and the response to hypoxic stress. Molecular cell 40, 294-309.

Mao, B., Zhao, G., Lv, X., Chen, H. Z., Xue, Z., Yang, B., Liu, D. P., and Liang, C. C. (2011). Sirt1 deacetylates c-Myc and promotes c-Myc/Max association. Int J Biochem Cell Biol 43, 1573-1581.

Marshall, G. M., Liu, P. Y., Gherardi, S., Scarlett, C. J., Bedalov, A., Xu, N., Traci, N., Valli, E., Ling, D., Thomas, W., et al. (2011). SIRT1 promotes N-Myc oncogenesis through a positive feedback loop involving the effects of MKP3 and ERK on N-Myc protein stability. PLoS Genet 7, e1002135.

Massudi, H., Grant, R., Braidy, N., Guest, J., Farnsworth, B., and Guillemin, G. J. (2012). Age-Associated Changes In Oxidative Stress and NAD(+) Metabolism In Human Tissue. PLoS One 7, e42357.

McBurney, M. W., Yang, X., Jardine, K., Hixon, M., Boekelheide, K., Webb, J. R., Lansdorp, P. M., and Lemieux, M. (2003). The mammalian SIR2alpha protein has a role in embryogenesis and gametogenesis. Mol Cell Biol 23, 38-54.

Menssen, A., Hydbring, P., Kapelle, K., Vervoorts, J., Diebold, J., Luscher, B., Larsson, L. G., and Hermeking, H. (2012). The c-MYC oncoprotein, the NAMPT enzyme, the SIRT1-inhibitor DBC1, and the SIRT1 deacetylase form a positive feedback loop. Proc Natl Acad Sci USA 109, E187-196.

Michel, S., Wanet, A., De Pauw, A., Rommelaere, G., Arnould, T., and Renard, P. (2012). Crosstalk between mitochondrial (dys)function and mitochondrial abundance. Journal of cellular physiology 227, 2297-2310.

Minamishima, Y. A., Moslehi, J., Bardeesy, N., Cullen, D., Bronson, R. T., and Kaelin, W. G., Jr. (2008). Somatic inactivation of the PHD2 prolyl hydroxylase causes polycythemia and congestive heart failure. Blood 111, 3236-3244.

Minor, R. K., Baur, J. A., Gomes, A. P., Ward, T. M., Csiszar, A., Mercken, E. M., Abdelmohsen, K., Shin, Y. K., Canto, C., Scheibye-Knudsen, M., et al. (2011). SRT1720 improves survival and healthspan of obese mice. Scientific reports 1, 70.

Moslehi, J., DePinho, R. A., and Sahin, E. (2012). Telomeres and mitochondria in the aging heart. Circ Res 110, 1226-1237.

Niemann, B., Chen, Y., Issa, H., Silber, R. E., and Rohrbach, S. (2010). Caloric restriction delays cardiac ageing in rats: role of mitochondria. Cardiovascular research 88, 267-276.

Oberdoerffer, P., Michan, S., McVay, M., Mostoslaysky, R., Vann, J., Park, S. K., Hartlerode, A., Stegmuller, J., Hafner, A., Loerch, P., et al. (2008). SIRT1 redistribution on chromatin promotes genomic stability but alters gene expression during aging. Cell 135, 907-918.

Osiewacz, H. D. (2011). Mitochondrial quality control in aging and lifespan control of the fungal aging model Podospora anserina. Biochem Soc Trans 39, 1488-1492.

Parisi, M. A., and Clayton, D. A. (1991). Similarity of human mitochondrial transcription factor 1 to high mobility group proteins. Science 252, 965-969.

Peterson, C. M., Johannsen, D. L., and Ravussin, E. (2012). Skeletal muscle mitochondria and aging: a review. J Aging Res 2012, 194821.

Pfluger, P. T., Herranz, D., Velasco-Miguel, S., Serrano, M., and Tschop, M. H. (2008). Sirt1 protects against high-fat diet-induced metabolic damage. Proc Natl Acad Sci USA 105, 9793-9798.

Powers, S. K., Wiggs, M. P., Duarte, J. A., Zergeroglu, A. M., and Demirel, H. A. (2012). Mitochondrial signaling contributes to disuse muscle atrophy. American journal of physiology Endocrinology and metabolism 303, E31-39.

Price, N. L., Gomes, A. P., Ling, A. J., Duarte, F. V., Martin-Montalvo, A., North, B. J., Agarwal, B., Ye, L., Ramadori, G., Teodoro, J. S., et al. (2012). SIRT1 is required for AMPK activation and the beneficial effects of resveratrol on mitochondrial function. Cell metabolism 15, 675-690.

Qin, W., Yang, T., Ho, L., Zhao, Z., Wang, J., Chen, L., Zhao, W., Thiyagarajan, M., MacGrogan, D., Rodgers, J. T., et al. (2006). Neuronal SIRT1 activation as a novel mechanism underlying the prevention of Alzheimer disease amyloid neuropathology by calorie restriction. J Biol Chem 281, 21745-21754.

Rasbach, K. A., Gupta, R. K., Ruas, J. L., Wu, J., Naseri, E., Estall, J. L., and Spiegelman, B. M. (2010). PGC-1alpha regulates a HIF2alpha-dependent switch in skeletal muscle fiber types. Proc Natl Acad Sci USA 107, 21866-21871.

Rodgers, J. T., Lerin, C., Haas, W., Gygi, S. P., Spiegelman, B. M., and Puigserver, P. (2005). Nutrient control of glucose homeostasis through a complex of PGC-1alpha and SIRT1. Nature 434, 113-118.

Sahin, E., Colla, S., Liesa, M., Moslehi, J., Muller, F. L., Guo, M., Cooper, M., Kotton, D., Fabian, A. J., Walkey, C., et al. (2011). Telomere dysfunction induces metabolic and mitochondrial compromise. Nature 470, 359-365.

Sanders, E. (2012). Pseudohypoxia, Mitochondrial Mutations, the Warburg Effect and Cancer. Biomedical Research 23, 109-131.

Santos, J. H., Meyer, J. N., Mandavilli, B. S., and Van Houten, B. (2006). Quantitative PCR-based measurement of nuclear and mitochondrial DNA damage and repair in mammalian cells. Methods Mol Biol 314, 183-199.

Scarpulla, R. C. (2011a). Metabolic control of mitochondrial biogenesis through the PGC-1 family regulatory network. Biochim Biophys Acta 1813, 1269-1278.

Scarpulla, R. C. (2011b). Nucleus-encoded regulators of mitochondrial function: Integration of respiratory chain expression, nutrient sensing and metabolic stress. Biochimica et biophysica acta.

Schriner, S. E., Linford, N. J., Martin, G. M., Treuting, P., Ogburn, C. E., Emond, M., Coskun, P. E., Ladiges, W., Wolf, N., Van Remmen, H., et al. (2005). Extension of murine life span by overexpression of catalase targeted to mitochondria. Science 308, 1909-1911.

Schulz, T. J., Zarse, K., Voigt, A., Urban, N., Birringer, M., and Ristow, M. (2007). Glucose restriction extends Caenorhabditis elegans life span by inducing mitochondrial respiration and increasing oxidative stress. Cell metabolism 6, 280-293.

Sequeira, J., Boily, G., Bazinet, S., Saliba, S., He, X., Jardine, K., Kennedy, C., Staines, W., Rousseaux, C., Mueller, R., et al. (2008). sirt1-null mice develop an autoimmune-like condition. Experimental cell research 314, 3069-3074.

Trifunovic, A., Hansson, A., Wredenberg, A., Rovio, A. T., Dufour, E., Khvorostov, I., Spelbrink, J. N., Wibom, R., Jacobs, H. T., and Larsson, N. G. (2005). Somatic mtDNA mutations cause aging phenotypes without affecting reactive oxygen species production. Proceedings of the National Academy of Sciences of the United States of America 102, 17993-17998.

Trifunovic, A., Wredenberg, A., Falkenberg, M., Spelbrink, J. N., Rovio, A. T., Bruder, C. E., Bohlooly, Y. M., Gidlof, S., Oldfors, A., Wibom, R., et al. (2004). Premature ageing in mice expressing defective mitochondrial DNA polymerase. Nature 429, 417-423.

Vermulst, M., Wanagat, J., Kujoth, G. C., Bielas, J. H., Rabinovitch, P. S., Prolla, T. A., and Loeb, L. A. (2008). DNA deletions and clonal mutations drive premature aging in mitochondrial mutator mice. Nature genetics 40, 392-394.

Wallace, D. C., Fan, W., and Procaccio, V. (2010). Mitochondrial energetics and therapeutics. Annual review of pathology 5, 297-348.

Wang, D., Malo, D., and Hekimi, S. (2010). Elevated mitochondrial reactive oxygen species generation affects the immune response via hypoxia-inducible factor-1alpha in long-lived Mclk1+/− mouse mutants. J Immunol 184, 582-590.

Wang, Y., Branicky, R., Stepanyan, Z., Carroll, M., Guimond, M. P., Hihi, A., Hayes, S., McBride, K., and Hekimi, S. (2009). The anti-neurodegeneration drug clioquinol inhibits the aging-associated protein CLK-1. The Journal of biological chemistry 284, 314-323.

Warburg, O. (1956). On the origin of cancer cells. Science 123, 309-314.

Williams, P. D., and Day, T. (2003). Antagonistic pleiotropy, mortality source interactions, and the evolutionary theory of senescence. Evolution 57, 1478-1488.

Williamson, J. R., Chang, K., Frangos, M., Hasan, K. S., Ido, Y., Kawamura, T., Nyengaard, J. R., van den Enden, M., Kilo, C., and Tilton, R. G. (1993). Hyperglycemic pseudohypoxia and diabetic complications. Diabetes 42, 801-813.

Yang, T., and Sauve, A. A. (2006). NAD metabolism and sirtuins: metabolic regulation of protein deacetylation in stress and toxicity. The AAPS journal 8, E632-643.

Yoshino, J., Mills, K. F., Yoon, M. J., and Imai, S. (2011). Nicotinamide mononucleotide, a key NAD(+) intermediate, treats the pathophysiology of diet- and age-induced diabetes in mice. Cell metabolism 14, 528-536.

Yuan, J., Minter-Dykhouse, K., and Lou, Z. (2009). A c-Myc-SIRT1 feedback loop regulates cell growth and transformation. J Cell Biol 185, 203-211.

Zhang, Q. J., Wang, Z., Chen, H. Z., Zhou, S., Zheng, W., Liu, G., Wei, Y. S., Cai, H., Liu, D. P., and Liang, C. C. (2008). Endothelium-specific overexpression of class III deacetylase SIRT1 decreases atherosclerosis in apolipoprotein E-deficient mice. Cardiovasc Res 80, 191-199.

Zhang, T., Berrocal, J. G., Frizzell, K. M., Gamble, M. J., DuMond, M. E., Krishnakumar, R., Yang, T., Sauve, A. A., and Kraus, W. L. (2009). Enzymes in the NAD+ salvage pathway regulate SIRT1 activity at target gene promoters. The Journal of biological chemistry 284, 20408-20417.

Zhang, T., Berrocal, J. G., Yao, J., DuMond, M. E., Krishnakumar, R., Ruhl, D. D., Ryu, K. W., Gamble, M. J., and Kraus, W. L. (2012). Regulation of poly(ADP-ribose) polymerase-1-dependent gene expression through promoter-directed recruitment of a nuclear NAD+ synthase. The Journal of biological chemistry 287, 12405-12416.

Bell, E. L., Emerling, B. M., Ricoult, S. J. H., and Guarente, L. (2011). SirT3 suppresses hypoxia inducible factor 1α and tumor growth by inhibiting mitochondrial ROS production. Oncogene. 30, 2986-2996.

Brautigan, D. L., Ferguson-Miller, S., and Margoliash, E. (1978). Mitochondrial cytochrome c: preparation and activity of native and chemically modified cytochromes c. Methods in enzymology 53, 128-164.

Emaus, R. K., Grunwald, R. and Lemasters, J. J. (1986). Rhodamine 123 as a probe of transmembrane potential in isolated rat-liver mitochondria: spectral and metabolic properties. Biochim. Biophys. Acta. 850, 436-448.

Gerhart-Hines, Z., Rodgers, J. T., Bare, O., Lerin, C., Kim, S. H., Mostoslaysky, R., Alt, F. W., Wu, Z., and Puigserver, P. (2007). Metabolic control of muscle mitochondrial function and fatty acid oxidation through SIRT1/PGC-1α lpha. EMBO J. 26, 1913-1923.

Gomes, A. P., Duarte, F. V., Nunes, P., Hubbard, B. P., Teodor, J. S., Varela, A. T., Jones, J. G., Sinclair, D. A., Palmeira, C. M., and Rolo, A. P. (2012). Berberine protects against high fat diet-induced dysfunction in muscle mitochondria by inducing SIRT1-dependent mitochondrial biogenesis. Biochim. Biophys. Acta. 1822, 185-195.

Rolo, A. P., Palmeira, C. M., and Wallace, K. B. (2003). Mitochondrially mediated synergistic cell killing by bile acids. Biochimica et biophysica acta 1637, 127-132.

Price, N. L., Gomes, A. P., Ling, A. J. Y., Duarte, F. V., Matin-Montalvo, A., North, B. J., Agarwal, B., Ye, L., Ramadori, G., Teodoro, J. S., Hubbard, B. P., Varela A. T., David, J. G., Varamini, B., Hafner, A., Moaddel, R., Rolo, A. P., Coppari, R., Palmeira, C. M., de Cabo, R., Baur, J. A., and Sinclair, D. A. (2012). SIRT1 is required for AMPK activation and the beneficial effects of resveratrol on mitochondrial function. Cell Metab. 15, 675-690.

Santos, J. H., Meyer, J. N., Mandavilli, B. S. and Van Houten, B. (2006). Quantitative PCR-based measurement of nuclear and mitochondrial DNA damage and repair in mammalian cells. Methods Mol. Biol. 314, 183-199.

Singer, T. P. (1974). Determination of the activity of succinate, NADH, choline, and alpha-glycerophosphate dehydrogenases. Methods of biochemical analysis 22, 123-175.

Zechner, C., Lai, L., Zechner, J. F., Gen, T., Yan. Z., Rumsey, J. W., Collia, D., Chen, Z., Wozniak, D. F., Leone, T. C. and Kelly, D. P. (2010). Total skeletal muscle PGC-1 deficiency uncouples mitochondrial derangements from fiber type determination and insulin sensitivity. Cell Metab. 12, 633-642.

Example 15: Investigation of Reversal of Warburg Metabolism Through Modulation of NAD+ Levels Methods
Aging Cohorts C57BL/6J mice of 3, 6, 22, or 24 months of age were obtained from the National Institutes of Aging mouse aging colony. Additionally 22 months old caloric restricted mice were also obtained from the National Institutes of Aging mouse aging colony. Mice were acclimated for at least one-week prior to sacrifice. 3, 6, 22 and 24-month-old mice were given interperitoneal (IP) injections of 500 mg NMN/kg body weight per day or the equivalent volume of PBS for 7 consecutive days at 5:00 pm and 7:00 am on day 8 and sacrificed 4 hr after last injection. All animal studies followed the guidelines of and were approved by the Harvard Institutional Animal Care and Use Committee Egln1 KO Mice Whole body adult-inducible Egln1 knockout mice (Minamishima et al, 2007) were treated with IP injection of tamoxifen for 3 days after which they were allowed to rest. The mice were given interperitoneal (IP) injections of 500 mg NMN/kg body weight per day or the equivalent volume of PBS for 7 consecutive days at 5:00 pm and 7:00 am on day 8 and sacrificed 4 hr after last injection. All animal studies followed the guidelines of and were approved by the Harvard Institutional Animal Care and Use Committee.

NMNAT1 Gene Silencing in Primary Myoblasts and NAMPT Gene Silencing in C2C12 Cells shNMNAT1#1, shNMNAT1#2, shNAMPT1#1 and shNAMPT#2 (Open Biosystems) and control shGFP lentivirus were produced by co-transfection of 293T cells with plasmids encoding psPAX2 (Addgene plasmid 12260), pMD2.G (Addgene plasmid 12259) using X-tremeGENE HP (Roche) in accordance with the manufacturer's protocol. Media was changed 24 hours post-transfection and the virus harvested after 48 hours, was filtered and used to infect primary myoblasts isolated as described before (Price et al, 2012) and C2C12 cells in the presence of 5 µg/mL polybrene (Sigma-Aldrich) via spin infection (2500 rpm, 30 minutes). Selection of resistant colonies was initiated 24 hours later using 2 µg/mL puromycin (Invivogen).

Gene Expression

RNA from skeletal muscle and aorta were extracted with RNeasy mini kit (Qiagen) according to the instructions and quantified using the NanoDrop 1000 spectrophotometer (Thermo Scientific). cDNA was synthesized with the iSCRIP cDNA synthesis kit (BioRad) using 600 ng of RNA. Quantitative RT-PCR reactions were performed using 1 µM of primers and LightCycler® 480 SYBR Green Master (Roche) on an LightCycler® 480 detection system (Roche). Calculations were performed by a comparative method ($2^{-\Delta CT}$) using 18S as an internal control. Primers were designed using the IDT software (IDT).

Immunoblot

Protein extracts from tissue were obtained by lysis in ice-cold lysis buffer (150 mM NaCl, 10 mM Tris HCl (pH 7.4), 1 mM EDTA, 1 mM EGTA, 1% Triton X-100, 0.5% NP-40) supplemented with a cocktail of protease and phosphatase inhibitors (Roche). Protein content was determined by the Bradford protein assay (Biorad), and 50 µg proteins were run on SDS-PAGE under reducing conditions. The separated proteins were then electrophoretically transferred to a polyvinylidene difluoride membrane (Perkin-Elmer). Proteins of interest were revealed with specific antibodies: anti-β-tubulin (Sigma-Aldrich), anti-HIF1α (Cayman) and anti-VHL (Cell Signaling) overnight at 4° C. The immunostaining was detected using horseradish peroxidase-conjugated anti-rabbit or anti-mouse immunoglobulin for 1 h at room temperature. Bands were revealed using Amersham ECL detection system (GE Healthcare).

HRE Activity

HIF-mediated transcriptional activity was measured using an HRE-luciferase plasmid (Bell et al., 2011). The plasmids were transfected using X-tremeGENE HP (Roche) in accordance with the manufacturer's protocol. Luciferase activity was measured using the Dual-Luciferase Reporter Assay System (Promega) with *Renilla* as the reference 48 h after transfection.

ATP Content

ATP content was measured with a commercial kit according to the manufacturer's instructions (Roche).

Lactate Levels

Lactate from skeletal muscle was quantified with a commercially available kit (BioVision) according to the manufacturer's instructions.

NAD+ Measurement

NAD+ from skeletal muscle was quantified with a commercially available kit (BioVision) according to the manufacturer's instructions and as described before (Gomes et al., 2012).

Results

Figure 25:
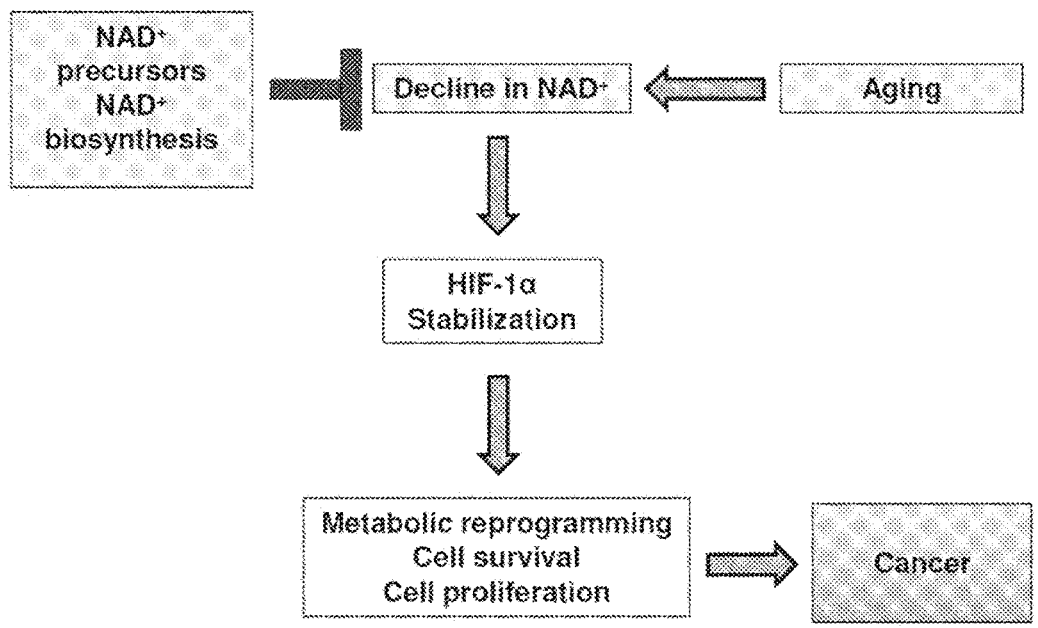
FIG. 25 presents a schematic depicting the connection between NAD+ levels and cancer.

FIG. 25 presents a schematic depicting the connection between NAD+ levels and cancer. FIG. 26 depicts HIF-1alpha levels and demonstrates that the downstream effects on metabolism promote cancer proliferation via the Warburg effect. FIGS. 27A and B demonstrate that HIF-1alpha stabilization and target genes are modulated by NAD biosynthesis (NMNAT-1 and NAMPT). The NAD+ biosynthetic pathway in mammals is depicted. FIG. 28 demonstrates that caloric restriction, a known intervention that suppresses most cancers, maintains NAD+ levels and shows the same effects as NMN on VHL/HIF1.

REFERENCES

Bell, E. L., Emerling, B. M., Ricoult, S. J. H., and Guarente, L. (2011). SirT3 suppresses hypoxia inducible factor 1α and tumor growth by inhibiting mitochondrial ROS production. Oncogene. 30, 2986-2996.

Gomes, A. P., Duarte, F. V., Nunes, P., Hubbard, B. P., Teodoro, J. S., Varela, A. T., Jones, J. G., Sinclair, D. A., Palmeira, C. M., and Rolo, A. P. (2012). Berberine protects against high fat diet-induced dysfunction in muscle mitochondria by inducing SIRT1-dependent mitochondrial biogenesis. Biochim Biophys Acta 1822, 185-195.

Minamishima, Y. A., Moslehi, J., Bardeesy, N., Cullen, D., Bronson, R. T., Kaelin Jr., W. G. (2007). Somativ inactivation of the PHD2 prolyl hydroxylase causes polycythemia and congestive heart failure. Blood 111(6): 3236-3244.

Price, N. L., Gomes, A. P., Ling, A. J., Duarte, F. V., Martin-Montalvo, A., North, B. J., Agarwal, B., Ye, L., Ramadori, G., Teodoro, J. S., et al. (2012). SIRT1 Is Required for AMPK Activation and the Beneficial Effects of Resveratrol on Mitochondrial Function. Cell Metab 15, 675-690.

EQUIVALENTS AND SCOPE

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

Those skilled in the art will recognize or be able to ascertain using no more than routine experimentation many equivalents to the specific embodiments of the invention described herein. Such equivalents are intended to be encompassed by the following claims. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention can be excluded from any one or more claims, for any reason, whether or not related to the existence of prior art.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

All references cited herein, including patents, published patent applications, and publications, are incorporated by reference in their entirety, particularly for the disclosure referenced herein.

What is claimed is:

1. A method for treating or preventing cancer in a subject in need thereof comprising administering to the subject an amount of nicotinamide mononucleotide (NMN), or a salt thereof, or a prodrug thereof, effective to increase the level of nicotinamide adenine dinucleotide (NAD+) in the subject.

2. The method of claim 1, wherein the NMN or salt thereof, or prodrug thereof, is administered at a dose of between 0.5-5 grams per day.

3. The method of claim 1, wherein the subject is a human.

4. The method of claim 1, wherein the NMN or salt thereof, or prodrug thereof, is administered as a pharmaceutical composition comprising a pharmaceutically acceptable carrier and the NMN or salt thereof, or prodrug thereof.

5. The method of claim 4, wherein the pharmaceutical composition is adapted for oral administration.

6. The method of claim 4, wherein the NMN or salt thereof, or prodrug thereof, is administered orally.

7. The method of claim 2, wherein the NMN or salt thereof, or prodrug thereof, is administered orally.

8. The method of claim 4, wherein the NMN or salt thereof, or prodrug thereof, is administered orally.

9. The method of claim 2, wherein the subject is a human.

10. The method of claim 4, wherein the subject is a human.

11. The method of claim 5, wherein the subject is a human.

12. The method of claim 2, wherein the NMN or salt thereof, or prodrug thereof, is administered as a pharmaceutical composition comprising a pharmaceutically acceptable carrier and the NMN or salt thereof, or prodrug thereof.

13. The method of claim 12, wherein the pharmaceutical composition is adapted for oral administration.

14. The method of claim 12, wherein the NMN or salt thereof, or prodrug thereof, is administered orally.

15. A method for treating or preventing cancer in a subject in need thereof, comprising administering to the subject an amount of NMN, or a salt thereof, effective to increase the level of NAD+ in the subject.

16. The method of claim 15, wherein the NMN or salt thereof is administered at a dose of between 0.5-5 grams per day.

17. The method of claim 15, wherein the NMN or salt thereof is administered as a pharmaceutical composition comprising a pharmaceutically acceptable carrier and the NMN or salt thereof.

18. The method of claim 17, wherein the pharmaceutical composition is adapted for oral administration.

19. The method of claim 17, wherein the NMN or salt thereof is administered orally.

* * * * *